United States Patent
Wilson et al.

(10) Patent No.: US 11,447,557 B2
(45) Date of Patent: Sep. 20, 2022

(54) ANTIBODIES AND METHODS OF USE THEREOF

(71) Applicants: Agenus Inc., Lexington, MA (US); Memorial Sloan-Kettering Cancer Center, New York, NY (US); Ludwig Institute for Cancer Research Ltd., Zurich (CH)

(72) Inventors: Nicholas S. Wilson, Somerville, MA (US); Jeremy D. Waight, Everett, MA (US); Gerd Ritter, New York, NY (US); David Schaer, Mamaroneck, NY (US); Daniel Hirschhorn-Cymerman, New York, NY (US); Taha Merghoub, Jersey City, NJ (US); Ekaterina V. Breous-Nystrom, Basel (CH); Volker Seibert, Lörrach (DE); Takemasa Tsuji, Williamsville, NY (US); Olivier Léger, Saint-Sixt (FR); Dennis J. Underwood, Jamaica Plain, MA (US); Marc Van Dijk, Bilthoven (NL)

(73) Assignees: Agenus Inc., Lexington, MA (US); Memorial Sloan-Kettering Cancer Center, New York, NY (US); Ludwig Institute for Cancer Research Ltd., Zurich (CH)

( * ) Notice: Subject to any disclaimer, the term of this patent is extended or adjusted under 35 U.S.C. 154(b) by 439 days.

(21) Appl. No.: 15/781,043

(22) PCT Filed: Dec. 2, 2016

(86) PCT No.: PCT/US2016/064642
§ 371 (c)(1),
(2) Date: Jun. 1, 2018

(87) PCT Pub. No.: WO2017/096179
PCT Pub. Date: Jun. 8, 2017

(65) Prior Publication Data
US 2020/0079861 A1    Mar. 12, 2020

Related U.S. Application Data

(60) Provisional application No. 62/419,911, filed on Nov. 9, 2016, provisional application No. 62/262,369, filed on Dec. 2, 2015.

(51) Int. Cl.
*C07K 16/28*    (2006.01)
*A61K 39/395*    (2006.01)
*A61K 45/06*    (2006.01)

(52) U.S. Cl.
CPC ...... *C07K 16/2878* (2013.01); *A61K 39/3955* (2013.01); *A61K 45/06* (2013.01); *C07K 2317/31* (2013.01); *C07K 2317/732* (2013.01); *C07K 2317/75* (2013.01); *C07K 2317/76* (2013.01)

(58) Field of Classification Search
CPC ............ C07K 16/2878; C07K 2317/31; C07K 2317/732; C07K 2317/75; A61K 39/3955; A61K 2039/505
See application file for complete search history.

(56) References Cited

U.S. PATENT DOCUMENTS

| 5,585,097 A | 12/1996 | Bolt et al. |
| 5,624,821 A | 4/1997 | Winter et al. |
| 5,648,260 A | 7/1997 | Winter et al. |
| 5,677,425 A | 10/1997 | Bodmer et al. |
| 5,693,780 A | 12/1997 | Newman et al. |
| 5,759,546 A | 6/1998 | Weinberg et al. |
| 5,869,046 A | 2/1999 | Presta et al. |

(Continued)

FOREIGN PATENT DOCUMENTS

| EP | 2 637 691 A2 | 9/2013 |
| EP | 2 100 615 B1 | 2/2016 |

(Continued)

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*

(Continued)

*Primary Examiner* — Brad Duffy
*Assistant Examiner* — Cheom-Gil Cheong
(74) *Attorney, Agent, or Firm* — Dechert LLP; Andrew T Wilkins; Sharla F. Flohr

(57) ABSTRACT

The present disclosure provides multispecific (e.g., bispecific) antibodies that specifically bind to human GITR and/or human OX40 as well as compositions comprising such antibodies. In a specific aspect, the multispecific antibodies specifically bind to human GITR and OX40 and modulate GITR and/or OX40 activity, e.g., enhance, activate, or induce GITR and/or OX40 activity, or reduce, deactivate, or inhibit GITR and/or OX40 activity. The present disclosure also provides methods for treating disorders, such as cancer, by administering a multispecific antibody that specifically binds to human GITR and/or OX40 and modulates GITR and/or OX40 activity, e.g., enhances, activates, or induces GITR and/or OX40 activity. Also provided are methods for treating autoimmune or inflammatory diseases or disorders, by administering a multispecific antibody that specifically binds to human GITR and/or OX40 and modulates GITR and/or OX40 activity, e.g., reduces, deactivates, or inhibits GITR and/or OX40 activity.

Figure 1B:
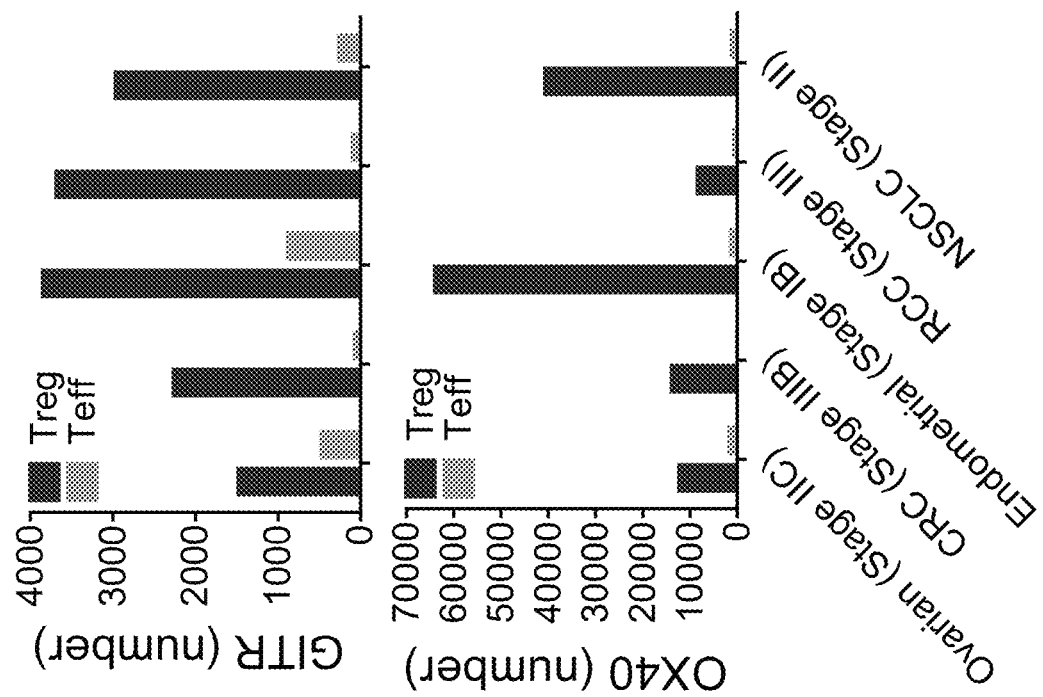

46 Claims, 19 Drawing Sheets
Specification includes a Sequence Listing.

(56) References Cited

U.S. PATENT DOCUMENTS

| | | |
|---|---|---|
| 6,121,022 A | 9/2000 | Presta et al. |
| 6,143,273 A | 11/2000 | Faure et al. |
| 6,165,745 A | 12/2000 | Ward et al. |
| 6,194,551 B1 | 2/2001 | Idusogie et al. |
| 6,197,524 B1 | 3/2001 | Romagnani |
| 6,207,156 B1 | 3/2001 | Kuchroo et al. |
| 6,277,375 B1 | 8/2001 | Ward |
| 6,277,962 B1 | 8/2001 | Godfrey et al. |
| 6,383,492 B1 | 5/2002 | Srivastava et al. |
| 6,391,306 B1 | 5/2002 | Srivastava et al. |
| 6,403,095 B1 | 6/2002 | Srivastava et al. |
| 6,410,026 B1 | 6/2002 | Srivastava |
| 6,436,404 B1 | 8/2002 | Srivastava et al. |
| 6,447,780 B1 | 9/2002 | Srivastava et al. |
| 6,447,781 B1 | 9/2002 | Srivastava |
| 6,503,184 B1 | 1/2003 | Ni et al. |
| 6,509,173 B1 | 1/2003 | Ni et al. |
| 6,566,082 B1 | 5/2003 | Weinberg et al. |
| 6,610,659 B1 | 8/2003 | Pramod |
| 6,645,495 B1 | 11/2003 | Kensil et al. |
| 6,737,056 B1 | 5/2004 | Presta |
| 6,808,710 B1 | 10/2004 | Wood et al. |
| 7,025,962 B1 | 4/2006 | Gormanb et al. |
| 7,029,678 B2 | 4/2006 | Momin et al. |
| 7,034,121 B2 | 4/2006 | Carreno et al. |
| 7,364,733 B2 | 4/2008 | Godfrey et al. |
| 7,387,271 B2 | 6/2008 | Noelle et al. |
| 7,402,431 B2 | 7/2008 | Har-Noy |
| 7,435,592 B2 | 10/2008 | Har-Noy |
| 7,465,446 B2 | 12/2008 | Lowy et al. |
| 7,470,428 B2 | 12/2008 | Kuchroo et al. |
| 7,488,802 B2 | 2/2009 | Collins et al. |
| 7,504,101 B2 | 3/2009 | Weinberg |
| 7,531,170 B1 | 5/2009 | Croft et al. |
| 7,534,808 B2 | 5/2009 | Evenou et al. |
| 7,550,140 B2 | 6/2009 | Bakker et al. |
| 7,563,443 B2 | 7/2009 | Grant et al. |
| 7,592,431 B2 | 9/2009 | Har-Noy |
| 7,635,472 B2 | 12/2009 | Kufer et al. |
| 7,648,989 B2 | 1/2010 | Van Eis et al. |
| 7,799,902 B2 | 9/2010 | Browning et al. |
| 7,807,156 B1 | 10/2010 | Croft et al. |
| 7,812,133 B2 | 10/2010 | Martin |
| 7,812,135 B2 | 10/2010 | Smith et al. |
| 7,820,672 B2 | 10/2010 | Von Matt |
| 7,829,084 B2 | 11/2010 | Ledbetter et al. |
| 7,858,589 B2 | 12/2010 | Kensil |
| 7,960,515 B2 | 6/2011 | Min et al. |
| 8,008,449 B2 | 8/2011 | Korman et al. |
| 8,101,175 B1 | 1/2012 | Croft et al. |
| 8,101,176 B2 | 1/2012 | Kuchroo et al. |
| 8,114,845 B2 | 2/2012 | Langermann et al. |
| 8,124,085 B2 | 2/2012 | Nielsen et al. |
| 8,133,983 B2 | 3/2012 | Bakker et al. |
| 8,142,778 B2 | 3/2012 | Davis et al. |
| 8,147,835 B2 | 4/2012 | Ledbetter et al. |
| 8,153,765 B2 | 4/2012 | Park et al. |
| 8,168,179 B2 | 5/2012 | Honjo et al. |
| 8,168,757 B2 | 5/2012 | Finnefrock et al. |
| 8,193,322 B2 | 6/2012 | Yan et al. |
| 8,197,810 B2 | 6/2012 | Ledbetter et al. |
| 8,226,946 B2 | 7/2012 | Chen |
| 8,236,930 B2 | 8/2012 | Min et al. |
| 8,263,073 B2 | 9/2012 | Korman et al. |
| 8,283,450 B2 | 10/2012 | Kato et al. |
| 8,329,197 B2 | 12/2012 | Noelle et al. |
| 8,388,967 B2 | 3/2013 | Smith et al. |
| 8,409,577 B2 | 4/2013 | Thompson et al. |
| 8,440,192 B2 | 5/2013 | Nielsen et al. |
| 8,481,029 B2 | 7/2013 | Glennie et al. |
| 8,541,002 B2 | 9/2013 | Truneh et al. |
| 8,551,477 B1 | 10/2013 | Croft et al. |
| 8,591,886 B2 | 11/2013 | Ponath et al. |
| 8,614,295 B2 | 12/2013 | Lawson et al. |
| 8,652,836 B2 | 2/2014 | Hu |
| 8,709,424 B2 | 4/2014 | Schebye et al. |
| 8,748,585 B2 | 6/2014 | Attinger et al. |
| 8,865,873 B2 | 10/2014 | Liu et al. |
| 8,956,615 B1 | 2/2015 | Croft et al. |
| 8,993,524 B2 | 3/2015 | Bedi et al. |
| 8,993,614 B2 | 3/2015 | Bartkovitz et al. |
| 9,005,612 B2 | 4/2015 | Ledbetter et al. |
| 9,005,619 B2 | 4/2015 | Kohrt et al. |
| 9,006,399 B2 | 4/2015 | Liu et al. |
| 9,028,823 B2 | 5/2015 | Smith et al. |
| 9,028,824 B2 | 5/2015 | Min et al. |
| 9,040,048 B2 | 5/2015 | Adams et al. |
| 9,102,733 B2 | 8/2015 | Endl et al. |
| 9,119,807 B2 | 9/2015 | Aarvak et al. |
| 9,132,281 B2 | 9/2015 | Zeng et al. |
| 9,161,976 B2 | 10/2015 | Noelle et al. |
| 9,163,085 B2 | 10/2015 | Liu |
| 9,228,016 B2 | 1/2016 | Wang et al. |
| 9,241,992 B2 | 1/2016 | Ponte et al. |
| 9,248,183 B2 | 2/2016 | Glennie et al. |
| 9,255,151 B2 | 2/2016 | Kwon |
| 9,255,152 B2 | 2/2016 | Kwon |
| 9,309,321 B2 | 4/2016 | Kwon |
| 9,352,001 B2 | 5/2016 | Har-Noy |
| 9,365,496 B2 | 6/2016 | Cerundolo et al. |
| 9,382,319 B2 | 7/2016 | Tso et al. |
| 9,409,987 B2 | 8/2016 | Toporik et al. |
| 9,428,570 B2 | 8/2016 | Lawson et al. |
| 9,441,044 B2 | 9/2016 | Bedi et al. |
| 9,464,139 B2 | 10/2016 | Beers et al. |
| 9,475,878 B2 | 10/2016 | Kato et al. |
| 9,475,880 B2 | 10/2016 | Simons et al. |
| 9,486,520 B2 | 11/2016 | Borrebaeck et al. |
| 9,493,563 B2 | 11/2016 | Blein et al. |
| 9,493,579 B2 | 11/2016 | Miller et al. |
| 9,511,127 B2 | 12/2016 | Har-Noy |
| 9,527,917 B2 | 12/2016 | Liu |
| 9,540,442 B2 | 1/2017 | Tsurushita et al. |
| 9,695,246 B2 | 7/2017 | Liu et al. |
| 9,700,532 B2 | 7/2017 | Cerundolo |
| 9,713,641 B2 | 7/2017 | Hicklin et al. |
| 9,738,723 B2 | 8/2017 | Hammond et al. |
| 9,758,589 B2 | 9/2017 | Kohrt et al. |
| 9,782,463 B2 | 10/2017 | Har-Noy |
| 9,790,281 B2 | 10/2017 | Simons et al. |
| 9,828,432 B2 | 11/2017 | Curti et al. |
| 9,834,610 B2 | 12/2017 | Tykocinski |
| 9,840,536 B2 | 12/2017 | Currie et al. |
| 9,850,306 B2 | 12/2017 | Bedi et al. |
| 9,873,735 B2 | 1/2018 | Adams et al. |
| 9,873,744 B1 | 1/2018 | Croft et al. |
| 9,926,374 B2 | 3/2018 | Glennie et al. |
| 10,155,818 B2 | 12/2018 | Seibert et al. |
| 10,259,882 B2 | 4/2019 | Van Dijk et al. |
| 10,280,226 B2 | 5/2019 | Seibert et al. |
| 10,577,426 B2 * | 3/2020 | Gonzalez ................ A61P 37/02 |
| 10,626,181 B2 | 4/2020 | Van Dijk et al. |
| 2002/0150993 A1 | 10/2002 | Ashkenazi et al. |
| 2003/0035790 A1 | 2/2003 | Chen et al. |
| 2003/0086930 A1 | 5/2003 | Mueller et al. |
| 2003/0133936 A1 | 7/2003 | Byrne et al. |
| 2003/0223989 A1 | 12/2003 | Pluenneke et al. |
| 2003/0232323 A1 | 12/2003 | Freeman et al. |
| 2004/0009174 A1 | 1/2004 | Arndt et al. |
| 2004/0022760 A1 | 2/2004 | McKenna et al. |
| 2004/0197312 A1 | 10/2004 | Moskalenko et al. |
| 2005/0002916 A1 | 1/2005 | Jooss |
| 2005/0014224 A1 | 1/2005 | Collins et al. |
| 2005/0048054 A1 | 3/2005 | Hanabuchi et al. |
| 2005/0123536 A1 | 6/2005 | Law |
| 2005/0226875 A1 | 10/2005 | Gomez-Navarro et al. |
| 2006/0148064 A1 | 7/2006 | Srivastava |
| 2006/0217531 A1 | 9/2006 | Godfrey et al. |
| 2006/0280728 A1 | 12/2006 | Weinberg et al. |
| 2006/0281072 A1 | 12/2006 | Bakker |
| 2007/0036783 A1 | 2/2007 | Humeau et al. |
| 2007/0092511 A1 | 4/2007 | Godfrey et al. |
| 2007/0243184 A1 | 10/2007 | Fischkoff et al. |
| 2008/0152665 A1 | 6/2008 | Leclerc et al. |

(56) References Cited

U.S. PATENT DOCUMENTS

| | | |
|---|---|---|
| 2008/0286286 A1 | 11/2008 | Liu et al. |
| 2008/0317751 A1 | 12/2008 | Heath |
| 2009/0004213 A1 | 1/2009 | Singh et al. |
| 2009/0069535 A1 | 3/2009 | Godfrey et al. |
| 2009/0087440 A1 | 4/2009 | Vicari et al. |
| 2009/0123477 A1 | 5/2009 | Hanke et al. |
| 2009/0130111 A1* | 5/2009 | Wu ................ A61P 37/00 424/139.1 |
| 2009/0175867 A1 | 7/2009 | Thompson et al. |
| 2009/0214533 A1 | 8/2009 | Clynes |
| 2009/0214560 A1 | 8/2009 | Min et al. |
| 2009/0285834 A1 | 11/2009 | Tomizawa |
| 2009/0317407 A1 | 12/2009 | Lacelle et al. |
| 2010/0008920 A1 | 1/2010 | Schneck et al. |
| 2010/0015143 A1 | 1/2010 | Hussell et al. |
| 2010/0061992 A1 | 3/2010 | Anderson et al. |
| 2010/0098712 A1 | 4/2010 | Adler et al. |
| 2010/0100131 A1 | 4/2010 | Wallenstein |
| 2010/0136030 A1 | 6/2010 | Salah-Eddine et al. |
| 2010/0196359 A1 | 8/2010 | Kato et al. |
| 2010/0196394 A1 | 8/2010 | Pardoll et al. |
| 2010/0203056 A1 | 8/2010 | Irving et al. |
| 2010/0233183 A1 | 9/2010 | Triebel et al. |
| 2010/0240873 A1 | 9/2010 | Godfrey et al. |
| 2010/0254978 A1 | 10/2010 | Lawson et al. |
| 2010/0278844 A1 | 11/2010 | Balkwill et al. |
| 2010/0285001 A1 | 11/2010 | Land et al. |
| 2011/0008368 A1 | 1/2011 | Liu et al. |
| 2011/0044953 A1 | 2/2011 | Allison et al. |
| 2011/0123552 A1 | 5/2011 | Bakker et al. |
| 2011/0150892 A1 | 6/2011 | Thudium et al. |
| 2011/0206681 A1 | 8/2011 | Min et al. |
| 2011/0256184 A1 | 10/2011 | Lei et al. |
| 2011/0262454 A1 | 10/2011 | Park et al. |
| 2011/0280903 A1 | 11/2011 | Noelle et al. |
| 2011/0305713 A1 | 12/2011 | Munn et al. |
| 2011/0318380 A1 | 12/2011 | Brix et al. |
| 2012/0014947 A1 | 1/2012 | Fu |
| 2012/0070450 A1 | 3/2012 | Ishikawa et al. |
| 2012/0128687 A1 | 5/2012 | Adler et al. |
| 2012/0141465 A1 | 6/2012 | Croft et al. |
| 2012/0141501 A1 | 6/2012 | Yoshida et al. |
| 2012/0142750 A1 | 6/2012 | Chen et al. |
| 2012/0219559 A1 | 8/2012 | Chen |
| 2012/0225086 A1 | 9/2012 | Min et al. |
| 2012/0251531 A1 | 10/2012 | Baehner et al. |
| 2012/0269825 A1 | 10/2012 | Liu et al. |
| 2013/0022623 A1 | 1/2013 | Karsunky et al. |
| 2013/0039911 A1 | 2/2013 | Bedi et al. |
| 2013/0071403 A1 | 3/2013 | Rolland et al. |
| 2013/0108641 A1 | 5/2013 | Baurin et al. |
| 2013/0177579 A1 | 7/2013 | Lin et al. |
| 2013/0183311 A1 | 7/2013 | Nielsen et al. |
| 2013/0183315 A1 | 7/2013 | Attinger et al. |
| 2013/0202623 A1 | 8/2013 | Chomont et al. |
| 2013/0211050 A1 | 8/2013 | Stennicke et al. |
| 2013/0243772 A1 | 9/2013 | Adams et al. |
| 2013/0280265 A1 | 10/2013 | Rolland et al. |
| 2013/0280275 A1* | 10/2013 | Liu ................ A61P 37/00 424/173.1 |
| 2013/0295091 A1 | 11/2013 | Esslinger et al. |
| 2013/0295107 A1 | 11/2013 | Tawara et al. |
| 2013/0323283 A1 | 12/2013 | Hancock et al. |
| 2013/0330344 A1 | 12/2013 | Lawson et al. |
| 2013/0336977 A1 | 12/2013 | Thompson et al. |
| 2014/0037621 A1 | 2/2014 | Tsurushita et al. |
| 2014/0044703 A1 | 2/2014 | Kato et al. |
| 2014/0079706 A1 | 3/2014 | Cannarile et al. |
| 2014/0127203 A1 | 5/2014 | Thompson et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0294759 A1 | 10/2014 | Chu et al. |
| 2014/0294765 A1 | 10/2014 | Cojocaru et al. |
| 2014/0294824 A1 | 10/2014 | Attinger et al. |
| 2014/0302033 A1 | 10/2014 | Adams et al. |
| 2014/0308276 A1 | 10/2014 | Liu et al. |
| 2014/0348841 A1 | 11/2014 | Schebye et al. |
| 2014/0377221 A1 | 12/2014 | Tufaro et al. |
| 2014/0377253 A1 | 12/2014 | Harding et al. |
| 2014/0377284 A1 | 12/2014 | Simons et al. |
| 2015/0017141 A1 | 1/2015 | June et al. |
| 2015/0037346 A1 | 2/2015 | Lesokhin et al. |
| 2015/0038682 A1 | 2/2015 | Tsurushita et al. |
| 2015/0056206 A1 | 2/2015 | Zhou |
| 2015/0064204 A1 | 3/2015 | Beers et al. |
| 2015/0086584 A1 | 3/2015 | Gilboa et al. |
| 2015/0119555 A1 | 4/2015 | Jung et al. |
| 2015/0132288 A1 | 5/2015 | Simons et al. |
| 2015/0015771 A1 | 6/2015 | Redmond et al. |
| 2015/0158947 A1 | 6/2015 | Cojocaru |
| 2015/0174268 A1 | 6/2015 | Li |
| 2015/0190505 A1 | 7/2015 | Yeung |
| 2015/0190506 A1 | 7/2015 | Cheung et al. |
| 2015/0202291 A1 | 7/2015 | Bosch et al. |
| 2015/0210765 A1 | 7/2015 | Roschke et al. |
| 2015/0218279 A1 | 8/2015 | Min et al. |
| 2015/0273033 A1 | 10/2015 | Bosch et al. |
| 2015/0307617 A1 | 10/2015 | Du et al. |
| 2015/0307620 A1 | 10/2015 | Vella et al. |
| 2015/0315281 A1 | 11/2015 | Liu et al. |
| 2015/0322119 A1 | 11/2015 | Engelhardt et al. |
| 2015/0329617 A1 | 11/2015 | Winther et al. |
| 2015/0353637 A1* | 12/2015 | Wang ................ G01N 33/6863 424/139.1 |
| 2015/0368349 A1 | 12/2015 | Gonzalez et al. |
| 2015/0374731 A1 | 12/2015 | Maio et al. |
| 2015/0377882 A1 | 12/2015 | Ashdown |
| 2016/0031974 A1 | 2/2016 | Adams et al. |
| 2016/0068604 A1 | 3/2016 | Liu et al. |
| 2016/0101128 A1 | 4/2016 | Wang et al. |
| 2016/0129095 A1 | 5/2016 | Noelle et al. |
| 2016/0137740 A1 | 5/2016 | Hammond et al. |
| 2016/0151515 A1 | 6/2016 | Joubert et al. |
| 2016/0152720 A1 | 6/2016 | Kim et al. |
| 2016/0159905 A1 | 6/2016 | Abdiche et al. |
| 2016/0159927 A1 | 6/2016 | Molloy et al. |
| 2016/0193239 A1 | 7/2016 | Baylin et al. |
| 2016/0207995 A1* | 7/2016 | Yansura ................ A61P 17/02 |
| 2016/0235842 A1 | 8/2016 | Goldstein et al. |
| 2016/0243218 A1 | 8/2016 | Gilboa |
| 2016/0289645 A1 | 10/2016 | Tufaro et al. |
| 2016/0304607 A1 | 10/2016 | Sadineni et al. |
| 2016/0347847 A1 | 12/2016 | Van Dijk et al. |
| 2016/0347848 A1 | 12/2016 | Hammond et al. |
| 2016/0347849 A1 | 12/2016 | Cai et al. |
| 2016/0355589 A1 | 12/2016 | Williams et al. |
| 2016/0355598 A1 | 12/2016 | Lawson et al. |
| 2017/0014496 A1 | 1/2017 | Fotin-Mleczek et al. |
| 2017/0042997 A1 | 2/2017 | Wirth |
| 2017/0051061 A1 | 2/2017 | Snyder et al. |
| 2017/0051069 A1 | 2/2017 | Simons et al. |
| 2017/0056391 A1 | 3/2017 | Li |
| 2017/0081417 A1 | 3/2017 | Kato et al. |
| 2017/0106048 A1 | 4/2017 | Kunz et al. |
| 2017/0137530 A1 | 5/2017 | Baehner et al. |
| 2017/0158770 A1 | 6/2017 | Bedi et al. |
| 2017/0165230 A1 | 6/2017 | Rudd et al. |
| 2017/0182156 A1 | 6/2017 | Khleif |
| 2017/0202902 A1 | 7/2017 | McLaughlin et al. |
| 2017/0209574 A1 | 7/2017 | Cao |
| 2017/0216403 A1 | 8/2017 | Wittrup et al. |
| 2017/0224777 A1 | 8/2017 | Wittrup et al. |
| 2017/0239338 A1 | 8/2017 | Szalay et al. |
| 2017/0240634 A1 | 8/2017 | Eisenbach-Schwartz |
| 2017/0261497 A1 | 9/2017 | Schneck et al. |
| 2017/0267759 A1 | 9/2017 | Liang et al. |
| 2017/0267773 A1 | 9/2017 | Liu et al. |
| 2017/0290914 A1 | 10/2017 | Liang et al. |
| 2017/0296659 A1 | 10/2017 | Lebwohl |
| 2017/0320950 A1 | 11/2017 | Snyder et al. |
| 2017/0340733 A1 | 11/2017 | Cao |
| 2017/0362295 A1 | 12/2017 | June et al. |
| 2017/0369586 A1 | 12/2017 | Simons et al. |

(56) References Cited

U.S. PATENT DOCUMENTS

| | | |
|---|---|---|
| 2018/0044428 A1 | 2/2018 | Gough et al. |
| 2018/0057608 A1 | 3/2018 | Jung et al. |
| 2018/0064765 A1 | 3/2018 | Petit et al. |
| 2018/0078625 A1 | 3/2018 | Moon et al. |
| 2018/0079821 A1 | 3/2018 | Tykocinski |
| 2018/0118823 A1 | 5/2018 | Thompson et al. |
| 2018/0194825 A1 | 7/2018 | Dubinett et al. |
| 2018/0194849 A1 | 7/2018 | Sahin et al. |
| 2018/0194850 A1 | 7/2018 | Faustman |
| 2018/0244793 A1 | 8/2018 | Gonzalez et al. |
| 2018/0355051 A1 | 12/2018 | Gonzalez et al. |
| 2019/0010239 A1 | 1/2019 | Gonzalez et al. |
| 2019/0062446 A1 | 2/2019 | Seibert et al. |
| 2019/0284291 A1 | 9/2019 | Van Dijk et al. |
| 2019/0309082 A1 | 10/2019 | Seibert et al. |
| 2019/0367627 A1 | 12/2019 | Wilson et al. |
| 2020/0079862 A1 | 3/2020 | Wilson et al. |
| 2020/0123265 A1 | 4/2020 | Wilson et al. |

FOREIGN PATENT DOCUMENTS

| | | |
|---|---|---|
| EP | 3 148 579 A1 | 4/2017 |
| EP | 3 292 152 A1 | 3/2018 |
| EP | 3 498 295 A1 | 6/2019 |
| JP | 2008-533993 A | 8/2008 |
| JP | 2008-278814 A | 11/2008 |
| WO | WO 1994029351 A2 | 12/1994 |
| WO | WO 1995001997 A1 | 1/1995 |
| WO | WO 1997034631 A1 | 9/1997 |
| WO | WO 1998023289 A1 | 6/1998 |
| WO | WO 1999042585 A1 | 8/1999 |
| WO | WO 2000037504 A2 | 6/2000 |
| WO | WO 2000042072 A2 | 7/2000 |
| WO | WO 2001014424 A2 | 3/2001 |
| WO | WO 2001077342 A1 | 10/2001 |
| WO | WO 2002028440 A1 | 4/2002 |
| WO | WO 2002060919 A2 | 8/2002 |
| WO | WO 2003106498 A2 | 12/2003 |
| WO | WO 2004056873 A1 | 7/2004 |
| WO | WO 2004073732 A1 | 9/2004 |
| WO | WO 2005049085 A1 | 6/2005 |
| WO | WO 2006105021 A2 | 10/2006 |
| WO | WO 2007133822 A1 | 11/2007 |
| WO | WO 2008106116 A2 | 9/2008 |
| WO | WO 2009079335 A1 | 6/2009 |
| WO | WO 2009100140 A1 | 8/2009 |
| WO | WO 2010005958 A2 | 1/2010 |
| WO | WO 2010054007 A1 | 5/2010 |
| WO | WO 2010056898 A2 | 5/2010 |
| WO | WO 2011028683 A1 | 3/2011 |
| WO | WO 2011086091 A1 | 7/2011 |
| WO | WO 2012064760 A2 | 5/2012 |
| WO | WO 2012130831 A1 | 10/2012 |
| WO | WO 2012163769 A1 | 12/2012 |
| WO | WO 2013008171 A1 | 1/2013 |
| WO | WO 2013022091 A1 | 2/2013 |
| WO | WO 2013028231 A1 | 2/2013 |
| WO | WO 2013038191 A2 | 3/2013 |
| WO | WO 2013039954 A1 | 3/2013 |
| WO | WO 2013049307 A2 | 4/2013 |
| WO | WO 2013068563 A2 | 5/2013 |
| WO | WO 2013083659 A1 | 6/2013 |
| WO | WO 2013092001 A1 | 6/2013 |
| WO | WO 2014121099 A1 | 8/2014 |
| WO | WO 2014148895 A1 | 9/2014 |
| WO | WO 2015009726 A2 | 1/2015 |
| WO | WO 2015009856 A2 | 1/2015 |
| WO | WO 2015026684 A1 | 2/2015 |
| WO | WO 2015095423 A2 | 6/2015 |
| WO | WO 2015095811 A2 | 6/2015 |
| WO | WO 2015116178 A1 | 8/2015 |
| WO | WO 2015135558 A1 | 9/2015 |
| WO | WO 2015145360 A1 | 10/2015 |
| WO | WO 2015153514 A1 | 10/2015 |
| WO | WO 2015174439 A1 | 11/2015 |
| WO | WO 2015184099 A1 | 12/2015 |
| WO | WO 2016028656 A1 | 2/2016 |
| WO | WO 2016028672 A1 | 2/2016 |
| WO | WO 2016054638 A1 | 4/2016 |
| WO | WO 2016057841 A1 | 4/2016 |
| WO | WO 2016059602 A2 | 4/2016 |
| WO | WO 2016062722 A1 | 4/2016 |
| WO | WO 2016066634 A2 | 5/2016 |
| WO | WO 2016075174 A1 | 5/2016 |
| WO | WO 2016081746 A2 | 5/2016 |
| WO | WO 2016100985 A2 | 6/2016 |
| WO | WO 2016111645 A1 | 7/2016 |
| WO | WO 2016154544 A1 | 9/2016 |
| WO | WO 2016168361 A1 | 10/2016 |
| WO | WO 2016168716 A1 | 10/2016 |
| WO | WO 2016179517 A1 | 11/2016 |
| WO | PCT/US2016/064642 | 12/2016 |
| WO | WO 2017096179 A1 | 6/2017 |
| WO | WO 2017096182 A1 | 6/2017 |
| WO | WO 2017096189 A1 | 6/2017 |
| WO | WO 2017096276 A1 | 6/2017 |
| WO | WO 2017096281 A1 | 6/2017 |
| WO | WO 2017157964 A1 | 9/2017 |
| WO | WO 2017186928 A1 | 11/2017 |
| WO | WO 2018089628 A1 | 5/2018 |

OTHER PUBLICATIONS

Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
"A comprehensive immuno-oncology Ecosystem" Cowen and Company 36th Annual Health Care Conference Mar. 2016.
"Agenus Announces Commencement of Phase 1-2 Clinical Trial of anti-OX40 Checkpoint Antibody INCAGN1949 in Patients with Solid Tumors"—PRNewswire—(Nov. 30, 2016).
"Agenus Presents Posters on Checkpoint Antibody Product Candidates at the American Association for Cancer Research (AACR) 2016 Annual Meeting" (Business Wire) (Apr. 18, 2016).
"Agenus R&D Day" (May 14, 2015).
"Agenus R&D Day" New York, NY (Nov. 19, 2015).
"Agenus, Driving the immune system to fight cancer and infectious disease," Mar. 2015.
"Agenus, Driving the immune system to fight cancer and infectious disease," May 15, 2015.
"Agonist Checkpoint Modulators: Challenges and Opportunities" PEGS Boston May 8, 2015.
"Emerging Leader in Immuno-Oncology", Lexington, MA (Nov. 2015).
"Four Agenus Abstracts Accepted for Presentation at the American Association for Cancer Research(AACR) 2017 Annual Meeting" PRNewswire (Mar. 7, 2017).
"Immuno-Oncology" RBS Immunotherapy Conference Mar. 27, 2014.
"Integrated Approach to Immuno-Oncology" Blair Maidstone I-0 Conference NYC (Mar. 31, 2016).
"Integrated Solutions in Immuno-Oncology" Apr. 2016.
"Integrated Solutions in Immuno-Oncology" May 2016.
"Targeting TNFR Family Members: Therapeutic opportunities in immuno-oncology and immuno-inflammation" PEGS Boston 2016.
Allan, et al. (Feb. 27, 2007) "Activation-Induced FOXP3 in Human T Effector Cells Does Not Suppress Proliferation or Cytokine Production", International Immunology, vol. 19, Issue 4, pp. 345-354.
Arch, R.H. and Thompson, C.B., (1998) "4-1BB and Ox40 are Members of a Tumor Necrosis Factor (TNF)-Nerve Growth Factor Receptor Subfamily That Bind TNF Receptor-Associated Factors and Activate Nuclear Factor κB" Molecular and Cell Biology 18(1):558-565.
Arnett, et al. (Mar. 1, 2011) "IBC's 21st Annual Antibody Engineering and 8th Annual Antibody Therapeutics International Con-

(56) References Cited

OTHER PUBLICATIONS ferences and 2010 Annual Meeting of the Antibody Society: Dec. 5-9, 2010, San Diego, CA USA", mAbs, vol. 3, No. 2, pp. 133-152.
Aspeslagh, S., et al. "Rationale for ANTI-OX40 Cancer Immunotherapy" European Journal of Cancer 52:50-66 (Jan. 2016).
Aspord, C., et al., "Plasmacytoid Dendritic Cells Support Melanoma Progression by Promoting Th2 and Regulatory Immunity through OX4OL and ICOSL" Cancer Immunol Res; 1(6):402-15 (2013).
Avogadri, et al. (Jun. 19, 2010) "Modulation of CTLA-4 and GITR for Cancer Immunotherapy", Cancer Immunology and Immunotherapy, vol. 344, pp. 211-244.
Back, J., "Dampening Pathological Immune Responses via Targeting OX40 with GBR830, an Antagonist Monoclonal Antibody" PEGS, Biologics for Autoimmune Disease, (May 12, 2015).
Baessler, et al. (Jan. 20, 2009) "Glucocorticoid-induced Tumor Necrosis Factor Receptor-related Protein Ligand Subverts Immunosurveillance of Acute Myeloid Leukemia in Humans", Cancer research, vol. 69, Issue 3, pp. 1037-1045.
Baltz, et al. (Mar. 14, 2007) "Cancer Immunoediting by GITR (Glucocorticoid-induced TNF-related Protein) Ligand in Humans: NK Cell/tumor Cell Interactions", The FASEB Journal, vol. 21, No. 10, pp. 2442-2454.
Baum, P.R., et al., "Identification of OX40 Ligand and Preliminary Characterization of its Activities on OX40 Receptor," Circulatory Shock 44(1):30-34, University Park Press, United States (1994).
Bellati, et al. (Jun. 1, 2009) "Immunology of Gynecologic Neoplasms: Analysis of the Prognostic Significance of the Immune Status", Current Cancer Drug Targets, vol. 9, No. 4, pp. 541-565.
Berrong, et al., "Immune combinational therapy targeting OX40 and IDO synergistically enhances efficacy of a cancer vaccine" J. Immunother. Cancer 2(Suppl 3): p. 226, Nature, United States (2014).
Berrong, Z., et al., "Antigen-Specific Antitumor Responses Induced by OX40 Agonist are Enhanced by the IDO Inhibitor Indoximod" Cancer Immunol Res 6(2):201-8 (2018).
Bianchini, et al. (May 10, 2011) "CD4(+) CD25(low) GITR(+) Cells: A Novel Human CD4(+) T-cell Population with Regulatory Activity", European Journal of Immunology, vol. 41, Issue 8, pp. 2269-2278.
Birebent, Brigitte (Nov. 26, 2004) "Suppressive Properties of Human CD25+CD4+ Regulatory T Cells are Dependent on CTLA-4 Expression", European journal of immunology, vol. 34, Issue 12, pp. 3485-3496.
Blazar et al., "Ligation of OX40 (CD134) regulates graft-versus-host disease (GVHD) and graft rejection in allogeneic bone marrow transplant recipients" Blood, 101(9):3741-8 (2003).
Bossen, et al. (May 19, 2006) "Interactions of Tumor Necrosis Factor (TNF) and TNF Receptor Family Members in the Mouse and Human", Journal of Biological Chemistry, American Society for Biochemistry and Molecular Biology, United States, vol. 281, No. 20, pp. 13964-13971.
Bournazos, S., and Ravetch, J.V., (2015) "FcY receptor pathways during active and passive immunization" Immunological Reviews 268:88-103.
Bowes, J., et al., (2012) "Reducing safety-related drug attrition: the use of in vitro pharmacological profiling" Nature Reviews Drug Discovery 11:911-922.
Bremnes, et al. (Apr. 2011) "The Role of Tumor-infiltrating Immune Cells and Chronic Inflammation at the Tumor Site on Cancer Development, Progression, and Prognosis: Emphasis on Non-Small Cell Lung Cancer", Journal of Thoracic Oncology, vol. 6, Issue 4, pp. 824-833.
Brennan, et al. (May-Jun. 2010) "Safety and Immunotoxicity Assessment of Immunomodulatory Monoclonal Antibodies", MAbs, vol. 2, No. 3, pp. 233-255.
Bruhns, et al. (Apr. 16, 2009) "Specificity and Affinity of Human Fcgamma Receptors and their Polymorphic Variants for Human IgG Subclasses", Blood, vol. 113, No. 16, pp. 3716-3725.
Buchan, S.L., et al., "Death receptor 3 is essential for generating optimal protective CD41 T-cell immunity against *Salmonella*" Eur. J. Immunol. 42: 580-588 (2012).
Buechele, et al. (Nov. 8, 2011) "Glucocorticoid-induced TNFR-related Protein (GITR) Ligand Modulates Cytokine Release and NK Cell Reactivity in Chronic Lymphocytic Leukemia (CLL)", Leukemia, vol. 26, No. 5, pp. 991-1000.
Bulliard, et al. (Aug. 26, 2013) "Activating Fcγ Receptors Contribute to the Antitumor Activities of Immunoregulatory Receptor-Targeting Antibodies", Journal of Experimental Medicine, vol. 210, No. 9, pp. 1685-1693.
Bulliard, et al. (Jul. 2014) "OX40 Engagement Depletes Intratumoral Tregs via Activating FcγRs, Leading to Antitumor Efficacy", Immunology and Cell Biology, vol. 92, No. 6, pp. 475-480.
Capello, D., et al., Immunoglobulin Kappa Chain Variable Region, Partial [*Homo sapiens*]. National Center for Biotechnology Information. GenBank Entry, Jul. 20, 1999 [Retrieved on Apr. 25, 2016] Retrieved from the Internet, URL: http://www.ncbi.nlm.nih.gov-protein-5578794, pp. 1-2.
Chan, et al. (May 1, 2010) "Therapeutic Antibodies for Autoimmunity and Inflammation", Nature Reviews Immunology, vol. 10, No. 5, pp. 301-316.
Chang, et al. (Apr. 28, 2014) "Inflammation-Related Factors Predicting Prognosis of Gastric Cancer", World Journal of Gastroenterology: WJG, vol. 20, No. 16, pp. 4586-4596.
Chapman, et al. (Feb. 2007) "Preclinical Safety Testing of Monoclonal Antibodies: The Significance of Species Relevance", Nature Reviews Drug Discovery, vol. 6, No. 2, pp. 120-126.
Chattopadhyay, et al. (Dec. 4, 2007) "Assembly and Structural Properties of Glucocorticoid-induced TNF Receptor Ligand: Implications for Function", Proceedings of the National Academy of Sciences USA, vol. 104, No. 49, pp. 19452-19457.
Chen, et al. (Jul. 25, 2013) "Oncology Meets Immunology: The Cancer-Immunity Cycle", Immunity, vol. 39, No. 1, pp. 1-10.
Chen, L., and Dallas, B.F., (2013) "Molecular mechanisms of T cell co-stimulation and co-inhibition" Nature Reviews Immunology 13(4):227-242.
Chu, et al. (Aug. 8, 2008) "Inhibition of B Cell Receptor-Mediated Activation of Primary Human B Cells by Coengagement of CD19 and Fc gamma RIIb With Fc-Engineered Antibodies", Molecular Immunology, vol. 45, No. 15, pp. 3926-3933.
Clackson, et al. (Aug. 15, 1991) "Making Antibody Fragments Using Phage Display Libraries", Nature, vol. 352, No. 6336, pp. 624-628.
Clouthier, et al. (Apr. 2014) "Cell-specific and Context-dependent Effects of GITR in Cancer, Autoimmunity, and Infection", Cytokine & Growth Factor Reviews, vol. 25, Issue 2, pp. 91-106.
Coe, et al. (Sep. 2010) "Depletion of Regulatory T Cells by Anti-GITR mAb as a Novel Mechanism for Cancer Immunotherapy", Cancer Immunology, Immunotherapy, vol. 59, No. 9, pp. 1367-1377.
Cohen, et al. (May 3, 2010) "Agonist Anti-GITR Monoclonal Antibody Induces Melanoma Tumor Immunity in Mice by Altering Regulatory T Cell Stability and Intra-tumor Accumulation", PloS One, vol. 5, No. 5, pp. e10436.
Cohen, et al. (May 2006) "Agonist Anti-GITR Antibody Enhances Vaccine-induced CD8(+) T-cell Responses and Tumor Immunity", Cancer Research, vol. 66, No. 9, pp. 4904-4912.
Coiffier (May 2007) "Rituximab Therapy in Malignant Lymphoma", Oncogene, vol. 26, No. 25, pp. 3603-3613.
Collins, A.V., et al., "The interaction properties of costimulatory molecules revisited" Immunity 17:201-210 (2002).
Compaan DM et al., "The Crystal Structure of the Costimulatory OX40-0X4OL Complex" Structure 14: 1321-1330 (2006).
Cote, et al. (Jan. 1, 2011) "Stimulation of the Glucocorticoid-induced TNF Receptor Family-related Receptor on CD8 T Cells Induces Protective and High-avidity T Cell Responses to Tumor-specific Antigens", The Journal of Immunology, American Association of Immunologists, United States, vol. 186, Issue 1, pp. 275-283.
Croft, M., "Control of immunity by the TNFR-related molecule OX40 (CD134)" Annul. Rev. Immunol. 28:57-78 (2010).

(56) References Cited

OTHER PUBLICATIONS

Croft, Michael (Jun. 2014) "The TNF Family in T Cell Differentiation and Function—unanswered Questions and Future Directions", Seminars in Immunology, vol. 26, Issue 3, pp. 183-190.
Cui, et al. (Mar. 15, 2010) "An Isoleucine-zipper Motif Enhances Costimulation of Human Soluble Trimeric GITR Ligand", Cellular & Molecular Immunology, vol. 7, No. 4, pp. 316-322.
Cunningham, et al. (Jun. 2, 1989) "High-Resolution Epitope Mapping of hGH-Receptor Interactions by Alanine-Scanning Mutagenesis", Science, vol. 244, No. 4908, pp. 1081-1085.
Curti, BD et al., "OX40 is a Potent Immune-Stimulating Target in Late-Stage Cancer Patients" Cancer Res. 73:7189-7198 (2013).
Cuzzocrea, et al. (Aug. 17, 2004) "Glucocorticoid-Induced TNF Receptor Family Gene (GITR) Knockout Mice Exhibit A Resistance to Splanchnic Artery Occlusion (SAO) Shock", Journal of leukocyte biology, vol. 76, Issue 5, pp. 933-940.
Cuzzocrea, et al. (Jul. 1, 2006) "Proinflammatory Role of Glucocorticoid-Induced TNF Receptor-Related Gene in Acute Lung Inflammation", The Journal of Immunology, vol. 177, No. 1, pp. 631-641.
Cuzzocrea, et al. (Nov. 29, 2006) "Geneticand Pharmacological Inhibition of GITR-GITRL Interaction Reduces Chronic Lung Injury Induced by Bleomycin Instillation", The FASEB Journal, vol. 21, No. 1, pp. 117-129.
Dall'Acqua, et al. (Aug. 18, 2006) "Properties of Human IgG1s Engineered for Enhanced Binding to the Neonatal Fc Receptor (FcRn)", Journal of Biology Chemistry, vol. 281, No. 33, pp. 23514-23524.
Dangl, et al. (Jul. 1988) "Segmental Flexibility and Complement Fixation of Genetically Engineered Chimeric Human, Rabbit and Mouse Antibodies", The EMBO Journal, vol. 7, No. 7, pp. 1989-1994.
Dunn, et al. (Nov. 1, 2002) "Cancer Immunoediting: From Immunosurveillance to Tumor Escape", Nature immunology, vol. 3, No. 11, pp. 991-998.
Dupage, et al. (2012) "Expression of Tumor-Specific Antigens Underlies Cancer Immunoediting", Nature, vol. 482, No. 7385, pp. 405-409.
EBioscience, an Affymetrix Company "Anti-Human CD357 (AITR/GITR) PE'," Product Brochure. Catalog No. 12-5875, (2012).
Ehrenstein, et al. (Nov. 2010) "The Importance of Natural IgM: Scavenger, Protector and Regulator", Nature Reviews Immunology, vol. 10, No. 11, pp. 778-786.
Ephrem, A., et al., (2013) "Modulation of Treg cells/T effector function by GITR signaling is context-dependent" Eur. J. Immunol. 43:2421-2429.
Esparza, et al. (May 1, 2006) "Signaling Triggered by Glucocorticoid-induced Tumor Necrosis Factor Receptor Family-related Gene: Regulation at the Interface Between Regulatory T Cells and Immune Effector Cells", Frontiers in Bio-science, vol. 11, pp. 1448-1465.
Extended European Search Report received for European Patent Application No. 18204948.6, 6 Pages, dated Mar. 22, 2019, 6 pages.
Finco, D., et al., "Cytokine release assays: current practices and future directions" Cytokine 66:143-155 (Jan. 2014).
Fromm, G., et al., "Gp96-Ig/Costimulator (OX4OL, ICOSL, or 4-1BBL) Combination Vaccine Improves T-cell Priming and Enhances Immunity, Memory, and Tumor Elimination" Cancer Immunol. Res. 4(9):766-78 (Jun. 2016).
Fujita, T., et al., (2006) "Functional characterization of OX40 expressed on human CD8+ T cells" Immunology Letters 106:27-33.
Furness, et al. (Jul. 2014) "Impact of Tumor Microenvironment and Fc Receptors on the Activity of Immunomodulatory Antibodies", Trends in Immunology, vol. 35, No. 7, pp. 290-298.
Galon, et al. (Sep. 29, 2006) "Type, Density, and Location of Immune Cells Within Human Colorectal Tumors Predict Clinical Outcome", Science, American Association for the Advancement of Science, United States, vol. 313, Issue 5795, pp. 1960-1964.
Genbank (Apr. 2, 1999) *Homo sapiens* glucocorticoid-induced TNFR-related protein ligand (TNFSF18) mRNA, complete cds, Accession No. AF125303.1, Retrieved from: <<https://www.ncbi.nlm.nih.gov/nuccore/AF125303>>, 1 Page.

Genbank (Oct. 7, 2016) Tumor Necrosis Factor Receptor Superfamily Member 18 Isoform 2 Precursor [*Homo sapiens*] "Accession No. NP_683699.1, Retrieved from: <<https://www.ncbi.nlm.nih.gov/protein/NP_683699.1/>>", 3 Pages.
Genbank (Oct. 30, 2007) *Homo sapiens* tumor necrosis factor receptor superfamily, member 18, mRNA (cDNA clone Image:100013446) Accession No. BC152386.1, Retrieved from: << https://www.ncbi.nlm.nih.gov/nuccore/BC152386>>, 2 Pages.
Genbank (Oct. 30, 2007) *Homo sapiens* tumor necrosis factor receptor superfamily, member 18, mRNA (cDNA clone MGC:166936 Image:100013440), complete cds, Accession No. BC152381.1, Retrieved from: <<https://www.ncbi.nlm.nih.gov/nuccore/BC152381>>, 2 Pages.
Genbank (Oct. 6, 2016) Tumor Necrosis Factor Ligand Superfamily Member 18 [*Homo sapiens*], Accession No. NP_005083.2, Retrieved from: <<https://www.ncbi.nlm.nih.gov/protein/NP005083>>, 3 Pages.
Genbank (Oct. 7, 2016) Tumor Necrosis Factor Receptor Superfamily Member 18 Isoform 1 Precursor [*Homo sapiens*] Accession No. NP_004186.1, Retrieved from: <<https://www.ncbi.nlm.nih.gov/protein/NP_004186.1/>> 3 Pages.
Genbank (Oct. 7, 2016) Tumor Necrosis Factor Receptor Superfamily Member 18 Isoform 3 Precursor [*Homo sapiens*] "Accession No. NP_683700.1, Retrieved from: <<https://www.ncbi.nlm.nih.gov/protein/NP_683700.1/>>", 3 Pages.
Genbank, "*Homo sapiens* cDNA FLJ50815 Complete CDS, Highly Similar to Tumor Necrosis Factor Ligand Superfamily member 4", Accession No. AK297932.1, accessed at https://www.ncbi.nlm.nih.gov-nuccore-AK297932.1.
Genbank, "*Homo sapiens* mRNA for Glycoprotein 34, Complete CDS," Accession No. D90224.1, accessed at https://www.ncbi.nlm.nih.gov-nuccore-D90224.1.
Gerondakis, et al. (Sep. 19, 2017) "NF-KB Control of T Cell Development", Nature Immunology, vol. 15, No. 1, pp. 15-25.
Glaus, et al. (May 2013) "In Vivo SPECT/CT Imaging of an Anti-GITR Antibody: A Novel Cancer Immunotherapeutic", The Journal of Nuclear Medicine, vol. 54, No. 2, 2 Pages.
Gobert, et al. (Mar. 2009) "Regulatory T Cells Recruited through CCL22/CCR4 are Selectively Activated in Lymphoid Infiltrates Surrounding Primary Breast Tumors and Lead to an Adverse Clinical Outcome", Cancer Research, vol. 69, No. 5, pp. 2000-2009.
Godfrey, W.R., et al., "Identification of a human OX-40 ligand, a costimulator of CD4+ T cells with homology to tumor necrosis factor" J. Exp. Med. 180:757-762 (1994).
Goede, et al. (Mar. 20, 2014) "Obinutuzumab Plus Chlorambucil in Patients with CLL and Coexisting Conditions", The New England Journal of Medicine, vol. 370, No. 12, pp. 1101-1110.
Golay, et al. (Nov. 14, 2013) "Glycoengineered CD20 Antibody Obinutuzumab Activates Neutrophils and Mediates Phagocytosis Through CD16B More Efficiently Than Rituximab", Blood, vol. 122, No. 20, pp. 3482-3491.
Gong, J et al. "A heat shock protein 70-Based vaccine with Enhanced Immunogenicity for clinical use," J Immunol, vol. 184, No. 1, pp. 488-496 (2010).
Gonzalez, et al. (Jul. 2016) "Abstract 3220: A Novel Agonist Antibody (INCAGN01876) That Targets the Costimulatory Receptor GITR", Cancer Research, American Association for Cancer Research Annual Meeting 2016, vol. 76, Issue 14, p. 3220.
Gonzalez, et al., "INCAGN1876, a Unique GITR Agonist Antibody That Facilitates GITR Oligomerization" 3643 Presented at the American Association for Cancer Research Annual Meeting 2017 Washington, DC, USA Apr. 1-5, 2017.
Gooden, et al. (Jun. 2011) "The Prognostic Influence of Tumor-Infiltrating Lymphocytes in Cancer: A Systematic Review with Meta-Analysis", British Journal of Cancer, vol. 105, No. 1, pp. 93-103.
Gough, M.J., et al., "Targeting macrophages in the tumour environment to enhance the efficacy of alpha-OX40 therapy" Immunology 136:437-447 (2012).
Gramaglia, I., et al., "OX-40 ligand: a potent costimulatory molecule for sustaining primary CD4 T cell responses" J. Immunol. 161:6510-6517 (1998).

(56) References Cited

OTHER PUBLICATIONS

Gramaglia, I., et al., "The OX40 Costimulatory Receptor Determines the Development of CD4 Memory by Regulating Primary Clonal Expansion" J. Immunol. 165:3043-3050 (2000).
Gravekamp, et al. (Jun. 2014) "Is Cancer Vaccination Feasible at Older Age?", Experimental Gerontology, vol. 54, pp. 138-144.
Grewal, Iqbal S. (2009) "Overview of TNF Superfamily: A Chest Full of Potential Therapeutic Targets", Advances in Experimental Medicine and Biology, vol. 647, pp. 1-7.
Grohmann, et al. (Apr. 8, 2007) "Reverse Signaling Through GITR Ligand Enables Dexamethasone to Activate IDO in Allergy", Nature Medicine, Nature Publishing Company, United States, 13, pp. 579-586.
Grosso, et al. (Feb. 2013) "CTLA-4 Blockade in Tumor Models: An Overview of Preclinical and Translational Research", Cancer Immunity, vol. 13, No. 1, pp. 1-14.
Guilliams, et al. (Jul. 18, 2014) "Dendritic Cells, Monocytes and Macrophages: A Unified Nomenclature Based on Ontogeny", Nature Reviews Immunology, vol. 14, No. 8, pp. 571-578.
Guilliams, M., et al., "The function of Fc gamma receptors in dendritic cells and macrophages" Nat. Rev. Immunol. 14:94-108 (Jan. 2014).
Guo, et al. (Feb. 27, 2014) "PD-1 Blockade and OX40 Triggering Synergistically Protects against Tumor Growth in a Murine Model of Ovarian Cancer", PLOS One, vol. 9, Issue 2, 10 Pages.
Gurney, et al. (Feb. 25, 1999) "Identification of a New Member of the Tumor Necrosis Factor Family and its Receptor, A Human Ortholog of Mouse GITR", Current biology, vol. 9, Issue 4, GenBank™ accession No. AF125303, Retrieved from: https://www.ncbi.nlm.nih.gov/nuccore/AF125303.1/, pp. 215-218.
Hanabuchi, et al. (May 1, 2006) "Human Plasmacytoid Predendritic Cells Activate NK Cells Through Glucocorticoid-Induced Tumor Necrosis Factor Receptor-Ligand (GITRL)", Blood, vol. 107, No. 9, pp. 3617-3623.
Hattori et al., "Blockade of the OX40 ligand prolongs corneal allograft survival" Eur. J. Immunol. 37(12):3597-604 (2007).
Hauer, J., et al., (2005) "TNF receptor (TNFR)-associated factor (TRAF) 3 serves as an inhibitor of TRAF2/5-mediated activation of the noncanonical NF-κB pathway by TRAF-binding TNFRs" PNAS 102(8):2874-7879.
Hebb, J.P., et al., "Administration of low-dose combination anti-CTLA4, anti-CD137, and anti-OX40 into murine tumor or proximal to the tumor draining lymph node induces systemic tumor regression" Cancer Immunol. Immunother. 67:47-60 (2018).
Herber, et al. (Jun. 2007) "Meeting Report: Mechanism and Therapeutic Reversal of Immune Suppression in Cancer,", Cancer Research, vol. 67, Issue 11, pp. 5067-5069.
Herter, et al. (Mar. 1, 2014) "Glycoengineering of Therapeutic Antibodies Enhances Monocyte/macrophage-mediated Phagocytosis and Cytotoxicity", The Journal of Immunology, vol. 192, No. 5, pp. 2252-2260.
Hindley, J.P., et al., (2011) "Analysis of the T-Cell Receptor Repertoires of Tumor-Infiltrating Conventional and Regulatory T Cells Reveals No Evidence for Conversion in Carcinogen-Induced Tumors" Cancer Res. 71(3):736-746.
Hirschhorn-Cymerman, D., et al., "OX40 engagement and chemotherapy combination provides potent antitumor immunity with concomitant regulatory T cell apoptosis" J. Exp. Med. 206:1103-1116 (2009).
Hogarth, et al. (Mar. 30, 2012) "Fc Receptor-Targeted Therapies for the Treatment of Inflammation, Cancer and Beyond", Nature Reviews Drug Discovery, vol. 11, No. 4, pp. 311-331.
Hombach, A.A., et al., "OX40 costimulation by a chimeric antigen receptor abrogates CD28 and IL-2 induced IL-10 secretion by redirected CD4+ T cells" OncoImmunology 1(4):458-466 (2012).
Hulett, et al. (Sep. 8, 1995) "Multiple Regions of Human Fc Gamma RII (CD32) Contribute to the Binding of IgG", The Journal of Biological Chemistry, vol. 270, No. 36, pp. 21188-21194.

"Human GITR/TNFRSF18 Antibody Summary", Retrieved from: https://www.rndsystems.com/products/human-gitr-tnfrsf18-antibody-110416_mab689, 7 Pages (Jun. 10, 2010).
Imai-Nishiya, et al. (Nov. 30, 2007) "Double Knockdown of α1, 6-Fucosyltransferase (FUT8) and GDP-Mannose 4, 6-Dehydratase (GMD) in Antibody-Producing Cells: A New Strategy for Generating Fully Non-Fucosylated Therapeutic Antibodies with Enhanced ADCC", BMC biotechnology, vol. 7, No. 1, pp. 1-13.
Imura, A., et al., "The human OX40-gp34 system directly mediates adhesion of activated T cells to vascular endothelial cells" J. Exp. Med. 183:2185-2195 (1996).
International Preliminary Report on Patentability for PCT/US2016/031257 dated Nov. 7, 2017.
International Search Report and Written Opinion received for PCT Patent Application No. PCT/US2015/032895, dated Oct. 21, 2015, 15 Pages (dated Oct. 21, 2015).
International Search Report and Written Opinion received for PCT Patent Application No. PCT/US2016/031257, dated Jul. 18, 2016, 16 Pages.
Jacobsen (Jan. 1, 2011) "Molecular and Functional Characterization of Cynomolgus Monkey IgG Subclasses", Journal of Immunology, vol. 186, No. 1, pp. 341-349.
Janco, Jo Marie Tran. (Mar. 20, 2015) "Tumor-Infiltrating Dendritic Cells in Cancer Pathogenesis", The Journal of Immunology, vol. 194, Issue 7, pp. 2985-2991.
Jensen, S.M., et al., "Signaling through OX40 enhances antitumor immunity" Semin Oncol. 37(5):524-32, Elsevier, Netherlands (2010).
Ji, et al. (May 15, 2004) "Cutting Edge: The Natural Ligand for Glucocorticoid-induced TNF Receptor-related Protein Abrogates Regulatory T Cell Suppression", Journal of Immunology, vol. 172, Issue 10, pp. 5823-5827.
Kamb, et al. (Dec. 8, 2006) "Why is Cancer Drug Discovery So Difficult?", Nature Reviews Drug Discovery, pp. 115-120.
Kanamaru, et al. (Jun. 15, 2004) "Costimulation via Glucocorticoid-Induced TNF Receptor in Both Conventional and CD25+ Regulatory CD4+ T Cells", The Journal of Immunology, vol. 172, Issue 12, pp. 7306-7314.
Katschke, et al. (Jun. 4, 2007) "A Novel Inhibitor of the Alternative Pathway of Complement Reverses Inflammation and Bone Destruction in Experimental Arthritis", The Journal of Experimental Medicine, vol. 204, No. 6, pp. 1319-1325.
Kim, et al. (Aug. 17, 2015) "Glucocorticoid-induced Tumor Necrosis Factor Receptor-related Protein Co-stimulation Facilitates Tumor Regression by Inducing IL-9-producing Helper T Cells", Nature Medicine, vol. 21, No. 9, pp. 1010-1017.
Kim, et al. (Aug. 26, 2013) "Fcγ Receptors Enable Anticancer Action of Proapoptotic and Immune-Modulatory Antibodies", Journal of Experimental Medicine, vol. 210, No. 9, pp. 1647-1651.
Kim, et al. (Jun. 2013) "Tumor-infiltrating Lymphocytes, Tumor Characteristics, and Recurrence in Patients with Early Breast Cancer", American Journal of Clinical Oncology, vol. 36, No. 3, pp. 224-231.
Kim, et al. (Nov. 15, 2015) "Authentic GITR Signaling Fails to Induce Tumor Regression unless Foxp3+ Regulatory T Cells are Depleted", Journal of Immunology, vol. 195, No. 10, pp. 4721-4729.
Kim, et al. (Nov. 2006) "Glucocorticoid-induced Tumor Necrosis Factor Receptor Family Related Protein (GITR) Mediates Inflammatory Activation of Macrophages that Can Destabilize Atherosclerotic Plaques", Immunology, vol. 119, Issue 3, pp. 421-429.
Kim, et al. (Nov. 26, 2003) "Cloning and Characterization of GITR Ligand", Genes and Immunity, vol. 4, No. 8, pp. 564-569.
Kim, et al. (Oct. 24, 2007) "Guided Selection of Human Antibody Light Chains Against TAG-72 Using a Phage Display Chain Shuffling Approach", The Journal of Microbiology, vol. 45, No. 6, pp. 572-577.
Kirk, Rebecca (Jun. 1, 2010) "Risk Factors. CD8+:FOXP3+ Cell Ratio is a Novel Survival Marker for Colorectal Cancer", Nature Reviews Clinical Oncology, vol. 7, No. 6, p. 299.
Kjaergaard, J., et al., "Therapeutic efficacy of OX-40 receptor antibody depends on tumor immunogenicity and anatomic site of tumor growth" Cancer Res. 60:5514-5521 (2000).

(56) References Cited

OTHER PUBLICATIONS

Knee, et al. (Nov. 2016) "Rationale for Anti-GITR Cancer Immunotherapy", European Journal of Cancer, vol. 67, pp. 1-10.
Ko, et al. (Aug. 2007) "A Combination of Chemoimmunotherapies Can Efficiently Break Self-Tolerance and Induce Antitumor Immunity in a Tolerogenic Murine Tumor Model", Cancer Research, vol. 67, No. 15, pp. 7477-7486.
Ko, et al. (Oct. 3, 2005) "Treatment of Advanced Tumors with Agonistic Anti-GITR Mab and its Effects on Tumor-infiltrating Foxp3+Cd25+Cd4+ Regulatory T Cells", The Journal of Experimental Medicine, vol. 202, No. 7, pp. 885-891.
Kober (Oct. 28, 2008) "The Capacity of the TNF Family Members 4-1BBL, OX40L, CD70, GITRL, CD30L and LIGHT to Costimulate Human T Cells", European Journal of Immunology, vol. 38, Issue 10, pp. 2678-2688.
Koene, H.R., et al., "Fc gammaRIIIa-158V/F polymorphism influences the binding of IgG by natural killer cell Fc gammaRIIIa, independently of the Fc gammaRIIIa-48L-R-H phenotype" Blood 90:1109-1114 (1997).
Krause, P., et al., "Prostaglandin E2 enhances T cell proliferation by inducing the co-stimulating molecules OX4OL, CD70 and 4-1BBL on dendritic cells" Blood 113(11):2451-2460 (2008).
Krausz, et al. (May 1, 2007) "GITR-GITRL System, A Novel Player in Shock and Inflammation", The Scientific World Journal, vol. 7, pp. 533-566.
Kunitomi, A., et al., "Vascular endothelial cells provide T cells with costimulatory signals via the OX40-gp34 system" J. Leukoc. Biol. 68:111-118 (2000).
Kwon, et al. (1999) "Identification of a Novel Activation-Inducible Protein of the Tumor Necrosis Factor Receptor Superfamily and its Ligand", Journal of Biological Chemistry, vol. 274, No. 10, pp. 6056-6061.
Lacal, et al. (Oct. 1, 2013) "Glucocorticoid-induced Tumor Necrosis Factor Receptor Family-related Ligand Triggering Upregulates Vascular Cell Adhesion Molecule-1 and Intercellular Adhesion Molecule-1 and Promotes Leukocyte Adhesion", The Journal of Pharmacology and Experimental Therapeutics, vol. 347, Issue 1, pp. 164-172.
Lazar, G.A., et al., (2006) "Engineered antibody Fc variants with enhanced effector function" PNAS 103(11):4005-4010.
Leach, et al. (Mar. 22, 1996) "Enhancement of Antitumor Immunity by CTLA-4 Blockade", Science, vol. 271, No. 5256, pp. 1734-1736.
Levings, et al. (Nov. 11, 2002) "Human CD25+CD4+ T Suppressor Cell Clones Produce Transforming Growth Factor Beta, but not Interleukin 10, and are Distinct from Type 1 T Regulatory Cells", The Journal of Experimental Medicine, vol. 196, No. 10, pp. 1335-1346.
Li, et al. (Aug. 19, 2011) "Inhibitory Fcγ Receptor Engagement Drives Adjuvant and Anti-Tumor Activities of Agonistic CD40 Antibodies", Science, vol. 333, Issue 6045, pp. 1030-1034.
Li, et al. (Aug. 2003) "Expression of Glucocorticoid Induced TNF Receptor Family Related Protein (GITR) on Peripheral T Cells from Normal Human Donors and Patients with Non-Infectious Uveitis", Journal of autoimmunity, vol. 21, No. 1, pp. 83-92.
Liao, et al. (Feb. 3, 2014) "Glucocorticoid-Induced TNF Receptor Family-Related Protein Ligand is Requisite for Optimal Functioning of Regulatory CD4(+) T Cells", Frontiers in Immunology, vol. 5, Article 35, pp. 1-7.
Lightle, S et al. "Mutations within a human IgG2 antibody form distinct and homogenous disulfide isomers but do not affect Fc gamma receptor or C1q binding," Protein Sci, vol. 19, No. 4, pp. 753-762 (Apr. 1, 2010).
Linch, S.N., et al., "Combination OX40 agonism/CTLA-4 blockade with HER2 vaccination reverses T-cell anergy and promotes survival in tumor-bearing mice" Proc. Natl. Acad. Sci. USA 113:E319-327 (Jan. 2016).
Linch, S.N., et al., "Combined OX40 ligation plus CTLA-4 blockade more than the sum of its parts" OncoImmunology 3:e28245 (Mar. 2014).
Linch, S.N., et al., "OX40 Agonists and Combination Immunotherapy: Putting the Pedal to the Metal" Front. Oncol. 5(34):E319-E327 (Feb. 2015).
Linton, P., et al., "Costimulation via OX4OL Expressed by B Cells is Sufficient to Determine the Extent of Primary CD4 Cell Expansion and Th2 Cytokine Secretion In Vivo" J. Exp. Med. vol. 197(7):875-83 (2003).
Liu, et al. (Nov. 2011) "CD8+cytotoxic T cell and FOXP3+ Regulatory T Cell Infiltration in Relation to Breast Cancer Survival and Molecular Subtypes", Breast Cancer Research and Treatment, vol. 130, Issue 2, pp. 645-655.
Li-Weber, et al. (Jul. 1, 2003) "Regulation of IL4 Gene Expression by T Cells and Therapeutic Perspectives", Nature Reviews Immunology, vol. 3, No. 7, pp. 534-543.
Locksley (Feb. 23, 2001) "The TNF and TNF Receptor Superfamilies: Integrating Mammalian Biology", Cell, vol. 104, Issue 4, pp. 487-501.
Lu, et al. (Feb. 7, 2014) "Combined PD-1 Blockade and GITR Triggering Induce a Potent Antitumor Immunity in Murine Cancer Models and Synergizes with Chemotherapeutic Drugs", Journal of Translational Medicine, vol. 12, No. 36, pp. 1-11.
Mahmud et al., "Costimulation via the tumor-necrosis factor receptor superfamily couples TCR signal strength to the thymic differentiation of regulatory T cells" Nature Immunology 15:473-481 (Mar. 2014).
Mahne, et al. (Mar. 2017) "Dual Roles for Regulatory T-cell Depletion and Costimulatory Signaling in Agonistic GITR Targeting for Tumor Immunotherapy", Cancer Research, vol. 77, Issue 5, pp. 1108-1118.
Mallett, S., et al., "Characterization of the MRC OX40 antigen of activated CD4 positive T lymphocytes—a molecule related to nerve growth factor receptor" EMBO J. 9:1063-1068 (1990).
Marabelle, A., et al., "Depleting tumor-specific Tregs at a single site eradicates disseminated tumors" 123(6):2447-2463 (2013).
Mathai, et al. (Jul. 2012) "Role of Foxp3-positive Tumor-infiltrating Lymphocytes in the Histologic Features and Clinical Outcomes of Hepatocellular Carcinoma", The American Journal of Surgical Pathology, vol. 36, Issue 7, pp. 980-986.
Matsushita, et al. (Feb. 8, 2012) "Cancer Exome Analysis Reveals a T-Cell-Dependent Mechanism of Cancer Immunoediting", Nature, vol. 482, No. 7385, pp. 400-404.
McHugh, et al. (Feb. 2002) "CD4+ CD25+ Immunoregulatory T Cells: Gene Expression Analysis Reveals a Functional Role for the Glucocorticoid-Induced TNF Receptor", Immunity, vol. 16, Issue 2, pp. 311-323.
Mei, et al. (Feb. 6, 2014) "Tumor-infiltrating Inflammation and Prognosis in Colorectal Cancer: Systematic Review and Meta-analysis", British Journal of Cancer, pp. 1595-1605.
Melero, et al. (Mar. 2013) "Agonist Antibodies to TNFR Molecules that Costimulate T and NK Cells", Clinical Cancer Research, vol. 19, Issue 5, pp. 1044-1053.
Mellman, et al. (Dec. 21, 2011) "Cancer Immunotherapy Comes of Age", Nature, vol. 480, No. 7378, pp. 480-489.
Mellor, J.D., et al., (2013) "A critical review of the role of Fc gamma receptor polymorphisms in the response to monoclonal antibodies in cancer" Journal of Hematology & Oncology 6:1-10.
Messenheimer, D.J., et al., "Timing of PD-1 Blockade is Critical to Effective Combination Immunotherapy with Anti-OX40" Clin. Cancer Res. 1-13 (2017).
Meylan, F., et al., "TL1A and DR3, a TNF family ligand-receptor pair that promotes lymphocyte costimulation, mucosal hyperplasia, and autoimmune inflammation" Immunological Reviews 244: 188-196 (2011).
Miltenyi Biotec "Human Anti-GITR Antibodies," Product Brochure. Catalog Nos. 130-092-895, 130-092-575, 130-092-886, and 130-092-855, (2012).
Mimoto, et al. (Oct. 2013) "Engineered Antibody Fc Variant with Selectively Enhanced FcγRIIb Binding Over Both FcγRIIa(R131) and FcγRIIa(H131)", Protein Engineering, Design and Selection, vol. 26, No. 10, pp. 589-598.

(56) References Cited

OTHER PUBLICATIONS

Mitsui, et al. (May 2010) "Two Distinct Mechanisms of Augmented Antitumor Activity by Modulation of Immunostimulatory/inhibitory Signals", Clinical Cancer Research, vol. 16, Issue 10, pp. 2781-2791.
Miura, S., et al., "Molecular cloning and characterization of a novel glycoprotein, gp34, that is specifically induced by the human T-cell leukemia virus type I transactivator p40tax" Mol. Cell Biol. 11:1313-1325 (1991).
Montler, R., et al., "OX40, PD-1 and CTLA-4 are selectively expressed on tumor-infiltrating T cells in head and neck cancer" Clinical & Translational Immunology 5:e70 (Apr. 2016).
Moran, A.E., et al., "The TNFRs OX40, 4-1BB, and CD40 as targets for cancer immunotherapy" Current Opinion in Immunology 25:230-237 (2013).
Moreau, et al. (Mar. 1996) "Transient Increase in Symptoms Associated with Cytokine Release in Patients with Multiple Sclerosis", Brain, vol. 119, No. 1, pp. 225-237.
Murphy, et al. (2014) "Anaphylaxis Caused by Repetitive Doses of a GITR Agonist Monoclonal Antibody in Mice", Blood, vol. 123, Issue 14, pp. 2172-2180.
Murphy, K.A., et al., "CD8+ T Cell-Independent Tumor Regression Induced by FC-OX4OL and Therapeutic Vaccination in a Mouse model of Glioma" J. Immunol. 192:224-233 (Jan. 2014).
NCBI (Feb. 20, 2017) TNFRSF18 TNF Receptor Superfamily Member 18 [*Homo sapiens* (human)], Gene ID: 8784, Retrieved from: <<https://www.ncbi.nlm.nih.gov/gene/8784>>, 9 Pages.
Neubling, T., et al., "The Immune Checkpoint Modulator OX40 and its Ligand OX4OL in NK-Cell Immunosurveillance and Acute Myeloid Leukemia" Cancer Immunology Research 6(2):209-22 (2018).
Nimmerjahn, et al. (Apr. 2007) "Antibodies, Fc Receptors and Cancer", Current Opinion in Immunology, vol. 19, No. 2, pp. 239-245.
Nimmerjahn, et al. (Jan. 2006) "Fc gamma Receptors: Old Friends and New Family Members", Immunity, vol. 24, Issue 1, pp. 19-28.
Nimmerjahn, et al. (May 1, 2012) "Translating Basic Mechanisms of IgG Effector Activity into Next Generation Cancer Therapies", Cancer Immunity, vol. 12, No. 13, 7 Pages.
Nimmerjahn, F., et al., "Fc gamma receptors as regulators of immune responses" Nat. Rev. Immunol. 8:34-47 (2008).
Nishikawa, H., et al., (2005) "Definition of target antigens for naturally occurring CD4+ CD25+ regulatory T cells" J. Exp. Med. 201(5):681-686.
Nishioka, et al. (Dec. 22, 2008) "In Vivo Expansion of CD4+ Foxp3+ regulatory T Cells Mediated by GITR Molecules", Immunology Letters, vol. 121, Issue 2, pp. 97-104.
Nocentini, et al. (2007) "GITR/GITRL: More Than an Effector T Cell Co-Stimulatory System", European journal of immunology, vol. 37, No. 5, pp. 1165-1169.
Nocentini, et al. (2009) "GITR: A Modulator of Immune Response and Inflammation", Advances in Experimental Medicine and Biology, pp. 156-173.
Nocentini, et al. (2012) "Pharmacological Modulation of GITRL/GITR System: Therapeutic Perspectives", British journal of pharmacology, vol. 165, No. 7, pp. 2089-2099.
Nocentini, et al. (Jun. 10, 1997) "A New Member of the Tumor Necrosis Factor/Nerve Growth Factor Receptor Family Inhibits T Cell Receptor-Induced Apoptosis", Proceedings of the National Academy of Sciences, vol. 94, No. 12, pp. 6216-6221.
Nocentini, et al. (Mar. 22, 2005) "GITR: A Multifaceted Regulator of Immunity Belonging to the Tumor Necrosis Factor Receptor Superfamily", European journal of immunology, vol. 35, No. 4, pp. 1016-1022.
"Nomenclature and Symbolism for Amino Acids and Peptides. Recommendations 1983", The Biochemical Journal, IUPAC-IUB Joint Commission on Biochemical Nomenclature (JCBN), vol. 219, No. 2, pp. 345-373 (1984).

Nosho, et al. (Aug. 31, 2010) "Tumor-infiltrating T-cell Subsets, Molecular Changes in Colorectal Cancer, and Prognosis: Cohort Study and Literature Review", The Journal of Pathology, vol. 222, Issue 4, pp. 350-366.
Oble, et al. (Jan. 2009) "Focus on TILs: Prognostic Significance of Tumor Infiltrating Lymphocytes in Human Melanoma", Cancer Immunity, vol. 9, Issue 1, pp. 1-20.
Ohshima, Y., et al., "Expression and function of OX40 ligand on human dendritic cells" J. Immunol. 159:3838-3848 (1997).
Oken, et al. (Dec. 1982) "Toxicity and response criteria of the Eastern Cooperative Oncology Group", American Journal of Clinical Oncology, vol. 5, No. 6, pp. 649-655.
OncoMed Pharmaceuticals (Sep. 2015) "OncoMed Presents Immuno-Oncology Data for GITRL-Fc Candidate at the Inaugural International Cancer Immunotherapy Conference".
Ono, et al. (Apr. 15, 2006) "Control of Autoimmune Myocarditis and Multiorgan Inflammation by Glucocorticoid-induced TNF Receptor Family-related Protein(high), Foxp3-expressing CD25+ and CD25− Regulatory T Cells", Journal of Immunology, vol. 176, Issue 8, pp. 4748-4756.
Park, Moon Soo (2005) "The Role of AITR and AITRL in the Lumbar Disc Herniation", Yonsei University Department of Medicine, vol. 48, No. 5, pp. 839-846.
Patel, et al. (May 17, 2016) "Agonist Anti-GITR Monoclonal Antibody and Stereotactic Radiation Induce Immune-mediated Survival Advantage in Murine Intracranial Glioma", Journal for Immunotherapy of Cancer, vol. 4, No. 28, pp. 1-13.
Paterson, D.J., et al., "Antigens of activated rat T lymphocytes including a molecule of 50,000 Mr detected only on CD4 positive T blasts" Mol. Immunol. 24:1281-1290 (1987).
Piao, et al. (Aug. 2009) "Enhancement of T-cell-mediated Antitumor Immunity via the Ectopically Expressed Glucocorticoid-induced Tumor Necrosis Factor Receptor-related Receptor Ligand (GITRL) on Tumours", Immunology, vol. 127, No. 4, pp. 489-499.
Piconese S et al., "Human OX40 Tunes the Function of Regulatory T Cells in Tumor and Nontumor Areas of Hepatitis C Virus-Infected Liver Tissue" Hepatology 60:1494-1507 (Jun. 2014).
Piconese S et al., "OX40 triggering blocks suppression by regulatory T cells and facilitates tumor rejection" J. Exp. Med. 205:825-839 (2008).
Piconese, S., et al., "Hardcore' OX40+ immunosuppressive regulatory T cells in hepatic cirrhosis and cancer" OncoImmunology 3:e29257 (Jun. 2014).
Placke, et al. (2010) "Glucocorticoid-induced TNFR-related (GITR) Protein and its Ligand in Antitumor Immunity: Functional Role and Therapeutic Modulation", Clinical and Developmental Immunology, vol. 2010, No. 239083, 10 Pages.
Ponte, et al. (Jun. 2010) "Enhancement of Humoral and Cellular Immunity with an Anti-glucocorticoid-induced Tumor Necrosis Factor Receptor Monoclonal Antibody", Immunology, vol. 130, Issue 2, pp. 231-242.
Prell, R.A., et al., "OX40-mediated memory T cell generation is TNF receptor-associated factor 2 dependent" J. Immunol. 171:5997-6005 (2003).
Presta (Aug. 2008) "Molecular Engineering and Design of Therapeutic Antibodies", Current Opinion in Immunology, vol. 20, No. 4, pp. 460-470.
Preston, et al. (Nov. 14, 2013) "The Ratios of CD8+ T Cells to CD4+CD25+ FOXP3+ and FOXP3− T Cells Correlate with Poor Clinical Outcome in Human Serous Ovarian Cancer", PLoS One, vol. 8, No. 11, pp. e80063.
Rader, et al. (Jul. 21, 1998) "A Phage Display Approach for Rapid Antibody Humanization: Designed Combinatorial V Gene Libraries", Proceedings of the National Academy of Sciences, vol. 95, No. 15, pp. 8910-8915.
Ramirez-Montagut, et al. (Jun. 1, 2006) "Glucocorticoid-induced TNF Receptor Family Related Gene Activation Overcomes Tolerance/ignorance to Melanoma Differentiation Antigens and Enhances Antitumor Immunity", The Journal of Immunology, vol. 176, Issue 11, pp. 6434-6442.
Ravetch, et al. (Oct. 6, 2000) "Immune Inhibitory Receptors", Science, vol. 290, Issue 5489, pp. 84-89.

(56) References Cited

OTHER PUBLICATIONS

Redmond, W. L., et al., "Dual Anti-OX40/IL-2 Therapy Augments Tumor Immunotherapy via IL-2R-Mediated Regulation of OX40 Expression" PLoS ONE 7(4): e34467 (2012).
Redmond, W.L., et al., "Combined Targeting of Costimulatory (OX40) and Coinhibitory (CTLA-4) Pathways Elicits Potent Effector T Cells Capable of Driving Robust Antitumor Immunity" Cancer Immunol Res. 2(2):142-53 (2013).
Redmond, W.L., et al., "Targeting OX40 and OX40L for the treatment of autoimmunity and cancer" Crit. Rev. Immunol. 27:415-436 (2007).
Richard, A.C., et al., "The TNF-Family Ligand TL1A and its Receptor DR3 Promote T Cell-Mediated Allergic Immunopathology by Enhancing Differentiation and Pathogenicity of IL-9-Producing T Cells" The Journal of Immunology 194:3567-3582 (Mar. 2015).
Rodman & Renshaw Annual Global Investment Conference Sep. 2015.
Rogers, P.R., et al., "OX40 promotes Bcl-xL and Bcl-2 expression and is essential for long-term survival of CD4 T cells" Immunity 15:445-455 (2001).
Ronchetti, et al. (Apr. 2012) "CD8+ T Cells: GITR Matters", The Scientific World Journal, vol. 2012, Article ID 308265, 7 Pages.
Ronchetti, et al. (Apr. 2012) "Glucocorticoid-induced Tumor Necrosis Factor Receptor-related Protein: A Key Marker of Functional Regulatory T Cells", Journal of Immunology Research, vol. 2015, Article ID 171520, 17 Pages.
Ronchetti, et al. (Feb. 25, 2004) "Frontline: GITR, A Member of the Tnf Receptor Superfamily, is Costimulatory to Mouse T Lymphocyte Subpopulations", European journal of immunology, vol. 34, No. 3, pp. 613-622.
Ronchetti, et al. (Jul. 1, 2002) "Role of GITR in Activation Response of T Lymphocytes", Blood, vol. 100, No. 1, pp. 350-352.
Rosenzweig, et al. (Sep. 22, 2016) "Development of TRX518, An Aglycosyl Humanized Monoclonal Antibody (Mab) Agonist of huGITR", Journal of Clinical Oncology, vol. 28, No. 15, pp. e13028.
Ruby, C.E., et al., "Cutting Edge: OX40 Agonists Can Drive Regulatory T Cell Expansion if the Cytokine Milieu is Right" J. Immunol. 183:4853-4857 (2009).
Sagiv-Barfi, I., et al., "Eradication of spontaneous-malignancy by local immunotherapy" Sci. Transl. Med. 10, eaan4488 (2018).
Sainz-Perez, A., et al., (2012) "The T-cell receptor repertoire of tumor-infiltrating regulatory T lymphocytes is skewed towards public sequences" Cancer Research.
Salek-Ardakani, S., et al., "OX40 (CD134) controls memory T helper 2 cells that drive lung inflammation" J. Exp. Med. 198(2):315-24 (2003).
Salgado, et al. (Sep. 11, 2014) "The Evaluation of Tumor-infiltrating Lymphocytes (TILs) in Breast Cancer: Recommendations by an International TILs Working Group 2014", Annals of Oncology, vol. 26, No. 2, pp. 259-271.
Saxena, A. and Wu, D., et al., (2016) "Advances in Therapeutic Fc engineering—Modulation of igG-Associated effector Functions and Serum Half-life" 7:570.
Schaer, et al. (Apr. 15, 2014) "Targeting Tumor-necrosis Factor Receptor Pathways for Tumor Immunotherapy", Journal for Immunotherapy of Cancer, vol. 2, No. 7, 9 Pages.
Schaer, et al. (Apr. 2012) "Modulation of GITR for Cancer Immunotherapy", Current Opinion in Immunology, vol. 24, No. 2, pp. 217-224.
Schaer, et al. (Nov. 2013) "GITR Pathway Activation Abrogates Tumor Immune Suppression Through Loss of Regulatory T Cell Lineage Stability", Cancer Immunology Research, vol. 1, No. 5, pp. 320-331.
Schreiber, T.H., "Immunobiology of TNFSFI5 and TNFRSF25" Immunol. Res. 57:3-11 (2013).
Schreiber, T.H., et al., "T Cell Costimulation by TNFRSF4 and TNFRSF25 in the Context of Vaccination" The Journal of Immunology 189:3311-3318 (2012).
Schreiber, T.H., et al., "Therapeutic Treg expansion in mice by TNFRSF25 prevents allergic lung inflammation" J. Clin. Invest. 120(10):3629-3640 (2010).
Schwende, et al. (Apr. 1, 1996) "Differences in the State of Differentiation of THP-1 Cells Induced by Phorbol Ester and 1 ,25-dihydroxyvitamin D3", Journal of Leukocyte Biology, vol. 59, Issue 4, pp. 555-561.
Selby, et al. (Jul. 2013) "Anti-CTLA-4 Antibodies of IgG2a Isotype Enhance Antitumor Activity Through Reduction of Intratumoral Regulatory T Cells", Cancer Immunology Research, vol. 1, No. 1, pp. 32-42.
Seshasayee D et al., "In vivo blockade of OX40 ligand inhibits thymic stromal lymphopoietin driven atopic inflammation" J. Clin. Invest. 117:3868-3878 (2007).
Sharma et al., (2015) "Immune Checkpoint Targeting in Cancer Therapy: Towards Combination Strategies With Curative Potential" Cell 161(2): 205-214.
Sheridan, C. "IDO inhibitors move center stage in immuno-oncology," Nature Biotech, vol. 33, No. 4, pp. 321-322 (Apr. 7, 2015).
Shevach, et al. (Aug. 1, 2006) "The GITR-GITRL Interaction: Co-Stimulation or Contrasuppression of Regulatory Activity", Nature Reviews Immunology, vol. 6, No. 8, pp. 613-618.
Shields, R.L., et al., "High resolution mapping of the binding site on human IgG1 for Fc gamma RI, Fc gamma RII, Fc gamma RIII, and FcRn and design of IgG1 variants with improved binding to the Fc gamma R" J. Biol. Chem. 276:6591-6604 (2001).
Shimizu, et al. (Jan. 22, 2002) "Stimulation of CD25+ CD4+ regulatory T Cells Through GITR Breaks Immunological Self-Tolerance", Nature Immunology, vol. 3, No. 2, pp. 135-142.
Shirabe, et al. (Dec. 2010) "Tumor-infiltrating Lymphocytes and Hepatocellular Carcinoma: Pathology and Clinical Management", International Journal of Clinical Oncology, vol. 15, No. 6, pp. 552-558.
Shrimali, R.K., et al., "Concurrent PD-1 Blockade Negates the Effects of OX40 Agonist Antibody in Combination Immunotherapy through Inducing T-cell Apoptosis" Cancer Immunol. Res. 5(9):755-66 (2017).
Simpson, et al. (Aug. 26, 2013) "Fc-Dependent Depletion of Tumor-Infiltrating Regulatory T Cells Co-Defines the Efficacy of Anti-Ctla-4 Therapy Against Melanoma", Journal of Experimental Medicine, vol. 210, No. 9, pp. 1695-1710.
Smith, et al. (Apr. 17, 2012) "Mouse Model Recapitulating Human Fcγ Receptor Structural and Functional Diversity", Proceedings of the National Academy of Sciences, vol. 109, No. 16, pp. 6181-6186.
Smith, et al. (Mar. 25, 1994) "The TNF Receptor Superfamily of Cellular and Viral Proteins: Activation, Costimulation, and Death", Cell, vol. 76, Issue 6, pp. 959-962.
Smyth, et al. (Apr. 29, 2014) "Targeting Regulatory T Cells in Tumor Immunotherapy", Immunology and Cell Biology, vol. 92, Issue 6, pp. 473-474.
Snell, et al. (Dec. 15, 2010) "CD8 T Cell-Intrinsic GITR is Required for T Cell Clonal Expansion and Mouse Survival Following Severe Influenza Infection", The Journal of Immunology 185.12, pp. 7223-7234.
Snell, et al. (Oct. 21, 2011) "T-cell intrinsic Effects of GITR and 4-1 BB during Viral Infection and Cancer Immunotherapy", Immunological Reviews, vol. 244, Issue 1, pp. 197-217.
So, T., et al., "Immune Regulation and Control of Regulatory T cells by OX40 and 4-1BB" Cytokine Growth Factor Rev. 19(3-4):253-262 (2008).
So, T., et al., (2015) "TNF Receptor-Associated Factor (TRAF) Signaling Network in CD4+ T-Lymphocytes" J. Exp. Med. 236:139-154.
Soroosh P et al., "OX40-OX40 Ligand Interaction through T Cell-T Cell Contact Contributes to CD4 T Cell Longevity" J. Immunol. 176:5975-5987 (2006).
Stebbings, et al. (Sep. 1, 2007) ""Cytokine Storm" in the Phase I Trial of Monoclonal Antibody TGN1412: Better Understanding the Causes to Improve Preclinical Testing of Immunotherapeutics", Journal of Immunology, vol. 179, No. 5, pp. 3325-3331.
Stephens, et al. (Oct. 15, 2004) "Engagement of Glucocorticoid-induced TNFR Family-related Receptor on Effector T Cells by its

(56) References Cited

OTHER PUBLICATIONS

Ligand Mediates Resistance to Suppression by CD4+CD25+ T Cells", Journal of Immunology, vol. 173, No. 8, pp. 5008-5020.
Strbo et al. "Secreted heat shock protein gp96-Ig: next generation vaccines for cancer and infectious diseases," Immunologic Res, vol. 57, No. 1, pp. 311-325 (2013).
Strohl (Dec. 2009) "Optimization of Fc-Mediated Effector Functions of Monoclonal Antibodies", Current Opinion in Biotechnology, vol. 20, No. 6, pp. 685-691.
Sugamura K. et al., "Therapeutic targeting of the effector T-cell co-stimulatory molecule OX40" Nat. Rev. Immunol. 4:420-431 (2004).
Supplemental Partial European Search Report from EP 16871583.7 dated Jul. 3, 2019.
Swiss-Prot (Feb. 15, 2017) Tumor Necrosis Factor Ligand Superfamily Member 18 (TNF18_HUMAN) Accession No. Q9UNG2, Retrieved From: <<http://www.uniprot.org/uniprot/Q9UNG2>> 11 Pages.
Swiss-Prot (Nov. 1, 1999) Tumor Necrosis Factor Receptor Superfamily Member 18 (TNR18_HUMAN), Accession No. Q9Y5U5-1, Retrieved From: <<http://www.uniprot.org/uniprot/Q9Y5U5#Q9Y5U5-1>>, 11 Pages.
Swiss-Prot, Tumor Necrosis Factor Receptor Superfamily Member 18 (TNR18_HUMAN), Accession No. Q9Y5U5-2, Retrieved From: <<http://www.uniprot.org/uniprot/Q9Y5U5#Q9Y5U5-2>>.
Swiss-Prot, Tumor Necrosis Factor Receptor Superfamily Member 18 (TNR18_HUMAN), Accession No. Q9Y5U5-3, Retrieved From: <<http://www.uniprot.org/uniprot/Q9Y5U5#Q9Y5U5-3>>.
Talmadge, James E. (Apr. 2011) "Immune Cell Infiltration of Primary and Metastatic Lesions: Mechanisms and Clinical Impact", Seminars in Cancer Biology, vol. 21, Issue 2, pp. 131-138.
Tanaka, A. and Sakaguchi, S. (2016) "Regulatory T cells in cancer immunotherapy" Cell Research 27:109-118.
Taylor, L., et al., "Identification of a Soluble OX40 Isoform: Development of a Specific and Quantitative Immunoassay," Journal of Immunological Methods 255(1-2):67-72, Elsevier, Netherlands (2001).
Tian, et al. (Oct. 15, 2012) "Up-Regulation of GITRL on Dendritic Cells by WGP Improves Anti-Tumor Immunity in Murine Lewis Lung Carcinoma", PloS one, vol. 7, No. 10, pp. e46936.
Tone, et al. (Apr. 15, 2014) "Gene Expression in the GITR Locus is Regulated by NF-KB and Foxp3 Through an Enhancer", Journal of Immunology, vol. 192, Issue 8, pp. 3915-3924.
Tone, et al. (Dec. 9, 2003) "Mouse Glucocorticoid-Induced Tumor Necrosis Factor Receptor Ligand is Costimulatory for T Cells", Proceedings of the National Academy of Sciences, vol. 100, No. 25, pp. 15059-15064.
Triplett, TA, et al., "STAT3 Signaling is Required for Optimal Regression of Large Established Tumors in Mice Treated with Anti-OX40 and TGF-beta Receptor Blockade" Cancer Immunol. Res. 3(5):526-35 (Jan. 2015).
Turk, et al. (Sep. 20, 2004) "Concomitant Tumor Immunity to a Poorly Immunogenic Melanoma is Prevented by Regulatory T Cells", The Journal of Experimental Medicine, vol. 200, No. 6, pp. 771-782.
Twohig, J.P., et al., "The death receptor 3-TL1A pathway is essential for efficient development of antiviral CD4+ and CD8+ T-cell immunity" FASEB J. 26:3575-3586 (2012).
Twohig, J.P., et al., (2011)"The role of tumor necrosis factor receptor superfamily members in mammalian brain development, function and homeostasis" Rev Neurosci. 22(5):509-533.
U.S. Appl. No. 16/744,163, filed Jan. 15, 2020.
U.S. Appl. No. 16/784,469, filed Feb. 7, 2020.
U.S. Appl. No. 16/808,074, filed Mar. 3, 2020.
U.S. Appl. No. 16/906,587, filed Jun. 19, 2020.
Ukyo et al. "Costimulation through OX40 is crucial for induction of an alloreactive human T-cell response" Immunology 109(2):226-31 (2003).
Valzasina, et al. (Dec. 9, 2004) "Triggering of OX40 (CD134) on CD4+CD25+ T Cells Blocks Their Inhibitory Activity: a Novel Regulatory Role for OX40 and its Comparison with GITR", Blood, vol. 105, No. 7, pp. 2845-2851.
Van Olffen, et al. (Jun. 15, 2009) "GITR Triggering Induces Expansion of Both Effector and Regulatory CD4+ T Cells In Vivo", Journal of Immunology, vol. 182, No. 12, pp. 7490-7500.
Vesely, MD., et al., "Natural innate and adaptive immunity to cancer" Annu. Rev. Immunol. 29:235-271 (2011).
Vessillier, et al. (Sep. 2015) "Cytokine Release Assays for the Prediction of Therapeutic mAb Safety in First-In Man Trials—Whole Blood Cytokine Release Assays are Poorly Predictive for TGN1412 Cytokine Storm", Journal of Immunological Methods, vol. 424, pp. 43-52.
Vidal, et al. (Aug. 2010) "In Vitro Cytokine Release Assays for Predicting Cytokine Release Syndrome: The Current State-of-the-Science", Report of a European Medicines Agency Workshop, Cytokine, vol. 51, No. 2, pp. 213-215.
Vilgelm, A.E., et al., (2016) "Combinatorial approach to cancer immunotherapy: strength in numbers" J. Leukoc. Biol. 100:275-290.
Voo, K.S., et al., "Antibodies Targeting Human OX40 Expand Effector T Cells and Block Inducible and Natural Regulatory T Cell Function" The Journal of Immunology 191(7):3641-50 (2013).
Vu, M.D., et al., (2007) "OX40 costimulation turns off Foxp3+ Tregs" Blood 110:2501-2510.
Waight, et al. (Feb. 1, 2015) "Cutting Edge: Epigenetic Regulation of Foxp3 Defines a Stable Population of CD4+ Regulatory T cells in Tumors from Mice and Humans", Journal of Immunology, vol. 194, No. 3, pp. 878-882.
Warncke, et al. (May 1, 2012) "Different Adaptations of IgG Effector Function in Human and Nonhuman Primates and Implications for Therapeutic Antibody Treatment", Journal of Immunology, vol. 188, No. 9, pp. 4405-4411.
Watanabe, A., et al., "Combination of Adoptive Cell Transfer and Antibody Injection Can Eradicate Established Tumors in Mice—An in vivo study using anti-OX40mAb, anti-CD25mAb and anti-CTLA4mAb" Immunopharmacology and Immunotoxicology 32(2):238-245 (2010).
Watts, T.H. (2005) "TNF/TNFR Family Members in Costimulation of T Cell Responses" Annu. Rev. Immunol. 23:23-68.
Weinberg AD et al., "Blocking OX-40/OX-40 Ligand Interaction In Vitro and In Vivo Leads to Decreased T Cell Function and Amelioration of Experimental Allergic Encephalomyelitis" J. Immunol. 162: 1818-1826 (1999).
Weinberg, A.D., et al., "Engagement of the OX-40 Receptor in Vivo Enhances Antitumor Immunity," Journal of Immunology 164(4):2160-2169, American Association of Immunologists, United States (2000).
Weinberg, A.D., et al., "Science gone translational: the OX40 agonist story" Immunol Rev. 244(1):218-231 (2011).
Weinberg, A.D., et al., "Selective depletion of myelin-reactive T cells with the anti-OX40 antibody ameliorates autoimmune encephalomyelitis" Nat. Med. 2:183-189 (1996).
Weinberg, AD et al. "Anti-OX40 (CD134) administration to non-human primates: immunomodulatory effects and toxicokinetic study," J Immunotherapy, vol. 29, No. 6, pp. 575-585 (2006).
Weixler, B., et al., "OX40 expression enhances the prognostic significance of CD8 positive lymphocyte infiltration in colorectal cancer" Oncotarget6(35): 37588-99 (Nov. 2015).
Wells, James A. (1991) "Systematic Mutational Analyses of Protein-protein Interfaces", Methods in Enzymology, vol. 202, pp. 390-411.
Weng, et al. (Nov. 1, 2003) "Two Immunoglobulin G Fragment C Receptor Polymorphisms Independently Predict Response to Rituximab in Patients with Follicular Lymphoma", Journal of Clinical Oncology, vol. 21, No. 21, pp. 3940-3947.
White, et al. (Aug. 15, 2011) "Interaction with FcγRIIB is Critical for the Agonistic Activity of Anti-CD40 Monoclonal Antibody", Journal of Immunology, vol. 187, Issue 4, pp. 1754-1763.
White, et al. (Jan. 12, 2015) "Conformation of the human immunoglobulin G2 hinge imparts superagonistic properties to immunostimulatory anticancer antibodies", Cancer Cell, vol. 27, Issue 1, pp. 138-148.

(56) References Cited

OTHER PUBLICATIONS

Wilson, et al. (2005) "Regulation of Antigen Presentation and Cross-Presentation in the Dendritic Cell Network: Facts, Hypothesis, and Immunological Implications", Advances in Immunology, vol. 86, pp. 241-305.

Wilson, et al. (Jan. 18, 2011) "An Fcγ Receptor-Dependent Mechanism Drives Antibody-Mediated Target-Receptor Signaling in Cancer Cells", Cancer Cell, vol. 19, No. 1, pp. 101-113.

Wing, et al. (Oct. 10, 2008) "CTLA-4 Control over Foxp3+ Regulatory T Cell Function", Science, vol. 322, No. 5899, pp. 271-275.

Wolchok, et al. (Dec. 2009) "Guidelines for the Evaluation of Immune Therapy Activity in Solid Tumors: Immune-Related Response Criteria", Clinical Cancer Research, vol. 15, No. 23, pp. 7412-7420.

Wolchok, et al. (Oct. 2008) "The Mechanism of Anti-CTLA-4 Activity and the Negative Regulation of T-cell Activation", The Oncologist, vol. 13, No. 4, pp. 2-9.

Wolf, et al. (Dec. 2012) "A Whole Blood In Vitro Cytokine Release Assay with Aqueous Monoclonal Antibody Presentation for the Prediction of Therapeutic Protein Induced Cytokine Release Syndrome in Humans", Cytokine, vol. 60, No. 3, pp. 828-837.

Wu, T., et al., "The Effect of OX40-0X40L and CD27-CD70 Pathways on Allogeneic Islet Graft Rejection" Transplantation Proceedings 33:217-218 (2001).

Xiao, X., et al., "The Costimulatory Receptor OX40 Inhibits Interleukin-17 Expression through Activation of Repressive Chromatin Remodeling Pathways" Immunity 44:1271-1283 (Jun. 2016).

Xie, F., et al., "Characterization and Application of Two Novel Monoclonal Antibodies Against Human OX40: Costimulation of T Cells and Expression on Tumor as Well as Normal Gland Tissues," Tissue Antigens 67(4):307-317, Wiley Blackwell, England (2006).

Xie, Ping (Jun. 13, 2013) "TRAF Molecules in Cell Signaling and in Human Diseases", Journal of Molecular Signaling, vol. 8, No. 1, pp. 1-31.

Yao, et al. (Feb. 2013) "Advances in Targeting Cell Surface Signaling Molecules for Immune Modulation", Nature Reviews Drug Discovery, vol. 12, No. 2, pp. 130-146.

Yoon, et al. (Aug. 6, 2012) "Prognostic Impact of FoxP3+ Regulatory T Cells in Relation to CD8+ T Lymphocyte Density in Human Colon Carcinomas", PLoS One, vol. 7, No. 8, pp. e42274.

Yu, et al. (Oct. 17, 2003) "Identification of a Ligand for Glucocorticoid-Induced Tumor Necrosis Factor Receptor Constitutively Expressed in Dendritic Cells", Biochemical and biophysical research communications, vol. 310, No. 2, pp. 433-438.

Yu, G., et al., "Combinational Immunotherapy with Allo-Dribble Vaccines and Anti-OX40 Co-Stimulation Leads to Generation of Cross-Reactive Effector T Cells and Tumor Regression" Scientific Reports 6:37558 (Nov. 2016).

Zhan, et al. (Oct. 15, 2008) "Glucocorticoid-induced TNF Receptor Expression by T Cells is Reciprocally Regulated by NF-kappaB and NFAT", Journal of Immunology, vol. 181, Issue 8, pp. 5405-5413.

Zhang, D., et al., "Fc engineering approaches to enhance the agonism and effector functions of an anti-OX40 antibody" J. of Biochem. 291:27134-27146 (Dec. 2016).

Zhang, et al. (Apr. 1, 2010) "Regulatory T Cell Depletion Enhances Tumor Specific CD8 T-cell Responses, Elicited by Tumor Antigen NY-ES0-1 b in Hepatocellular Carcinoma Patients, in Vitro", International Journal of Oncology, vol. 36, Issue 4, pp. 841-848.

Zheng, et al. (May 1, 2004) "Natural and Induced CD4+CD25+ Cells Educate CD4+CD25-Cells to Develop Suppressive Activity: The Role of IL-2, TGF-β, and IL-1 0", The Journal of Immunology, vol. 172, Issue 9, pp. 5213-5221.

Zhou, et al. (Apr. 8, 2008) "Human Glucocorticoid-induced TNF Receptor Ligand Regulates its Signaling Activity Through Multiple Oligomerization States", Proceedings of the National Academy of Sciences USA, vol. 105, No. 14, pp. 5465-5470.

Zhou, et al. (Oct. 2010) "Mature B Cells are Critical to T-cell-mediated Tumor Immunity Induced by an Agonist Anti-GITR Monoclonal Antibody", Journal of Immunotherapy, vol. 33, Issue 8, pp. 789-797.

Zhou, P., et al., (2007) "Pivotal Roles of CD4 Effector T cells in Mediating Agonistic Anti-GITR mAb-Induced-Immune Activation and Tumor Immunity in CT26 Tumors" Journal of Immunology 179:7365-7375.

Zipfel, et al. (Oct. 2009) "Complement Regulators and Inhibitory Proteins", Nature Reviews Immunology, vol. 9, No. 10, pp. 729-740.

Zou, et al. (Apr. 2006) "Regulatory T cells, Tumor Immunity and Immunotherapy", Nature Reviews Immunology, vol. 6, No. 4, pp. 295-307.

U.S. Appl. No. 16/906,587, filed Jun. 19, 2020, Nicholas S. Wilson.

* cited by examiner

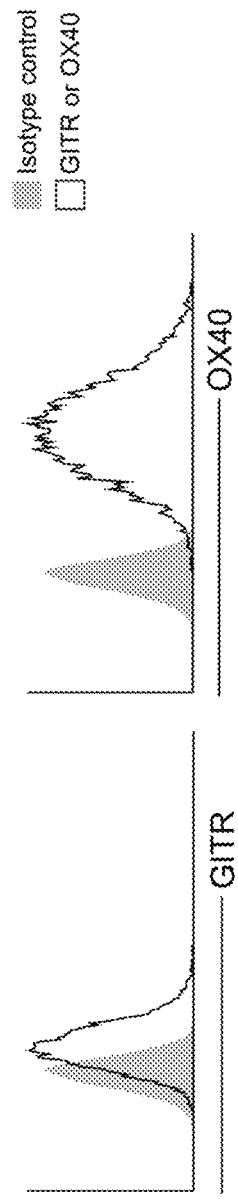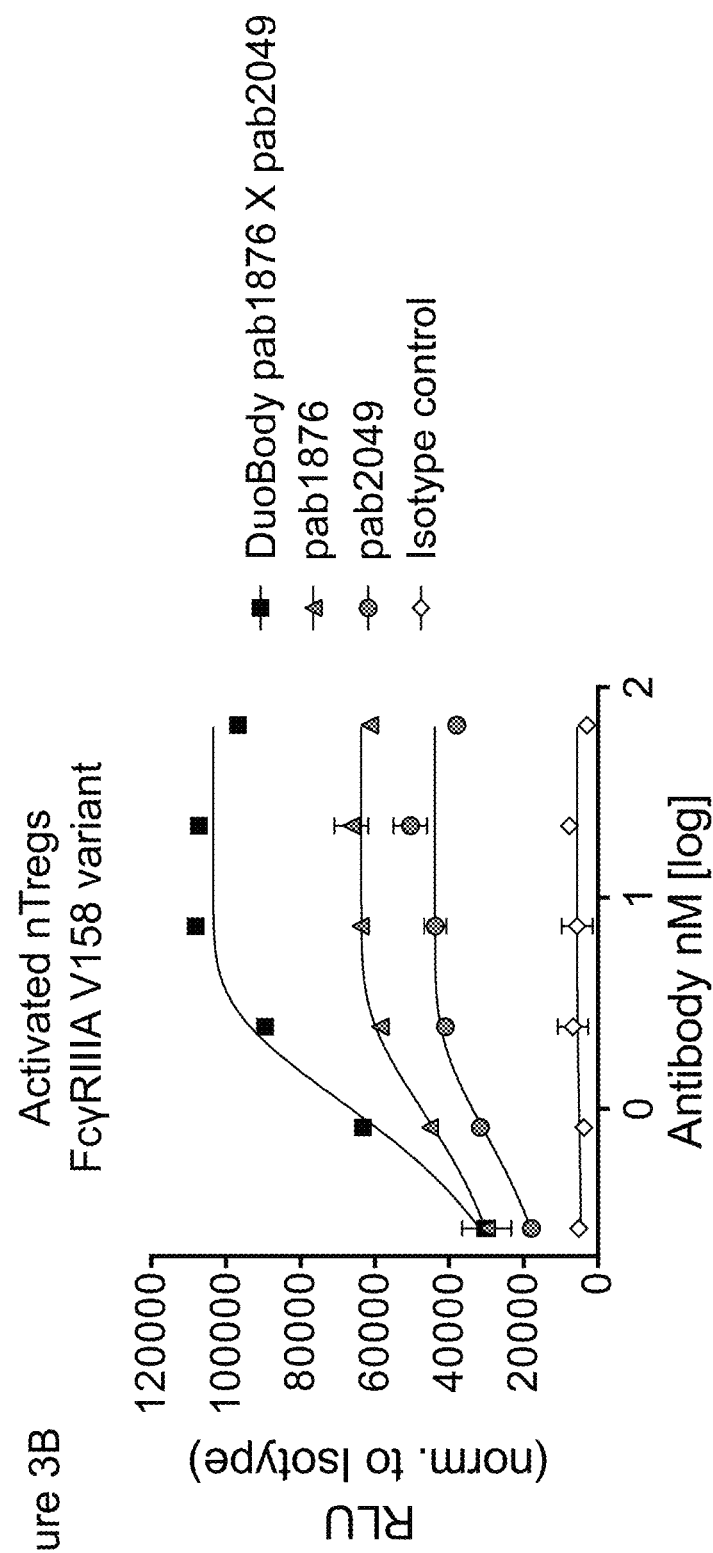
Figure 3A
Figure 3B

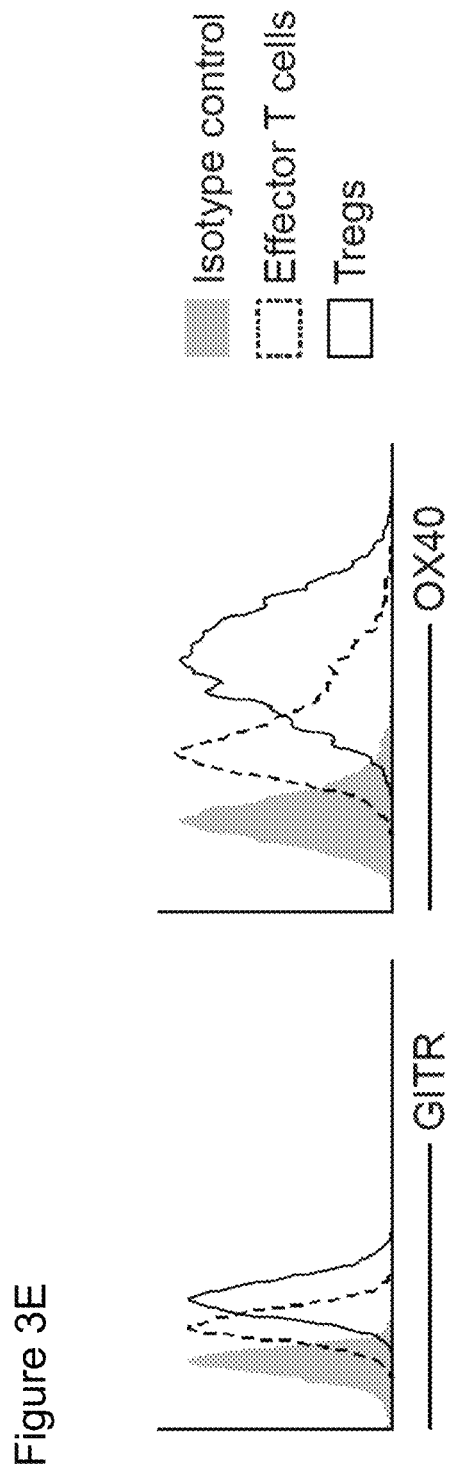

| Mutant | construct number | pab1876 | pab1967 | pab1975 | pab1979 | m6C8 |
|---|---|---|---|---|---|---|
| T54A | 4526 | + | + | + | + | + |
| T55A | 4527 | + | + | + | + | + |
| R56A | 4528 | + | + | + | + | + |
| C57A | 4529 | + | + | + | + | + |
| C58A | 4530 | +/- | +/- | +/- | +/- | +/- |
| R59A | 4531 | + | + | + | + | + |
| D60A | 4532 | - | +/- | +/- | +/- | + |
| Y61A | 4533 | + | + | + | + | + |
| P62A | 4534 | + | + | + | + | + |
| G63A | 4535 | +/- | +/- | +/- | +/- | + |
| E64A | 4536 | + | + | + | + | + |
| E65A | 4537 | + | + | + | + | + |
| C66A | 4538 | + | + | + | + | + |
| C67A | 4539 | + | + | + | + | + |
| S68A | 4540 | + | + | + | + | + |
| E69A | 4541 | + | + | + | + | + |
| W70A | 4542 | + | + | + | + | + |
| D71A | 4543 | + | + | + | + | + |
| C72A | 4544 | + | + | + | + | + |
| M73A | 4545 | + | + | + | + | + |
| C74A | 4546 | | | | | |
| V75A | 4547 | + | + | + | + | + |
| Q76A | 4548 | + | + | + | + | + |
| P28A | 4595 | + | + | + | + | + |
| T29A | 4596 | + | + | + | + | + |
| G30A | 4597 | + | + | + | + | + |
| G31A | 4598 | + | + | + | + | + |
| P32A | 4599 | + | + | + | + | + |

Figure 11A

```
                     SEQ ID NO: 46   MARHSAMCASGTLCCLALLCAASLGQRPTGPGLGPGRLLLGTGKDARCCRVHPTRCCRDYPGEECCSEWDCMCVQPEFH
                                              10        20        30        40        50        60        70        80 human GITR          SEQ ID NO: 41   MAQHGAMGAFRALCGLALLCALSLGQRPTGPGLGPGRLLLGTGTDARCCRVHFTRCCRDYPGEECCSEWDCMCVQPEFH   80
V1M/Q62P/S63G cyno GITR              ..R....C.CGT..C........A......................K......P........V..............   80
V1M cyno GITR                        ..R....C.CGT..C........A......................K......P........V..............   80

CGNPCCTTCQHHPCPSGGGVQPGGKFSFGFRCVQCALGTFSRGHDGHEKPWTDCTQFGFLTVFPGNKTHWAVCVPGSPPA
                                              90       100       110       120       130       140       150       160 human GITR                          CGDPCCTTCRHHPCPPGGGVQSGGKFSFGFQCTDCASGTFSGGHEGHCKPWTDCTQFGFLTVFPGNKTHRAVCVPGSPPA  160
V1M/Q62P/S63G cyno GITR              ...N.......Q......S....P.........R.V..I.....R..D...............................  160
V1M cyno GITR                        ...N.......Q......S....P.........R.V..I.....R..D...............................  160
                                                                              **

EPPGWLTIVLLAVAACVLLLTSAQLGLHIWQLG--------KTGLLLEVPPSTEQASSCQFPEEERGRLAEEKGRLGDIN
                                             170       180       190       200       210       220       230       240 human GITR                          EPLGWLTVVLLAVAACVLLLTSAQLGLHIWQLRSQCMWPRETGLLLEVPPSTEQARSCQFPEEERGERSAEEKGRLGDIN  240
V1M/Q62P/S63G cyno GITR              ..P..................................G------K.........S.......................  233
V1M cyno GITR                        ..P..................................G------K.........S.......................  233 human GITR                          V.                                                                                243
V1M/Q62P/S63G cyno GITR              V..                                                                               235
V1M cyno GITR                        .                                                                                 234
```

Figure 12

|       | pab1949w | pab2049 | pab1928 |
|-------|----------|---------|---------|
| W58A  | -        | +       | -       |
| N60A  | -        | -       | +       |
| R62A  | -        | -       | +       |
| R80A  | -        | -       | +       |
| L88A  | -        | -       | +       |
| P93A  | -        | -       | +       |
| P99A  | -        | +       | +       |
| P115A | -        | +       | +       |

SEQUENCE LISTING

<160> NUMBER OF SEQ ID NOS: 139

<210> SEQ ID NO 1
<211> LENGTH: 5
<212> TYPE: PRT
<213> ORGANISM: Artificial sequence

```
<220> FEATURE:
<223> OTHER INFORMATION: GITR HCDR1 consensus
<220> FEATURE:
<221> NAME/KEY: MISC_FEATURE
<222> LOCATION: (1)..(1)
<223> OTHER INFORMATION: Xaa is Asp, Gly or Glu
<220> FEATURE:
<221> NAME/KEY: MISC_FEATURE
<222> LOCATION: (5)..(5)
<223> OTHER INFORMATION: Xaa is Tyr or His

<400> SEQUENCE: 1

Xaa Tyr Ala Met Xaa
1               5

<210> SEQ ID NO 2
<211> LENGTH: 17
<212> TYPE: PRT
<213> ORGANISM: Artificial sequence
<220> FEATURE:
<223> OTHER INFORMATION: GITR HCDR2 consensus
<220> FEATURE:
<221> NAME/KEY: MISC_FEATURE
<222> LOCATION: (1)..(1)
<223> OTHER INFORMATION: Xaa is Val or Leu
<220> FEATURE:
<221> NAME/KEY: MISC_FEATURE
<222> LOCATION: (8)..(8)
<223> OTHER INFORMATION: Xaa is Asp or Gly
<220> FEATURE:
<221> NAME/KEY: MISC_FEATURE
<222> LOCATION: (10)..(10)
<223> OTHER INFORMATION: Xaa is Thr or Ser
<220> FEATURE:
<221> NAME/KEY: MISC_FEATURE
<222> LOCATION: (16)..(16)
<223> OTHER INFORMATION: Xaa is Lys, Arg or Gln
<220> FEATURE:
<221> NAME/KEY: MISC_FEATURE
<222> LOCATION: (17)..(17)
<223> OTHER INFORMATION: Xaa is Asp, Glu or Gly

<400> SEQUENCE: 2

Xaa Ile Arg Thr Tyr Ser Gly Xaa Val Xaa Tyr Asn Gln Lys Phe Xaa
1               5                   10                  15

Xaa

<210> SEQ ID NO 3
<211> LENGTH: 9
<212> TYPE: PRT
<213> ORGANISM: Artificial sequence
<220> FEATURE:
<223> OTHER INFORMATION: GITR HCDR3 consensus
      (pab1876/pab1967/pab1975/pab1979 HCDR3)

<400> SEQUENCE: 3

Ser Gly Thr Val Arg Gly Phe Ala Tyr
1               5

<210> SEQ ID NO 4
<211> LENGTH: 17
<212> TYPE: PRT
<213> ORGANISM: Artificial sequence
<220> FEATURE:
<223> OTHER INFORMATION: GITR LCDR1 consensus
<220> FEATURE:
<221> NAME/KEY: MISC_FEATURE
<222> LOCATION: (10)..(10)
<223> OTHER INFORMATION: Xaa is Gly or Ser

<400> SEQUENCE: 4
```

```
Lys Ser Ser Gln Ser Leu Leu Asn Ser Xaa Asn Gln Lys Asn Tyr Leu
1               5                   10                  15
Thr

<210> SEQ ID NO 5
<211> LENGTH: 7
<212> TYPE: PRT
<213> ORGANISM: Artificial sequence
<220> FEATURE:
<223> OTHER INFORMATION: GITR LCDR2 consensus
      (pab1876/pab1967/pab1975/pab1979 LCDR2)

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: GITR LCDR3 consensus
<220> FEATURE:
<221> NAME/KEY: MISC_FEATURE
<222> LOCATION: (3)..(3)
<223> OTHER INFORMATION: Xaa is Asp or Glu
<220> FEATURE:
<221> NAME/KEY: MISC_FEATURE
<222> LOCATION: (6)..(6)
<223> OTHER INFORMATION: Xaa is Tyr or Phe

<400> SEQUENCE: 6

Gln Asn Xaa Tyr Ser Xaa Pro Tyr Thr
1               5

<210> SEQ ID NO 7
<211> LENGTH: 5
<212> TYPE: PRT
<213> ORGANISM: Artificial sequence
<220> FEATURE:
<223> OTHER INFORMATION: pab1876 HCDR1

<400> SEQUENCE: 7

Asp Tyr Ala Met Tyr
1               5

<210> SEQ ID NO 8
<211> LENGTH: 5
<212> TYPE: PRT
<213> ORGANISM: Artificial sequence
<220> FEATURE:
<223> OTHER INFORMATION: pab1967 HCDR1

<400> SEQUENCE: 8

Gly Tyr Ala Met His
1               5

<210> SEQ ID NO 9
<211> LENGTH: 5
<212> TYPE: PRT
<213> ORGANISM: Artificial sequence
<220> FEATURE:
<223> OTHER INFORMATION: pab1975/pab1979 HCDR1

<400> SEQUENCE: 9

Glu Tyr Ala Met His
1               5
```

```
<210> SEQ ID NO 10
<211> LENGTH: 17
<212> TYPE: PRT
<213> ORGANISM: Artificial sequence
<220> FEATURE:
<223> OTHER INFORMATION: pab1876 HCDR2

<400> SEQUENCE: 10

Val Ile Arg Thr Tyr Ser Gly Asp Val Thr Tyr Asn Gln Lys Phe Lys
1               5                   10                  15

Asp

<210> SEQ ID NO 11
<211> LENGTH: 17
<212> TYPE: PRT
<213> ORGANISM: Artificial sequence
<220> FEATURE:
<223> OTHER INFORMATION: pab1967 HCDR2

<400> SEQUENCE: 11

Leu Ile Arg Thr Tyr Ser Gly Gly Val Ser Tyr Asn Gln Lys Phe Arg
1               5                   10                  15

Glu

<210> SEQ ID NO 12
<211> LENGTH: 17
<212> TYPE: PRT
<213> ORGANISM: Artificial sequence
<220> FEATURE:
<223> OTHER INFORMATION: pab1975 HCDR2

<400> SEQUENCE: 12

Leu Ile Arg Thr Tyr Ser Gly Gly Val Ser Tyr Asn Gln Lys Phe Gln
1               5                   10                  15

Gly

<210> SEQ ID NO 13
<211> LENGTH: 17
<212> TYPE: PRT
<213> ORGANISM: Artificial sequence
<220> FEATURE:
<223> OTHER INFORMATION: pab1979 HCDR2

<400> SEQUENCE: 13

Val Ile Arg Thr Tyr Ser Gly Gly Val Ser Tyr Asn Gln Lys Phe Gln
1               5                   10                  15

Glu

<210> SEQ ID NO 14
<211> LENGTH: 17
<212> TYPE: PRT
<213> ORGANISM: Artificial sequence
<220> FEATURE:
<223> OTHER INFORMATION: pab1876/pab1975/pab1979 LCDR1

<400> SEQUENCE: 14

Lys Ser Ser Gln Ser Leu Leu Asn Ser Gly Asn Gln Lys Asn Tyr Leu
1               5                   10                  15

Thr

<210> SEQ ID NO 15
<211> LENGTH: 17
<212> TYPE: PRT
```

<213> ORGANISM: Artificial sequence
<220> FEATURE:
<223> OTHER INFORMATION: pab1967 LCDR1

<400> SEQUENCE: 15

Lys Ser Ser Gln Ser Leu Leu Asn Ser Ser Asn Gln Lys Asn Tyr Leu
1               5                   10                  15
Thr

<210> SEQ ID NO 16
<211> LENGTH: 9
<212> TYPE: PRT
<213> ORGANISM: Artificial sequence
<220> FEATURE:
<223> OTHER INFORMATION: pab1876/pab1975/pab1979 LCDR3

<400> SEQUENCE: 16

Gln Asn Asp Tyr Ser Tyr Pro Tyr Thr
1               5

<210> SEQ ID NO 17
<211> LENGTH: 9
<212> TYPE: PRT
<213> ORGANISM: Artificial sequence
<220> FEATURE:
<223> OTHER INFORMATION: pab1967 LCDR3

<400> SEQUENCE: 17

Gln Asn Glu Tyr Ser Phe Pro Tyr Thr
1               5

<210> SEQ ID NO 18
<211> LENGTH: 118
<212> TYPE: PRT
<213> ORGANISM: Artificial sequence
<220> FEATURE:
<223> OTHER INFORMATION: pab1876 VH

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 19
<211> LENGTH: 113
<212> TYPE: PRT
<213> ORGANISM: Artificial sequence
<220> FEATURE:
<223> OTHER INFORMATION: pab1876 VL -continued

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 20
<211> LENGTH: 118
<212> TYPE: PRT
<213> ORGANISM: Artificial sequence
<220> FEATURE:
<223> OTHER INFORMATION: pab1967 VH

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Gly Tyr
            20                  25                  30

Ala Met His Trp Val Arg Gln Ala Pro Gly Gln Gly Leu Glu Trp Met
        35                  40                  45

Gly Leu Ile Arg Thr Tyr Ser Gly Gly Val Ser Tyr Asn Gln Lys Phe
50                  55                  60

Arg Glu Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Ile Thr Val Ser Ser
        115

<210> SEQ ID NO 21
<211> LENGTH: 113
<212> TYPE: PRT
<213> ORGANISM: Artificial sequence
<220> FEATURE:
<223> OTHER INFORMATION: pab1967 VL

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val

```
                     50                  55                  60
Pro Asp Arg Phe Thr Gly Ser Gly Ser Gly Thr Asp Phe Thr Leu Thr
 65                  70                  75                  80

Ile Ser Ser Val Gln Ala Glu Asp Val Ala Val Tyr His Cys Gln Asn
                     85                  90                  95

Glu Tyr Ser Phe Pro Tyr Thr Phe Gly Gln Gly Thr Lys Leu Glu Ile
                    100                 105                 110

Lys

<210> SEQ ID NO 22
<211> LENGTH: 118
<212> TYPE: PRT
<213> ORGANISM: Artificial sequence
<220> FEATURE:
<223> OTHER INFORMATION: pab1975 VH

<400> SEQUENCE: 22

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Glu Tyr
                 20                  25                  30

Ala Met His Trp Val Arg Gln Ala Pro Gly Gln Gly Leu Glu Trp Met
             35                  40                  45

Gly Leu Ile Arg Thr Tyr Ser Gly Gly Val Ser Tyr Asn Gln Lys Phe
 50                  55                  60

Gln Gly Arg Ala Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Lys Ser Gly Thr Val Arg Gly Phe Ala Tyr Trp Gly Gln Gly Thr
                100                 105                 110

Leu Val Thr Val Ser Ser
            115

<210> SEQ ID NO 23
<211> LENGTH: 113
<212> TYPE: PRT
<213> ORGANISM: Artificial sequence
<220> FEATURE:
<223> OTHER INFORMATION: pab1975/pab1979 VL

<400> SEQUENCE: 23

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Ser Tyr Pro Tyr Thr Phe Gly Gln Gly Thr Lys Leu Glu Ile
                100                 105                 110

Lys
```

<210> SEQ ID NO 24
<211> LENGTH: 118
<212> TYPE: PRT
<213> ORGANISM: Artificial sequence
<220> FEATURE:
<223> OTHER INFORMATION: pab1979 VH

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ala Met His Trp Val Arg Gln Ala Pro Gly Gln Gly Leu Glu Trp Met
        35                  40                  45

Gly Val Ile Arg Thr Tyr Ser Gly Gly Val Ser Tyr Asn Gln Lys Phe
    50                  55                  60

Gln Glu Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial sequence
<220> FEATURE:
<223> OTHER INFORMATION: GITR VH consensus
<220> FEATURE:
<221> NAME/KEY: MISC_FEATURE
<222> LOCATION: (24)..(24)
<223> OTHER INFORMATION: Xaa is Gly or Ala
<220> FEATURE:
<221> NAME/KEY: MISC_FEATURE
<222> LOCATION: (31)..(31)
<223> OTHER INFORMATION: Xaa is Asp, Gly or Glu
<220> FEATURE:
<221> NAME/KEY: MISC_FEATURE
<222> LOCATION: (35)..(35)
<223> OTHER INFORMATION: Xaa is Tyr or His
<220> FEATURE:
<221> NAME/KEY: MISC_FEATURE
<222> LOCATION: (48)..(48)
<223> OTHER INFORMATION: Xaa is Ile or Met
<220> FEATURE:
<221> NAME/KEY: MISC_FEATURE
<222> LOCATION: (50)..(50)
<223> OTHER INFORMATION: Xaa is Val or Leu
<220> FEATURE:
<221> NAME/KEY: MISC_FEATURE
<222> LOCATION: (57)..(57)
<223> OTHER INFORMATION: Xaa is Asp or Gly
<220> FEATURE:
<221> NAME/KEY: MISC_FEATURE
<222> LOCATION: (59)..(59)
<223> OTHER INFORMATION: Xaa is Thr or Ser
<220> FEATURE:
<221> NAME/KEY: MISC_FEATURE
<222> LOCATION: (65)..(65)
<223> OTHER INFORMATION: Xaa is Lys, Arg or Gln
<220> FEATURE:
<221> NAME/KEY: MISC_FEATURE
<222> LOCATION: (66)..(66)
<223> OTHER INFORMATION: Xaa is Asp, Glu or Gly
<220> FEATURE:

-continued

```
<221> NAME/KEY: MISC_FEATURE
<222> LOCATION: (68)..(68)
<223> OTHER INFORMATION: Xaa is Ala or Val
<220> FEATURE:
<221> NAME/KEY: MISC_FEATURE
<222> LOCATION: (74)..(74)
<223> OTHER INFORMATION: Xaa is Lys or Thr
<220> FEATURE:
<221> NAME/KEY: MISC_FEATURE
<222> LOCATION: (114)..(114)
<223> OTHER INFORMATION: Xaa is Val or Ile

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Xaa Ser Gly Tyr Thr Phe Thr Xaa Tyr
                20                  25                  30

Ala Met Xaa Trp Val Arg Gln Ala Pro Gly Gln Gly Leu Glu Trp Xaa
            35                  40                  45

Gly Xaa Ile Arg Thr Tyr Ser Gly Xaa Val Xaa Tyr Asn Gln Lys Phe
    50                  55                  60

Xaa Xaa Arg Xaa Thr Met Thr Val Asp Xaa Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Xaa Thr Val Ser Ser
        115

<210> SEQ ID NO 26
<211> LENGTH: 113
<212> TYPE: PRT
<213> ORGANISM: Artificial sequence
<220> FEATURE:
<223> OTHER INFORMATION: GITR VL consensus
<220> FEATURE:
<221> NAME/KEY: MISC_FEATURE
<222> LOCATION: (33)..(33)
<223> OTHER INFORMATION: Xaa is Gly or Ser
<220> FEATURE:
<221> NAME/KEY: MISC_FEATURE
<222> LOCATION: (69)..(69)
<223> OTHER INFORMATION: Xaa is Ser or Thr
<220> FEATURE:
<221> NAME/KEY: MISC_FEATURE
<222> LOCATION: (84)..(84)
<223> OTHER INFORMATION: Xaa is Leu or Val
<220> FEATURE:
<221> NAME/KEY: MISC_FEATURE
<222> LOCATION: (93)..(93)
<223> OTHER INFORMATION: Xaa is His or Tyr
<220> FEATURE:
<221> NAME/KEY: MISC_FEATURE
<222> LOCATION: (97)..(97)
<223> OTHER INFORMATION: Xaa is Asp or Glu
<220> FEATURE:
<221> NAME/KEY: MISC_FEATURE
<222> LOCATION: (100)..(100)
<223> OTHER INFORMATION: Xaa is Tyr or Phe

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Xaa Asn Gln Lys Asn Tyr Leu Thr Trp Tyr Gln Gln Lys Pro Gly Gln
```

```
                35                  40                  45
Pro Pro Lys Leu Leu Ile Tyr Trp Ala Ser Thr Arg Glu Ser Gly Val
 50                  55                  60

Pro Asp Arg Phe Xaa Gly Ser Gly Ser Gly Thr Asp Phe Thr Leu Thr
 65                  70                  75                  80

Ile Ser Ser Xaa Gln Ala Glu Asp Val Ala Val Tyr Xaa Cys Gln Asn
                 85                  90                  95

Xaa Tyr Ser Xaa Pro Tyr Thr Phe Gly Gln Gly Thr Lys Leu Glu Ile
                100                 105                 110

Lys

<210> SEQ ID NO 27
<211> LENGTH: 98
<212> TYPE: PRT
<213> ORGANISM: Artificial sequence
<220> FEATURE:
<223> OTHER INFORMATION: GITR VH germline IGHV1-2*02

<400> SEQUENCE: 27

Gln Val Gln Leu Val Gln Ser Gly Ala Glu Val Lys Lys Pro Gly Ala
 1                   5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
                 35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg

<210> SEQ ID NO 28
<211> LENGTH: 101
<212> TYPE: PRT
<213> ORGANISM: Artificial sequence
<220> FEATURE:
<223> OTHER INFORMATION: GITR VL germline IGKV4-1*01

<400> SEQUENCE: 28

Asp Ile Val Met Thr Gln Ser Pro Asp Ser Leu Ala Val Ser Leu Gly
 1                   5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro
                100

<210> SEQ ID NO 29
```

```
<211> LENGTH: 448
<212> TYPE: PRT
<213> ORGANISM: Artificial sequence
<220> FEATURE:
<223> OTHER INFORMATION: pab1876 HC IgG1

<400> SEQUENCE: 29
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Gly | Ser | Gly | Tyr | Thr | Phe | Thr | Asp | Tyr |
| | | | 20 | | | | | 25 | | | | | 30 | | |
| Ala | Met | Tyr | Trp | Val | Arg | Gln | Ala | Pro | Gly | Gln | Gly | Leu | Glu | Trp | Ile |
| | | | 35 | | | | | 40 | | | | | 45 | | |
| Gly | Val | Ile | Arg | Thr | Tyr | Ser | Gly | Asp | Val | Thr | Tyr | Asn | Gln | Lys | Phe |
| | | | 50 | | | | | 55 | | | | | 60 | | |
| Lys | Asp | Arg | Ala | Thr | Met | Thr | Val | Asp | Lys | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Ala | Lys | Ser | Gly | Thr | Val | Arg | Gly | Phe | Ala | Tyr | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | | 115 | | | | | 120 | | | | | 125 | | |
| Leu | Ala | Pro | Ser | Ser | Lys | Ser | Thr | Ser | Gly | Gly | Thr | Ala | Ala | Leu | Gly |
| | | | 130 | | | | | 135 | | | | | 140 | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Val | Val | Thr | Val | Pro | Ser | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Arg | Val | Glu | Pro | Lys | Ser | Cys | Asp | Lys | Thr |
| | | | 210 | | | | | 215 | | | | | 220 | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | | 275 | | | | | 280 | | | | | 285 | | |
| Lys | Thr | Lys | Pro | Arg | Glu | Glu | Gln | Tyr | Asn | Ser | Thr | Tyr | Arg | Val | Val |
| | | | 290 | | | | | 295 | | | | | 300 | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Glu | Glu | Met | Thr | Lys | Asn | Gln | Val | Ser | Leu | Thr | Cys |
| | | | 355 | | | | | 360 | | | | | 365 | | |
| Leu | Val | Lys | Gly | Phe | Tyr | Pro | Ser | Asp | Ile | Ala | Val | Glu | Trp | Glu | Ser |
| | | | 370 | | | | | 375 | | | | | 380 | | |

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 30
<211> LENGTH: 448
<212> TYPE: PRT
<213> ORGANISM: Artificial sequence
<220> FEATURE:
<223> OTHER INFORMATION: pab1876 HC IgG1 N297A

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 31
<211> LENGTH: 448
<212> TYPE: PRT
<213> ORGANISM: Artificial sequence
<220> FEATURE:
<223> OTHER INFORMATION: pab1876 HC IgG1 F405L

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met Tyr Trp Val Arg Gln Ala Pro Gly Gln Gly Leu Glu Trp Ile
            35                  40                  45

Gly Val Ile Arg Thr Tyr Ser Gly Asp Val Thr Tyr Asn Gln Lys Phe
        50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Leu Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 32
<211> LENGTH: 448
<212> TYPE: PRT
<213> ORGANISM: Artificial sequence
<220> FEATURE:
<223> OTHER INFORMATION: pab1876 HC IgG1 F405L N297A

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

-continued

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Leu Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 33
<211> LENGTH: 448
<212> TYPE: PRT
<213> ORGANISM: Artificial sequence
<220> FEATURE:
<223> OTHER INFORMATION: pab1876 HC IgG1 F405L L234F L235E D265A

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60
```

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Leu Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 34
<211> LENGTH: 448
<212> TYPE: PRT
<213> ORGANISM: Artificial sequence
<220> FEATURE:

<223> OTHER INFORMATION: pab1876 HC IgG1 K409R

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

Ser Asp Gly Ser Phe Phe Leu Tyr Ser Arg Leu Thr Val Asp Lys Ser
              405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 35
<211> LENGTH: 448
<212> TYPE: PRT
<213> ORGANISM: Artificial sequence
<220> FEATURE:
<223> OTHER INFORMATION: pab1876 HC IgG1 K409R N297A

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 36
<211> LENGTH: 445
<212> TYPE: PRT
<213> ORGANISM: Artificial sequence
<220> FEATURE:
<223> OTHER INFORMATION: pab1876 HC IgG4 S228P

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Tyr Asn Gln Lys Phe
50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
    195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240
```

```
Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 37
<211> LENGTH: 220
<212> TYPE: PRT
<213> ORGANISM: Artificial sequence
<220> FEATURE:
<223> OTHER INFORMATION: pab1876w LC

<400> SEQUENCE: 37

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

-continued

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 38
<211> LENGTH: 220
<212> TYPE: PRT
<213> ORGANISM: Artificial sequence
<220> FEATURE:
<223> OTHER INFORMATION: pab1876 LC T109S

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Asn
                85                  90                  95

Asp Tyr Ser Tyr Pro Tyr Thr Phe Gly Gln Gly Thr Lys Leu Glu Ile
            100                 105                 110

Lys Arg Ser Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 39
<211> LENGTH: 448
<212> TYPE: PRT
<213> ORGANISM: Artificial sequence
<220> FEATURE:
<223> OTHER INFORMATION: pab1876 HC IgG1 K409R L234F L235E D265A

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30
```

```
Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
        50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Lys Ser Gly Thr Val Arg Gly Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445
```

```
<210> SEQ ID NO 40
<211> LENGTH: 216
<212> TYPE: PRT
<213> ORGANISM: Homo sapiens

<400> SEQUENCE: 40

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Leu Gly Trp Leu Thr Val Val
    130                 135                 140

Leu Leu Ala Val Ala Ala Cys Val Leu Leu Leu Thr Ser Ala Gln Leu
145                 150                 155                 160

Gly Leu His Ile Trp Gln Leu Arg Ser Gln Cys Met Trp Pro Arg Glu
                165                 170                 175

Thr Gln Leu Leu Leu Glu Val Pro Pro Ser Thr Glu Asp Ala Arg Ser
            180                 185                 190

Cys Gln Phe Pro Glu Glu Glu Arg Gly Glu Arg Ser Ala Glu Glu Lys
        195                 200                 205

Gly Arg Leu Gly Asp Leu Trp Val
    210                 215

<210> SEQ ID NO 41
<211> LENGTH: 241
<212> TYPE: PRT
<213> ORGANISM: Homo sapiens

<400> SEQUENCE: 41

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110
```

```
Ile Asp Cys Ala Ser Gly Thr Phe Ser Gly Gly His Glu Gly His Cys
        115                 120                 125
Lys Pro Trp Thr Asp Cys Thr Gln Phe Gly Phe Leu Thr Val Phe Pro
    130                 135                 140
Gly Asn Lys Thr His Asn Ala Val Cys Val Pro Gly Ser Pro Pro Ala
145                 150                 155                 160
Glu Pro Leu Gly Trp Leu Thr Val Val Leu Ala Val Ala Ala Cys
                165                 170                 175
Val Leu Leu Leu Thr Ser Ala Gln Leu Gly Leu His Ile Trp Gln Leu
                180                 185                 190
Arg Ser Gln Cys Met Trp Pro Arg Glu Thr Gln Leu Leu Leu Glu Val
            195                 200                 205
Pro Pro Ser Thr Glu Asp Ala Arg Ser Cys Gln Phe Pro Glu Glu Glu
        210                 215                 220
Arg Gly Glu Arg Ser Ala Glu Glu Lys Gly Arg Leu Gly Asp Leu Trp
225                 230                 235                 240
Val

<210> SEQ ID NO 42
<211> LENGTH: 255
<212> TYPE: PRT
<213> ORGANISM: Homo sapiens

<400> SEQUENCE: 42

Met Ala Gln His Gly Ala Met Gly Ala Phe Arg Ala Leu Cys Gly Leu
1               5                   10                  15
Ala Leu Leu Cys Ala Leu Ser Leu Gly Gln Arg Pro Thr Gly Gly Pro
                20                  25                  30
Gly Cys Gly Pro Gly Arg Leu Leu Leu Gly Thr Gly Thr Asp Ala Arg
            35                  40                  45
Cys Cys Arg Val His Thr Thr Arg Cys Cys Arg Asp Tyr Pro Gly Glu
        50                  55                  60
Glu Cys Cys Ser Glu Trp Asp Cys Met Cys Val Gln Pro Glu Phe His
65                  70                  75                  80
Cys Gly Asp Pro Cys Cys Thr Thr Cys Arg His His Pro Cys Pro Pro
                85                  90                  95
Gly Gln Gly Val Gln Ser Gln Gly Lys Phe Ser Phe Gly Phe Gln Cys
                100                 105                 110
Ile Asp Cys Ala Ser Gly Thr Phe Ser Gly Gly His Glu Gly His Cys
        115                 120                 125
Lys Pro Trp Thr Asp Cys Cys Trp Arg Cys Arg Arg Pro Lys Thr
    130                 135                 140
Pro Glu Ala Ala Ser Ser Pro Arg Lys Ser Gly Ala Ser Asp Arg Gln
145                 150                 155                 160
Arg Arg Arg Gly Gly Trp Glu Thr Cys Gly Cys Glu Pro Gly Arg Pro
                165                 170                 175
Pro Gly Pro Pro Thr Ala Ala Ser Pro Ser Gly Ala Pro Gln Ala
                180                 185                 190
Ala Gly Ala Leu Arg Ser Ala Leu Gly Arg Ala Leu Leu Pro Trp Gln
            195                 200                 205
Gln Lys Trp Val Gln Glu Gly Gly Ser Asp Gln Arg Pro Gly Pro Cys
        210                 215                 220
Ser Ser Ala Ala Ala Ala Gly Pro Cys Arg Arg Glu Arg Glu Thr Gln
225                 230                 235                 240
```

```
Ser Trp Pro Pro Ser Ser Leu Ala Gly Pro Asp Gly Val Gly Ser
                245                 250                 255

<210> SEQ ID NO 43
<211> LENGTH: 234
<212> TYPE: PRT
<213> ORGANISM: Homo sapiens

<400> SEQUENCE: 43

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Lys Thr Gln Leu Leu Leu Glu Val Pro Pro Ser Thr Glu Asp Ala
        195                 200                 205

Arg Ser Cys Gln Phe Pro Glu Glu Glu Arg Gly Glu Arg Ser Ala Glu
    210                 215                 220

Glu Lys Gly Arg Leu Gly Asp Leu Trp Val
225                 230

<210> SEQ ID NO 44
<211> LENGTH: 234
<212> TYPE: PRT
<213> ORGANISM: Cynomolgus monkey

<400> SEQUENCE: 44

Val Ala Arg His Gly Ala Met Cys Ala Cys Gly Thr Leu Cys Cys Leu
1               5                   10                  15

Ala Leu Leu Cys Ala Ala Ser Leu Gly Gln Arg Pro Thr Gly Gly Pro
                20                  25                  30

Gly Cys Gly Pro Gly Arg Leu Leu Leu Gly Thr Gly Lys Asp Ala Arg
            35                  40                  45

Cys Cys Arg Val His Pro Thr Arg Cys Cys Arg Asp Tyr Gln Ser Glu
        50                  55                  60

Glu Cys Cys Ser Glu Trp Asp Cys Val Cys Val Gln Pro Glu Phe His
65                  70                  75                  80
```

```
Cys Gly Asn Pro Cys Cys Thr Thr Cys Gln His His Pro Cys Pro Ser
                85                  90                  95

Gly Gln Gly Val Gln Pro Gln Gly Lys Phe Ser Phe Gly Phe Arg Cys
            100                 105                 110

Val Asp Cys Ala Leu Gly Thr Phe Ser Arg Gly His Asp Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Pro Gly Trp Leu Thr Ile Val Leu Leu Ala Val Ala Ala Cys
                165                 170                 175

Val Leu Leu Leu Thr Ser Ala Gln Leu Gly Leu His Ile Trp Gln Leu
            180                 185                 190

Gly Lys Thr Gln Leu Leu Leu Glu Val Pro Pro Ser Thr Glu Asp Ala
        195                 200                 205

Ser Ser Cys Gln Phe Pro Glu Glu Glu Arg Gly Glu Arg Leu Ala Glu
    210                 215                 220

Glu Lys Gly Arg Leu Gly Asp Leu Trp Val
225                 230

<210> SEQ ID NO 45
<211> LENGTH: 234
<212> TYPE: PRT
<213> ORGANISM: Cynomolgus monkey

<400> SEQUENCE: 45

Met Ala Arg His Gly Ala Met Cys Ala Cys Gly Thr Leu Cys Cys Leu
1               5                   10                  15

Ala Leu Leu Cys Ala Ala Ser Leu Gly Gln Arg Pro Thr Gly Gly Pro
            20                  25                  30

Gly Cys Gly Pro Gly Arg Leu Leu Leu Gly Thr Gly Lys Asp Ala Arg
        35                  40                  45

Cys Cys Arg Val His Pro Thr Arg Cys Cys Arg Asp Tyr Gln Ser Glu
    50                  55                  60

Glu Cys Cys Ser Glu Trp Asp Cys Val Cys Val Gln Pro Glu Phe His
65                  70                  75                  80

Cys Gly Asn Pro Cys Cys Thr Thr Cys Gln His His Pro Cys Pro Ser
                85                  90                  95

Gly Gln Gly Val Gln Pro Gln Gly Lys Phe Ser Phe Gly Phe Arg Cys
            100                 105                 110

Val Asp Cys Ala Leu Gly Thr Phe Ser Arg Gly His Asp Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Pro Gly Trp Leu Thr Ile Val Leu Leu Ala Val Ala Ala Cys
                165                 170                 175

Val Leu Leu Leu Thr Ser Ala Gln Leu Gly Leu His Ile Trp Gln Leu
            180                 185                 190

Gly Lys Thr Gln Leu Leu Leu Glu Val Pro Pro Ser Thr Glu Asp Ala
        195                 200                 205

Ser Ser Cys Gln Phe Pro Glu Glu Glu Arg Gly Glu Arg Leu Ala Glu
    210                 215                 220
```

```
Glu Lys Gly Arg Leu Gly Asp Leu Trp Val
225                 230

<210> SEQ ID NO 46
<211> LENGTH: 234
<212> TYPE: PRT
<213> ORGANISM: Artificial sequence
<220> FEATURE:
<223> OTHER INFORMATION: V1M/Q62P/S63G cynomolgus GITR immature protein

<400> SEQUENCE: 46

Met Ala Arg His Gly Ala Met Cys Ala Cys Gly Thr Leu Cys Cys Leu
1               5                   10                  15

Ala Leu Leu Cys Ala Ala Ser Leu Gly Gln Arg Pro Thr Gly Gly Pro
                20                  25                  30

Gly Cys Gly Pro Gly Arg Leu Leu Leu Gly Thr Gly Lys Asp Ala Arg
            35                  40                  45

Cys Cys Arg Val His Pro Thr Arg Cys Cys Arg Asp Tyr Pro Gly Glu
        50                  55                  60

Glu Cys Cys Ser Glu Trp Asp Cys Val Cys Val Gln Pro Glu Phe His
65                  70                  75                  80

Cys Gly Asn Pro Cys Cys Thr Thr Cys Gln His His Pro Cys Pro Ser
                85                  90                  95

Gly Gln Gly Val Gln Pro Gln Gly Lys Phe Ser Phe Gly Phe Arg Cys
            100                 105                 110

Val Asp Cys Ala Leu Gly Thr Phe Ser Arg Gly His Asp Gly His Cys
        115                 120                 125

Lys Pro Trp Thr Asp Cys Thr Gln Phe Gly Phe Leu Thr Val Phe Pro
130                 135                 140

Gly Asn Lys Thr His Asn Ala Val Cys Val Pro Gly Ser Pro Pro Ala
145                 150                 155                 160

Glu Pro Pro Gly Trp Leu Thr Ile Val Leu Leu Ala Val Ala Ala Cys
                165                 170                 175

Val Leu Leu Leu Thr Ser Ala Gln Leu Gly Leu His Ile Trp Gln Leu
            180                 185                 190

Gly Lys Thr Gln Leu Leu Leu Glu Val Pro Pro Ser Thr Glu Asp Ala
        195                 200                 205

Ser Ser Cys Gln Phe Pro Glu Glu Glu Arg Gly Glu Arg Leu Ala Glu
    210                 215                 220

Glu Lys Gly Arg Leu Gly Asp Leu Trp Val
225                 230

<210> SEQ ID NO 47
<211> LENGTH: 5
<212> TYPE: PRT
<213> ORGANISM: Artificial sequence
<220> FEATURE:
<223> OTHER INFORMATION: pab2049/pab1949 HCDR1

<400> SEQUENCE: 47

Gly Ser Ala Met His
1               5

<210> SEQ ID NO 48
<211> LENGTH: 19
<212> TYPE: PRT
<213> ORGANISM: Artificial sequence
<220> FEATURE:
<223> OTHER INFORMATION: pab2049/pab1949 HCDR2
```

```
<400> SEQUENCE: 48

Arg Ile Arg Ser Lys Ala Asn Ser Tyr Ala Thr Ala Tyr Ala Ala Ser
1               5                   10                  15

Val Lys Gly

<210> SEQ ID NO 49
<211> LENGTH: 10
<212> TYPE: PRT
<213> ORGANISM: Artificial sequence
<220> FEATURE:
<223> OTHER INFORMATION: pab2049/pab1949 HCDR3

<400> SEQUENCE: 49

Gly Ile Tyr Asp Ser Ser Gly Tyr Asp Tyr
1               5                   10

<210> SEQ ID NO 50
<211> LENGTH: 16
<212> TYPE: PRT
<213> ORGANISM: Artificial sequence
<220> FEATURE:
<223> OTHER INFORMATION: pab2049/pab1949 LCDR1

<400> SEQUENCE: 50

Arg Ser Ser Gln Ser Leu Leu His Ser Asn Gly Tyr Asn Tyr Leu Asp
1               5                   10                  15

<210> SEQ ID NO 51
<211> LENGTH: 7
<212> TYPE: PRT
<213> ORGANISM: Artificial sequence
<220> FEATURE:
<223> OTHER INFORMATION: pab2049/pab1949 LCDR2

<400> SEQUENCE: 51

Leu Gly Ser Asn Arg Ala Ser
1               5

<210> SEQ ID NO 52
<211> LENGTH: 9
<212> TYPE: PRT
<213> ORGANISM: Artificial sequence
<220> FEATURE:
<223> OTHER INFORMATION: pab2049 LCDR3

<400> SEQUENCE: 52

Met Gln Gly Ser Lys Trp Pro Leu Thr
1               5

<210> SEQ ID NO 53
<211> LENGTH: 9
<212> TYPE: PRT
<213> ORGANISM: Artificial sequence
<220> FEATURE:
<223> OTHER INFORMATION: pab1949 LCDR3

<400> SEQUENCE: 53

Met Gln Ala Leu Gln Thr Pro Leu Thr
1               5

<210> SEQ ID NO 54
<211> LENGTH: 121
<212> TYPE: PRT
<213> ORGANISM: Artificial sequence
<220> FEATURE:
```

<223> OTHER INFORMATION: pab2049/pab1949 VH

<400> SEQUENCE: 54

Glu Val Gln Leu Val Glu Ser Gly Gly Gly Leu Val Gln Pro Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Gly Tyr Asp Tyr Trp Gly
            100                 105                 110

Gln Gly Thr Leu Val Thr Val Ser Ser
        115                 120

<210> SEQ ID NO 55
<211> LENGTH: 112
<212> TYPE: PRT
<213> ORGANISM: Artificial sequence
<220> FEATURE:
<223> OTHER INFORMATION: pab2049 VL

<400> SEQUENCE: 55

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Ser Lys Trp Pro Leu Thr Phe Gly Gly Gly Thr Lys Leu Glu Ile Lys
            100                 105                 110

<210> SEQ ID NO 56
<211> LENGTH: 112
<212> TYPE: PRT
<213> ORGANISM: Artificial sequence
<220> FEATURE:
<223> OTHER INFORMATION: pab1949 VL

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro

```
                  50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Leu Thr Phe Gly Gly Gly Thr Lys Val Glu Ile Lys
                100                 105                 110

<210> SEQ ID NO 57
<211> LENGTH: 100
<212> TYPE: PRT
<213> ORGANISM: Artificial Sequence
<220> FEATURE:
<223> OTHER INFORMATION: OX40 HC germline  IGHV3-73*01

<400> SEQUENCE: 57

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
                 20                  25                  30

Ala Met His Trp Val Arg Gln Ala Ser Gly Lys Gly Leu Glu Trp Val
             35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 58
<211> LENGTH: 100
<212> TYPE: PRT
<213> ORGANISM: Artificial sequence
<220> FEATURE:
<223> OTHER INFORMATION: OX40 LC germline  IGKV2-28*01

<400> SEQUENCE: 58

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 59
<211> LENGTH: 451
<212> TYPE: PRT
<213> ORGANISM: Artificial sequence
<220> FEATURE:
```

<223> OTHER INFORMATION: pab2049/pab1949 HC IgG1

<400> SEQUENCE: 59

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 60
<211> LENGTH: 451
<212> TYPE: PRT
<213> ORGANISM: Artificial sequence
<220> FEATURE:
<223> OTHER INFORMATION: pab2049/pab1949 HC IgG1 N297A

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
            85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
        290                 295                 300

-continued

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 61
<211> LENGTH: 451
<212> TYPE: PRT
<213> ORGANISM: Artificial sequence
<220> FEATURE:
<223> OTHER INFORMATION: pab2049/pab1949 HC IgG1 K409R

<400> SEQUENCE: 61

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 62
<211> LENGTH: 451
<212> TYPE: PRT
<213> ORGANISM: Artificial sequence
<220> FEATURE:
<223> OTHER INFORMATION: pab2049/pab1949 HC IgG1 K409R N297A

<400> SEQUENCE: 62

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 63
<211> LENGTH: 451
<212> TYPE: PRT
<213> ORGANISM: Artificial sequence
<220> FEATURE:
<223> OTHER INFORMATION: pab2049/pab1949 HC K409R L234F L235E D265A

<400> SEQUENCE: 63

Glu Val Gln Leu Val Glu Ser Gly Gly Gly Leu Val Gln Pro Gly Gly
1               5                   10                  15

-continued

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
            85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                    405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser

-continued

```
                435                 440                 445
Pro Gly Lys
    450

<210> SEQ ID NO 64
<211> LENGTH: 451
<212> TYPE: PRT
<213> ORGANISM: Artificial sequence
<220> FEATURE:
<223> OTHER INFORMATION: pab2049/pab1949 HC F405L

<400> SEQUENCE: 64

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
                    340                 345                 350
Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 65
<211> LENGTH: 451
<212> TYPE: PRT
<213> ORGANISM: Artificial sequence
<220> FEATURE:
<223> OTHER INFORMATION: pab2049/pab1949 HC F405L N297A

<400> SEQUENCE: 65

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                245                 250                 255
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 66
<211> LENGTH: 448
<212> TYPE: PRT
<213> ORGANISM: Artificial sequence
<220> FEATURE:
<223> OTHER INFORMATION: pab2049/pab1949 HC IgG4 S228P

<400> SEQUENCE: 66

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
            85                  90                  95

Tyr Cys Thr Ser Gly Ile Tyr Asp Ser Ser Gly Tyr Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
```

145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 67
<211> LENGTH: 219
<212> TYPE: PRT
<213> ORGANISM: Artificial sequence
<220> FEATURE:
<223> OTHER INFORMATION: pab2049w LC

<400> SEQUENCE: 67

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ala Gly Thr Asp Phe Thr Leu Lys Ile 65                  70                  75                  80

Ser Arg Val Glu Ala Glu Asp Val Gly Ile Tyr Tyr Cys Met Gln Gly
                85                  90                  95

Ser Lys Trp Pro Leu Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 68
<211> LENGTH: 219
<212> TYPE: PRT
<213> ORGANISM: Artificial sequence
<220> FEATURE:
<223> OTHER INFORMATION: pab2049 LC T109S

<400> SEQUENCE: 68

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Ser Lys Trp Pro Leu Thr Phe Gly Gly Gly Thr Lys Leu Glu Ile Lys
                100                 105                 110

Arg Ser Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys

<210> SEQ ID NO 69
<211> LENGTH: 219
<212> TYPE: PRT
<213> ORGANISM: Artificial sequence
<220> FEATURE:
<223> OTHER INFORMATION: Pab1949w LC

<400> SEQUENCE: 69

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 70
<211> LENGTH: 219
<212> TYPE: PRT
<213> ORGANISM: Artificial sequence
<220> FEATURE:
<223> OTHER INFORMATION: Pab1949 LC T109S

<400> SEQUENCE: 70

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 71
<211> LENGTH: 451
<212> TYPE: PRT
<213> ORGANISM: Artificial sequence
<220> FEATURE:
<223> OTHER INFORMATION: pab2049/pab1949 HC F405L L234F L235E D265A

<400> SEQUENCE: 71

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

```
Asp Lys Thr His Thr Cys Pro Pro Cys Pro Ala Glu Phe Glu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 72
<211> LENGTH: 249
<212> TYPE: PRT
<213> ORGANISM: Homo sapiens

<400> SEQUENCE: 72

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140
```

```
Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
            165                 170                 175

Arg Pro Val Glu Val Pro Gly Gly Arg Ala Val Ala Ala Ile Leu Gly
        180                 185                 190

Leu Gly Leu Val Leu Gly Leu Leu Gly Pro Leu Ala Ile Leu Leu Ala
            195                 200                 205

Leu Tyr Leu Leu Arg Arg Asp Gln Arg Leu Pro Pro Asp Ala His Lys
        210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245

<210> SEQ ID NO 73
<211> LENGTH: 277
<212> TYPE: PRT
<213> ORGANISM: Homo sapiens

<400> SEQUENCE: 73

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
```

Thr Leu Ala Lys Ile
        275

<210> SEQ ID NO 74
<211> LENGTH: 447
<212> TYPE: PRT
<213> ORGANISM: Artificial Sequence
<220> FEATURE:
<223> OTHER INFORMATION: pab1876 HC IgG1

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu

```
                340             345             350
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 75
<211> LENGTH: 447
<212> TYPE: PRT
<213> ORGANISM: Artificial Sequence
<220> FEATURE:
<223> OTHER INFORMATION: pab1876 HC IgG1 N297A

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met Tyr Trp Val Arg Gln Ala Pro Gly Gln Gly Leu Glu Trp Ile
            35                  40                  45

Gly Val Ile Arg Thr Tyr Ser Gly Asp Val Thr Tyr Asn Gln Lys Phe
        50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Ala Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
            435                 440                 445

<210> SEQ ID NO 76
<211> LENGTH: 447
<212> TYPE: PRT
<213> ORGANISM: Artificial Sequence
<220> FEATURE:
<223> OTHER INFORMATION: pab1876 HC IgG1 F405L

<400> SEQUENCE: 76

Gln Val Gln Leu Val Gln Ser Gly Ala Glu Val Lys Lys Pro Gly Ala
1               5                   10                  15
Ser Val Lys Val Ser Cys Lys Gly Ser Gly Tyr Thr Phe Thr Asp Tyr
            20                  25                  30
Ala Met Tyr Trp Val Arg Gln Ala Pro Gly Gln Gly Leu Glu Trp Ile
            35                  40                  45
Gly Val Ile Arg Thr Tyr Ser Gly Asp Val Thr Tyr Asn Gln Lys Phe
            50                  55                  60
Lys Asp Arg Ala Thr Met Thr Val Asp Lys Ser Ile Ser Thr Ala Tyr
65                  70                  75                  80
Met Glu Leu Ser Arg Leu Arg Ser Asp Asp Thr Ala Val Tyr Tyr Cys
            85                  90                  95
Ala Lys Ser Gly Thr Val Arg Gly Phe Ala Tyr Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
```

```
            180                 185                 190
Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Leu Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 77
<211> LENGTH: 447
<212> TYPE: PRT
<213> ORGANISM: Artificial Sequence
<220> FEATURE:
<223> OTHER INFORMATION: pab1876 HC IgG1 F405L N297A

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met Tyr Trp Val Arg Gln Ala Pro Gly Gln Gly Leu Glu Trp Ile
            35                  40                  45

Gly Val Ile Arg Thr Tyr Ser Gly Asp Val Thr Tyr Asn Gln Lys Phe
        50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
```

```
                100              105                110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Ala Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Leu Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 78
<211> LENGTH: 447
<212> TYPE: PRT
<213> ORGANISM: Artificial Sequence
<220> FEATURE:
<223> OTHER INFORMATION: pab1876 HC IgG1 F405L L234F L235E D265A

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
```

```
                 20                  25                  30
Ala Met Tyr Trp Val Arg Gln Ala Pro Gly Gln Gly Leu Glu Trp Ile
             35                  40                  45
Gly Val Ile Arg Thr Tyr Ser Gly Asp Val Thr Tyr Asn Gln Lys Phe
         50                  55                  60
Lys Asp Arg Ala Thr Met Thr Val Asp Lys Ser Ile Ser Thr Ala Tyr
65                  70                  75                  80
Met Glu Leu Ser Arg Leu Arg Ser Asp Thr Ala Val Tyr Tyr Cys
                 85                  90                  95
Ala Lys Ser Gly Thr Val Arg Gly Phe Ala Tyr Trp Gly Gln Gly Thr
             100                 105                 110
Leu Val Thr Val Ser Ser Ala Ser Thr Lys Gly Pro Ser Val Phe Pro
         115                 120                 125
Leu Ala Pro Ser Ser Lys Ser Thr Ser Gly Gly Thr Ala Ala Leu Gly
         130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                 165                 170                 175
Ser Ser Gly Leu Tyr Ser Leu Ser Ser Val Val Thr Val Pro Ser Ser
             180                 185                 190
Ser Leu Gly Thr Gln Thr Tyr Ile Cys Asn Val Asn His Lys Pro Ser
         195                 200                 205
Asn Thr Lys Val Asp Lys Arg Val Glu Pro Lys Ser Cys Asp Lys Thr
         210                 215                 220
His Thr Cys Pro Pro Cys Pro Ala Pro Glu Phe Glu Gly Gly Pro Ser
225                 230                 235                 240
Val Phe Leu Phe Pro Pro Lys Pro Lys Asp Thr Leu Met Ile Ser Arg
                 245                 250                 255
Thr Pro Glu Val Thr Cys Val Val Val Ala Val Ser His Glu Asp Pro
             260                 265                 270
Glu Val Lys Phe Asn Trp Tyr Val Asp Gly Val Glu Val His Asn Ala
         275                 280                 285
Lys Thr Lys Pro Arg Glu Glu Gln Tyr Asn Ser Thr Tyr Arg Val Val
         290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                 325                 330                 335
Ile Ser Lys Ala Lys Gly Gln Pro Arg Glu Pro Gln Val Tyr Thr Leu
             340                 345                 350
Pro Pro Ser Arg Glu Glu Met Thr Lys Asn Gln Val Ser Leu Thr Cys
         355                 360                 365
Leu Val Lys Gly Phe Tyr Pro Ser Asp Ile Ala Val Glu Trp Glu Ser
         370                 375                 380
Asn Gly Gln Pro Glu Asn Asn Tyr Lys Thr Thr Pro Pro Val Leu Asp
385                 390                 395                 400
Ser Asp Gly Ser Phe Leu Leu Tyr Ser Lys Leu Thr Val Asp Lys Ser
                 405                 410                 415
Arg Trp Gln Gln Gly Asn Val Phe Ser Cys Ser Val Met His Glu Ala
             420                 425                 430
Leu His Asn His Tyr Thr Gln Lys Ser Leu Ser Leu Ser Pro Gly
         435                 440                 445
```

<210> SEQ ID NO 79
<211> LENGTH: 447
<212> TYPE: PRT
<213> ORGANISM: Artificial Sequence
<220> FEATURE:
<223> OTHER INFORMATION: pab1876 HC IgG1 K409R

<400> SEQUENCE: 79

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 80
<211> LENGTH: 447
<212> TYPE: PRT
<213> ORGANISM: Artificial Sequence
<220> FEATURE:
<223> OTHER INFORMATION: pab1876 HC IgG1 K409R N297A

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met Tyr Trp Val Arg Gln Ala Pro Gly Gln Gly Leu Glu Trp Ile
            35                  40                  45

Gly Val Ile Arg Thr Tyr Ser Gly Asp Val Thr Tyr Asn Gln Lys Phe
        50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
        435                 440                 445
```

<210> SEQ ID NO 81
<211> LENGTH: 444
<212> TYPE: PRT
<213> ORGANISM: Artificial Sequence
<220> FEATURE:
<223> OTHER INFORMATION: pab1876 HC IgG4 S228P

<400> SEQUENCE: 81

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Ala Met Tyr Trp Val Arg Gln Ala Pro Gly Gln Gly Leu Glu Trp Ile
            35                  40                  45

Gly Val Ile Arg Thr Tyr Ser Gly Asp Val Thr Tyr Asn Gln Lys Phe
        50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205
```

```
Asn Thr Lys Val Asp Lys Arg Val Glu Ser Lys Tyr Gly Pro Pro Cys
            210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 82
<211> LENGTH: 447
<212> TYPE: PRT
<213> ORGANISM: Artificial Sequence
<220> FEATURE:
<223> OTHER INFORMATION: pab1876 HC IgG1 K409R L234F L235E D265A

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 83
<211> LENGTH: 450
<212> TYPE: PRT
<213> ORGANISM: Artificial Sequence
<220> FEATURE:
<223> OTHER INFORMATION: pab2049/pab1949 HC F405L L234F L235E D265A

<400> SEQUENCE: 83

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45
```

-continued

```
Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87
<211> LENGTH: 5
<212> TYPE: PRT
<213> ORGANISM: Artificial Sequence
<220> FEATURE:
<223> OTHER INFORMATION: H-CDR1 anti-GITR consensus
<220> FEATURE:
<221> NAME/KEY: MISC_FEATURE
<222> LOCATION: (1)..(1)
<223> OTHER INFORMATION: Xaa is Asp, Glu or Gly
<220> FEATURE:
<221> NAME/KEY: MISC_FEATURE
<222> LOCATION: (3)..(3)
<223> OTHER INFORMATION: Xaa is Ala or Val
<220> FEATURE:
<221> NAME/KEY: MISC_FEATURE
<222> LOCATION: (5)..(5)
<223> OTHER INFORMATION: Xaa is Tyr or His

<400> SEQUENCE: 87

Xaa Tyr Xaa Met Xaa
1               5

<210> SEQ ID NO 88
<211> LENGTH: 17
<212> TYPE: PRT
<213> ORGANISM: Artificial Sequence
<220> FEATURE:
<223> OTHER INFORMATION: H-CDR2 anti-GITR consensus
<220> FEATURE:
<221> NAME/KEY: MISC_FEATURE
<222> LOCATION: (1)..(1)
<223> OTHER INFORMATION: Xaa is Val or Leu
<220> FEATURE:
<221> NAME/KEY: MISC_FEATURE
<222> LOCATION: (3)..(3)
<223> OTHER INFORMATION: Xaa is Arg, Lys or Gln
<220> FEATURE:
<221> NAME/KEY: MISC_FEATURE
<222> LOCATION: (5)..(5)
<223> OTHER INFORMATION: Xaa is Tyr or Phe
<220> FEATURE:
<221> NAME/KEY: MISC_FEATURE
<222> LOCATION: (8)..(8)
<223> OTHER INFORMATION: Xaa is Asp, Glu or Gly
<220> FEATURE:
<221> NAME/KEY: MISC_FEATURE
<222> LOCATION: (9)..(9)
<223> OTHER INFORMATION: Xaa is Val or Leu
<220> FEATURE:
<221> NAME/KEY: MISC_FEATURE
<222> LOCATION: (10)..(10)
<223> OTHER INFORMATION: Xaa is Thr or Ser
<220> FEATURE:
<221> NAME/KEY: MISC_FEATURE

```
<222> LOCATION: (16)..(16)
<223> OTHER INFORMATION: Xaa is Lys, Arg or Gln
<220> FEATURE:
<221> NAME/KEY: MISC_FEATURE
<222> LOCATION: (17)..(17)
<223> OTHER INFORMATION: Xaa is Asp, Glu or Gly

<400> SEQUENCE: 88

Xaa Ile Xaa Thr Xaa Ser Gly Xaa Xaa Xaa Tyr Asn Gln Lys Phe Xaa
1               5                   10                  15

Xaa

<210> SEQ ID NO 89

<400> SEQUENCE: 89

000

<210> SEQ ID NO 90
<211> LENGTH: 17
<212> TYPE: PRT
<213> ORGANISM: Artificial Sequence
<220> FEATURE:
<223> OTHER INFORMATION: L-CDR1 anti-GITR consensus
<220> FEATURE:
<221> NAME/KEY: MISC_FEATURE
<222> LOCATION: (10)..(10)
<223> OTHER INFORMATION: Xaa is Gly or Ser
<220> FEATURE:
<221> NAME/KEY: MISC_FEATURE
<222> LOCATION: (17)..(17)
<223> OTHER INFORMATION: Xaa is Thr or Ser

<400> SEQUENCE: 90

Lys Ser Ser Gln Ser Leu Leu Asn Ser Xaa Asn Gln Lys Asn Tyr Leu
1               5                   10                  15

Xaa

<210> SEQ ID NO 91

<400> SEQUENCE: 91

000

<210> SEQ ID NO 92
<211> LENGTH: 9
<212> TYPE: PRT
<213> ORGANISM: Artificial Sequence
<220> FEATURE:
<223> OTHER INFORMATION: L-CDR3 anti-GITR consensus
<220> FEATURE:
<221> NAME/KEY: MISC_FEATURE
<222> LOCATION: (3)..(3)
<223> OTHER INFORMATION: Xaa is Asp or Glu
<220> FEATURE:
<221> NAME/KEY: MISC_FEATURE
<222> LOCATION: (6)..(6)
<223> OTHER INFORMATION: Xaa is Tyr, Phe or Ser

<400> SEQUENCE: 92

Gln Asn Xaa Tyr Ser Xaa Pro Tyr Thr
1               5

<210> SEQ ID NO 93
<211> LENGTH: 330
<212> TYPE: PRT
<213> ORGANISM: Artificial Sequence
<220> FEATURE:
<223> OTHER INFORMATION: Human IgG1 constant region consensus sequence
```

```
<220> FEATURE:
<221> NAME/KEY: MISC_FEATURE
<222> LOCATION: (97)..(97)
<223> OTHER INFORMATION: Xaa is Lys or Arg
<220> FEATURE:
<221> NAME/KEY: MISC_FEATURE
<222> LOCATION: (239)..(239)
<223> OTHER INFORMATION: Xaa is Asp or Glu
<220> FEATURE:
<221> NAME/KEY: MISC_FEATURE
<222> LOCATION: (241)..(241)
<223> OTHER INFORMATION: Xaa is Leu or Met
<220> FEATURE:
<221> NAME/KEY: MISC_FEATURE
<222> LOCATION: (314)..(314)
<223> OTHER INFORMATION: Xaa is Gly or Ala

<400> SEQUENCE: 93
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Lys |
| 1 | | | | 5 | | | | | 10 | | | | | 15 |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Xaa | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Xaa | Glu |
| 225 | | | | | 230 | | | | | 235 | | | | | 240 |
| Xaa | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Xaa | Leu | His | Asn | His | Tyr | Thr |
| 305 | | | | | 310 | | | | | 315 | | | | | 320 |

Gln Lys Ser Leu Ser Leu Ser Pro Gly Lys
                325                 330

<210> SEQ ID NO 94
<211> LENGTH: 330
<212> TYPE: PRT
<213> ORGANISM: Artificial Sequence
<220> FEATURE:
<223> OTHER INFORMATION: Human IgG1 G1m3 allotype

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 330

<212> TYPE: PRT
<213> ORGANISM: Artificial Sequence
<220> FEATURE:
<223> OTHER INFORMATION: Human IgG1 G1m17,1 allotype

<400> SEQUENCE: 95

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 96
<211> LENGTH: 330
<212> TYPE: PRT
<213> ORGANISM: Artificial Sequence
<220> FEATURE:
<223> OTHER INFORMATION: Human IgG1, G1m17,1,2 allotype

<400> SEQUENCE: 96

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330

<210> SEQ ID NO 97
<211> LENGTH: 327
<212> TYPE: PRT
<213> ORGANISM: Artificial Sequence
<220> FEATURE:
<223> OTHER INFORMATION: Human IgG4 wild type constant regions

<400> SEQUENCE: 97

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Ser Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 98
<211> LENGTH: 327
<212> TYPE: PRT
<213> ORGANISM: Artificial Sequence
<220> FEATURE:
<223> OTHER INFORMATION: IgG4 constant regions S228P modification

<400> SEQUENCE: 98

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 99
<211> LENGTH: 326
<212> TYPE: PRT
<213> ORGANISM: Artificial Sequence
<220> FEATURE:
<223> OTHER INFORMATION: Human IgG2 wild type constant region

<400> SEQUENCE: 99

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95
```

```
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 100
<211> LENGTH: 326
<212> TYPE: PRT
<213> ORGANISM: Artificial Sequence
<220> FEATURE:
<223> OTHER INFORMATION: IgG2 constant region C127S modification

<400> SEQUENCE: 100

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

```
Thr Leu Met Ile Ser Arg Thr Pro Glu Val Thr Cys Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 101
<211> LENGTH: 118
<212> TYPE: PRT
<213> ORGANISM: Artificial Sequence
<220> FEATURE:
<223> OTHER INFORMATION: 231-32-15 VH

<400> SEQUENCE: 101

Gln Val Gln Leu Leu Gln Ser Gly Thr Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met Tyr Trp Val Lys Gln Ser His Ala Lys Ser Leu Glu Trp Ile
        35                  40                  45

Gly Val Ile Arg Thr Tyr Ser Gly Asp Val Thr Tyr Asn Gln Lys Phe
    50                  55                  60

Lys Asp Lys Ala Thr Met Thr Val Asp Lys Ser Ser Ile Ala Tyr
65                  70                  75                  80

Met Glu Leu Ala Arg Leu Ser Ser Glu Asp Ser Ala Ile Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 102
<211> LENGTH: 113
<212> TYPE: PRT
<213> ORGANISM: Artificial Sequence
```

-continued

```
<220> FEATURE:
<223> OTHER INFORMATION: 231-32-15 VL

<400> SEQUENCE: 102

Asp Ile Val Met Thr Gln Ser Pro Ser Ser Leu Thr Val Thr Ala Gly
1               5                   10                  15

Glu Lys Val Ile Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr His Cys Gln Asn
                85                  90                  95

Asp Tyr Ser Tyr Pro Tyr Thr Phe Gly Gly Gly Thr Lys Leu Glu Ile
            100                 105                 110

Lys

<210> SEQ ID NO 103
<211> LENGTH: 113
<212> TYPE: PRT
<213> ORGANISM: Artificial Sequence
<220> FEATURE:
<223> OTHER INFORMATION: pab1875 VL

<400> SEQUENCE: 103

Asp Ile Val Met Thr Gln Ser Pro Pro Thr Leu Ser Leu Ser Pro Gly
1               5                   10                  15

Glu Arg Val Thr Leu Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Ala Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr His Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 104
<211> LENGTH: 119
<212> TYPE: PRT
<213> ORGANISM: Artificial Sequence
<220> FEATURE:
<223> OTHER INFORMATION: m6C8 VH

<400> SEQUENCE: 104

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45
```

```
Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser
            115

<210> SEQ ID NO 105
<211> LENGTH: 107
<212> TYPE: PRT
<213> ORGANISM: Artificial Sequence
<220> FEATURE:
<223> OTHER INFORMATION: m6C8 VL

<400> SEQUENCE: 105

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val His Ser
65                  70                  75                  80

Glu Asp Leu Ala Glu Tyr Phe Cys Gln Gln Tyr Asn Thr Asp Pro Leu
                85                  90                  95

Thr Phe Gly Ala Gly Thr Lys Leu Glu Ile Lys
            100                 105

<210> SEQ ID NO 106
<211> LENGTH: 452
<212> TYPE: PRT
<213> ORGANISM: Artificial Sequence
<220> FEATURE:
<223> OTHER INFORMATION: Pab1928 (Hu106-122) HC

<400> SEQUENCE: 106

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser Ala Ser Thr Lys Gly Pro
```

```
            115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Arg Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys
    450

<210> SEQ ID NO 107
<211> LENGTH: 214
<212> TYPE: PRT
<213> ORGANISM: Artificial Sequence
<220> FEATURE:
<223> OTHER INFORMATION: Pab1928 (Hu106-122) LC T109S

<400> SEQUENCE: 107

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
```

```
                 20                  25                  30
Val Ala Trp Tyr Gln Gln Lys Pro Gly Lys Ala Pro Lys Leu Leu Ile
         35                  40                  45

Tyr Ser Ala Ser Tyr Leu Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Thr Pro Arg
                 85                  90                  95

Thr Phe Gly Gln Gly Thr Lys Leu Glu Ile Lys Arg Ser Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 108
<211> LENGTH: 330
<212> TYPE: PRT
<213> ORGANISM: Artificial Sequence
<220> FEATURE:
<223> OTHER INFORMATION: Synthetic peptide

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

-continued

```
                165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 109
<211> LENGTH: 330
<212> TYPE: PRT
<213> ORGANISM: Artificial Sequence
<220> FEATURE:
<223> OTHER INFORMATION: Synthetic peptide

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

-continued

```
            195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

<210> SEQ ID NO 118
<211> LENGTH: 450
<212> TYPE: PRT
<213> ORGANISM: Artificial Sequence
<220> FEATURE:
<223> OTHER INFORMATION: pab2049/pab1949 HC IgG1

<400> SEQUENCE: 118

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Lys | Leu | Ser | Cys | Ala | Ala | Ser | Gly | Phe | Thr | Phe | Ser | Gly | Ser |
| | | | 20 | | | | | 25 | | | | | 30 | | |
| Ala | Met | His | Trp | Val | Arg | Gln | Ala | Ser | Gly | Lys | Gly | Leu | Glu | Trp | Val |
| | | 35 | | | | | 40 | | | | | 45 | | | |
| Gly | Arg | Ile | Arg | Ser | Lys | Ala | Asn | Ser | Tyr | Ala | Thr | Ala | Tyr | Ala | Ala |
| 50 | | | | | 55 | | | | | 60 | | | | | |
| Ser | Val | Lys | Gly | Arg | Phe | Thr | Ile | Ser | Arg | Asp | Asp | Ser | Lys | Asn | Thr |
| 65 | | | | | 70 | | | | | 75 | | | | | 80 |
| Ala | Tyr | Leu | Gln | Met | Asn | Ser | Leu | Lys | Thr | Glu | Asp | Thr | Ala | Val | Tyr |
| | | | | 85 | | | | | 90 | | | | | 95 | |
| Tyr | Cys | Thr | Ser | Gly | Ile | Tyr | Asp | Ser | Ser | Gly | Tyr | Asp | Tyr | Trp | Gly |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| 130 | | | | | 135 | | | | | 140 | | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | | 195 | | | | | 200 | | | | | 205 | | |
| Lys | Pro | Ser | Asn | Thr | Lys | Val | Asp | Lys | Arg | Val | Glu | Pro | Lys | Ser | Cys |
| 210 | | | | | 215 | | | | | 220 | | | | | |
| Asp | Lys | Thr | His | Thr | Cys | Pro | Pro | Cys | Pro | Ala | Pro | Glu | Leu | Leu | Gly |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Tyr | Asn | Ser | Thr | Tyr |
| 290 | | | | | 295 | | | | | 300 | | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 119
<211> LENGTH: 450
<212> TYPE: PRT
<213> ORGANISM: Artificial Sequence
<220> FEATURE:
<223> OTHER INFORMATION: pab2049/pab1949 HC IgG1 N297A

<400> SEQUENCE: 119

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 120
<211> LENGTH: 450
<212> TYPE: PRT
<213> ORGANISM: Artificial Sequence
<220> FEATURE:
<223> OTHER INFORMATION: pab2049/pab1949 HC IgG1 K409R

<400> SEQUENCE: 120

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 121
<211> LENGTH: 450
<212> TYPE: PRT
<213> ORGANISM: Artificial Sequence
<220> FEATURE:
<223> OTHER INFORMATION: pab2049/pab1949 HC IgG1 K409R N297A

<400> SEQUENCE: 121

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60
```

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 122
<211> LENGTH: 450
<212> TYPE: PRT

<213> ORGANISM: Artificial Sequence
<220> FEATURE:
<223> OTHER INFORMATION: pab2049/pab1949 HC K409R L234F L235E D265A

<400> SEQUENCE: 122

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
                385                 390                 395                 400
Val Leu Asp Ser Asp Gly Ser Phe Phe Leu Tyr Ser Arg Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly
    450

<210> SEQ ID NO 123
<211> LENGTH: 450
<212> TYPE: PRT
<213> ORGANISM: Artificial Sequence
<220> FEATURE:
<223> OTHER INFORMATION: pab2049/pab1949 HC F405L

<400> SEQUENCE: 123

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290             295             300
Arg Val Ser Val Leu Thr Val Leu His Gln Asp Trp Leu Asn Gly
305                     310                     315             320

Lys Glu Tyr Lys Cys Lys Val Ser Asn Lys Ala Leu Pro Ala Pro Ile
                325                     330                     335

Glu Lys Thr Ile Ser Lys Ala Lys Gly Gln Pro Arg Glu Pro Gln Val
                340                     345                     350

Tyr Thr Leu Pro Pro Ser Arg Glu Glu Met Thr Lys Asn Gln Val Ser
                355                     360                     365

Leu Thr Cys Leu Val Lys Gly Phe Tyr Pro Ser Asp Ile Ala Val Glu
                370                     375                     380

Trp Glu Ser Asn Gly Gln Pro Glu Asn Asn Tyr Lys Thr Thr Pro Pro
385                     390                     395                     400

Val Leu Asp Ser Asp Gly Ser Phe Leu Leu Tyr Ser Lys Leu Thr Val
                405                     410                     415

Asp Lys Ser Arg Trp Gln Gln Gly Asn Val Phe Ser Cys Ser Val Met
                420                     425                     430

His Glu Ala Leu His Asn His Tyr Thr Gln Lys Ser Leu Ser Leu Ser
                435                     440                     445

Pro Gly
    450

<210> SEQ ID NO 124
<211> LENGTH: 450
<212> TYPE: PRT
<213> ORGANISM: Artificial Sequence
<220> FEATURE:
<223> OTHER INFORMATION: pab2049/pab1949 HC F405L N297A

<400> SEQUENCE: 124

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 125
<211> LENGTH: 447
<212> TYPE: PRT
<213> ORGANISM: Artificial Sequence
<220> FEATURE:
<223> OTHER INFORMATION: pab2049/pab1949 HC IgG4 S228P

<400> SEQUENCE: 125

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
```

```
            100                 105                 110
Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 126
<211> LENGTH: 329
<212> TYPE: PRT
<213> ORGANISM: Artificial Sequence
<220> FEATURE:
<223> OTHER INFORMATION: Human IgG1 constant region consensus sequence
<220> FEATURE:
<221> NAME/KEY: MISC_FEATURE
<222> LOCATION: (97)..(97)
<223> OTHER INFORMATION: Xaa can be Lys or Arg
<220> FEATURE:
<221> NAME/KEY: MISC_FEATURE
<222> LOCATION: (239)..(239)
```

<223> OTHER INFORMATION: Xaa can be Asp or Glu
<220> FEATURE:
<221> NAME/KEY: MISC_FEATURE
<222> LOCATION: (241)..(241)
<223> OTHER INFORMATION: Xaa can be Leu or Met
<220> FEATURE:
<221> NAME/KEY: MISC_FEATURE
<222> LOCATION: (314)..(314)
<223> OTHER INFORMATION: Xaa can be Gly or Ala

<400> SEQUENCE: 126

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Xaa Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Xaa Leu His Asn His Tyr Thr
305                 310                 315                 320

Gln Lys Ser Leu Ser Leu Ser Pro Gly
                325

<210> SEQ ID NO 127
<211> LENGTH: 329
<212> TYPE: PRT

<213> ORGANISM: Artificial Sequence
<220> FEATURE:
<223> OTHER INFORMATION: Human IgG1 G1m3 allotype

<400> SEQUENCE: 127

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Arg | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | | | | | | | |
| | | | | 325 | | | | | | | | | | | |

<210> SEQ ID NO 128
<211> LENGTH: 329
<212> TYPE: PRT
<213> ORGANISM: Artificial Sequence
<220> FEATURE:
<223> OTHER INFORMATION: Human IgG1 G1m17,1 allotype

<400> SEQUENCE: 128

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 129
<211> LENGTH: 329
<212> TYPE: PRT
<213> ORGANISM: Artificial Sequence
<220> FEATURE:
<223> OTHER INFORMATION: Human IgG1, G1m17,1,2 allotype

<400> SEQUENCE: 129

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Gly Leu His Asn His Tyr Thr
305                 310                 315                 320

Gln Lys Ser Leu Ser Leu Ser Pro Gly
            325

<210> SEQ ID NO 130
<211> LENGTH: 326
<212> TYPE: PRT
<213> ORGANISM: Artificial Sequence
<220> FEATURE:
<223> OTHER INFORMATION: Human IgG4 wild type constant regions

<400> SEQUENCE: 130

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Ser Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 131
<211> LENGTH: 326
<212> TYPE: PRT
<213> ORGANISM: Artificial Sequence
<220> FEATURE:
<223> OTHER INFORMATION: IgG4 constant regions S228P modification

<400> SEQUENCE: 131

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 132
<211> LENGTH: 325
<212> TYPE: PRT
<213> ORGANISM: Artificial Sequence
<220> FEATURE:
<223> OTHER INFORMATION: Human IgG2 wild type constant region

<400> SEQUENCE: 132

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

```
Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 133
<211> LENGTH: 325
<212> TYPE: PRT
<213> ORGANISM: Artificial Sequence
<220> FEATURE:
<223> OTHER INFORMATION: IgG2 constant region C127S modification

<400> SEQUENCE: 133

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160
```

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 134
<211> LENGTH: 451
<212> TYPE: PRT
<213> ORGANISM: Artificial Sequence
<220> FEATURE:
<223> OTHER INFORMATION: Pab1928 (Hu106-122) HC

<400> SEQUENCE: 134

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

```
Val Pro Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
    435                 440                 445

Ser Pro Gly
    450

<210> SEQ ID NO 135
<211> LENGTH: 329
<212> TYPE: PRT
<213> ORGANISM: Artificial Sequence
<220> FEATURE:
<223> OTHER INFORMATION: IgG1 constant region comprising the F405L
      mutation

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 136
<211> LENGTH: 329
<212> TYPE: PRT
<213> ORGANISM: Artificial Sequence
<220> FEATURE:
<223> OTHER INFORMATION: IgG1 constant region comprising the K409R
      mutation

<400> SEQUENCE: 136

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro

```
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 137
<211> LENGTH: 82
<212> TYPE: PRT
<213> ORGANISM: Homo sapiens

<400> SEQUENCE: 137

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Asp Glu
    50                  55                  60

Glu Cys Cys Ser Glu Trp Asp Cys Met Cys Val Gln Pro Glu Phe His
65                  70                  75                  80

Cys Gly

<210> SEQ ID NO 138
<211> LENGTH: 82
<212> TYPE: PRT
<213> ORGANISM: Homo sapiens

<400> SEQUENCE: 138

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30
```

```
Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly

<210> SEQ ID NO 139
<211> LENGTH: 84
<212> TYPE: PRT
<213> ORGANISM: Homo sapiens

<400> SEQUENCE: 139

Phe His Cys Gly Asp Pro Cys Cys Thr Thr Cys Arg His His Pro Cys
1               5                   10                  15

Pro Pro Gly Gln Gly Val Gln Ser Gln Gly Lys Phe Ser Phe Gly Phe
            20                  25                  30

Gln Cys Ile Asp Cys Ala Ser Gly Thr Phe Ser Gly Gly His Glu Gly
            35                  40                  45

His Cys Lys Pro Trp Thr Asp Cys Thr Gln Phe Gly Phe Leu Thr Val
    50                  55                  60

Phe Pro Gly Asn Lys Thr His Asn Ala Val Cys Val Pro Gly Ser Pro
65                  70                  75                  80

Pro Ala Glu Pro
```

ANTIBODIES AND METHODS OF USE THEREOF

1. RELATED APPLICATIONS

The instant application claims priority to U.S. Provisional Application No. 62/262,369, filed on Dec. 2, 2015, and 62/419,911, filed on Nov. 9, 2016, the disclosures of which are herein incorporated by reference in their entireties.

2. SEQUENCE LISTING

The instant application contains a sequence listing which has been submitted electronically in ASCII format and is hereby incorporated by reference in its entirety (said ASCII copy, created on Dec. 1, 2016, is named 3617_016PC02_SeqListing.txt and is 274,675 bytes in size).

3. FIELD

The present disclosure relates to multispecific antibodies, e.g., bispecific antibodies, that specifically bind to human glucocorticoid-induced TNFR family related receptor (GITR) and/or human OX40 receptor ("OX40"), compositions comprising such antibodies, and methods of producing and using those antibodies.

4. BACKGROUND

The contributions of the innate and adaptive immune response in the control of human tumor growth are well-characterized (Vesely M D et al., (2011) Annu Rev Immunol 29: 235-271). As a result, antibody-based strategies have emerged that aim to enhance T cell responses for the purpose of cancer therapy, such as targeting T cell expressed stimulatory receptors with agonist antibodies, or inhibitory receptors with functional antagonists (Mellman I et al., (2011) Nature 480: 480-489). Antibody-mediated agonist and antagonist approaches have shown preclinical, and more recently clinical, activity.

Two important stimulators of immune responses are glucocorticoid-induced TNFR-related protein (GITR) and OX40 receptor ("OX40"). Both GITR and OX40 are members of the tumor necrosis factor receptor superfamily (TNFRSF).

GITR (also known as activation-inducible TNFR family receptor (AITR), GITR-D, CD357, and tumor necrosis factor receptor superfamily member 18 (TNFRSF18)), is expressed in many components of the innate and adaptive immune system and stimulates both acquired and innate immunity (Nocentini G et al., (1994) PNAS 94: 6216-6221; Hanabuchi S et al., (2006) Blood 107:3617-3623; Nocentini G & Riccardi C (2005) Eur J Immunol 35: 1016-1022; Nocentini G et al., (2007) Eur J Immunol 37:1165-1169). It is expressed in several cells and tissues, including T, B, dendritic (DC) and Natural Killer (NK) cells and is activated by its ligand, GITRL, mainly expressed on Antigen Presenting Cells (APCs), on endothelial cells, and also in tumor cells. The GITR/GITRL system participates in the development of autoimmune/inflammatory responses and potentiates response to infection and tumors. For example, treating animals with GITR-Fc fusion protein ameliorates autoimmune/inflammatory diseases while GITR triggering is effective in treating viral, bacterial, and parasitic infections, as well in boosting immune response against tumors (Nocentini G et al., (2012) Br J Pharmacol 165: 2089-99). These effects are due to several concurrent mechanisms including: co-activation of effector T-cells, inhibition of regulatory T (Treg) cells, NK-cell co-activation, activation of macrophages, modulation of dendritic cell function, and regulation of the extravasation process. The membrane expression of GITR is increased following T cell activation (Hanabuchi S et al., (2006) supra; Nocentini G & Riccardi C supra). Its triggering coactivates effector T lymphocytes (McHugh R S et al., (2002) Immunity 16: 311-323; Shimizu J et al., (2002) Nat Immunol 3: 135-142; Roncheti S et al., (2004) Eur J Immunol 34: 613-622; Tone M et al., (2003) PNAS 100: 15059-15064). GITR activation increases resistance to tumors and viral infections, is involved in autoimmune/inflammatory processes and regulates leukocyte extravasation (Nocentini G & Riccardi C (2005) supra; Cuzzocrea S et al., (2004) J Leukoc Biol 76: 933-940; Shevach E M & Stephens G L (2006) Nat Rev Immunol 6: 613-618; Cuzzocrea S et al., (2006) J Immunol 177: 631-641; Cuzzocrea S et al., (2007) FASEB J 21: 117-129).

Human GITR is expressed at very low levels in peripheral (non-activated) T cells. After T cell activation, GITR is strongly up-regulated for several days in both $CD4^+$ and $CD8^+$ cells (Kwon B et al., (1999) J Biol Chem 274: 6056-6061; Gurney A L et al., (1999) Curr Biol 9: 215-218; Ronchetti S et al., (2004) supra; Shimizu J et al., (2002) supra; Ji H B et al., (2004) supra; Ronchetti S et al., (2002) Blood 100: 350-352; Li Z et al., (2003) J Autoimmun 21: 83-92), with $CD4^+$ cells having a higher GITR expression than $CD8^+$ cells (Kober J et al., (2008) Eur J Immunol 38(10): 2678-88; Bianchini R et al., (2011) Eur J Immunol 41(8): 2269-78)

OX40 (also known as CD134, tumor necrosis factor receptor superfamily member 4 (TNFRSF4), TXGP1L, ACT35, and ACT-4) modulates T cell, Natural Killer T (NKT) cell, and NK cell function (Sugamura K et al., (2004) Nat Rev Immunol 4: 420-431). OX40 can be upregulated by antigen-specific T cells following T cell receptor (TCR) stimulation by professional antigen presenting cells (APCs) displaying MHC class I or II molecules loaded with a cognate peptide (Sugamura K et al., (2004) Nat Rev Immunol 4: 420-431). Upon maturation APCs such as dendritic cells (DCs) upregulate stimulatory B7 family members (e.g., CD80 and CD86), as well as accessory co-stimulatory molecules including OX40 ligand (OX40L), which help to sculpt the kinetics and magnitude of the T cell immune response, as well as effective memory cell differentiation. Notably, other cell types can also express constitutive and/or inducible levels of OX40L such as B cells, vascular endothelial cells, mast cells, and in some instances activated T cells (Soroosh P et al., (2006) J Immunol 176: 5975-5987). OX40:OX40L co-engagement is believed to drive the higher order clustering of receptor trimers and subsequent signal transduction (Compaan D M et al., (2006) Structure 14: 1321-1330).

OX40 expression by T cells within the tumor microenvironment has been observed in murine and human tumor tissues (Bulliard Y et al., (2014) Immunol Cell Biol 92: 475-480 and Piconese S et al., (2014) Hepatology 60: 1494-1507). OX40 is highly expressed by intratumoral populations of regulatory T cells (Tregs) relative to conventional T cell populations, a feature attributed to their proliferative status (Waight J D et al., (2015) J Immunol 194: 878-882 and Bulliard Y et al., (2014) Immunol Cell Biol 92: 475-480). Early studies demonstrated that OX40 agonist antibodies were able to elicit tumor rejection in mouse models (Weinberg A D et al., (2000) J Immunol 164: 2160-2169 and Piconese S et al., (2008) J Exp Med 205: 825-839). A mouse antibody that agonizes human OX40 signaling has also been shown to enhance immune functions in cancer patients (Curti B D et al., (2013) Cancer Res 73: 7189-7198).

OX40 and OX40L interactions also have been associated with immune responses in inflammatory and autoimmune diseases and disorders, including mouse models of asthma/atopy, encephalomyelitis, rheumatoid arthritis, colitis/inflammatory bowel disease, graft-versus-host disease (e.g., transplant rejection), diabetes in non-obese diabetic mice, and atherosclerosis (Croft M et al., (2009) Immunol Rev 229(1): 173-191, and references cited therein). Reduced symptomatology associated with the diseases and disorders has been reported in OX40- and OX40L-deficient mice, in mice receiving anti-OX40 liposomes loaded with a cytostatic drug, and in mice in which OX40 and OX40L interactions were blocked with an anti-OX40L blocking antibody or a recombinant OX40 fused to the Fc portion of human immunoglobulin (Croft M et al.; Boot E P J et al., (2005) Arthritis Res Ther 7: R604-615; Weinberg A D et al., (1999) J Immunol 162: 1818-1826). Treatment with a blocking anti-OX40L antibody was also shown to inhibit Th2 inflammation in a rhesus monkey model of asthma (Croft M et al., Seshasayee D et al., (2007) J Clin Invest 117: 3868-3878). Additionally, polymorphisms in OX40L have been associated with lupus (Croft M et al.)

Given the role of human GITR and OX40 in modulating immune responses, provided herein are antibodies that specifically bind to GITR and/or OX40 and the use of these antibodies to modulate GITR and/or OX40 activity.

5. SUMMARY

In one aspect, provided herein are multispecific (e.g., bispecific) antibodies that bind to GITR and/or OX40. In one instance, an isolated multispecific (e.g., bispecific) antibody comprises a first antigen-binding domain that specifically binds to OX40 (e.g., human OX40) and a second antigen-binding domain that specifically binds to GITR (e.g., human GITR).

In one instance, an antibody comprises a first antigen-binding domain that specifically binds to human OX40 and a TNF superfamily protein. In one instance, an antibody comprises a TNF superfamily protein and a second antigen-binding domain that specifically binds to human GITR. A TNF superfamily protein can replace the first antigen-binding domain or the second antigen-binding domain in any multispecific (e.g., bispecific) antibody provided herein.

In one instance, an isolated multispecific (e.g., bispecific) antibody that specifically binds to human OX40 comprises: (a) a first antigen-binding domain that specifically binds to human OX40; comprising: (i) a heavy chain variable domain (VH)-complementarity determining region (CDR) 1 comprising the amino acid sequence of GSAMH (SEQ ID NO:47); (ii) a VH-CDR2 comprising the amino acid sequence of RIRSKANSYATAYAASVKG (SEQ ID NO:48); (iii) a VH-CDR3 comprising the amino acid sequence of GIYDSSGYDY (SEQ ID NO:49); (iv) a light chain variable domain (VL)-CDR1 comprising the amino acid sequence of RSSQSLLHSNGYNYLD (SEQ ID NO:50); (v) a VL-CDR2 comprising the amino acid sequence of LGSNRAS (SEQ ID NO:51); and (vi) a VL-CDR3 comprising the amino acid sequence of MQGSKWPLT (SEQ ID NO:52) or MQALQTPLT (SEQ ID NO:53); and (b) a second antigen-binding domain.

In one instance, an isolated multispecific (e.g., bispecific) antibody that specifically binds to human OX40 comprises: (a) a first antigen-binding domain that specifically binds to the same epitope of human OX40 as an antibody comprising a VH comprising the amino acid sequence of SEQ ID NO:54 and a VL comprising the amino acid sequence of SEQ ID NO:55 or 56; and (b) a second antigen-binding domain.

In one instance an isolated multispecific (e.g., bispecific) antibody that specifically binds to human OX40 comprises: (a) a first antigen-binding domain that specifically binds to human OX40 and exhibits, as compared to binding to a human OX40 sequence of SEQ ID NO:72, reduced or absent binding to a protein identical to SEQ ID NO:72 except for the presence of an amino acid mutation selected from the group consisting of: N60A, R62A, R80A, L88A, P93A, P99A, P115A, and a combination thereof, numbered according to SEQ ID NO: 72; and (b) a second antigen-binding domain.

In one instance, an isolated multispecific (e.g., bispecific) antibody that specifically binds to human OX40 comprises: (a) a first antigen-binding domain that specifically binds to human OX40 comprising a VH and a VL, wherein the VH comprises the amino acid sequence of SEQ ID NO:54; and (b) a second antigen-binding domain.

In one instance, an isolated multispecific (e.g., bispecific) antibody that specifically binds to human OX40 comprises: (a) a first antigen-binding domain that specifically binds to human OX40 comprising a VH and a VL, wherein the VL comprises the amino acid sequence of SEQ ID NO:55 or SEQ ID NO:56; (b) a second antigen-binding domain.

In one instance, an isolated multispecific (e.g., bispecific) antibody that specifically binds to human GITR comprises: (a) a first antigen-binding domain; and (b) a second antigen-binding domain that specifically binds to human GITR comprising (i) a VH-CDR1 comprising the amino acid sequence of $X_1YX_2MX_3$ (SEQ ID NO:87), wherein $X_1$ is D, E or G; $X_2$ is A or V; and $X_3$ is Y or H; (ii) a VH-CDR2 comprising the amino acid sequence of $X_1IX_2TX_3SGX_4X_5X_6YNQKFX_7X_8$ (SEQ ID NO:88), wherein $X_1$ is V or L; $X_2$ is R, K or Q; $X_3$ is Y or F; $X_4$ is D, E or G; $X_5$ is V or L; $X_6$ is T or S; $X_7$ is K, R or Q; and $X_8$ is D, E or G; (iii) a VH-CDR3 comprising the amino acid sequence of SGTVRGFAY (SEQ ID NO:3); (iv) a VL-CDR1 comprising the amino acid sequence of KSSQSLLNSX$_1$NQKNYLX$_2$ (SEQ ID NO:90), wherein $X_1$ is G or S; and $X_2$ is T or S; (v) a VL-CDR2 comprising the amino acid sequence of WASTRES (SEQ ID NO:5); and (vi) a VL-CDR3 comprising the amino acid sequence of QNX$_1$YSX$_2$PYT (SEQ ID NO:92), wherein $X_1$ is D or E; and $X_2$ is Y, F or S.

In one instance, an isolated multispecific (e.g., bispecific) antibody that specifically binds to human GITR comprises: (a) a first antigen-binding domain; and (b) a second antigen-binding domain that specifically binds to the same epitope of human GITR as an antibody comprising a VH comprising the amino acid sequence of SEQ ID NO:18 and a VL comprising the amino acid sequence of SEQ ID NO:19.

In one instance, an isolated multispecific (e.g., bispecific) antibody that specifically binds to human GITR comprises: (a) a first antigen-binding domain; and (b) a second antigen-binding domain that specifically binds to an epitope of human GITR comprising at least one amino acid in residues 60-63 of SEQ ID NO:41.

In one instance, an isolated multispecific (e.g., bispecific) antibody that specifically binds to human GITR comprises: (a) a first antigen-binding domain; and (b) a second antigen-binding domain that specifically binds to each of i) human GITR comprising residues 26 to 241 of SEQ ID NO:41 and ii) a variant of *cynomolgus* GITR, the variant comprising residues 26-234 of SEQ ID NO:46, wherein the antibody does not specifically bind to *cynomolgus* GITR comprising residues 26-234 of SEQ ID NO:44.

In one instance, an isolated multispecific (e.g., bispecific) antibody that specifically binds to human GITR comprises: (a) a first antigen-binding domain; and (b) a second antigen-binding domain that specifically binds to human GITR and exhibits, as compared to binding to a human GITR sequence of residues 26 to 241 of SEQ ID NO:41, reduced or absent binding to a protein identical to residues 26 to 241 of SEQ ID NO:41 except for the presence of a D60A or G63A amino acid substitution, numbered according to SEQ ID NO:41.

In one instance, an isolated multispecific (e.g., bispecific) antibody that specifically binds to human GITR comprises: (a) a first antigen-binding domain; and (b) a second antigen-binding domain that specifically binds to human GITR and comprises a VH and a VL, wherein the VH comprises an amino acid sequence selected from the group consisting of SEQ ID NOs:18, 20, 22, 24, and 25.

In one instance, an isolated multispecific (e.g., bispecific) antibody that specifically binds to human GITR comprises: (a) a first antigen-binding domain; and (b) a second antigen-binding domain that specifically binds to human GITR and comprises a VH and a VL, wherein the VL comprises an amino acid sequence selected from the group consisting of SEQ ID NOs:19, 21, 23, and 26.

In one instance, the isolated multispecific (e.g., bispecific) antibody that specifically binds to human OX40 comprises the second antigen-binding domain. In one instance, the second antigen-binding domain specifically binds to a TNFR superfamily protein. In one instance, the TNFR superfamily protein is selected from the group consisting of: GITR, OX40 (e.g., wherein the second antigen-binding domain binds to a different OX40 epitope than the first antigen-binding domain), CD137, DR3, CD40, BAFFR, CD27, and HVEM.

In one instance, the isolated multispecific (e.g., bispecific) antibody that specifically binds to human GITR comprises the first antigen-binding domain. In one instance, the first antigen-binding domain specifically binds to a TNFR superfamily protein. In one instance, the TNFR superfamily protein is selected from the group consisting of: GITR (e.g., wherein the first antigen-binding domain binds to a different GITR epitope than the second antigen-binding domain) OX40, CD137, DR3, CD40, BAFFR, CD27, and HVEM.

In one instance, the second antigen-binding domain specifically binds to the TNFR superfamily protein human GITR. In one instance, the second antigen-binding domain that binds to human GITR comprises: (i) a VH-CDR1 comprising the amino acid sequence of $X_1YX_2MX_3$ (SEQ ID NO:87), wherein $X_1$ is D, E or G; $X_2$ is A or V; and $X_3$ is Y or H; (ii) a VH-CDR2 comprising the amino acid sequence of $X_1IX_2TX_3SGX_4X_5X_6YNQKFX_7X_8$ (SEQ ID NO:88), wherein $X_1$ is V or L; $X_2$ is R, K Q; $X_3$ is Y F; $X_4$ is D, E G; $X_5$ is V or L; $X_6$ is T or S; $X_7$ is K, R or Q; and $X_8$ is D, E or G; (iii) a VH-CDR3 comprising the amino acid sequence of SGTVRGFAY (SEQ ID NO:3); (iv) a VL-CDR1 comprising the amino acid sequence of KSSQSLLNSX$_1$NQKNYLX$_2$ (SEQ ID NO:90), wherein X$_1$ is G or S; and X$_2$ is T or S; (v) a VL-CDR2 comprising the amino acid sequence of WASTRES (SEQ ID NO:5); and (vi) a VL-CDR3 comprising the amino acid sequence of QNX$_1$YSX$_2$PYT (SEQ ID NO:92), wherein X$_1$ is D or E; and X$_2$ is Y, F or S. In one instance, the second antigen-binding domain that specifically binds to human GITR binds to the same epitope of human GITR as an antibody comprising a VH comprising the amino acid sequence of SEQ ID NO:18 and a VL comprising the amino acid sequence of SEQ ID NO:19. In one instance, the second antigen-binding domain that specifically binds to human GITR binds to an epitope of human GITR comprising at least one amino acid in residues 60-63 of SEQ ID NO:41. In one instance, the second antigen-binding domain that specifically binds to human GITR binds to each of i) human GITR comprising residues 26 to 241 of SEQ ID NO:41 and ii) a variant of *cynomolgus* GITR, the variant comprising residues 26-234 of SEQ ID NO:46, wherein the second antigen-binding domain does not specifically bind to *cynomolgus* GITR comprising residues 26-234 of SEQ ID NO:44. In one instance, the second antigen-binding domain that specifically binds to human GITR exhibits, as compared to binding to a human GITR sequence of residues 26 to 241 of SEQ ID NO:41, reduced or absent binding to a protein identical to residues 26 to 241 of SEQ ID NO:41 except for the presence of a D60A or G63A amino acid substitution, numbered according to SEQ ID NO:41. In one instance, the second antigen-binding domain that specifically binds to human GITR comprises a VH and a VL, wherein the VH comprises an amino acid sequence selected from the group consisting of SEQ ID NOs:18, 20, 22, 24, and 25. In one instance, the second antigen-binding domain that specifically binds to human GITR comprises a VH and a VL, wherein the VL comprises an amino acid sequence selected from the group consisting of SEQ ID NOs:19, 21, 23, and 26.

In one instance, the first antigen-binding domain specifically binds to the TNFR superfamily protein human OX40. In one instance, the first antigen-binding domain that specifically binds to human OX40 comprises: (i) a VH-CDR1 comprising the amino acid sequence of GSAMH (SEQ ID NO:47); (ii) a VH-CDR2 comprising the amino acid sequence of RIRSKANSYATAYAASVKG (SEQ ID NO:48); (iii) a VH-CDR3 comprising the amino acid sequence of GIYDSSGYDY (SEQ ID NO:49); (iv) a VL-CDR1 comprising the amino acid sequence of RSSQSLLHSNGYNYLD (SEQ ID NO:50); (v) a VL-CDR2 comprising the amino acid sequence of LGSNRAS (SEQ ID NO:51); and (vi) a VL-CDR3 comprising the amino acid sequence of MQGSKWPLT (SEQ ID NO:52) or MQALQTPLT (SEQ ID NO:53). In one instance, the first antigen-binding domain that specifically binds to human OX40 binds to the same epitope of human OX40 as an antibody comprising a VH comprising the amino acid sequence of SEQ ID NO:54 and a VL comprising the amino acid sequence of SEQ ID NO:55 or 56. In one instance, the first antigen-binding domain that specifically binds to human OX40 exhibits, as compared to binding to a human OX40 sequence of SEQ ID NO:72, reduced or absent binding to a protein identical to SEQ ID NO:72 except for the presence of an amino acid mutation selected from the group consisting of: N60A, R62A, R80A, L88A, P93A, P99A, P115A, and a combination thereof, numbered according to SEQ ID NO: 72. In one instance, the first antigen-binding domain that specifically binds to human OX40 comprises a VH and a VL, and the VH comprises the amino acid sequence of SEQ ID NO:54. In one instance, the first antigen-binding domain that specifically binds to human OX40 comprises a VH and a VL, and the VL comprises the amino acid sequence of SEQ ID NO:55 or SEQ ID NO:56.

In one instance, the second antigen-binding domain that specifically binds to human GITR comprises: (i) a VH-CDR1 comprising the amino acid sequence of $X_1YAMX_2$ (SEQ ID NO:1), wherein $X_1$ is D, G, or E; and $X_2$ is Y or H; (ii) a VH-CDR2 comprising the amino acid sequence of $X_1IRTYSGX_2VX_3YNQKFX_4X_5$ (SEQ ID NO:2), wherein $X_1$ is V or L; $X_2$ is D or G; $X_3$ is T or S; $X_4$ is K, R, or Q;

and $X_5$ is D, E, or G; (iii) a VH-CDR3 comprising the amino acid sequence of SGTVRGFAY (SEQ ID NO:3); (iv) a VL-CDR1 comprising the amino acid sequence of KSSQSLLNSX$_1$NQKNYLT (SEQ ID NO:4), wherein $X_1$ is G or S; (v) a VL-CDR2 comprising the amino acid sequence of WASTRES (SEQ ID NO:5); and (vi) a VL-CDR3 comprising the amino acid sequence of QNX$_1$YSX$_2$PYT (SEQ ID NO:6), wherein $X_1$ is D or E; and $X_2$ is Y or F.

In one instance, the second antigen-binding domain that specifically binds to human GITR comprises a VH-CDR1 comprising an amino acid sequence selected from the group consisting of SEQ ID NOs:7-9. In one instance, the second antigen-binding domain that specifically binds to human GITR comprises a VH-CDR2 comprising an amino acid sequence selected from the group consisting of SEQ ID NOs:10-13. In one instance, the second antigen-binding domain that specifically binds to human GITR comprises a VL-CDR1 comprising the amino acid sequence of SEQ ID NO:14 or 15. In one instance, the second antigen-binding domain that specifically binds to human GITR comprises a VL-CDR3 comprising the amino acid sequence of SEQ ID NO:16 or 17.

In one instance, the second antigen-binding domain that specifically binds to human GITR comprises VH-CDR1, VH-CDR2, and VH-CDR3 sequences set forth in SEQ ID NOs:7, 10, and 3; SEQ ID NOs:8, 11, and 3; SEQ ID NOs:9, 12, and 3; or SEQ ID NOs:9, 13, and 3, respectively; and/or VL-CDR1, VL-CDR2, and VL-CDR3 sequences set forth in SEQ ID NOs:14, 5, and 16; or SEQ ID NOs:15, 5, and 17, respectively.

In one instance, the second antigen-binding domain that specifically binds to human GITR comprises VH-CDR1, VH-CDR2, VH-CDR3, VL-CDR1, VL-CDR2, and VL-CDR3 sequences set forth in SEQ ID NOs:7, 10, 3, 14, 5, and 16, respectively.

In one instance, the second antigen-binding domain that specifically binds to human GITR comprises a VH comprising the amino acid sequence set forth in SEQ ID NO:25. In one instance, the second antigen-binding domain that specifically binds to human GITR comprises a VH comprising an amino acid sequence at least 75%, 80%, 85%, 90%, 95%, or 99% identical to an amino acid sequence selected from the group consisting of SEQ ID NOs:18, 20, 22, and 24. In one instance, the second antigen-binding domain that specifically binds to human GITR comprises a VH comprising an amino acid sequence selected from the group consisting of SEQ ID NOs:18, 20, 22, and 24. In one instance, the second antigen-binding domain that specifically binds to human GITR comprises a VH comprising the amino acid sequence of SEQ ID NO:18.

In one instance, the second antigen-binding domain that specifically binds to human GITR comprises a heavy chain comprising an amino acid sequence selected from the group consisting of SEQ ID NOs:29-36. In one instance, the second antigen-binding domain that specifically binds to human GITR comprises a heavy chain comprising an amino acid sequence selected from the group consisting of SEQ ID NOs:74-81. In one instance, the second antigen-binding domain that specifically binds to human GITR comprises a heavy chain comprising the amino acid sequence of SEQ ID NO:31. In one instance, the second antigen-binding domain that specifically binds to human GITR comprises a heavy chain comprising the amino acid sequence of SEQ ID NO:76. In one instance, the second antigen-binding domain that specifically binds to human GITR comprises a heavy chain comprising the amino acid sequence of SEQ ID NO:32. In one instance, the second antigen-binding domain that specifically binds to human GITR comprises a heavy chain comprising the amino acid sequence of SEQ ID NO:77. In one instance, the second antigen-binding domain that specifically binds to human GITR comprises a heavy chain comprising the amino acid sequence of SEQ ID NO:34. In one instance, the second antigen-binding domain that specifically binds to human GITR comprises a heavy chain comprising the amino acid sequence of SEQ ID NO:79. In one instance, the second antigen-binding domain that specifically binds to human GITR comprises a heavy chain comprising the amino acid sequence of SEQ ID NO:35. In one instance, the second antigen-binding domain that specifically binds to human GITR comprises a heavy chain comprising the amino acid sequence of SEQ ID NO:80.

In one instance, the second antigen-binding domain that specifically binds to human GITR comprises a VH comprising an amino acid sequence derived from a human IGHV1-2 germline sequence.

In one instance, the second antigen-binding domain that specifically binds to human GITR comprises a VL comprising the amino acid sequence of SEQ ID NO:26. In one instance, the second antigen-binding domain that specifically binds to human GITR comprises a VL comprising amino acid sequence at least 75%, 80%, 85%, 90%, 95%, or 99% identical to an amino acid sequence selected from the group consisting of SEQ ID NOs:19, 21, and 23. In one instance, the second antigen-binding domain that specifically binds to human GITR comprises a VL comprising an amino acid sequence selected from the group consisting of SEQ ID NOs:19, 21, and 23. In one instance, the second antigen-binding domain that specifically binds to human GITR comprises a VL comprising the amino acid sequence of SEQ ID NO:19.

In one instance, the second antigen-binding domain that specifically binds to human GITR comprises a light chain comprising the amino acid sequence of SEQ ID NO:37. In one instance, the second antigen-binding domain that specifically binds to human GITR comprises a light chain comprising the amino acid sequence of SEQ ID NO:38.

In one instance, the second antigen-binding domain that specifically binds to human GITR comprises a VL comprising an amino acid sequence derived from a human IGKV4-1 germline sequence.

In one instance, the second antigen-binding domain that specifically binds to human GITR comprises VH and VL sequences set forth in SEQ ID NOs:18 and 19, SEQ ID NOs:20 and 21, SEQ ID NOs:22 and 23, or SEQ ID NOs:24 and 23, respectively. In one instance, the second antigen-binding domain that specifically binds to human GITR comprises a VH comprising the sequence set forth in SEQ ID NO:18 and a VL comprising the sequence set forth in SEQ ID NO:19.

In one instance, the second antigen-binding domain that specifically binds to human GITR comprises a heavy chain comprising the amino acid sequence of SEQ ID NO:31 and a light chain comprising the amino acid sequence of SEQ ID NO:37. In one instance, the second antigen-binding domain that specifically binds to human GITR comprises a heavy chain comprising the amino acid sequence of SEQ ID NO:76 and a light chain comprising the amino acid sequence of SEQ ID NO:37. In one instance, the second antigen-binding domain that specifically binds to human GITR comprises a heavy chain comprising the amino acid sequence of SEQ ID NO:32 and a light chain comprising the amino acid sequence of SEQ ID NO:37. In one instance, the second antigen-binding domain that specifically binds to human GITR comprises a heavy chain comprising the amino acid sequence of SEQ ID NO:77 and a light chain comprising the amino acid sequence of SEQ ID NO:37. In one instance, the second antigen-binding domain that specifically binds to human GITR comprises a heavy chain comprising the amino acid sequence of SEQ ID NO:34 and a light chain comprising the amino acid sequence of SEQ ID NO:37. In one instance, the second antigen-binding domain that specifically binds to human GITR comprises a heavy chain comprising the amino acid sequence of SEQ ID NO:79 and a light chain comprising the amino acid sequence of SEQ ID NO:37. In one instance, the second antigen-binding domain that specifically binds to human GITR comprises a heavy chain comprising the amino acid sequence of SEQ ID NO:35 and a light chain comprising the amino acid sequence of SEQ ID NO:37. In one instance, the second antigen-binding domain that specifically binds to human GITR comprises a heavy chain comprising the amino acid sequence of SEQ ID NO:80 and a light chain comprising the amino acid sequence of SEQ ID NO:37. In one instance, the second antigen-binding domain that specifically binds to human GITR comprises a heavy chain comprising the amino acid sequence of SEQ ID NO:29 and a light chain comprising the amino acid sequence of SEQ ID NO:37. In one instance, the second antigen-binding domain that specifically binds to human GITR comprises a heavy chain comprising the amino acid sequence of SEQ ID NO:74 and a light chain comprising the amino acid sequence of SEQ ID NO:37. In one instance, the second antigen-binding domain that specifically binds to human GITR comprises a heavy chain comprising the amino acid sequence of SEQ ID NO:30 and a light chain comprising the amino acid sequence of SEQ ID NO:37. In one instance, the second antigen-binding domain that specifically binds to human GITR comprises a heavy chain comprising the amino acid sequence of SEQ ID NO:75 and a light chain comprising the amino acid sequence of SEQ ID NO:37.

In one instance, the second antigen-binding domain that specifically binds to human GITR comprises a heavy chain variable region having an amino acid sequence derived from a human IGHV1-2 germline sequence and a light chain variable region having an amino acid sequence derived from a human IGKV4-1 germline sequence.

In one instance, the first antigen-binding domain that specifically binds to human OX40 comprises a VH comprising an amino acid sequence that is at least 75%, 80%, 85%, 90%, 95%, or 99% identical to the amino acid sequence of SEQ ID NO:54. In one instance, the first antigen-binding domain that specifically binds to human OX40 comprises a VH comprising the amino acid sequence of SEQ ID NO:54.

In one instance, the first antigen-binding domain that specifically binds to human OX40 comprises a heavy chain comprising an amino acid sequence selected from the group consisting of SEQ ID NOs:59-66. In one instance, the first antigen-binding domain that specifically binds to human OX40 comprises a heavy chain comprising an amino acid sequence selected from the group consisting of SEQ ID NOs:118-125. In one instance, the first antigen-binding domain that specifically binds to human OX40 comprises a heavy chain comprising the amino acid sequence of SEQ ID NO:61. In one instance, the first antigen-binding domain that specifically binds to human OX40 comprises a heavy chain comprising the amino acid sequence of SEQ ID NO:120. In one instance, the first antigen-binding domain that specifically binds to human OX40 comprises a heavy chain comprising the amino acid sequence of SEQ ID NO:62. In one instance, the first antigen-binding domain that specifically binds to human OX40 comprises a heavy chain comprising the amino acid sequence of SEQ ID NO:121. In one instance, the first antigen-binding domain that specifically binds to human OX40 comprises a heavy chain comprising the amino acid sequence of SEQ ID NO:64. In one instance, the first antigen-binding domain that specifically binds to human OX40 comprises a heavy chain comprising the amino acid sequence of SEQ ID NO:123. In one instance, the first antigen-binding domain that specifically binds to human OX40 comprises a heavy chain comprising the amino acid sequence of SEQ ID NO:65. In one instance, the first antigen-binding domain that specifically binds to human OX40 comprises a heavy chain comprising the amino acid sequence of SEQ ID NO:124.

In one instance, the first antigen-binding domain that specifically binds to human OX40 comprises a VH comprising an amino acid sequence derived from a human IGHV3-73 germline sequence.

In one instance, the first antigen-binding domain that specifically binds to human OX40 comprises a VL comprising an amino acid sequence at least 75%, 80%, 85%, 90%, 95%, or 99% identical to the amino acid sequence of SEQ ID NO:55 or SEQ ID NO:56. In one instance, the first antigen-binding domain that specifically binds to human OX40 comprises a VL-CDR3 comprising the amino acid sequence of SEQ ID NO:52. In one instance, the first antigen-binding domain that specifically binds to human OX40 comprises a VL comprising the amino acid sequence of SEQ ID NO:55. In one instance, the first antigen-binding domain that specifically binds to human OX40 comprises a light chain comprising the amino acid sequence of SEQ ID NO:67. In one instance, the first antigen-binding domain that specifically binds to human OX40 comprises a light chain comprising the amino acid sequence of SEQ ID NO:68.

In one instance, the first antigen-binding domain that specifically binds to human OX40 comprises a VL-CDR3 comprising the amino acid sequence of SEQ ID NO:53. In one instance, the first antigen-binding domain that specifically binds to human OX40 comprises a VL comprising the amino acid sequence of SEQ ID NO:56. In one instance, the first antigen-binding domain that specifically binds to human OX40 comprises a light chain comprising the amino acid sequence of SEQ ID NO:69. In one instance, the first antigen-binding domain that specifically binds to human OX40 comprises a light chain comprising the amino acid sequence of SEQ ID NO:70.

In one instance, the first antigen-binding domain that specifically binds to human OX40 comprises a VL comprising an amino acid sequence derived from a human IGKV2-28 germline sequence.

In one instance, the first antigen-binding domain that specifically binds to human OX40 comprises the VH and VL sequences set forth in SEQ ID NOs:54 and 55 or SEQ ID NOs:54 and 56, respectively. In one instance, the first antigen-binding domain that specifically binds to human OX40 comprises a heavy chain comprising the amino acid sequence of SEQ ID NO:59 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:118 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:64 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:123 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:65 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:124 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:61 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:120 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:62 and a light chain comprising the amino acid sequence of SEQ ID NO:67 or 69. In one instance, the first antigen-binding domain that specifically binds to human OX40 comprises a heavy chain comprising the amino acid sequence of SEQ ID NO:121 and a light chain comprising the amino acid sequence of SEQ ID NO:67 or 69.

In one instance, the first antigen-binding domain that specifically binds to human OX40 comprises a VH comprising an amino acid sequence derived from a human IGHV3-73 germline sequence and a VL comprising an amino acid sequence derived from a human IGKV2-28 germline sequence.

In one instance, the first antigen-binding domain that specifically binds to human OX40 comprises the VH sequence set forth in SEQ ID NO:54 and the VL sequence set forth in SEQ ID NO:55 or 56, and the second antigen-binding domain that specifically binds to human GITR comprises the VH sequence set forth in SEQ ID NO:18 and the VL sequence set forth in SEQ ID NO:19. In one instance, the first antigen-binding domain that specifically binds to human OX40 comprises the heavy chain sequence set forth in SEQ ID NO:59 and the light chain sequence set forth in SEQ ID NO:67 or 69, and the second antigen-binding domain that specifically binds to human GITR comprises the heavy chain sequence set forth in SEQ ID NO:29 and the light chain sequence set forth in SEQ ID NO:37. In one instance, the first antigen-binding domain that specifically binds to human OX40 comprises the heavy chain sequence set forth in SEQ ID NO:118 and the light chain sequence set forth in SEQ ID NO:67 or 69, and wherein the second antigen-binding domain that specifically binds to human GITR comprises the heavy chain sequence set forth in SEQ ID NO:74 and the light chain sequence set forth in SEQ ID NO:37. In one instance, the first antigen-binding domain that specifically binds to human OX40 comprises the heavy chain sequence set forth in SEQ ID NO:61 and the light chain sequence set forth in SEQ ID NO:67 or 69, and the second antigen-binding domain that specifically binds to human GITR comprises the heavy chain sequence set forth in SEQ ID NO:31 and the light chain sequence set forth in SEQ ID NO:37. In one instance, the first antigen-binding domain that specifically binds to human OX40 comprises the heavy chain sequence set forth in SEQ ID NO:120 and the light chain sequence set forth in SEQ ID NO:67 or 69, and wherein the second antigen-binding domain that specifically binds to human GITR comprises the heavy chain sequence set forth in SEQ ID NO:76 and the light chain sequence set forth in SEQ ID NO:37. In one instance, the first antigen-binding domain that specifically binds to human OX40 comprises the heavy chain sequence set forth in SEQ ID NO:62 and the light chain sequence set forth in SEQ ID NO:67 or 69, and the second antigen-binding domain that specifically binds to human GITR comprises the heavy chain sequence set forth in SEQ ID NO:32 and the light chain sequence set forth in SEQ ID NO:37. In one instance, the first antigen-binding domain that specifically binds to human OX40 comprises the heavy chain sequence set forth in SEQ ID NO:121 and the light chain sequence set forth in SEQ ID NO:67 or 69, and wherein the second antigen-binding domain that specifically binds to human GITR comprises the heavy chain sequence set forth in SEQ ID NO:77 and the light chain sequence set forth in SEQ ID NO:37. In one instance, the first antigen-binding domain that specifically binds to human OX40 comprises the heavy chain sequence set forth in SEQ ID NO:64 and the light chain sequence set forth in SEQ ID NO:67 or 69, and the second antigen-binding domain that specifically binds to human GITR comprises the heavy chain sequence set forth in SEQ ID NO:34 and the light chain sequence set forth in SEQ ID NO:37. In one instance, the first antigen-binding domain that specifically binds to human OX40 comprises the heavy chain sequence set forth in SEQ ID NO:123 and the light chain sequence set forth in SEQ ID NO:67 or 69, and wherein the second antigen-binding domain that specifically binds to human GITR comprises the heavy chain sequence set forth in SEQ ID NO:79 and the light chain sequence set forth in SEQ ID NO:37. In one instance, the first antigen-binding domain that specifically binds to human OX40 comprises the heavy chain sequence set forth in SEQ ID NO:65 and the light chain sequence set forth in SEQ ID NO:67 or 69, and the second antigen-binding domain that specifically binds to human GITR comprises the heavy chain sequence set forth in SEQ ID NO:35 and the light chain sequence set forth in SEQ ID NO:37. In one instance, the first antigen-binding domain that specifically binds to human OX40 comprises the heavy chain sequence set forth in SEQ ID NO:124 and the light chain sequence set forth in SEQ ID NO:67 or 69, and wherein the second antigen-binding domain that specifically binds to human GITR comprises the heavy chain sequence set forth in SEQ ID NO:80 and the light chain sequence set forth in SEQ ID NO:37. In one instance, the first antigen-binding domain that specifically binds to human OX40 comprises the light chain sequence set forth in SEQ ID NO:67. In one instance, the first antigen-binding domain that specifically binds to human OX40 comprises the light chain sequence set forth in SEQ ID NO:69.

In one instance, the first antigen-binding domain that specifically binds to human OX40 comprises a VH derived from a human IGHV3-73 germline sequence and a VL derived from a human IGKV2-28 germline sequence, and the second antigen-binding domain that specifically binds to human GITR comprises a VH derived from a human IGHV1-2 germline sequence and a VL derived from a human IGKV4-1 germline sequence.

In one instance, the antibody is a kappa-lambda body, a dual-affinity re-targeting molecule (DART), a knob-in-hole antibody, a strand-exchange engineered domain body (SEEDbody) or a DuoBody® antibody (Genmab A/S).

In one instance, the first antigen-binding domain comprises a heavy chain constant region selected from the group consisting of human IgG$_1$, human IgG$_2$, human IgG$_3$, human IgG$_4$, human IgA$_1$, and human IgA$_2$, and the second antigen-binding domain comprises a heavy chain constant region selected from the group consisting of human IgG$_1$, human IgG$_2$, human IgG$_3$, human IgG$_4$, human IgA$_1$, and human IgA$_2$. In one instance, the heavy chain constant region of the first antigen-binding domain is human IgG$_1$, and the heavy chain constant region of the second antigen-binding domain is human IgG$_1$.

In one instance, the (a) the first antigen-binding domain comprises a first heavy chain constant region comprising an F405L amino acid mutation; and (b) the second antigen-binding domain comprises a second heavy chain constant region comprising a K409R amino acid mutation, numbered according to the EU numbering system. In one instance, (a) the first antigen-binding domain comprises a first heavy chain constant region comprising a K409R amino acid mutation; and (b) the second antigen-binding domain comprises a heavy chain constant region comprising an F405L amino acid mutation, numbered according to the EU numbering system. In one instance, the heavy chain constant region of the first antigen-binding domain is an IgG$_1$. In one instance, the heavy chain constant region of the second antigen-binding domain is an IgG$_1$.

In one instance, the first antigen-binding domain comprises a light chain constant region selected from the group consisting of human IgG$_\kappa$ and IgG$_\lambda$, and the second antigen-binding domain comprises a light chain constant region selected from the group consisting of human IgG$_\kappa$ and IgG$_\lambda$.

In one instance, the second antigen-binding domain exhibits, as compared to binding to a human GITR sequence of residues 26 to 241 of SEQ ID NO:41, reduced or absent binding to a protein identical to residues 26 to 241 of SEQ ID NO:41 except for the presence of a D60A substitution, numbered according to SEQ ID NO:41. In one instance, the second antigen-binding domain exhibits, as compared to binding to a human GITR sequence of residues 26 to 241 of SEQ ID NO:41, reduced or absent binding to a protein identical to residues 26 to 241 of SEQ ID NO:41 except for the presence of a G63A substitution, numbered according to SEQ ID NO: 41. In one instance, the second antigen-binding domain that binds to human GITR binds to at least one residue selected from the group consisting of residues 60, 62, and 63 of SEQ ID NO:41. In one instance, the second antigen-binding domain that binds to human GITR binds to at least one residue selected from the group consisting of residues 62 and 63 of SEQ ID NO:41. In one instance, the second antigen-binding domain that binds to human GITR binds to at least one residue selected from the group consisting of residues 60 and 63 of SEQ ID NO:41. In one instance, the second antigen-binding domain that binds to human GITR binds to an epitope comprising residues 60-63 of SEQ ID NO:41.

In one instance, the antibody (i) shows increased binding to cells expressing human GITR and human OX40 as compared to a monospecific bivalent antibody that binds to human GITR and contains the same VH and VL as the second antigen-binding domain that binds to human GITR; and/or (ii) shows increased binding to cells expressing human GITR and human OX40 as compared to a monospecific bivalent antibody that binds to human OX40 and contains the same VH and VL as the first antigen-binding domain that binds to human OX40.

In one instance, the antibody (i) shows decreased binding to GITR-positive, OX40-negative cells as compared to a monospecific bivalent antibody that binds to human GITR and contains the same VH and VL as the second antigen-binding domain that binds to human GITR; and/or (ii) shows decreased binding to GITR-negative, OX40-positive cells as compared to a monospecific bivalent antibody that binds to human OX40 and contains the same VH and VL as the first antigen-binding domain that binds to human OX40.

In one instance, the antibody (i) induces stronger natural killer cell-mediated cytotoxicity towards regulatory T cells as compared to a monospecific bivalent antibody that binds to human GITR and contains the same VH and VL as the second antigen-binding domain that binds to human GITR; and/or (ii) induces stronger natural killer cell-mediated cytotoxicity towards regulatory T cells as compared to a monospecific bivalent antibody that binds to human OX40 and contains the same VH and VL as the first antigen-binding domain that binds to human OX40.

In one instance, the antibody inhibits binding of human GITR ligand to human GITR. In one instance, the antibody inhibits binding of human OX40 ligand to human OX40.

In one instance, the antibody, when bound to activated regulatory T cells, binds to activating Fc gamma receptors selected from the group consisting of CD16, CD32A and CD64 to a greater extent than the antibody, when bound to activated effector T cells, binds to the activating Fc gamma receptors selected from the group consisting of CD16, CD32A and CD64. In one instance, the activating Fc gamma receptor is expressed on a cell selected from the group consisting of myeloid-derived effector cells and lymphocyte-derived effector cells.

In one instance, the antibody is agonistic to human GITR and/or human OX40. In one instance, the antibody induces, activates, or enhances an activity of human GITR. In one instance, the antibody induces, activates, or enhances an activity of human OX40.

In one instance, the first antigen-binding domain comprises a human IgG$_1$ heavy chain constant region that comprises a N297A mutation or a N297Q mutation and/or the second antigen-binding domain comprises a human IgG$_1$ heavy chain constant region that comprises a N297A mutation or a N297Q mutation, numbered according to the EU numbering system.

In one instance, the antibody is antagonistic to human GITR and/or human OX40. In one instance, the antibody deactivates, reduces, or inhibits an activity of human GITR. In one instance, the antibody deactivates, reduces, or inhibits an activity of human OX40. In one instance, the antibody inhibits or reduces human GITR signaling. In one instance, the antibody inhibits or reduces human OX40 signaling. In one instance, the antibody inhibits or reduces human GITR signaling induced by human GITR ligand. In one instance, the antibody inhibits or reduces human OX40 signaling induced by human OX40 ligand.

In one instance, the antibody decreases CD4+ T cell proliferation induced by synovial fluid from rheumatoid arthritis patients. In one instance, the antibody increases survival of NOG mice transplanted with human PBMCs. In one instance, the antibody increases proliferation of regulatory T cells in a GVHD model.

In one instance, the antibody further comprises a detectable label.

Also provided herein are compositions. In one instance, the composition comprises (i) a nucleic acid molecule encoding the light chain variable region or light chain of the first antigen-binding fragment of an antibody provided herein, (ii) a nucleic acid molecule encoding the heavy chain variable region or heavy chain of the first antigen-binding fragment of an antibody provided herein, (iii) a nucleic acid molecule encoding the light chain variable region or light chain of the second antigen-binding fragment of an antibody provided herein, and (iv) a nucleic acid molecule encoding the heavy chain variable region or heavy chain of the second antigen-binding fragment of an antibody provided herein.

Also provided herein are host cells. In one instance, a host cell comprises (i) a nucleic acid molecule encoding the light chain variable region or light chain of the first antigen-binding fragment of an antibody provided herein, (ii) a nucleic acid molecule encoding the heavy chain variable region or heavy chain of the first antigen-binding fragment of an antibody provided herein, (iii) a nucleic acid molecule encoding the light chain variable region or light chain of the second antigen-binding fragment of an antibody provided herein, and (iv) a nucleic acid molecule encoding the heavy chain variable region or heavy chain of the second antigen-binding fragment of an antibody provided herein. In one instance, the host cell is selected from the group consisting of E. coli, Pseudomonas, Bacillus, Streptomyces, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture. Also provided herein are methods of making the multispecific (e.g., bispecific) antibodies that bind to GITR and/or OX40. In one instance, the method comprises culturing a host cell provided herein so that the nucleic acid molecules are expressed and the antibody is produced Also provided herein are methods of using the multispecific (e.g., bispecific) antibodies that bind to GITR and/or OX40. In one instance, a method for detecting cells expressing GITR and OX40 in a sample comprises contacting the sample with an antibody provided herein.

Also provided herein are pharmaceutical compositions. In one instance, a pharmaceutical composition comprises an antibody provided herein and a pharmaceutically acceptable excipient.

Also provided herein are kits. In one instance, a kit comprises an antibody or pharmaceutical composition provided herein and a) a detection reagent, b) a GITR and/or OX40 antigen, c) a notice that reflects approval for use or sale for human administration, or d) a combination thereof.

Also provided herein are methods of using the antibodies and pharmaceutical compositions provided herein. In one instance, a method of modulating an immune response in a subject comprises administering to the subject an effective amount of an antibody or pharmaceutical composition provided herein. In one instance, a method for enhancing or inducing an immune response in a subject comprises administering to the subject an effective amount of an antibody or pharmaceutical composition provided herein.

In one instance, a method of treating cancer in a subject comprises administering to the subject an effective amount of an antibody or pharmaceutical composition provided herein. In one instance, the cancer is selected from the group consisting of melanoma, renal cancer, prostate cancer, colon cancer, and lung cancer. In one instance, the method further comprises administering to the subject an inhibitor of indoleamine-2,3-dioxygenase (IDO). In one instance, the inhibitor is epacadostat. In one instance, the inhibitor is F001287. In one instance, the inhibitor is indoximod. In one instance, the inhibitor is NLG919. In one instance, the method further comprises administering to the subject a vaccine. In one instance, the vaccine comprises a heat shock protein peptide complex (HSPPC) comprising a heat shock protein complexed with an antigenic peptide. In one instance, the heat shock protein is hsp70 or hsc70 and is complexed with a tumor-associated antigenic peptide. In one instance, the heat shock protein is gp96 protein and is complexed with a tumor-associated antigenic peptide, wherein the HSPPC is derived from a tumor obtained from a subject. In one instance, the method further comprises administering to the subject a checkpoint targeting agent. In one instance, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, and an agonist anti-OX40 antibody.

In one instance, a method of treating an infectious disease comprises administering to the subject an effective amount of an antibody or pharmaceutical composition provided herein.

In one instance, a method for reducing or inhibiting an immune response in a subject comprises administering to the subject an effective amount of an antibody or pharmaceutical composition provided herein.

In one instance, a method for treating an autoimmune or inflammatory disease or disorder in a subject comprises administering to the subject an effective amount of an antibody or pharmaceutical composition provided herein. In one instance, the autoimmune or inflammatory disease or disorder is selected from the group consisting of transplant rejection, graft-versus-host disease, vasculitis, asthma, rheumatoid arthritis, dermatitis, inflammatory bowel disease, uveitis, lupus, colitis, diabetes, multiple sclerosis, and airway inflammation.

In one instance, the subject is human.

6. BRIEF DESCRIPTION OF THE FIGURES

Figure 1A:
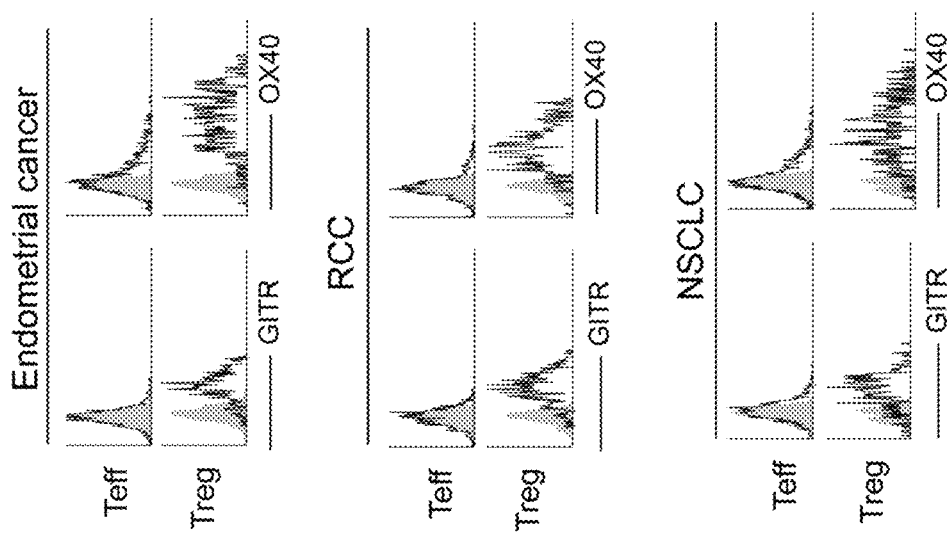

FIGS. 1A and 1B: FIG. 1A is a set of histograms showing the expression of GITR and OX40 on intratumoral effector T cells (Teff: CD4+ CD127+ CD25+/− FOXP3−) and regulatory T cells (Treg: CD4+ CD127− CD25+ FOXP3+) from endometrial cancer tumor tissue, renal cell carcinoma (RCC) tumor tissue, and non-small cell lung cancer (NSCLC) tumor tissue. FIG. 1B is a set of bar graphs showing the predicted number of GITR and OX40 receptors on the surface of Tregs and Teff cells from ovarian cancer tumor tissue, colorectal cancer (CRC) tumor tissue, endometrial cancer tumor tissue, RCC tumor tissue, and NSCLC tumor tissue.

Figure 2A:
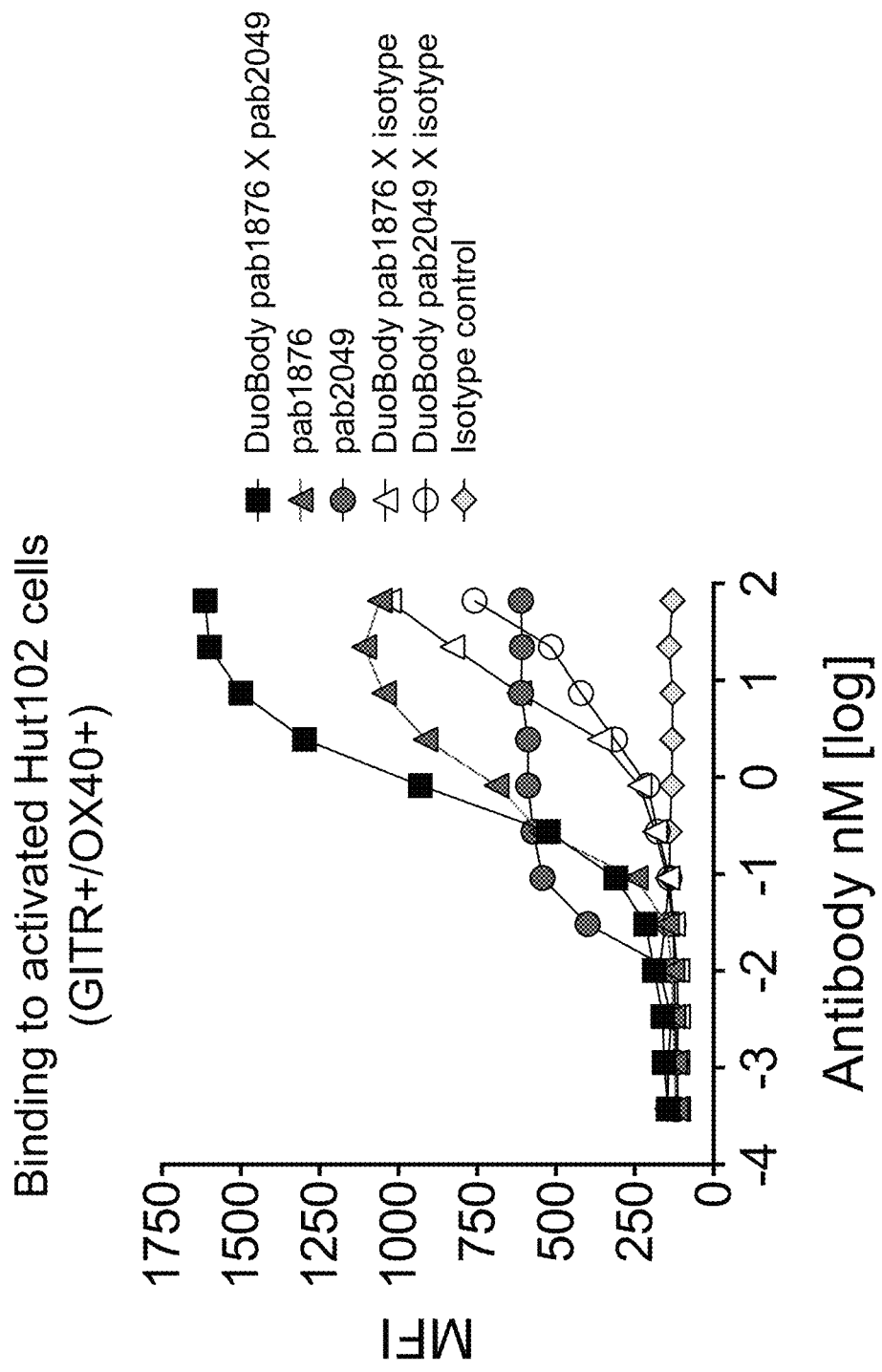
Figure 2B:
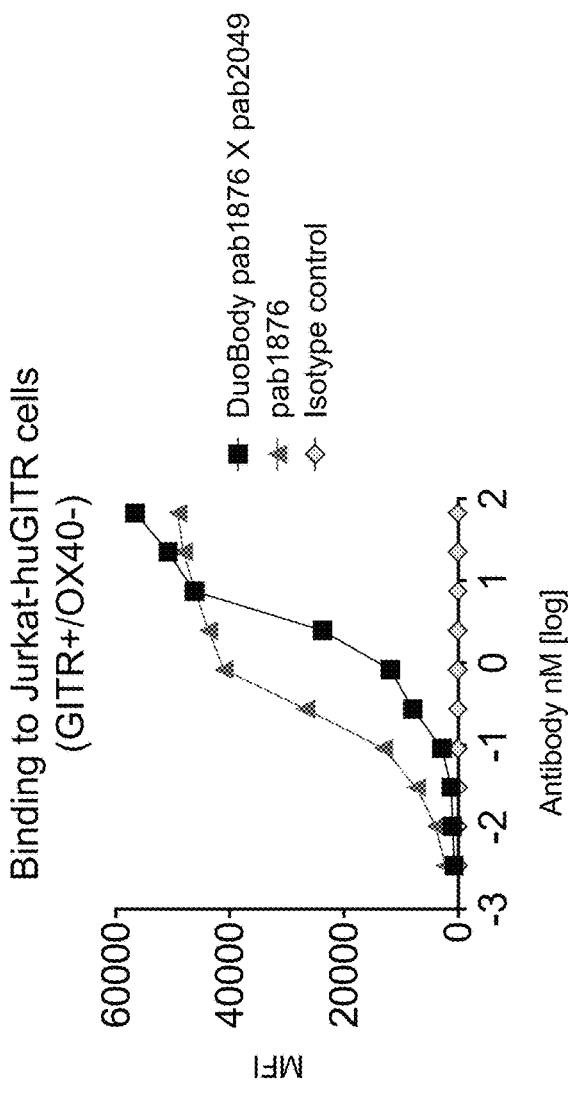
Figure 2C:
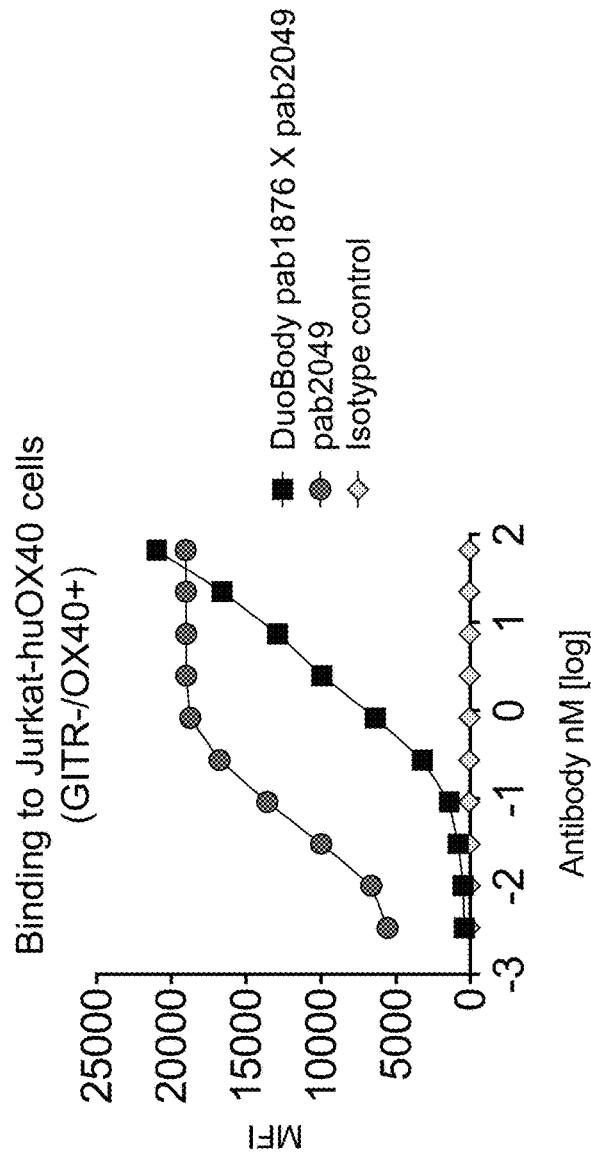

FIGS. 2A, 2B, and 2C are graphs showing the binding of test antibodies to activated Hut102 cells that co-expressed GITR and OX40 (FIG. 2A), Jurkat cells expressing GITR (FIG. 2B), and Jurkat cells expressing OX40 (FIG. 2C). The mean fluorescence intensity (MFI) is plotted against a range of antibody concentrations. The test antibodies used were DuoBody pab1876×pab2049 (FIGS. 2A-2C), a bivalent monospecific antibody pab1876 (FIGS. 2A and 2B), a bivalent monospecific antibody pab2049 (FIGS. 2A and 2C), DuoBody pab1876×isotype (FIG. 2A), DuoBody pab2049×isotype (FIG. 2A), and an isotype control antibody (FIGS. 2A-2C).

Figure 3C:
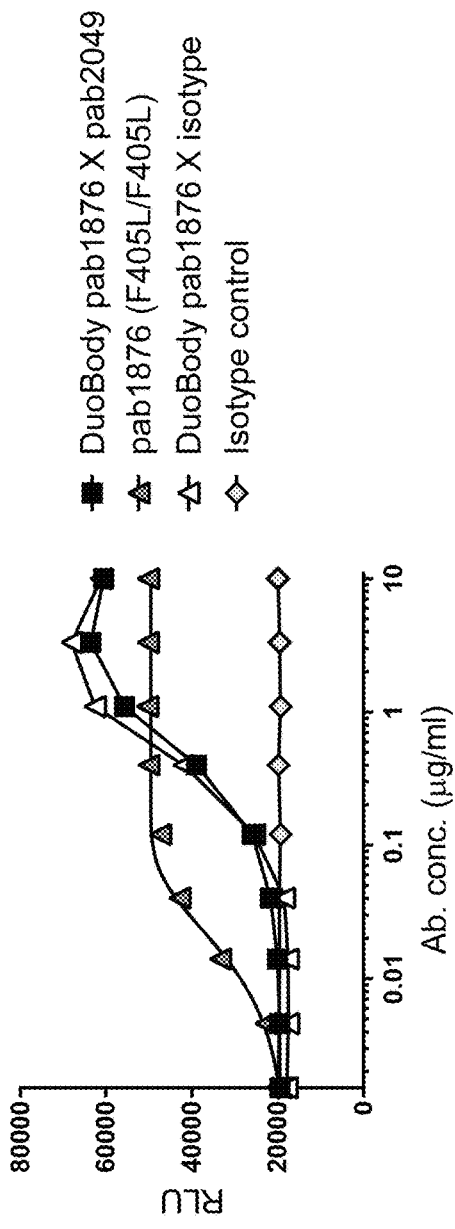
Figure 3D:
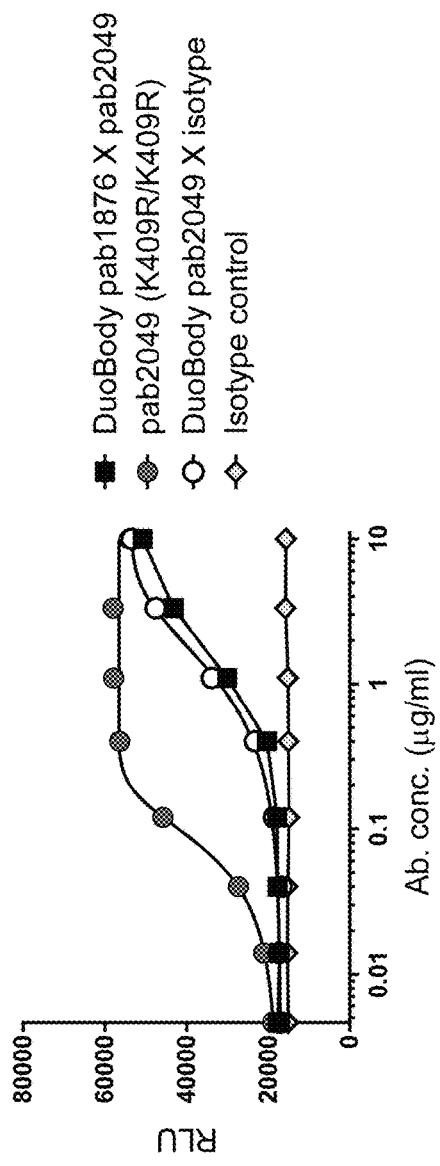
Figure 3F:
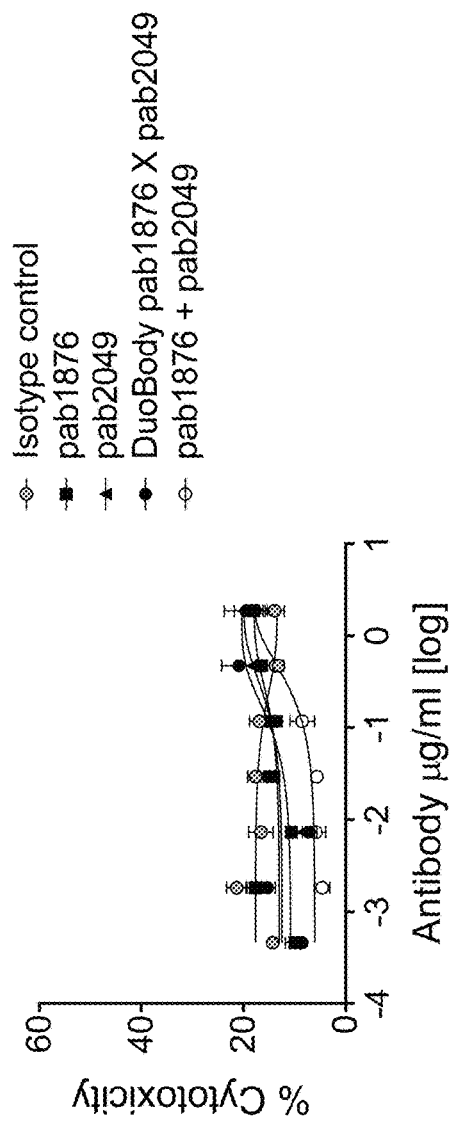
Figure 3G:
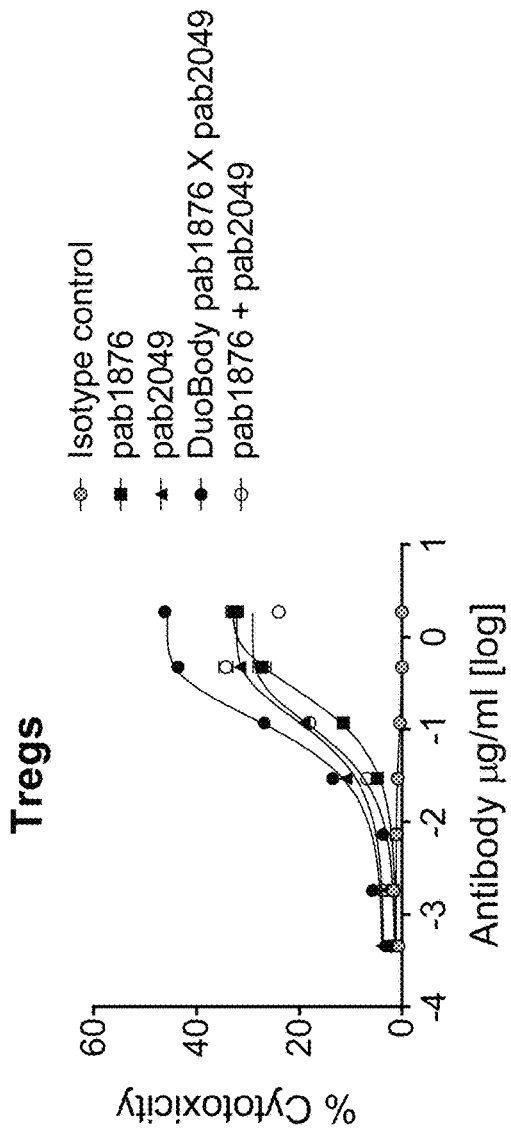

FIG. 3A is a set of histograms showing the expression of GITR and OX40 on activated natural regulatory T (nTreg) cells. FIG. 3B is the result of a reporter assay where test antibodies were examined for their ability to activate a reporter cell line expressing FcγRIIIA$^{V158}$ when the antibodies were bound to activated nTregs. The test antibodies used were DuoBody pab1876×pab2049, the bivalent monospecific antibody pab1876, the bivalent monospecific antibody pab2049, and an isotype control antibody. The relative light units (RLU) are normalized to the RLU values in the samples treated with the isotype control antibody at the highest concentration tested and plotted against a dose titration of antibody concentrations. FIGS. 3C and 3D are the result from a similar reporter assay where test antibodies were examined for their ability to activate FcγRIIIAV158-expressing reporter cells when the antibodies were bound to Jurkat cells expressing GITR (FIG. 3C) or Jurkat cells expressing OX40 (FIG. 3D). The test antibodies used were DuoBody pab1876×pab2049, the bivalent monospecific antibody pab1876 (F405L/F405L), the bivalent monospecific antibody pab2049 (K409R/K409R), and an isotype control antibody. RLUs are plotted against a range of antibody concentrations. FIGS. 3E, 3F, and 3G are the result from an assay measuring NK cell-mediated lysis of activated effector T cells or activated Tregs in the presence of an isotype control antibody, pab1876, pab2049, DuoBody pab1876×pab2049, or a combination of pab1876 and pab2049. FIG. 3E is a pair of histograms showing the expression of GITR (left) or OX40 (right) on activated effector T cells or Tregs as measured by flow cytometry. In FIGS. 3F and 3G, % cytotoxicity is plotted against a titration of antibody concentrations.

Figure 4A:
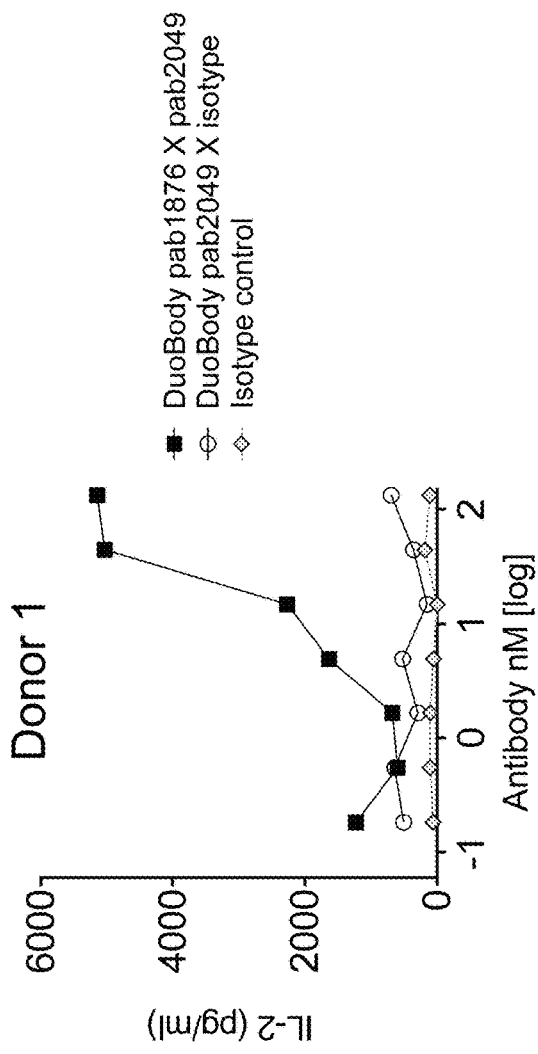
Figure 4B:
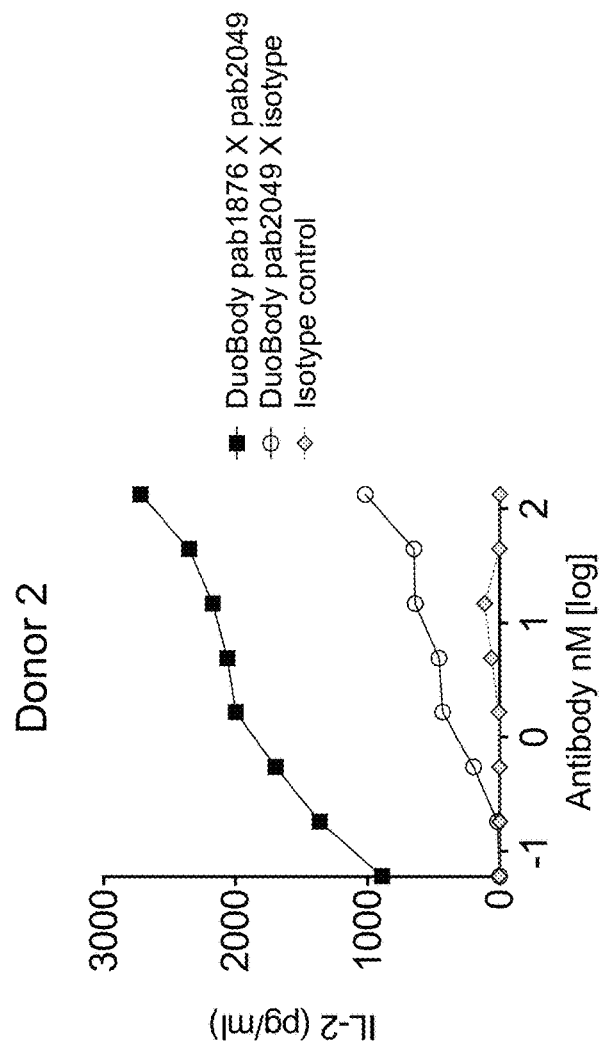

FIGS. 4A and 4B are graphs depicting the functional activity of DuoBody pab1876×pab2049 on primary human T cells from two donors following *Staphylococcus* Enterotoxin A (SEA) stimulation. The concentration of IL-2 is plotted at a dose titration of DuoBody pab1876×pab2049, DuoBody pab2049×isotype and an isotype control antibody.

Figure 5A:
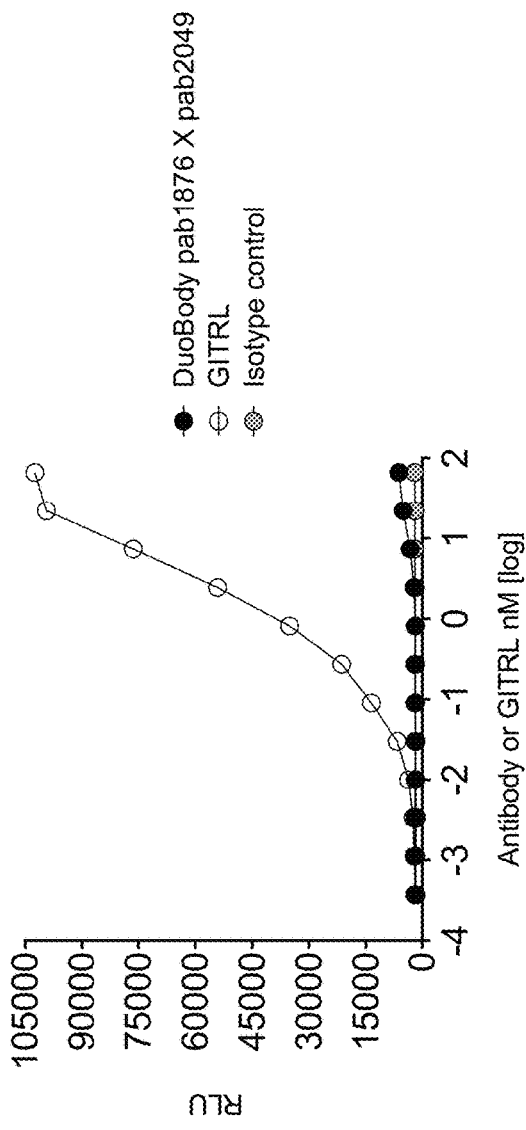
Figure 5B:
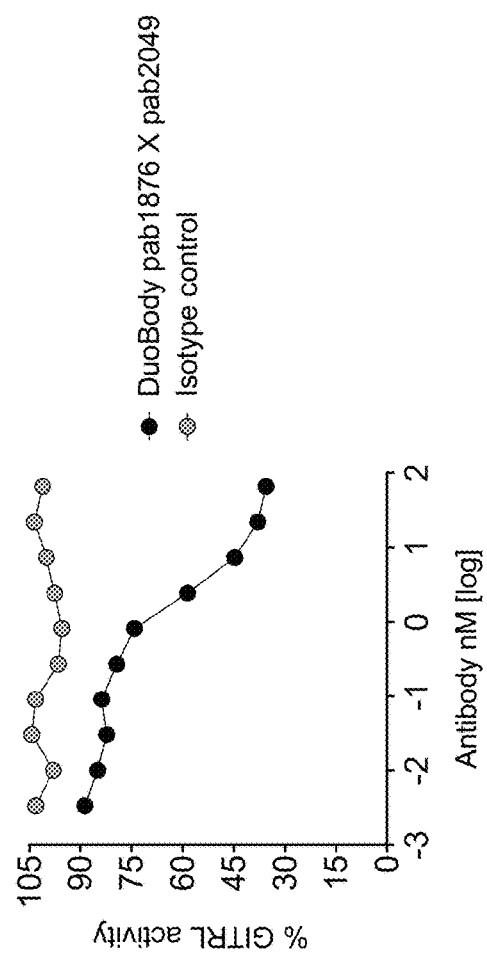

FIGS. 5A and 5B: FIG. 5A is the result of a reporter assay where DuoBody pab1876×pab2049, trimeric GITRL, and an isotype control antibody were tested for their ability to activate Jurkat-huGITR-NF-κB-luciferase reporter cells. The relative light units (RLU), are plotted against a range of antibody or GITRL concentrations. FIG. 5B is the result of a reporter assay where DuoBody pab1876×pab2049 and an isotype control antibody were examined for their capacity to block GITRL-induced NF-κB signaling. In this report assay, Jurkat-huGITR-NF-κB-luciferase reporter cells were pre-incubated with DuoBody pab1876 pab2049 or an isotype control antibody before activated by trimeric GITRL. The % GITRL activity in the presence of a dose titration of antibody concentrations is shown.

Figure 6A:
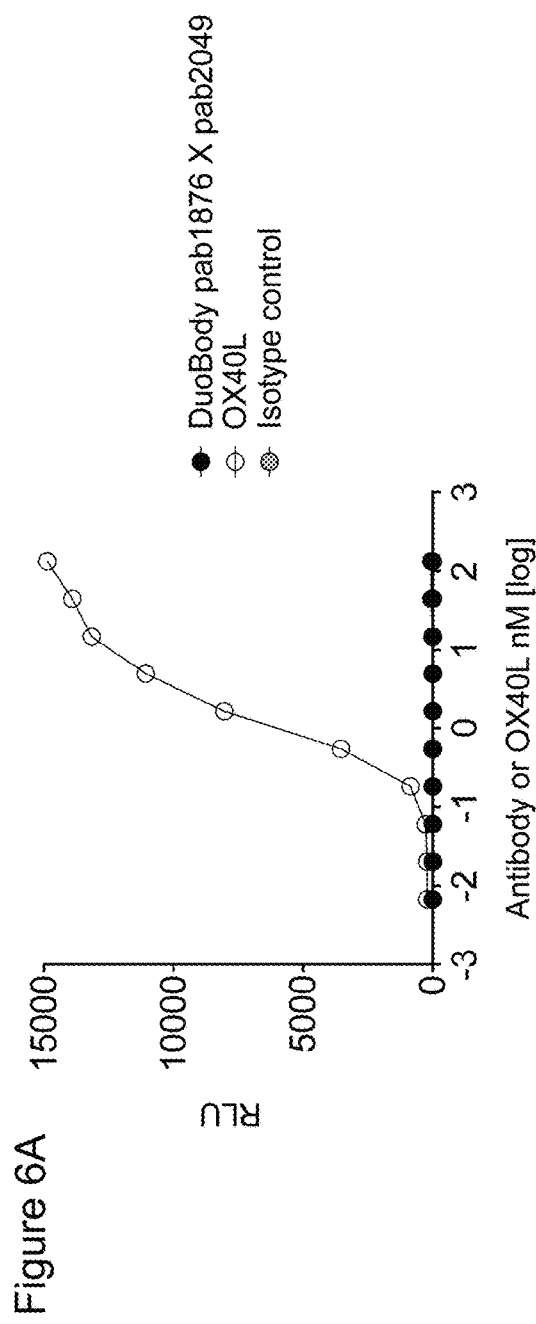
Figure 6B:
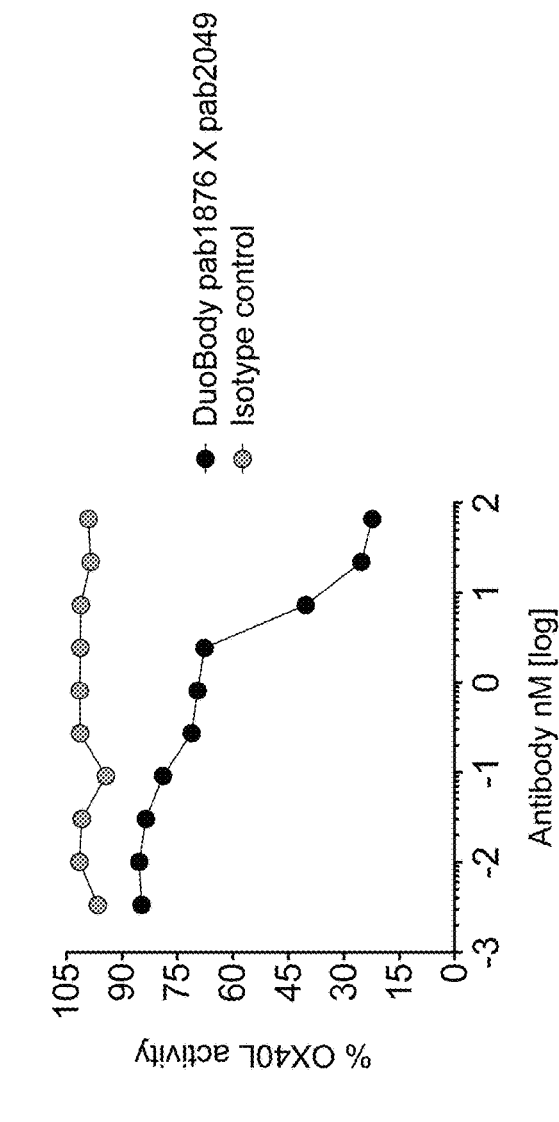

FIGS. 6A and 6B: FIG. 6A depicts NF-κB-luciferase signal from Jurkat-huOX40-NF-κB-luciferase reporter cells triggered by multimeric OX40L, DuoBody pab1876×pab2049 or an isotype control antibody. RLUs are plotted against a dose titration of OX40L or antibody concentrations. FIG. 6B is the result of a reporter assay where Jurkat-huOX40-NF-κB-luciferase reporter cells were pre-incubated with DuoBody pab1876×pab2049 or an isotype control antibody before activated by multimeric OX40L. The % OX40L activity is plotted against a range of antibody concentrations.

Figure 7:
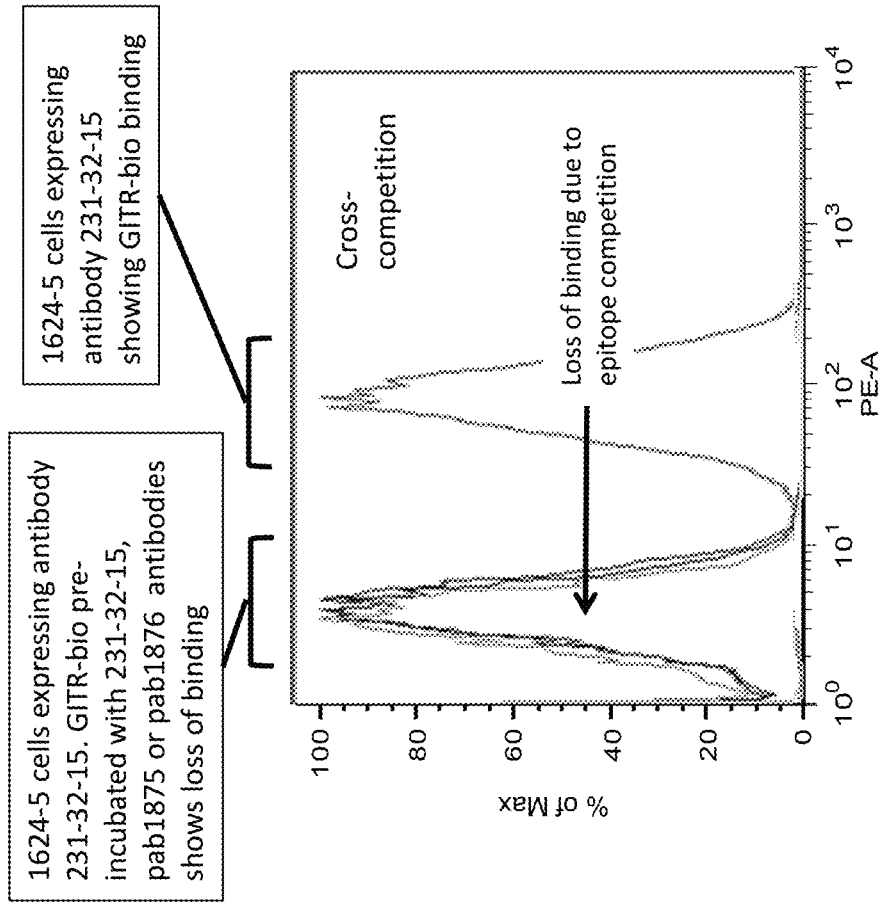

FIG. 7 is a histogram showing the loss of binding of 1624-5 pre-B cells expressing the chimeric parental 231-32-15 antibody to biotinylated GITR (GITR-bio) when GITR-bio was pre-incubated with chimeric parental 231-32-15, pab1875 or pab1876 antibodies. FIG. 7 right-hand profile depicts the binding of 1624-5 pre-B cells expressing the chimeric parental 231-32-15 antibody to GITR-bio. In the left-hand profile, however, there is loss of binding of 1624-5 cells expressing the chimeric parental 231-32-15 antibody to GITR-bio following pre-incubation of GITR-bio with either the chimeric parental 231-32-15, pab1875 or pab1876 antibodies.

Figure 8:
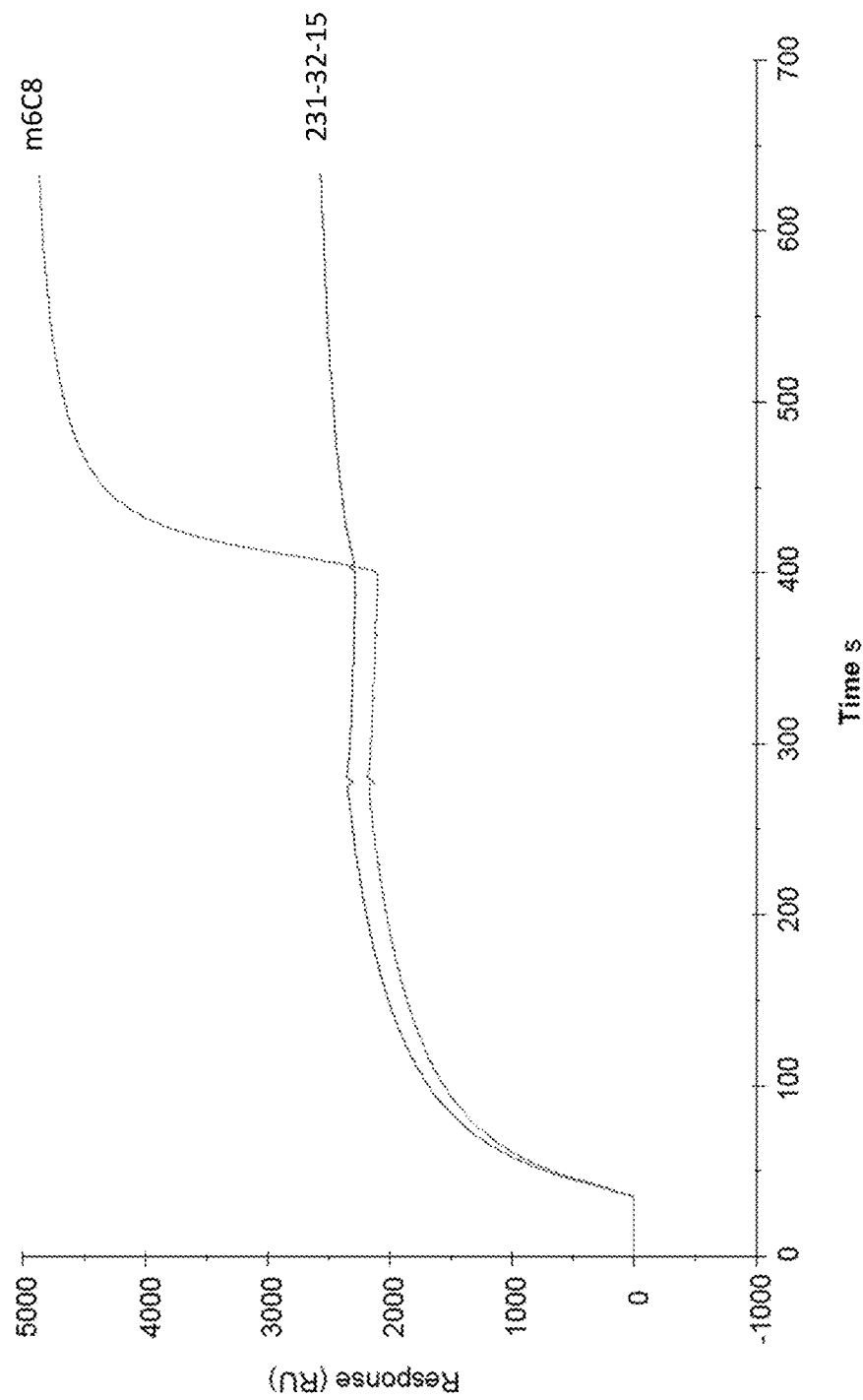

FIG. 8 shows the results of an epitope competition assay measured by surface plasmon resonance (BIAcore® T100/200). GITR antigen was immobilized on a CM5 sensor chip and the anti-GITR antibodies applied at a concentration of 300 nM. Chimeric parental 231-32-15 antibody was applied first followed by the application of the murine antibody 6C8.

Figure 9A:
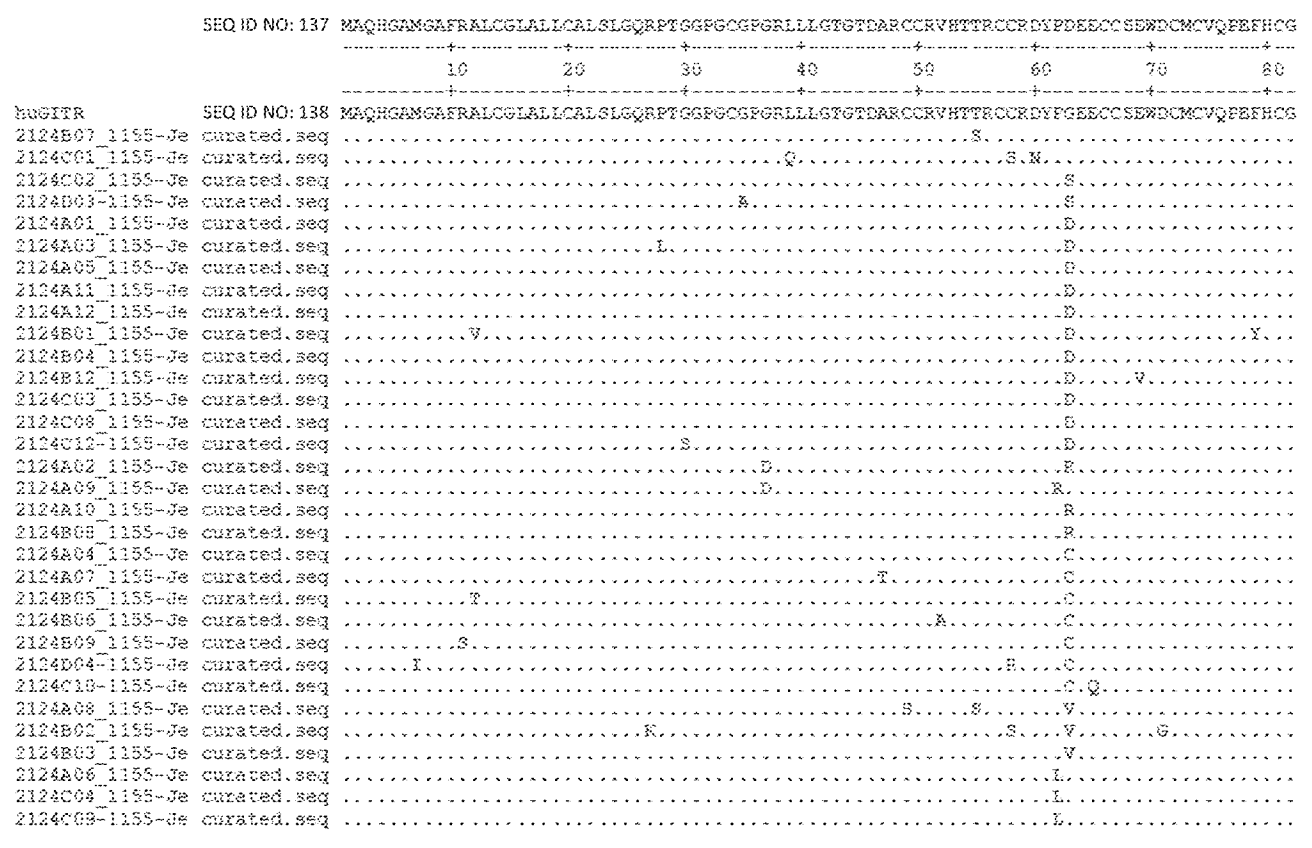
Figure 9B:
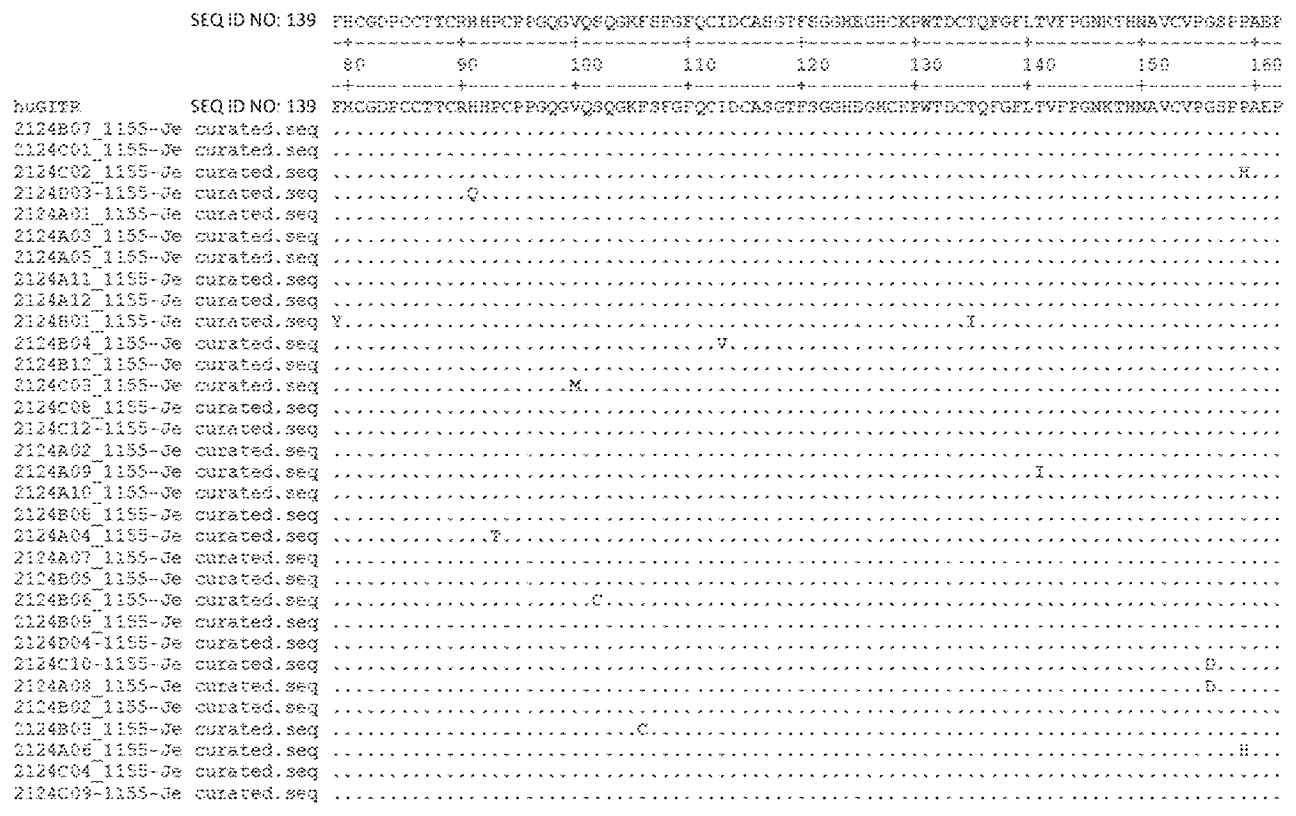

FIGS. 9A and 9B are the results of an epitope mapping experiment using a cellular library expressing GITR variants generated by error prone PCR. Shown in FIGS. 9A and 9B is an alignment of sequences from the GITR variants that bind to a polyclonal anti-GITR antibody but do not bind to the anti-GITR chimeric parental 231-32-15 antibody.

Figure 10B:
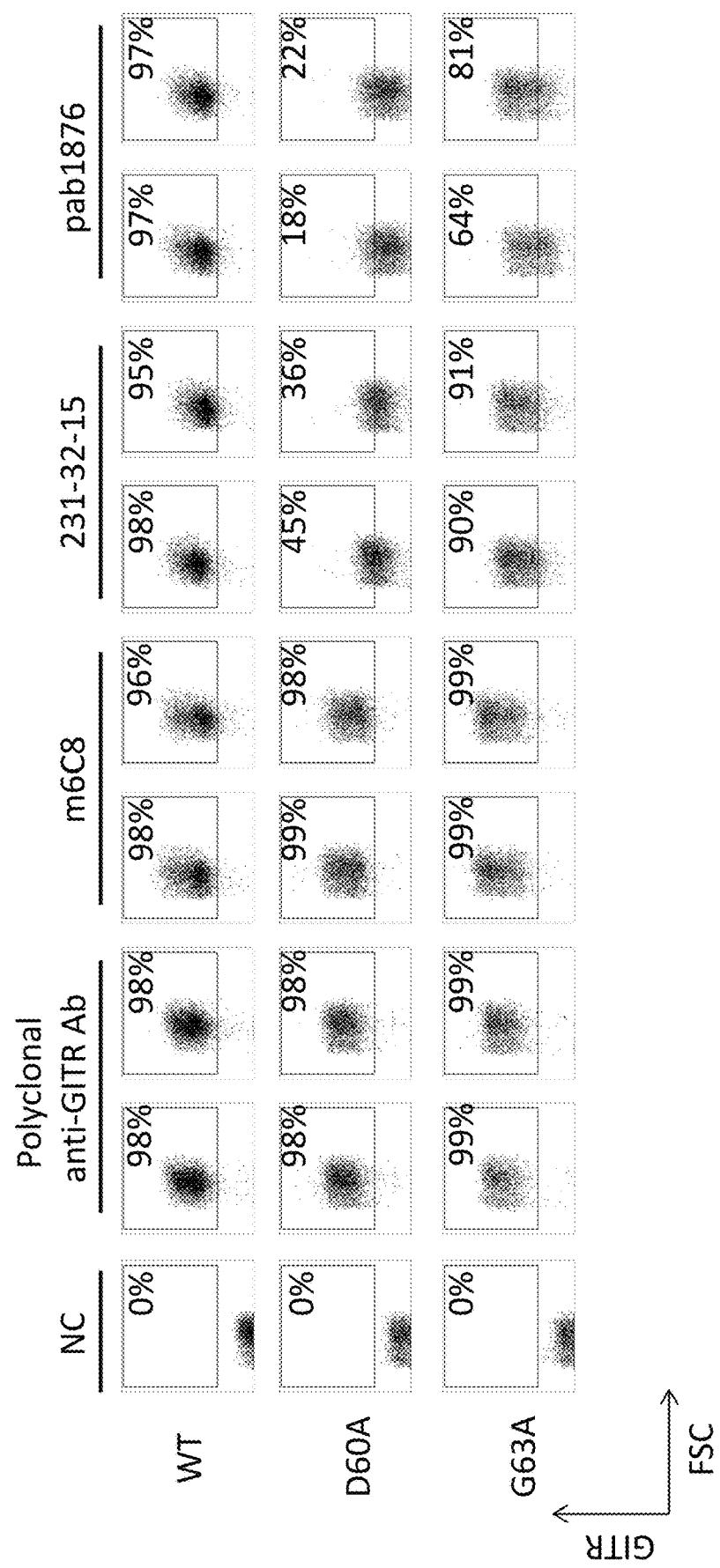

FIGS. 10A and 10B are the result of an epitope mapping experiment using alanine scanning. The following positions in human GITR (numbered according to SEQ ID NO:41) were separately mutated to an Alanine: P28A, T29A, G30A, G31A, P32A, T54A, T55A, R56A, C57A, C58A, R59A, D60A, Y61A, P62A, G63A, E64A, E65A, C66A, C67A, S68A, E69A, W70A, D71A, C72A, M73A, C74A, V75A and Q76A. The antibodies tested in the experiment shown in FIG. 10A included: the monoclonal anti-GITR antibodies pab1876, pab1967, pab1975, pab1979 and m6C8; and a polyclonal anti-GITR antibody (AF689, R&D systems). FIG. 10A is a table summarizing the binding of pab1876, pab1967, pab1975, pab1979 and the reference antibody m6C8 to 1624-5 cells expressing human GITR alanine mutants. FIG. 10B is a set of flow cytometry plots showing the staining of 1624-5 cells expressing wild type human GITR, D60A mutant, or G63A mutant using the monoclonal antibody 231-32-15, pab1876, or m6C8, or a polyclonal antibody. The percentage of GITR positive cells is indicated in each plot.

Figure 11B:
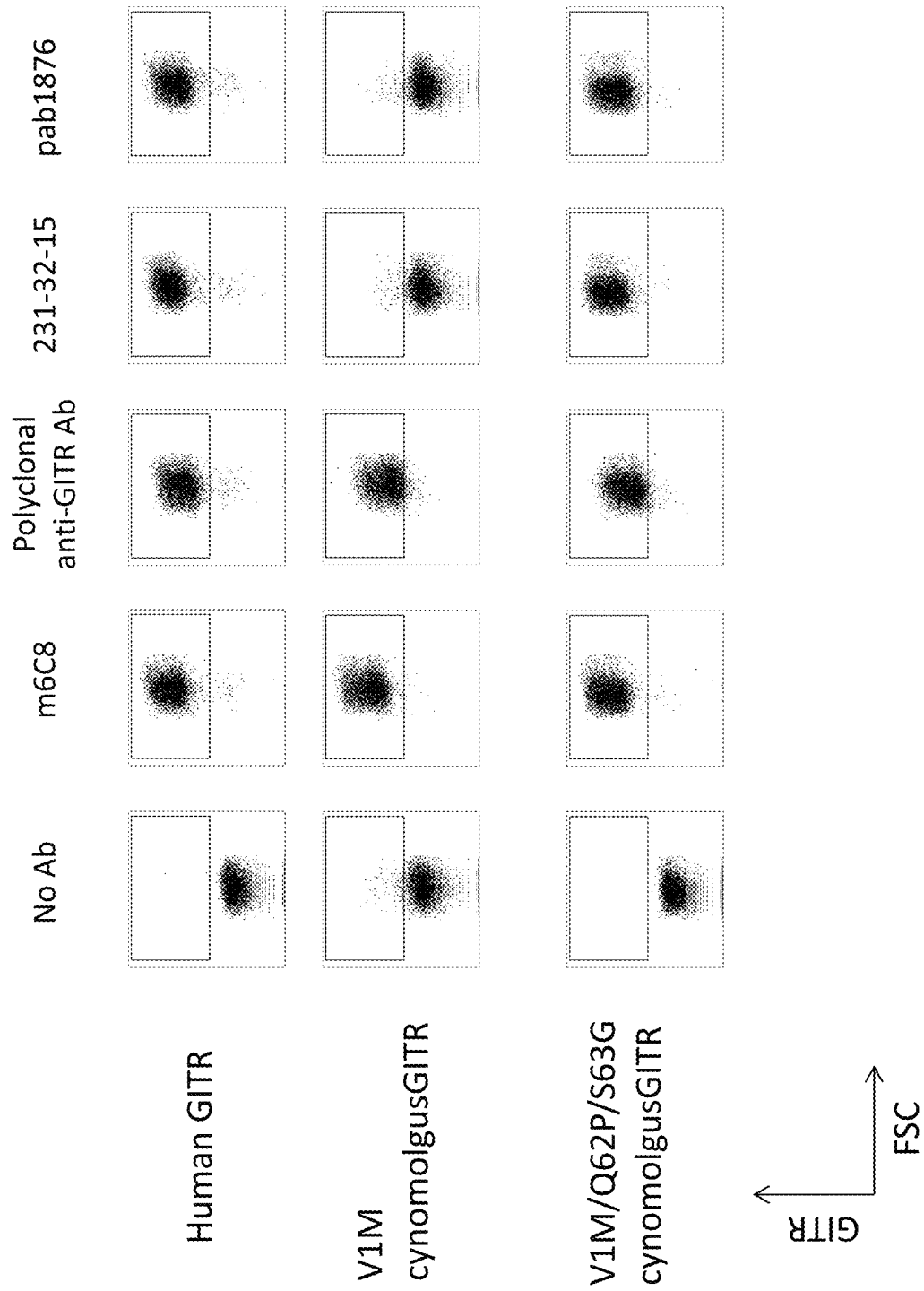

FIG. 11A is a sequence alignment of human GITR, V1M *cynomolgus* GITR, and V1M/Q62P/S63G *cynomolgus* GITR, highlighting the positions 62 and 63 where two amino acids from *cynomolgus* GITR (GlnSer) were replaced by corresponding residues in human GITR (ProGly). FIG. 11B is a set of flow cytometry plots showing the staining of 1624-5 cells expressing human GITR, V1M *cynomolgus* GITR, or V1M/Q62P/S63G *cynomolgus* GITR using the monoclonal antibody 231-32-15, pab1876, or m6C8, or a polyclonal anti-GITR antibody.

FIG. 12 is a table summarizing the binding of the monoclonal anti-OX40 antibodies pab1949w, pab2049, and pab1928 to 1624-5 cells expressing human OX40 alanine mutants.

7. DETAILED DESCRIPTION

Provided herein are multispecific antibodies (e.g., bispecific antibodies) that specifically bind to GITR (e.g., human GITR) and/or OX40 (e.g., human OX40).

For example, multispecific (e.g., bispecific) antibodies provided herein can contain a first antigen-binding domain that binds to OX40 and a second antigen-binding domain. The second antigen-binding domain can be distinct from the first antigen-binding domain. The second antigen-binding domain can bind to a different antigen (i.e., an antigen that is not OX40) than the first antigen-binding domain. The second antigen-binding domain can bind to a different epitope than the first antigen-binding domain. In one instance, antibodies provided herein contain a first antigen-binding domain that specifically binds to OX40 (e.g., human OX40) and a second antigen-binding domain that specifically binds to a TNFR superfamily protein. The TNFR superfamily protein can be, for example, GITR, OX40, CD137, DR3, CD40, BAFFR, CD27, or HVEM. In one instance, antibodies provided herein contain a first antigen-binding domain that specifically binds to OX40 (e.g., human OX40) and a second antigen-binding domain that specifically binds to GITR (e.g., human GITR).

In another example, antibodies provided herein can contain a first antigen-binding domain and a second antigen-binding domain that binds to GITR. The first antigen-binding domain can be distinct from the second antigen-binding domain. The first antigen-binding domain can bind to a different antigen (i.e., an antigen that is not GITR) than the first antigen-binding domain. The second antigen-binding domain can bind to a different epitope than the first antigen-binding domain. In one instance, antibodies provided herein contain a first antigen-binding domain that specifically binds to a TNFR superfamily protein and a second antigen-binding domain that specifically binds to GITR (e.g., human GITR). The TNFR superfamily protein can be, for example, GITR, OX40, CD137, DR3, CD40, BAFFR, CD27, or HVEM. In another example, antibodies provided herein contain a first antigen-binding domain that binds to OX40 and a second antigen-binding domain that binds to GITR. In one instance, antibodies provided herein contain a first antigen-binding domain that specifically binds to OX40 (e.g., human OX40) and a second antigen-binding domain that specifically binds to GITR (e.g., human GITR).

Also provided herein are antibodies that comprise an antigen-binding domain that specifically binds to OX40 (e.g., human OX40) and a TNF superfamily protein. Such antibodies can bind to cells expressing OX40 (e.g., human OX40) and a receptor for the TNF superfamily protein. Also provided herein are antibodies that comprise a TNF superfamily protein and an antigen-binding domain that specifically binds to GITR (e.g., human GITR). Such antibodies can bind to cells expressing a receptor for the TNF superfamily protein and GITR (e.g., human GITR). The TNF superfamily protein can be, for example, GITR ligand, OX40 ligand, CD137 ligand, DR3 ligand, CD40 ligand, BAFFR ligand, CD27 ligand, or HVEM ligand. A TNF superfamily protein can replace the first antigen-binding domain or the second antigen-binding domain in any multispecific (e.g., bispecific) antibody provided herein.

In one aspect, provided herein is a multispecific (e.g., bispecific) antibody that specifically binds to GITR and OX40 and enhances, induces, or increases one or more GITR and/or OX40 activities. In another aspect, provided herein is a multispecific (e.g., bispecific) antibody that specifically binds to GITR and OX40 and reduces, inhibits, or decreases one or more GITR or OX40 activities. In a specific embodiment, the antibody is isolated.

Also provided are isolated nucleic acids (polynucleotides), such as complementary DNA (cDNA), encoding such antibodies. Further provided are vectors (e.g., expression vectors) and cells (e.g., host cells) comprising nucleic acids (polynucleotides) encoding such antibodies. Also provided are methods of making such antibodies. In other aspects, provided herein are methods and uses for inducing, increasing, or enhancing GITR and/or OX40 activity, and treating certain conditions, such as cancer. Further provided are methods and uses for inhibiting, decreasing, or reducing GITR and/or OX40 activity, and treating certain conditions, such as inflammatory or autoimmune diseases and disorders. Related compositions (e.g., pharmaceutical compositions), kits, and detection methods are also provided.

7.1 Terminology

As used herein, the terms "about" and "approximately," when used to modify a numeric value or numeric range, indicate that deviations of 5% to 10% above and 5% to 10% below the value or range remain within the intended meaning of the recited value or range.

As used herein, B is a "substantially increasing function" of A over a specified domain of A values if B substantially increases as A increases over the specified domain, e.g., in a given experiment, or using mean values from multiple experiments. This definition allows for a value of B corresponding to a specified value of A to be up to 1%, 2%, 3%, 4%, 5%, 10%, 15%, or 20% lower relative to a value of B corresponding to any lower value of A.

As used herein, B is a "substantially decreasing function" of A over a specified domain of A values if B substantially decreases as A increases over the specified domain, e.g., in a given experiment, or using mean values from multiple experiments. This definition allows for a value of B corresponding to a specified value of A to be up to 1%, 2%, 3%, 4%, 5%, 10%, 15%, or 20% higher relative to a value of B corresponding to any lower value of A.

As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$, IgG$_2$, or IgG$_4$) or subclass thereof. In a specific embodiment, the antibody is a humanized monoclonal antibody. In another specific embodiment, the antibody is a human monoclonal antibody, e.g., that is an immunoglobulin. In certain embodiments, an antibody described herein is an IgG$_1$, IgG$_2$, or IgG$_4$ antibody.

"Multispecific" antibodies are antibodies with at least two different antigen-binding sites. Multispecific antibodies include bispecific antibodies that contain two different antigen-binding sites (exclusive of the Fc region). Multispecific antibodies can include, for example, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, heteroconjugate antibodies, linked single chain antibodies or linked-single-chain Fvs (scFv), camelized antibodies, affybodies, linked Fab fragments, F(ab')$_2$ fragments, chemically-linked Fvs, and disulfide-linked Fvs (sdFv). Multispecific antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclass (e.g., IgG$_{2a}$ or IgG$_{2b}$) of immunoglobulin molecule. In certain embodiments, multispecific antibodies described herein are IgG antibodies, or a class (e.g., human IgG$_1$, IgG$_2$, or IgG$_4$) or subclass thereof.

As used herein, the terms "antigen-binding domain," "antigen-binding region," "antigen-binding site," and similar terms refer to the portion of antibody molecules which comprises the amino acid residues that confer on the antibody molecule its specificity for the antigen (e.g., the complementarity determining regions (CDR)). The antigen-binding region can be derived from any animal species, such as rodents (e.g., mouse, rat, or hamster) and humans.

A used herein, the term "anti-GITR/OX40" antibody refers to a multispecific antibody (e.g., a bispecific antibody) that contains an antigen-binding domain that binds to GITR (e.g., human GITR) and an antigen-binding domain that binds to OX40 (e.g., human OX40).

As used herein, the terms "variable region" or "variable domain" are used interchangeably and are common in the art. The variable region typically refers to a portion of an antibody, generally, a portion of a light or heavy chain, typically about the amino-terminal 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., IgG$_1$, IgG$_2$, IgG$_3$, and IgG$_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques. In a specific embodiment, the epitope of an antibody is determined using alanine scanning mutagenesis studies.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that immunospecifically bind to an antigen bind to the antigen with a $K_A$ that is at least 2 logs, 2.5 logs, 3 logs, 4 logs or greater than the $K_A$ when the molecules bind non-specifically to another antigen. In the context of multispecific (e.g., bispecific) antibodies, the terms "immunospecifically binds," "immunospecifically recognizes," "specifically binds," and "specifically recognizes" refer to antibodies that have distinct specificities for more than one antigen or for more than one epitope on a single antigen. For example, a bispecific antibody may, e.g., specifically bind each of human OX40 and human GITR, e.g., with distinct antigen-binding domains.

In another specific embodiment, antigen-binding domains that immunospecifically bind to an antigen do not cross react with other proteins under similar binding conditions. In another specific embodiment, antigen-binding domains that immunospecifically bind to GITR antigen do not cross react with other non-GITR proteins. In another specific embodiment, antigen-binding domains that immunospecifically bind to OX40 antigen do not cross react with other non-OX40 proteins. In a specific embodiment, provided herein is an antibody containing an antigen-binding domain that binds to GITR or OX40 with higher affinity than to another unrelated antigen. In certain embodiments, provided herein is an antibody containing an antigen-binding domain that binds to GITR or OX40 (e.g., human GITR or human OX40) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-GITR antigen-binding domain described herein to an unrelated, non-GITR protein is less than 10%, 15%, or 20% of the binding of the antigen-binding domain to GITR protein as measured by, e.g., a radioimmunoassay. In a specific embodiment, the extent of binding of an anti-OX40 antigen-binding domain described herein to an unrelated, non-OX40 protein is less than 10%, 15%, or 20% of the binding of the antigen-binding domain to OX40 protein as measured by, e.g., a radioimmunoassay.

In a specific embodiment, provided herein is an antibody containing an antigen-binding domain that binds to human GITR with higher affinity than to another species of GITR and/or an antigen-binding domain that binds to human OX40 with higher affinity than to another species of OX40. In certain embodiments, provided herein is an antibody containing an antigen-binding domain that binds to human GITR with a 5%, 10%, 15%, 20%, 25%, 30%, 35%, 40%, 45%, 50%, 55%, 60%, 65%, 70% or higher affinity than to another species of GITR as measured by, e.g., a radioimmunoassay, surface plasmon resonance, or kinetic exclusion assay and/or that binds to human OX40 with a 5%, 10%, 15%, 20%, 25%, 30%, 35%, 40%, 45%, 50%, 55%, 60%, 65%, 70% or higher affinity than to another species of OX40 as measured by, e.g., a radioimmunoassay, surface plasmon resonance, or kinetic exclusion assay. In a specific embodiment, an antibody described herein, which binds to human GITR and human OX40, will bind to another species of GITR and/or OX40 protein with less than 10%, 15%, or 20% of the binding of the antibody to the human GITR and/or OX40 protein as measured by, e.g., a radioimmunoassay, surface plasmon resonance, or kinetic exclusion assay.

As used herein, the terms "glucocorticoid-induced TNFR family related receptor" or "GITR" or "GITR polypeptide" refer to GITR including, but not limited to, native GITR, an isoform of GITR, or an interspecies GITR homolog of GITR. GITR is also known as activation-inducible TNFR family receptor (AITR), GITR-D, CD357, and tumor necrosis factor receptor superfamily member 18 (TNFRSF18). GenBank™ accession numbers BC152381 and BC152386 provide human GITR nucleic acid sequences. Swiss-Prot accession number Q9Y5U5-1 (TNR18_HUMAN; SEQ ID NO:41) and GenBank™ accession number NP_004186 provide exemplary human GITR amino acid sequences for isoform 1. This amino acid sequence is 241 amino acids in length with the first 25 amino acid residues encoding the signal sequence. Isoform 1 is a type I membrane protein. An exemplary mature amino acid sequence of human GITR is provided as SEQ ID NO:40. In contrast, isoform 2 is a secreted form of human GITR and is approximately 255 amino acids in length. Swiss-Prot accession number Q9Y5U5-2 and GenBank™ accession number NP_683699 provide exemplary human GITR amino acid sequences for isoform 2. Isoform 3 of human GITR is approximately 234 amino acids in length. Swiss-Prot accession number Q9Y5U5-3 and GenBank™ accession number NP_683700 (isoform 3 precursor) provide exemplary human GITR amino acid sequences for isoform 3. In a specific embodiment, the GITR is human GITR. In another specific embodiment, the GITR is human GITR isoform 1 (SEQ ID NO:41). In certain embodiments, the GITR is human isoform 2 (SEQ ID NO:42) or isoform 3 (SEQ ID NO:43). Human GITR is designated GeneID: 8784 by Entrez Gene. SEQ ID NO:44 provides the *cynomolgus* GITR amino acid sequence, and amino acids 26-234 of SEQ ID NO:44 represent the mature form of *cynomolgus* GITR. As used herein, the term "human GITR" refers to GITR comprising the polypeptide sequence of SEQ ID NO:40.

As used herein, the terms "GITR ligand" and "GITRL" refer to glucocorticoid-induced TNFR-related protein ligand. GITRL is otherwise known as activation-induced TNF-related ligand (AITRL) and tumor necrosis factor ligand superfamily member 18 (TNFSF18). GenBank™ accession number AF125303 provides an exemplary human GITRL nucleic acid sequence. GenBank™ accession number NP_005083 and Swiss-Prot accession number Q9UNG2 provide exemplary human GITRL amino acid sequences.

As used herein, the terms "OX40 receptor" or "OX40" or "OX40 polypeptide" refer to OX40 including, but not limited to, native OX40, an isoform of OX40, or an interspecies OX40 homolog of OX40. OX40 is also known as tumor necrosis factor receptor superfamily member 4 (TNFRSF4), ACT35, CD134, IMD16, and TXGP1L. GenBank™ accession numbers BC105070 and BC105072 provide human OX40 nucleic acid sequences. Refseq number NP_003318.1 provides the amino acid sequence of human OX40. The immature amino acid sequence of human OX40 is provided as SEQ ID NO:73. The mature amino acid sequence of human OX40 is provided as SEQ ID NO:72. Human OX40 is designated GeneID: 7293 by Entrez Gene. RefSeq numbers XM_005545122.1 and XP_005545179.1 provide predicted *cynomolgus* OX40 nucleic acid sequences and amino acid sequences, respectively. A soluble isoform of human OX40 has also been reported (Taylor L et al., (2001) J Immunol Methods 255: 67-72). As used herein, the term "human OX40" refers to OX40 comprising the polypeptide sequence of SEQ ID NO:72.

As used herein, the terms "OX40 ligand" and "OX40L" refer to tumor necrosis factor ligand superfamily member 4 (TNFSF4). OX40L is otherwise known as CD252, GP34, TXGP1, and CD134L. GenBank™ accession numbers D90224.1 and AK297932.1 provide exemplary human OX40L nucleic acid sequences. RefSeq number NP_003317.1 and Swiss-Prot accession number P23510-1 provide exemplary human OX40L amino acid sequences for isoform 1. RefSeq number NP_001284491.1 and Swiss-Prot accession number P23510-2 provide exemplary human OX40L amino acid sequences for isoform 2. Human OX40L is designated GeneID: 7292 by Entrez Gene.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell are not necessarily identical to the parent cell transfected with the nucleic acid molecule, e.g., due to mutations or environmental influences that may occur in succeeding generations or integration of the nucleic acid molecule into the host cell genome.

As used herein, the term "effective amount" in the context of the administration of a therapy to a subject refers to the amount of a therapy that achieves a desired prophylactic or therapeutic effect.

As used herein, the terms "subject" and "patient" are used interchangeably. The subject can be an animal. In some embodiments, the subject is a mammal such as a non-primate (e.g., cow, pig, horse, cat, dog, rat, etc.) or a primate (e.g., monkey or human), most preferably a human. In some embodiments, the subject is a *cynomolgus* monkey. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

As used herein, the binding between a test antibody and a first antigen is "substantially weakened" relative to the binding between the test antibody and a second antigen if the binding between the test antibody and the first antigen is reduced by at least 30%, 40%, 50%, 60%, 70%, or 80% relative to the binding between the test antibody and the second antigen, as measured in e.g., a flow cytometry analysis, or in a given experiment, or using mean values from multiple experiments, as assessed by, e.g., an assay comprising the following steps: (a) expressing on the surface of cells (e.g., 1624-5 cells) the first antigen or the second antigen; (b) staining the cells expressing the first antigen or the second antigen using, e.g., 2 µg/ml of the test antibody or a polyclonal antibody in a flow cytometry analysis and recording mean fluorescence intensity (MFI) values, e.g., as the mean from more than one measurement, wherein the polyclonal antibody recognizes both the first antigen and the second antigen; (c) dividing the MFI value of the test antibody for the cells expressing the second antigen by the MFI value of the polyclonal antibody for the cells expressing the second antigen (MFI ratio$_2$); (d) dividing the MFI value of the test antibody for the cells expressing the first antigen by the MFI value of the polyclonal antibody for the cells expressing the first antigen (MFI ratio$_1$); and (e) determining the percentage of reduction in binding by calculating 100%*(1−(MFI ratio$_1$/MFI ratio$_2$)).

The determination of "percent identity" between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877. Such an algorithm is incorporated into the NBLAST and XBLAST programs of Altschul S F et al., (1990) J Mol Biol 215: 403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

7.2 Multispecific Antibodies that Bind to GITR and/or OX40

In a specific aspect, provided herein are multispecific antibodies (e.g., bispecific antibodies) which specifically bind to GITR and/or OX40 (e.g., human GITR and human OX40). For instance, a multispecific (e.g., bispecific) antibody provided herein can comprise a first antigen-binding domain that binds to OX40 and a second antigen-binding domain. A multispecific (e.g., bispecific) antibody provided herein can also comprise a first antigen-binding domain and a second antigen-binding domain that binds to GITR. These multispecific (e.g., bispecific) antibodies can also bind to other tumor necrosis factor receptor (TNFR) superfamily proteins, e.g., those that are co-regulated with GITR and/or OX40. Such multispecific antibodies advantageously show greater specificity for certain subsets of immune cells containing the combination of target proteins than monospecific bivalent antibodies that only bind to one TNFR superfamily protein.

For example, provided herein are antibodies that comprise a first antigen-binding domain that binds to OX40 and a second antigen-binding domain that binds to a tumor necrosis factor receptor (TNFR) superfamily protein, such as GITR, OX40, CD137, or DR3. In another example, provided herein are antibodies that comprise a first antigen-binding domain that binds to a TNFR superfamily protein, such as GITR, OX40, CD137, or DR3, and a second antigen-binding domain that binds to GITR.

Also provided herein are multispecific (e.g., bispecific) antibodies that comprise a first antigen-binding domain that binds to OX40 and a second antigen-binding domain that binds to GITR.

The antibodies provided herein that contain an OX40 antigen-binding domain and a GITR antigen-binding domain can show increased binding to cells expressing GITR and OX40 (e.g., T regulatory cells) as compared, for example, to a monospecific bivalent antibody that binds to GITR and contains the same GITR antigen-binding domain; and/or as compared to a monospecific bivalent antibody that binds to OX40 and contains the same OX40 antigen-binding domain.

The antibodies provided herein that contain an OX40 antigen-binding domain and a GITR antigen-binding domain can also show decreased binding to GITR-positive, OX40-negative cells (e.g., at low concentrations) as compared to a monospecific bivalent antibody that binds to GITR and contains the same GITR antigen-binding domain.

The antibodies provided herein that contain an OX40 antigen-binding domain and a GITR antigen-binding domain can also show decreased binding to GITR-negative, OX40-positive cells (e.g., at low concentrations) as compared to a monospecific bivalent antibody that binds to OX40 and contains the same OX40 antigen-binding domain.

In certain embodiments, a multispecific (e.g., bispecific) antibody described herein which specifically binds to GITR and OX40 can bind to human CD4+ T cells and human CD8+ T cells. In certain embodiments, an antibody described herein binds to human CD4+ cells and *cynomolgus* monkey CD4+ T cells. The antibodies provided herein which specifically bind to GITR and OX40 can show enhanced binding to regulatory T cells as compared to effector T cells. In some instances, the antibodies provided herein which specifically bind to GITR and OX40 show enhanced binding to intratumoral regulatory T cells as compared to intratumoral effector T cells.

The multispecific (e.g., bispecific) antibodies provided herein that specifically bind to GITR and OX40 can inhibit binding of human GITR ligand to human GITR and/or inhibit binding of human OX40 ligand to human OX40.

In one instance, an antibody provided herein that specifically binds to GITR and OX40 contains a combination of CDRs shown in a single row of Table 1 below.

TABLE 1

| CDR sequences of exemplary anti-GITR/OX40 antibodies* | | | | | | | | | | | |
|---|---|---|---|---|---|---|---|---|---|---|---|
| GITR-Binding Sequence SEQ ID NO. | | | | | | OX40-Binding Sequence SEQ ID NO. | | | | | |
| VH CDR1 | VH CDR2 | VH CDR3 | VL CDR1 | VL CDR2 | VL CDR3 | VH CDR1 | VH CDR2 | VH CDR3 | VL CDR1 | VL CDR2 | VL CDR3 |
| 7 | 10 | 3 | 14 | 5 | 16 | 47 | 48 | 49 | 50 | 51 | 52 |
| 8 | 11 | 3 | 15 | 5 | 17 | 47 | 48 | 49 | 50 | 51 | 52 |
| 9 | 12 | 3 | 14 | 5 | 16 | 47 | 48 | 49 | 50 | 51 | 52 |
| 9 | 13 | 3 | 14 | 5 | 16 | 47 | 48 | 49 | 50 | 51 | 52 |
| 1 | 2 | 3 | 4 | 5 | 6 | 47 | 48 | 49 | 50 | 51 | 52 |
| 87 | 88 | 3 | 90 | 5 | 92 | 47 | 48 | 49 | 50 | 51 | 52 |
| 7 | 10 | 3 | 14 | 5 | 16 | 47 | 48 | 49 | 50 | 51 | 53 |
| 8 | 11 | 3 | 15 | 5 | 17 | 47 | 48 | 49 | 50 | 51 | 53 |
| 9 | 12 | 3 | 14 | 5 | 16 | 47 | 48 | 49 | 50 | 51 | 53 |
| 9 | 13 | 3 | 14 | 5 | 16 | 47 | 48 | 49 | 50 | 51 | 53 |
| 1 | 2 | 3 | 4 | 5 | 6 | 47 | 48 | 49 | 50 | 51 | 53 |
| 87 | 88 | 3 | 90 | 5 | 92 | 47 | 48 | 49 | 50 | 51 | 53 |

*The CDRs in Table 1 are determined according to Kabat.

In one instance, an antibody provided herein that specifically binds to GITR and OX40 contains a combination of two heavy chain variable domains and two light chain variable domains shown in a single row of Table 2 below.

TABLE 2

Heavy chain variable domain (VH) and light chain variable domain (VL) sequences of exemplary anti-GITR/OX40 antibodies

| GITR VH (SEQ ID NO:) | GITR VL (SEQ ID NO:) | OX40 VH (SEQ ID NO:) | OX40 VL (SEQ ID NO:) |
|---|---|---|---|
| 18 | 19 | 54 | 55 |
| 20 | 21 | 54 | 55 |
| 22 | 23 | 54 | 55 |
| 24 | 23 | 54 | 55 |
| 25 | 26 | 54 | 55 |
| 18 | 19 | 54 | 56 |
| 20 | 21 | 54 | 56 |
| 22 | 23 | 54 | 56 |
| 24 | 23 | 54 | 56 |
| 25 | 26 | 54 | 56 |

In one instance, an antibody provided herein that specifically binds to GITR and OX40 contains a combination of two heavy chains and two light chains shown in a single row of Table 3 below.

TABLE 3

Heavy chain (HC) and light chain (LC) sequences of exemplary anti-GITR/OX40 DuoBody antibodies

| Antibody | GITR HC (SEQ ID NO:) | GITR LC (SEQ ID NO:) | OX40 HC (SEQ ID NO:) | OX40 LC (SEQ ID NO:) |
|---|---|---|---|---|
| pab1876w (F405L) X pab2049w (K409R) | 31 | 37 | 61 | 67 |
| pab1876w (F405L/N297A) X pab2049w (K409R/N297A) | 32 | 37 | 62 | 67 |
| pab1876w (F405L/L234F/L235E/D265A) X pab2049w (K409R/L234F/L235E/D265A) | 33 | 37 | 63 | 67 |
| pab1876w (F405L) X pab1949w (K409R) | 31 | 37 | 61 | 69 |
| pab1876w (F405L/N297A) X pab1949w (K409R/N297A) | 32 | 37 | 62 | 69 |
| pab1876w (F405L/L234F/L235E/D265A) X pab1949w (K409R/L234F/L235E/D265A) | 33 | 37 | 63 | 69 |
| pab1876w (K409R) X pab2049w (F405L) | 34 | 37 | 64 | 67 |
| pab1876w (K409R/N297A) X pab2049w (F405L/N297A) | 35 | 37 | 65 | 67 |
| pab1876w (K409R/L234F/L235E/D265A) X pab2049w (F405L/L234F/L235E/D265A) | 39 | 37 | 71 | 67 |
| pab1876w (K409R) X pab1949w (F405L) | 34 | 37 | 64 | 69 |
| pab1876w (K409R/N297A) X pab1949w (F405L/N297A) | 35 | 37 | 65 | 69 |
| pab1876w (K409R/L234F/L235E/D265A) X pab1949w (F405L/L234F/L235E/D265A) | 39 | 37 | 71 | 69 |
| pab1876w (F405L) X pab2049w (K409R) without heavy chain terminal lysine | 76 | 37 | 120 | 67 |
| pab1876w (F405L/N297A) X pab2049w (K409R/ N297A) without heavy chain terminal lysine | 77 | 37 | 121 | 67 |
| pab1876w (F405L/L234F/L235E/D265A) X pab2049w (K409R/L234F/L235E/D265A) without heavy chain terminal lysine | 78 | 37 | 122 | 67 |
| pab1876w (F405L) X pab1949w (K409R) without heavy chain terminal lysine | 76 | 37 | 120 | 69 |
| pab1876w (F405L/N297A) X pab1949w (K409R/N297A) without heavy chain terminal lysine | 77 | 37 | 121 | 69 |
| pab1876w (F405L/L234F/L235E/D265A) X pab1949w (K409R/L234F/L235E/D265A) without heavy chain terminal lysine | 78 | 37 | 122 | 69 |
| pab1876w (K409R) X pab2049w (F405L) without heavy chain terminal lysine | 79 | 37 | 123 | 67 |
| pab1876w (K409R/N297A) X pab2049w (F405L/N297A) without heavy chain terminal lysine | 80 | 37 | 124 | 67 |
| pab1876w (K409R/L234F/L235E/D265A) X pab2049w (F405L/L234F/L235E/D265A) without heavy chain terminal lysine | 82 | 37 | 83 | 67 |
| pab1876w (K409R) X pab1949w (F405L) without heavy chain terminal lysine | 79 | 37 | 123 | 69 |

TABLE 3-continued

Heavy chain (HC) and light chain (LC) sequences of exemplary anti-GITR/OX40 DuoBody antibodies

| Antibody | GITR HC (SEQ ID NO:) | GITR LC (SEQ ID NO:) | OX40 HC (SEQ ID NO:) | OX40 LC (SEQ ID NO:) |
|---|---|---|---|---|
| pab1876w (K409R/N297A) X pab1949w (F405L/N297A) without heavy chain terminal lysine | 80 | 37 | 124 | 69 |
| pab1876w (K409R/L234F/ L235E/D265A) X pab1949w (F405L/L234F/ L235E/D265A) without heavy chain terminal lysine | 82 | 37 | 83 | 69 |

A multispecific antibody, e.g., a bispecific antibody, that binds to GITR and/or OX40 as provided herein can be prepared by chemically linking two different monoclonal antibodies or by fusing two hybridoma cell lines to produce a hybrid-hybridoma. Other multivalent formats that can be used include, for example, Kk-bodies, dAbs, diabodies, TandAbs, nanobodies, SMIPs, DNLs, strand-exchange engineered domain bodies (SEEDbodies), Affibodies, Fynomers, Kunitz Domains, Albu-dabs, DARTs, DVD-IG, Covx-bodies, peptibodies, scFv-Igs, SVD-Igs, dAb-Igs, Knobs-in-Holes, DuoBody antibodies and triomAbs. Exemplary bispecific formats are discussed in Garber et al., *Nature Reviews Drug Discovery* 13:799-801 (2014), which is herein incorporated by reference in its entirety.

Exemplary bispecific antibody molecules of the invention comprise (i) a single antibody that has two arms comprising different antigen-binding regions, one with a specificity to a first antigen such as OX40 and one with a specificity to a second antigen such as GITR, (ii) a single antibody that has one antigen-binding region or arm specific to a first antigen such as OX40 and a second antigen-binding region or arm specific to a second antigen such as GITR, (iii) a single chain antibody that has a first specificity to a first antigen such as OX40 and a second specificity to a second antigen such as GITR, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab)$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody.

Examples of different classes of bispecific antibodies include but are not limited to IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Examples of Fab fusion bispecific antibodies include but are not limited to F(ab)$_2$ (Medarex/AMGEN), Dual-Action or Bis-Fab (Genentech), Dock-and-Lock (DNL) (Immuno-Medics), Bivalent Bispecific (Biotecnol) and Fab-Fv (UCB-Celltech). Examples of ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), and dual targeting heavy chain only domain antibodies.

In particular embodiments, a multispecific (e.g., bispecific) antibody can be a chimeric antibody or a humanized antibody. In certain embodiments, a multispecific (e.g., bispecific) antibody can be a F(ab')$_2$ fragment.

In certain embodiments, the multispecific (e.g., bispecific) antibody, that binds to GITR and/or OX40, is a DuoBody antibody.

In certain embodiments, a first antigen-binding domain that binds to OX40 as described herein comprises a human IgG$_1$ heavy chain constant region comprising a F405L mutation, and a second antigen-binding domain that binds to GITR as described herein comprises a human IgG$_1$ heavy chain constant region comprising a K409R mutation, numbered according to the EU numbering system.

In certain embodiments, a first antigen-binding domain that binds to OX40 as described herein comprises a human IgG$_1$ heavy chain constant region comprising a K409R mutation, and a second antigen-binding domain that binds to GITR as described herein comprises a human IgG$_1$ heavy chain constant region comprising a F405L mutation, numbered according to the EU numbering system.

As provided herein, multispecific antibodies (e.g. bispecific antibodies) that bind to GITR and/or OX40 can agonize or antagonize GITR and/or OX40 activity. Antibodies that agonize GITR and/or OX40 function include antibodies that cluster GITR and/or OX40. Clustering can result, e.g., as a result of Fc-Fc receptor (FcR) interaction. Thus, antibodies that agonize GITR and/or OX40 include antibodies with increased Fc-receptor binding. Mutations that increase Fc-receptor binding are known in the art and include, for example, antibodies with an afucosylated Fc, and antibodies with mutations such as S267E/L328F (the SELF mutant) and S239D/A330L/I332E, numbered according to the EU numbering system. In some embodiments, a multispecific (e.g., bispecific) agonist antibody that binds to GITR and/or OX40 comprises an IgG2 constant region containing C127S, numbered according to Kabat. Antibodies that antagonize GITR and/or OX40 function include antibodies with diminished Fc-receptor binding. Mutations that diminish Fc-receptor binding are known in the art and include, for example, N297A; N297Q; D265A; L234F/L235E; L234F/L235E/N297Q; L234F/L235E/P331S; D265A/N297Q; and L234F/L235E/D265A/N297Q/P331S, numbered according to the EU numbering system. In some embodiments, a multispecific (e.g., bispecific) antagonist antibody that binds to GITR and/or OX40 comprises an IgG1 constant region containing N297A, numbered according to the EU numbering system. In some embodiments, a multispecific (e.g., bispecific) antagonist antibody that binds to GITR and/or OX40 comprises an IgG1 constant region containing N297Q, numbered according to the EU numbering system. In some embodiments, a multispecific (e.g., bispecific) antagonist antibody that binds to GITR and/or OX40 comprises an IgG1 constant region containing D265A, numbered according to the EU numbering system. In some embodiments, a multispecific (e.g., bispecific) antagonist antibody that binds to GITR and/or OX40 comprises an IgG1 constant region containing L234F/L235E/D265A, numbered according to the EU numbering system. In some embodiments, a multispecific (e.g., bispecific) antagonist antibody that binds to GITR and/or OX40 comprises an IgG1 constant region containing a mutation selected from the group consisting of D265A, P329A, and a combination thereof, numbered according to the EU numbering system.

In some embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, with numbering according to the EU numbering system, e.g., to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo. In some embodiments, one, two or more amino acid mutations (i.e., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), with numbering according to the EU numbering system. In a specific embodiment, the constant region of the $IgG_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU numbering system.

In a specific embodiment, an antibody described herein comprises the constant domain of an $IgG_1$ with an N297Q or N297A amino acid substitution, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain of an antibody described herein are altered to thereby alter the ability of the antibody to fix complement. This approach is described further in International Publication No. WO 94/29351. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072.

In certain embodiments, an antibody described herein comprises the constant domain of an $IgG_1$ with a mutation (e.g., substitution) at position 267, 328, or a combination thereof, numbered according to the EU numbering system. In certain embodiments, an antibody described herein comprises the constant domain of an $IgG_1$ with a mutation (e.g., substitution) selected from the group consisting of S267E, L328F, and a combination thereof, numbered according to the EU numbering system. In certain embodiments, an antibody described herein comprises the constant domain of an $IgG_1$ with a S267E/L328F mutation (e.g., substitution), numbered according to the EU numbering system. In certain embodiments, an antibody described herein comprising the constant domain of an $IgG_1$ with a S267E/L328F mutation (e.g., substitution) has an increased binding affinity for FcγRIIA, FcγRIIB, or FcγRIIA and FcγRIIB, numbered according to the EU numbering system.

In certain embodiments, an antibody described herein comprises the constant region of an $IgG_4$ antibody and the serine at amino acid residue 228 of the heavy chain, numbered according to the EU numbering system, is substituted for proline.

In certain embodiments, an antibody described herein comprises the constant region of an $IgG_2$ antibody and the cysteine at amino acid residue 127 of the heavy chain, numbered according to Kabat, is substituted for serine.

Antibodies with reduced fucose content have been reported to have an increased affinity for Fc receptors, such as, e.g., FcγRIIIa. Accordingly, in certain embodiments, the antibodies described herein have reduced fucose content or no fucose content. Such antibodies can be produced using techniques known to one skilled in the art. For example, the antibodies can be expressed in cells deficient or lacking the ability of fucosylation. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content. Alternatively, antibodies with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies thereof with no fucose content or reduced fucose content.

Engineered glycoforms may be useful for a variety of purposes, including but not limited to enhancing or reducing effector function. Methods for generating engineered glycoforms in an antibody described herein include but are not limited to those disclosed, e.g., in Umaña P et al., (1999) Nat Biotechnol 17: 176-180; Davies J et al., (2001) Biotechnol Bioeng 74: 288-294; Shields R L et al., (2002) J Biol Chem 277: 26733-26740; Shinkawa T et al., (2003) J Biol Chem 278: 3466-3473; Niwa R et al., (2004) Clin Cancer Res 1: 6248-6255; Presta L G et al., (2002) Biochem Soc Trans 30: 487-490; Kanda Y et al., (2007) Glycobiology 17: 104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosylation engineering technology (Glycart biotechnology AG, Zurich, Switzerland). See also, e.g., Ferrara C et al., (2006) Biotechnol Bioeng 93: 851-861; International Publication Nos. WO 07/039818; WO 12/130831; WO 99/054342; WO 03/011878; and WO 04/065540.

In certain embodiments, the technology used to engineer the Fc domain of an antibody described herein is the Xmab® Technology of Xencor (Monrovia, Calif.). See, e.g., U.S. Pat. Nos. 8,367,805; 8,039,592; 8,124,731; 8,188,231; U.S. Patent Publication No. 2006/0235208; International Publication Nos. WO 05/077981; WO 11/097527; and Richards J O et al., (2008) Mol Cancer Ther 7: 2517-2527.

In certain embodiments, amino acid residues in the constant region of an antibody described herein in the positions corresponding to positions L234, L235, and D265 in a human IgG1 heavy chain, numbered according to the EU numbering system, are not L, L, and D, respectively. This approach is described in detail in International Publication No. WO 14/108483. In a particular embodiment, the amino acids corresponding to positions L234, L235, and D265 in a human IgG1 heavy chain are F, E, and A; or A, A, and A, respectively, numbered according to the EU numbering system.

In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, with numbering according to the EU numbering system, e.g., to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody.

In certain embodiments, a multispecific (e.g., bispecific) antibody, which immunospecifically binds to GITR and OX40 (e.g., human GITR and OX40), increases GITR and/or OX40 (e.g., human GITR and/or OX40) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to GITR and/or OX40 (e.g., human GITR and/or OX40) activity without any antibody or with an unrelated antibody (e.g., an antibody that does not immunospecifically bind to GITR or OX40). For instance, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, increase GITR and/or OX40 (e.g., human GITR and/or OX40) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to GITR and/or OX40 (e.g., human GITR and/or OX40) activity without any antibody or with an unrelated antibody (e.g., an antibody that does not immunospecifically bind to GITR or OX40). Non-limiting examples of GITR and/or OX40 (e.g., human GITR and/or OX40) activity can include GITR and/or OX40 (e.g., human GITR and/or OX40) signaling, cell proliferation, cell survival, and cytokine production (e.g., IL-2, TNF-α, IFN-γ, IL-4, IL-10, and/or IL-13).

As provided herein, multispecific antibodies (e.g., bispecific antibodies) that bind to GITR and/or OX40 can agonize GITR and/or OX40 function, for example, by stimulating IL-2 release in SEA assay, e.g., as exemplified in the Examples, infra. For instance, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, in combination with *Staphylococcus* Enterotoxin A (SEA) (e.g., 100 ng/ml), induce IL-2 production in, e.g., PBMCs upon stimulation for, e.g., 5 days at, e.g., 37° C., 5% $CO_2$, and 97% humidity, as measured by, e.g., electrochemiluminescence. In some embodiments, the IL-2 production is a substantially increasing function of antibody concentrations between, e.g., 0.08 µg/ml and 20 µg/ml, 0.25 µg/ml and 20 µg/ml, 0.74 µg/ml and 20 µg/ml, 2.2 µg/ml and 20 µg/ml, or 6.7 µg/ml and 20 µg/ml. In certain embodiments, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, in combination with *Staphylococcus* Enterotoxin A (SEA), induce IL-2 production in, e.g., PBMCs, wherein the IL-2 production is a substantially increasing function of antibody concentrations between, e.g., 0.08 µg/ml and 20 µg/ml, 0.25 µg/ml and 20 µg/ml, 0.74 µg/ml and 20 µg/ml, 2.2 µg/ml and 20 µg/ml, or 6.7 µg/ml and 20 µg/ml as assessed in, e.g., an assay comprising the following steps: (a) culturing the PBMCs (e.g., $10^5$ cells in a well) in the absence or presence of varying concentrations (e.g., 20, 46.7, 2.2, 0.74, 0.25, and 0.08 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence.

In certain embodiments, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, in combination with *Staphylococcus* Enterotoxin A (SEA) (e.g., 100 ng/ml), induce IL-2 production in, e.g., PBMCs upon stimulation for, e.g., 5 days at, e.g., 37° C., 5% $CO_2$, and 97% humidity, as measured by, e.g., electrochemiluminescence. In some embodiments, the IL-2 production shows a sigmoidal dose response curve when the antibody is between, e.g., 0.08 µg/ml and 20 µg/ml, 0.25 µg/ml and 20 µg/ml, 0.74 µg/ml and 20 µg/ml, 2.2 µg/ml and 20 µg/ml, or 6.7 µg/ml and 20 µg/ml. In certain embodiments, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, in combination with *Staphylococcus* Enterotoxin A (SEA), induce IL-2 production in, e.g., PBMCs, wherein the IL-2 production shows a sigmoidal dose response curve when the antibody is between, e.g., 0.08 µg/ml and 20 µg/ml, 0.25 µg/ml and 20 µg/ml, 0.74 µg/ml and 20 µg/ml, 2.2 µg/ml and 20 µg/ml, or 6.7 µg/ml and 20 µg/ml as assessed in, e.g., an assay comprising the following steps: (a) culturing the PBMCs (e.g., $10^5$ cells in a well) in the absence or presence of varying concentrations (e.g., 20, 6.7, 2.2, 0.74, 0.25, and 0.08 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence. In certain embodiments, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, in combination with *Staphylococcus* Enterotoxin A (SEA) (e.g., 100 ng/ml), induce IL-2 production in, e.g., PBMCs upon stimulation for, e.g., 5 days at, e.g., 37° C., 5% $CO_2$, and 97% humidity, as measured by, e.g., electrochemiluminescence, wherein the IL-2 production is a substantially increasing function of antibody concentrations between, e.g., 0.08 µg/ml and 20 µg/ml, 0.25 µg/ml and 20 µg/ml, 0.74 µg/ml and 20 µg/ml, 2.2 µg/ml and 20 µg/ml, or 6.7 µg/ml and 20 µg/ml. In certain embodiments, an antibody that binds to GITR and OX40, e.g., an antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can, in combination with *Staphylococcus* Enterotoxin A (SEA), induce IL-2 production in, e.g., PBMCs, wherein the IL-2 production is a substantially increasing function of antibody concentrations between, e.g., 0.08 µg/ml and 20 µg/ml, 0.25 µg/ml and 20 µg/ml, 0.74 µg/ml and 20 µg/ml, 2.2 µg/ml and 20 µg/ml, or 6.7 µg/ml and 20 µg/ml, as assessed in, e.g., an assay comprising the following steps: (a) culturing the PBMCs (e.g., $10^5$ cells in a well) in the absence or presence of varying concentrations (e.g., 20, 6.7, 2.2, 0.74, 0.25, and 0.08 µg/ml) of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence.

In a specific aspect, provided herein are multispecific (e.g., bispecific) antagonistic antibodies, which immunospecifically bind to GITR and OX40 (e.g., human GITR and OX40).

In a specific aspect, a multispecific (e.g., bispecific) antibody as described herein, which immunospecifically binds to GITR and OX40 (e.g., human GITR and OX40), comprises a human immunoglobulin $IgG_1$ heavy chain constant region, wherein the amino acid sequence of the $IgG_1$ heavy chain constant region comprises a mutation selected from the group consisting of: N297A, D265A, L234F, L235E, N297Q, and P331S, numbered according to the EU numbering system. In certain embodiments, the mutation is N297A or D265 A, numbered according to the EU numbering system. In certain embodiments the mutation is L234F and L235E, numbered according to the EU numbering system. In certain embodiments, the mutation is L234F, L234E, and D265A, numbered according to the EU numbering system. In certain embodiments, the mutation is L234F, L234E, and N297Q, numbered according to the EU numbering system. In certain embodiments, the mutation is L234F, L235E, and P331S, numbered according to the EU numbering system. In certain embodiments, the mutation is D265A and N297Q, numbered according to the EU numbering system. In certain embodiments, the mutation is L234F, L235E, D265A, N297Q, and P331S, numbered according to the EU numbering system. In a specific aspect, a multispecific (e.g., bispecific) antibody as described herein, which immunospecifically binds to GITR and OX40 (e.g., human GITR and OX40), comprises a human immunoglobulin $IgG_1$ heavy chain constant region, wherein the amino acid sequence of the $IgG_1$ heavy chain constant region comprises a mutation selected from the group consisting of D265A, P329A, and a combination thereof, numbered according to the EU numbering system. In certain embodiments, the antibody is antagonistic.

In certain embodiments, an antagonist multispecific (e.g., bispecific) antibody described herein, which immunospecifically binds to GITR and OX40 (e.g., human GITR and OX40), decreases GITR and/or OX40 (e.g., human GITR and/or OX40) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to GITR and/or OX40 (e.g., human GITR and/or OX40) activity without any antibody or with an unrelated antibody (e.g., an antibody that does not immunospecifically bind to GITR or OX40). In certain embodiments, an antagonist multispecific (e.g., bispecific) antibody described herein, which immunospecifically binds to GITR and/or OX40 (e.g., human GITR and/or OX40), decreases GITR and/or OX40 (e.g., human GITR and/or OX40) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to GITR and/or OX40 (e.g., human GITR and/or OX40) activity without any antibody or with an unrelated antibody (e.g., an antibody that does not immunospecifically bind to GITR or OX40). Non-limiting examples of GITR and/or OX40 (e.g., human GITR and/or OX40) activity can include GITR and/or OX40 (e.g., human GITR and/or OX40) signaling, cell proliferation, cell survival, and cytokine production (e.g., IL-2, TNF-α, IFN-γ, IL-4, IL-10, and/or IL-13). In specific embodiments, GITR and/or OX40 activity is assessed as described in the Examples, infra.

As provided herein, antagonist multispecific antibodies (e.g., bispecific antibodies) that bind to GITR and/or OX40 can antagonize GITR and/or OX40 function, for example, by neutralize GITRL-induced signaling, e.g., as exemplified in the Examples, infra. For instance, an antagonist antibody that binds to GITR and OX40, e.g., an antagonist antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can neutralize GITRL-induced signaling as measured by, e.g., a luciferase assay. In certain embodiments, an antagonist antibody that binds to GITR and OX40, e.g., an antagonist antibody that binds to GITR and OX40 and comprises a combination of CDR sequences specified herein, a VH and/or VL sequence having at least 70%, at least 75%, at least 80%, at least 85%, at least 90%, at least 95%, at least 98%, at least 99% or 100% sequence identity with VH and/or VL sequences specified herein, or heavy and/or light chains specified herein, can neutralize GITRL-induced signaling as assessed in, e.g., a luciferase assay comprising the following steps: (a) culturing Jurkat-hu-GITR-NF-κB-luciferase cells in the absence or presence of varying concentrations of the antibody (e.g., 12-point dose titration, 0.05-10,000 ng/ml) and trimeric GITRL for 2 hours in RPMI media, supplemented with 10% heat-inactivated FBS, at 37° C. and 5% $CO_2$ and (b) detecting luciferase activity.

In certain embodiments, antagonist multispecific antibodies (e.g., bispecific antibodies) described herein that bind to GITR and/or OX40 block the interaction of GITR and/or OX40 with GITRL and/or OX40L (e.g., blocks the binding of GITRL and GITR and/or OX40L and OX40 to one another). In certain embodiments, antagonist multispecific antibodies (e.g., bispecific antibodies) described herein that bind to GITR and/or OX40 decrease GITR and/or OX40 activity (e.g., GITR and/or OX40 signaling) induced by GITRL and/or OX40L. In certain embodiments, antagonist multispecific antibodies (e.g., bispecific antibodies) described herein that bind to GITR and/or OX40 suppress T cell proliferation. In certain embodiments, antagonist multispecific antibodies (e.g., bispecific antibodies) described herein that bind to GITR and/or OX40 suppress production of cytokines (e.g., IL-2, TNFα, IFNγ, IL-4, IL-10, IL-13, or a combination thereof).

An antibody provided herein that binds to GITR and/or OX40 can be fused or conjugated (e.g., covalently or non-covalently linked) to a detectable label or substance. Examples of detectable labels or substances include enzyme labels, such as, glucose oxidase; radioisotopes, such as iodine ($^{125}$I, $^{121}$I) carbon ($^{14}$C), sulfur ($^{35}$S), tritium ($^3$H), indium ($^{121}$In) and technetium ($^{99}$Tc); luminescent labels, such as luminol; and fluorescent labels, such as fluorescein and rhodamine, and biotin. Such labeled antibodies can be used to detect OX40 (e.g., human OX40) protein. See, e.g., Section 7.5.2, infra.

7.2.1 OX40 Antigen-Binding Domains

In a particular embodiment, an OX40 antigen-binding domain described herein, which specifically binds to OX40 (e.g., human OX40), comprises a comprising a light chain variable region (VL) comprising:

(a) a VL CDR1 comprising, consisting of, or consisting essentially of the amino acid sequence RSSQSLLHSNGYNYLD (SEQ ID NO:50), (b) a VL CDR2 comprising, consisting of, or consisting essentially of the amino acid sequence LGSNRAS (SEQ ID NO:51), and (c) a VL CDR3 comprising, consisting of, or consisting essentially of the amino acid sequence MQALQTPLT (SEQ ID NO:52) or MQALQTPLT (SEQ ID NO:53), as shown in Table 4.

In some embodiments, the OX40 antigen-binding domain comprises the VL framework regions described herein.

In another embodiment, an antigen-binding domain described herein, which specifically binds to OX40 (e.g., human OX40), comprises a heavy chain variable region (VH) comprising:

(a) a VH CDR1 comprising, consisting of, or consisting essentially of the amino acid sequence GSAMH (SEQ ID NO:47), (b) a VH CDR2 comprising, consisting of, or consisting essentially of the amino acid sequence RIRSKANSYATAYAASVKG (SEQ ID NO:48), and (c) a VH CDR3 comprising, consisting of, or consisting essentially of the amino acid sequence GIYDSSGYDY (SEQ ID NO:49), as shown in Table 4.

In some embodiments, the OX40 antigen-binding domain comprises the VH frameworks described herein. In specific embodiments, the OX40 antigen-binding domain comprises the VH framework regions of an antibody described herein.

TABLE 4

VL CDR amino acid sequences of anti-OX40 antibodies *

| Antibody | VL CDR1 (SEQ ID NO:) | VL CDR2 (SEQ ID NO:) | VL CDR3 (SEQ ID NO:) |
|---|---|---|---|
| pab1949w | RSSQSLLHSNGYNYLD (50) | LGSNRAS (51) | MQALQTPLT (53) |
| pab2049w | RSSQSLLHSNGYNYLD (50) | LGSNRAS (51) | MQGSKWPLT (52) |

* The VL CDRs in Table 4 are determined according to Kabat.

TABLE 5

VH CDR amino acid sequences of anti-OX40 antibodies *

| Antibody (SEQ ID NO:) | VH CDR1 (SEQ ID NO:) | VH CDR2 (SEQ ID NO:) | VH CDR3 (SEQ ID NO:) |
|---|---|---|---|
| pab1949w | GSAMH (47) | RIRSKANSYATAYAA SVKG (48) | GIYDSSGYDY (49) |
| pab2049w | GSAMH (47) | RIRSKANSYATAYAA SVKG (48) | GIYDSSGYDY (49) |

* The VH CDRs in Table 5 are determined according to Kabat.

In certain embodiments, provided herein is an antigen-binding domain which specifically binds to OX40 (e.g., human OX40) and comprises light chain variable region (VL) CDRs and heavy chain variable region (VH) CDRs of pab1949w, or pab2049w, for example as set forth in Tables 4 and 5 (i.e., SEQ ID NOs:47-52 or SEQ ID NOs:47-51 and 53).

In certain embodiments, an OX40 antigen-binding domain comprises a light chain variable framework region that is derived from a human IGKV2-28 germline sequence (e.g., IGKV2-28*01, e.g., having amino acid sequence of SEQ ID NO:58).

In certain embodiments, the OX40 antigen-binding domain comprises a heavy chain variable framework region that is derived from human IGHV3-73 germline sequence (e.g., IGHV3-73*01, e.g., having amino acid sequence of SEQ ID NO:57).

In a specific embodiment, an antigen-binding domain that specifically binds to OX40 (e.g., human OX40) comprises a VL domain comprising the amino acid sequence of SEQ ID NO:55 or 56. In a specific embodiment, an antigen-binding domain that specifically binds to OX40 (e.g., human OX40) comprises a VL domain consisting of or consisting essentially of the amino acid sequence of SEQ ID NO:55 or 56.

In certain embodiments, an antigen-binding domain that specifically binds to OX40 (e.g., human OX40) comprises a VH domain comprising the amino acid sequence of SEQ ID NO:54. In some embodiments, an antigen-binding domain that specifically binds to OX40 (e.g., human OX40) comprises a VH domain consisting of or consisting essentially of the amino acid sequence of SEQ ID NO:54.

In certain embodiments, an antigen-binding domain that specifically binds to OX40 (e.g., human OX40) comprises a VH domain and a VL domain, wherein the VH domain and the VL domain comprise the amino acid sequences of SEQ ID NO:54 and SEQ ID NO:55 or 56, respectively. In certain embodiments, an antigen-binding domain that specifically binds to OX40 (e.g., human OX40) comprises a VH domain and a VL domain, wherein the VH domain and the VL domain consist of or consist essentially of the amino acid sequences of SEQ ID NO:54 and SEQ ID NO:55 or 56, respectively, e.g., as shown in Table 6.

TABLE 6

VH and VL sequences of exemplary anti-OX40 antibodies

| Antibody | VH (SEQ ID NO:) | VL (SEQ ID NO:) |
|---|---|---|
| pab2049w | 54 | 55 |
| pab1949w | 54 | 56 |

In specific aspects, provided herein is an antigen-binding domain comprising a light chain and heavy chain, e.g., a separate light chain and heavy chain. With respect to the light chain, in a specific embodiment, the light chain of an antigen-binding domain described herein is a kappa light chain. In another specific embodiment, the light chain of an antigen-binding domain described herein is a lambda light chain. In yet another specific embodiment, the light chain of an antigen-binding domain described herein is a human kappa light chain or a human lambda light chain. In a particular embodiment, an antigen-binding domain described herein, which immunospecifically binds to an OX40 polypeptide (e.g., human OX40) comprises a light chain wherein the amino acid sequence of the VL domain comprises the sequence set forth in SEQ ID NO:55 or 56, and wherein the constant region of the light chain comprises the amino acid sequence of a human kappa light chain constant region. In another particular embodiment, an antigen-binding domain described herein, which immunospecifically binds to OX40 (e.g., human OX40) comprises a light chain wherein the amino acid sequence of the VL domain comprises the sequence set forth in SEQ ID NO:55 or 56 and wherein the constant region of the light chain comprises the amino acid sequence of a human lambda light chain constant region. In a specific embodiment, an antigen-binding domain described herein, which immunospecifically binds to OX40 (e.g., human OX40) comprises a light chain wherein the amino acid sequence of the VL domain comprises the sequence set forth in SEQ ID NO:55 or 56 and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat E A et al., (1991) supra.

In a particular embodiment, an antigen-binding domain described herein, which specifically binds to OX40 (e.g., human OX40) comprises a light chain comprising the amino acid sequence set forth in SEQ ID NO:67 or 69.

With respect to the heavy chain, in a specific embodiment, the heavy chain of an antigen-binding domain described herein can be an alpha (α), delta (δ), epsilon (ε), gamma (γ) or mu (µ) heavy chain. In another specific embodiment, the heavy chain of an antigen-binding domain described can comprise a human alpha (α), delta (δ), epsilon (ε), gamma (γ) or mu (µ) heavy chain. In a particular embodiment, an antigen-binding domain described herein, which immunospecifically binds to OX40 (e.g., human OX40), comprises a heavy chain wherein the amino acid sequence of the VH domain can comprise the sequence set forth in SEQ ID NO:54 and wherein the constant region of the heavy chain comprises the amino acid sequence of a human gamma (γ) heavy chain constant region. In a specific embodiment, an antigen-binding domain described herein, which specifically binds to OX40 (e.g., human OX40), comprises a heavy chain wherein the amino acid sequence of the VH domain comprises the sequence set forth in SEQ ID NO:54, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In a particular embodiment, an antigen-binding domain described herein, which specifically binds to OX40 (e.g., human OX40), comprises a heavy chain comprising the amino acid sequence set forth in SEQ ID NO:61. In another embodiment, an antigen-binding domain described herein, which specifically binds to OX40 (e.g., human OX40), comprises a heavy chain comprising the amino acid sequence set forth in SEQ ID NO:62. In another embodiment, an antigen-binding domain described herein, which specifically binds to OX40 (e.g., human OX40), comprises a heavy chain comprising the amino acid sequence set forth in SEQ ID NO:63. In another embodiment, an antigen-binding domain described herein, which specifically binds to OX40 (e.g., human OX40), comprises a heavy chain comprising the amino acid sequence set forth in SEQ ID NO:64. In another embodiment, an antigen-binding domain described herein, which specifically binds to OX40 (e.g., human OX40), comprises a heavy chain comprising the amino acid sequence set forth in SEQ ID NO:65. In another embodiment, an antigen-binding domain described herein, which specifically binds to OX40 (e.g., human OX40), comprises a heavy chain comprising the amino acid sequence set forth in SEQ ID NO:71.

In a specific embodiment, an antigen-binding domain described herein, which immunospecifically binds to OX40 (e.g., human OX40), comprises a VL domain and a VH domain comprising any amino acid sequences described herein, wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In another specific embodiment, an antigen-binding domain described herein, which immunospecifically binds to OX40 (e.g., human OX40) comprises a VL domain and a VH domain comprising any amino acid sequences described herein, wherein the constant regions comprise the amino acid sequences of the constant regions of an IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule. In a particular embodiment, the constant regions comprise the amino acid sequences of the constant regions of a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In another specific embodiment, an antigen-binding domain described herein, which immunospecifically binds to OX40 (e.g., human OX40), comprises a VL domain and a VH domain comprising any amino acid sequences described herein, wherein the constant regions comprise the amino acid sequences of the constant regions of a human $IgG_1$ (e.g., allotypes G1m3, G1m17,1 or G1m17,1,2), human $IgG_2$, or human $IgG_4$. In a particular embodiment, an antigen-binding domain described herein, which immunospecifically binds to OX40 (e.g., human OX40), comprises a VL domain and a VH domain comprising any amino acid sequences described herein, wherein the constant regions comprise the amino acid sequences of the constant region of a human $IgG_1$ (allotype G1m3). Non-limiting examples of human constant regions are described in the art, e.g., see Kabat E A et al., (1991) supra.

In another embodiment, an antigen-binding domain described herein, which specifically binds to OX40 (e.g., human OX40), comprises a light chain comprising the amino acid sequence set forth in SEQ ID NO:67 and a heavy chain comprising the amino acid sequence set forth in SEQ ID NO:61, 62, 63, 64, 65, or 71. In another embodiment, an antigen-binding domain described herein, which specifically binds to OX40 (e.g., human OX40), comprises a light chain comprising the amino acid sequence set forth in SEQ ID NO:69 and a heavy chain comprising the amino acid sequence set forth in SEQ ID NO:61, 62, 63, 64, 65, or 71.

In certain embodiments, an antigen-binding domain described herein, which immunospecifically binds to OX40 (e.g., human OX40), comprises a VL domain having at least 70%, at least 75%, at least 80%, at least 85%, at least 90%, at least 95%, or at least 98% sequence identity to the amino acid sequence of the VL domain of pab1949w or pab2049w (i.e., SEQ ID NO:55 or 56), e.g., wherein the antigen-binding domain comprises VL CDRs that are identical to the VL CDRs of pab1949w or pab2049w.

In certain embodiments, an antigen-binding domain described herein, which immunospecifically binds to OX40 (e.g., human OX40), comprises a VH domain having at least 70%, at least 75%, at least 80%, at least 85%, at least 90%, at least 95%, or at least 98% sequence identity to the amino acid sequence of the VH domain of pab1949w or pab2049w (i.e., SEQ ID NO:54), e.g., wherein the antigen-binding domain comprises VH CDRs that are identical to the VH CDRs of pab1949w or pab2049w.

In certain embodiments, an antigen-binding domain described herein, which immunospecifically binds to OX40 (e.g., human OX40), comprises: (i) a VL domain having at least 70%, at least 75%, at least 80%, at least 85%, at least 90%, at least 95%, or at least 98% sequence identity to the amino acid sequence of the VL domain of pab1949w or pab2049w (i.e., SEQ ID NO:55 or 56); and (ii) a VH domain having at least 70%, at least 75%, at least 80%, at least 85%, at least 90%, at least 95%, or at least 98% sequence identity to the amino acid sequence of the VH domain of pab1949w or pab2049w (i.e., SEQ ID NO:54), e.g., wherein the antibody comprises VL CDRs and VH CDRs that are identical to the VL CDRs and VH CDRs of pab1949w or pab2049w.

In specific aspects, provided herein is an antigen-binding domain which competes (e.g., in a dose dependent manner) for specific binding to OX40 (e.g., human OX40), with an antigen-binding domain comprising a VL domain having the amino acid sequence set forth in SEQ ID NO:55 or 56, and a VH domain having the amino acid sequence set for the in SEQ ID NO:54.

In a specific embodiment, an antigen-binding domain described herein is one that is competitively blocked (e.g., in a dose dependent manner) by an antigen-binding domain comprising a VL domain having the amino acid sequence set forth in SEQ ID NO:55 or 56 and a VH domain having the amino acid sequence set forth in SEQ ID NO:54 for specific binding to OX40 (e.g., human OX40).

Assays known to one of skill in the art or described herein (e.g., X-ray crystallography, hydrogen/deuterium exchange coupled with mass spectrometry (e.g., liquid chromatography electrospray mass spectrometry), alanine scanning, ELISA assays, etc.) can be used to determine if two antibodies bind to the same epitope.

In a specific embodiment, an antigen-binding domain described herein immunospecifically binds to the same epitope as that bound by pab1949w or pab2049w or an epitope that overlaps the epitope.

In a specific aspect, the binding between an antigen-binding domain described herein and a variant OX40 is substantially weakened relative to the binding between the antigen-binding domain and a human OX40 sequence of SEQ ID NO:72, wherein the variant OX40 comprises the sequence of SEQ ID NO:72 except for an amino acid mutation (e.g., substitution) selected from the group consisting of: N60A, R62A, R80A, L88A, P93A, P99A, P115A, and a combination thereof or selected from the group consisting of N60A, R62A, R80A, L88A, and P93A, numbered according to SEQ ID NO: 72.

In some embodiments, the variant OX40 comprises the sequence of SEQ ID NO:72 except for any one mutation selected from the group consisting of: N60A, R62A, R80A, L88A, P93A, P99A, and P115A or selected from the group consisting of N60A, R62A, R80A, L88A, and P93A, numbered according to SEQ ID NO: 72. In some embodiments, the variant OX40 comprises the sequence of SEQ ID NO: 72 except for any two, three, four, five, six, or seven mutations selected from the group consisting of: W58A, N60A, R62A, R80A, L88A, P93A, P99A, and P115A or selected from the group consisting of N60A, R62A, R80A, L88A, and P93A, numbered according to SEQ ID NO: 72. In some embodiments, the variant OX40 comprises the sequence of SEQ ID NO:72 except for the amino acid mutations W58A, N60A, R62A, R80A, L88A, P93A, P99A, and P115A or except for the amino acid mutations of N60A, R62A, R80A, L88A, and P93A, numbered according to SEQ ID NO: 72.

In a specific aspect, an antigen-binding domain described herein binds to an epitope of a human OX40 sequence comprising, consisting essentially of, or consisting of a residue of SEQ ID NO:72 selected from the group consisting of: 58, 60, 62, 80, 88, 93, 99, 115, and a combination thereof or elected from the group consisting of: 60, 62, 80, 88, 93, and a combination thereof. In some embodiments, the epitope comprises, consists of, or consists essentially of any one residue, or any two, three, four, five, six, or seven residues, selected from the group consisting of: 58, 60, 62, 80, 88, 93, 99, and 115 of SEQ ID NO:72 or selected from the group consisting of: 60, 62, 80, 88, and 93 of SEQ ID NO:72. In some embodiments, the epitope comprises, consists essentially of, or consists of residues 58, 60, 62, 80, 88, 93, 99, and 115 of SEQ ID NO:72 or comprises residues 60, 62, 80, 88, and 93 of SEQ ID NO:72.

In a specific embodiment, an antigen-binding domain described herein binds to an epitope of SEQ ID NO:72 comprising, consisting essentially of, or consisting of a residue selected from the group consisting of: 58, 60, 62, 80, 88, 93, 99, 115, and a combination thereof or an epitope of SEQ ID NO:72 comprising, consisting essentially of, or consisting of a residue selected from the group consisting of: 60, 62, 80, 88, 93, and a combination thereof. In some embodiments, the epitope comprises any one residue, or any two, three, four, five, six, or seven residues, selected from the group consisting of: 58, 60, 62, 80, 88, 93, 99, and 115 of SEQ ID NO:72 or selected from the group consisting of: 60, 62, 80, 88, and 93 of SEQ ID NO:72. In some embodiments, the epitope comprises, consists of, or consists essentially of residues 58, 60, 62, 80, 88, 93, 99, and 115 of SEQ ID NO:72 or comprises residues 60, 62, 80, 88, and 93 of SEQ ID NO:72.

In a specific aspect, an antigen-binding domain described herein binds to at least one residue of SEQ ID NO:72 selected from the group consisting of: 58, 60, 62, 80, 88, 93, 99, 115, and a combination thereof or selected from the group consisting of: 60, 62, 80, 88, 93, and a combination thereof. In some embodiments, an antigen-binding domain described herein binds to any one residue, or any two, three, four, five, six, or seven residues, selected from the group consisting of: 58, 60, 62, 80, 88, 93, 99, and 115 of SEQ ID NO:72 or selected from the group consisting of: 60, 62, 80, 88, and 93 of SEQ ID NO:72. In some embodiments, an antigen-binding domain described herein binds to residues 58, 60, 62, 80, 88, 93, 99, and 115 of SEQ ID NO:72. In some embodiments, an antigen-binding domain described herein binds to residues 60, 62, 80, 88, and 93 of SEQ ID NO:72.

In a specific aspect, an antigen-binding domain described herein exhibits, as compared to binding to a human OX40 sequence of SEQ ID NO:72, reduced or absent binding to a protein identical to SEQ ID NO:72 except for the presence of an amino acid mutation (e.g., substitution) selected from the group consisting of: N60A, R62A, R80A, L88A, P93A, P99A, P115A, and a combination thereof or selected from the group consisting of: N60A, R62A, R80A, L88A, P93A, and a combination thereof, numbered according to SEQ ID NO: 72. In some embodiments, the protein is identical to SEQ ID NO:72 except for the presence of an amino acid mutation comprising any one mutation selected from the group consisting of: N60A, R62A, R80A, L88A, P93A, P99A, and P115A or selected from the group consisting of: N60A, R62A, R80A, L88A, and P93A, numbered according to SEQ ID NO: 72. In some embodiments, the protein is identical to SEQ ID NO:72 except for the presence of any two, three, four, five, six, or seven mutations selected from the group consisting of: W58A, N60A, R62A, R80A, L88A, P93A, P99A, and P115A or selected from the group consisting of N60A, R62A, R80A, L88A, and P93A, numbered according to SEQ ID NO: 72. In some embodiments, the protein is identical to SEQ ID NO:72 except for the presence of the amino acid substitutions W58A, N60A, R62A, R80A, L88A, P93A, P99A, and P115A or except for the presence of the amino acid substitutions N60A, R62A, R80A, L88A, and P93A, numbered according to SEQ ID NO: 72.

In certain embodiments, the epitope of an antigen-binding domain described herein is used as an immunogen to produce antibodies. See, e.g., Section 7.3 infra for methods for producing antibodies.

In specific aspects, an antigen-binding domain described herein, which immunospecifically binds to OX40 (e.g., human OX40), functions as an agonist when present in a monospecific bivalent format.

In certain embodiments, an antigen-binding domain described herein, which immunospecifically binds to OX40 (e.g., human OX40), increases OX40 (e.g., human OX40) activity, when present in a monospecific bivalent form, by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 (e.g., human OX40) activity without any antibody or with an unrelated antibody (e.g., an antibody that does not immunospecifically bind to OX40). In certain embodiments, an antigen-binding domain described herein, which immunospecifically binds to OX40 (e.g., human OX40), increases OX40 (e.g., human OX40) activity, when present in a monospecific bivalent form, by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) activity without any antibody or with an unrelated antibody (e.g., an antibody that does not immunospecifically bind to OX40). Non-limiting examples of OX40 (e.g., human OX40) activity can include OX40 (e.g., human OX40) signaling, cell proliferation, cell survival, and cytokine production (e.g., IL-2, TNF-α, IFN-γ, IL-4, IL-10, and/or IL-13). In certain embodiments, an antigen-binding domain described herein, which immunospecifically binds to OX40 (e.g., human OX40), induces, enhances, or increases an OX40 (e.g., human OX40) activity, when present in a monospecific bivalent form. In specific embodiments, an increase in an OX40 activity is assessed as described in the Examples, infra.

In certain embodiments, a multispecific (e.g., bispecific) antibody provided herein comprises an antigen-binding domain that binds to OX40 as described in U.S. Application No. 62/161,198, which is herein incorporated by reference in its entirety.

7.2.2 GITR Antigen-Binding Domains

In a particular embodiment, an antigen-binding domain described herein, which specifically binds to GITR (e.g., human GITR), comprises a light chain variable region (VL) comprising:

(a) a VL-CDR1 comprising the amino acid sequence of KSSQSLLNSX$_1$NQKNYLX$_2$ (SEQ ID NO:90), wherein X$_1$ is G or S; and X$_2$ is T or S;

(b) a VL-CDR2 comprising the amino acid sequence of WASTRES (SEQ ID NO:5); and (c) a VL-CDR3 comprising the amino acid sequence of QNX$_1$YSX$_2$PYT (SEQ ID NO:92), wherein X$_1$ is D or E; and X$_2$ is Y, F or S, as shown in Table 7.

In another embodiment, a GITR antigen-binding domain described herein, which specifically binds to GITR (e.g., human GITR), comprises a comprising a heavy chain variable region (VH) comprising:

(a) a VH-CDR1 comprising the amino acid sequence of X$_1$YX$_2$MX$_3$ (SEQ ID NO:87), wherein X$_1$ is D, E or G; X$_2$ is A or V; and X$_3$ is Y or H;

(b) a VH-CDR2 comprising the amino acid sequence of X$_1$IX$_2$TX$_3$SGX$_4$X$_5$X$_6$YNQKFX$_7$X$_8$ (SEQ ID NO:88), wherein X$_1$ is V or L; X$_2$ is R, K or Q; X$_3$ is Y or F; X$_4$ is D, E or G; X$_5$ is V or L; X$_6$ is T or S; X$_7$ is K, R or Q; and X$_8$ is D, E or G;

(c) a VH-CDR3 comprising the amino acid sequence of SGTVRGFAY (SEQ ID NO:3), as shown in Table 8.

In another particular embodiment, an antigen-binding domain described herein, which specifically binds to GITR (e.g., human GITR), comprises a light chain variable region (VL) comprising:

(a) a VL-CDR1 comprising the amino acid sequence of KSSQSLLNSX$_1$NQKNYLT (SEQ ID NO:4), wherein X$_1$ is G or S;

(b) a VL-CDR2 comprising the amino acid sequence of WASTRES (SEQ ID NO:5); and (c) a VL-CDR3 comprising the amino acid sequence of QNX$_1$YSX$_2$PYT (SEQ ID NO:6), wherein X$_1$ is D or E; and X$_2$ is Y or F, as shown in Table 7.

In another embodiment, a GITR antigen-binding domain described herein, which specifically binds to GITR (e.g., human GITR), comprises a comprising a heavy chain variable region (VH) comprising:

(a) a VH-CDR1 comprising the amino acid sequence of X$_1$YAMX$_2$ (SEQ ID NO:1), wherein X$_1$ is D, G, or E; and X$_2$ is Y or H;

(b) a VH-CDR2 comprising the amino acid sequence of X$_1$IRTYSGX$_2$VX$_3$YNQKFX$_4$X$_5$ (SEQ ID NO:2), wherein X$_1$ is V or L; X$_2$ is D or G; X$_3$ is T or S; X$_4$ is K, R, or Q; and X$_5$ is D, E, or G;

(c) a VH-CDR3 comprising the amino acid sequence of SGTVRGFAY (SEQ ID NO:3); as shown in Table 8.

TABLE 7

GITR VL CDR amino acid sequences *

| Antibody | VL CDR1 (SEQ ID NO:) | VL CDR2 (SEQ ID NO:) | VL CDR3 (SEQ ID NO:) |
|---|---|---|---|
| Consensus 1 | KSSQSLLNSX$_1$NQKNYLX$_2$, wherein X$_1$ is G or S; and X$_2$ is T or S (90) | WASTRES (5) | QNX$_1$YSX$_2$PYT, wherein X$_1$ is D or E; and X$_2$ is Y, F or S (92) |

TABLE 7-continued

GITR VL CDR amino acid sequences *

| Antibody | VL CDR1 (SEQ ID NO:) | VL CDR2 (SEQ ID NO:) | VL CDR3 (SEQ ID NO:) |
|---|---|---|---|
| Consensus 2 | KSSQSLLNSX$_1$NQKNYLT X$_1$ is G or S (4) | WASTRES (5) | QNX$_1$YSX$_2$PYT X$_1$ is D or E; and X$_2$ is Y or F (6) |
| pab1876w | KSSQSLLNSGNQKNYLT (14) | WASTRES (5) | QNDYSYPYT (16) |
| pab1967w | KSSQSLLNSSNQKNYLT (15) | WASTRES (5) | QNEYSFPYT (17) |
| pab1975w | KSSQSLLNSGNQKNYLT (14) | WASTRES (5) | QNDYSYPYT (16) |
| pab1979w | KSSQSLLNSGNQKNYLT (14) | WASTRES (5) | QNDYSYPYT (16) |

* The VL CDRs in Table 7 are determined according to Kabat.

TABLE 8

GITR VH CDR amino acid sequences *

| Antibody | VH CDR1 (SEQ ID NO:) | VH CDR2 (SEQ ID NO:) | VH CDR3 (SEQ ID NO:) |
|---|---|---|---|
| Consensus 1 | X$_1$YX$_2$MX$_3$ wherein X$_1$ is D, E or G; X$_2$ is A or V; and X$_3$ is Y or H (87) | X$_1$IX$_2$TX$_3$SGX$_4$X$_5$X$_6$YNQKFX$_7$X$_8$, wherein X$_1$ is V or L; X$_2$ is R, K or Q; X$_3$ is Y or F; X$_4$ is D, E or G; X$_5$ is V or L; X$_6$ is T or S; X$_7$ is K, R or Q; and X$_8$ is D, E or G (88) | SGTVRGFAY (3) |
| Consensus 2 | X$_1$YAMX$_2$ X$_1$ is D, G, or E; and X$_2$ is Y or H (1) | X$_1$IRTYSGX$_2$VX$_3$YNQKFX$_4$X$_5$ X$_1$ is V or L; X$_2$ is D or G; X$_3$ is T or S; X$_4$ is K, R, or Q; and X$_5$ is D, E, or G (2) | SGTVRGFAY (3) |
| pab1876w | DYAMY (7) | VIRTYSGDVTYNQKFKD (10) | SGTVRGFAY (3) |
| pab1967w | GYAMH (8) | LIRTYSGGVSYNQKFRE (11) | SGTVRGFAY (3) |
| pab1975w | EYAMH (9) | LIRTYSGGVSYNQKFQG (12) | SGTVRGFAY (3) |
| pab1979w | EYAMH (9) | VIRTYSGGVSYNQKFQE (13) | SGTVRGFAY (3) |

* The VH CDRs in Table 8 are determined according to Kabat.

In certain embodiments, provided herein is an antigen-binding domain which specifically binds to GITR (e.g., human GITR) and comprises light chain variable region (VL) CDRs and heavy chain variable region (VH) CDRs of pab1876, pab1967, pab1975, or pab1979, for example as set forth in Tables 1 and 2 (i.e., SEQ ID NOs:14, 5, 16, 7, 10, and 3; SEQ ID NOs:15, 5, 17, 8, 11, and 3; SEQ ID NOs:14, 5, 16, 9, 12, and 3; or SEQ ID NOs:14, 5, 16, 9, 13, and 3).

In certain embodiments, a GITR antigen-binding domain comprises a light chain variable framework region that is derived from human IGKV4-1 germline sequence (e.g., IGKV4-1*01, e.g., having amino acid sequence of SEQ ID NO:28).

In certain embodiments, the GITR antigen-binding domain comprises a heavy chain variable framework region that is derived from a human IGHV1-2 germline sequence (e.g., IGHV1-2*02, e.g., having amino acid sequence of SEQ ID NO:27).

In a specific embodiment, an antigen-binding domain that specifically binds to GITR (e.g., human GITR) comprises a VL domain comprising the amino acid sequence of SEQ ID NO:19, 21, 23, or 26. In a specific embodiment, an antigen-binding domain that specifically binds to GITR (e.g., human GITR) comprises a VL domain consisting of or consisting essentially of the amino acid sequence of SEQ ID NO:19, 21, 23, or 26.

In certain embodiments, an antigen-binding domain that specifically binds to GITR (e.g., human GITR) comprises a VH domain comprising the amino acid sequence of SEQ ID NO:18, 20, 22, 24, or 25. In some embodiments, an antigen-binding domain that specifically binds to GITR (e.g., human GITR) comprises a VH domain consisting of or consisting essentially of the amino acid sequence of SEQ ID NO:18, 20, 22, 24, or 25.

In certain embodiments, an antigen-binding domain that specifically binds to GITR (e.g., human GITR) comprises a VH domain and a VL domain, wherein the VH domain and the VL domain comprise the amino acid sequences of SEQ ID NOs:18 and 19; SEQ ID NOs:20 and 21; SEQ ID NOs:22 and 23; SEQ ID NOs:24 and 23; or SEQ ID NOs:25 and 26; respectively. In certain embodiments, an antigen-binding domain that specifically binds to GITR (e.g., human GITR)

comprises a VH domain and a VL domain, wherein the VH domain and the VL domain consist of or consist essentially of the amino acid sequences of SEQ ID NOs:18 and 19; SEQ ID NOs:20 and 21; SEQ ID NOs:22 and 23; SEQ ID NOs:24 and 23; or SEQ ID NOs:25 and 26; respectively, e.g., as shown in Table 9.

TABLE 9

VH and VL sequences of exemplary anti-GITR antibodies

| Antibody | VH (SEQ ID NO:) | VL (SEQ ID NO:) |
|---|---|---|
| pab1876w | 18 | 19 |
| pab1967w | 20 | 21 |
| pab1975w | 22 | 23 |
| pab1979w | 24 | 23 |

In specific aspects, provided herein is an antigen-binding domain comprising a light chain and heavy chain, e.g., a separate light chain and heavy chain. With respect to the light chain, in a specific embodiment, the light chain of an antigen-binding domain described herein is a kappa light chain. In another specific embodiment, the light chain of an antigen-binding domain described herein is a lambda light chain. In yet another specific embodiment, the light chain of an antigen-binding domain described herein is a human kappa light chain or a human lambda light chain. In a particular embodiment, an antigen-binding domain described herein, which immunospecifically binds to a GITR polypeptide (e.g., human GITR) comprises a light chain wherein the amino acid sequence of the VL domain comprises the sequence set forth in SEQ ID NO:19, 21, 23, or 26 and wherein the constant region of the light chain comprises the amino acid sequence of a human kappa light chain constant region. In another particular embodiment, an antigen-binding domain described herein, which immunospecifically binds to GITR (e.g., human GITR) comprises a light chain wherein the amino acid sequence of the VL domain comprises the sequence set forth in SEQ ID NO:19, 21, 23, or 26 and wherein the constant region of the light chain comprises the amino acid sequence of a human lambda light chain constant region. In a specific embodiment, an antigen-binding domain described herein, which immunospecifically binds to GITR (e.g., human GITR) comprises a light chain wherein the amino acid sequence of the VL domain comprises the sequence set forth in SEQ ID NO:19, 21, 23, or 26 and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat E A et al., (1991) supra.

In a particular embodiment, an antigen-binding domain described herein, which specifically binds to GITR (e.g., human GITR) comprises a light chain comprising the amino acid sequence set forth in SEQ ID NO:37 or 38.

With respect to the heavy chain, in a specific embodiment, the heavy chain of an antigen-binding domain described herein can be an alpha (α), delta (δ), epsilon (ε), gamma (γ) or mu (μ) heavy chain. In another specific embodiment, the heavy chain of an antigen-binding domain described can comprise a human alpha (α), delta (δ), epsilon (ε), gamma (γ) or mu (μ) heavy chain. In a particular embodiment, an antigen-binding domain described herein, which immunospecifically binds to GITR (e.g., human GITR), comprises a heavy chain wherein the amino acid sequence of the VH domain can comprise the sequence set forth in SEQ ID NO:18, 20, 22, 24, or 25 and wherein the constant region of the heavy chain comprises the amino acid sequence of a human gamma (γ) heavy chain constant region. In a specific embodiment, an antigen-binding domain described herein, which specifically binds to GITR (e.g., human GITR), comprises a heavy chain wherein the amino acid sequence of the VH domain comprises the sequence set forth in SEQ ID NO: 18, 20, 22, 24, or 25, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In a particular embodiment, an antigen-binding domain described herein, which specifically binds to GITR (e.g., human GITR), comprises a heavy chain comprising the amino acid sequence set forth in SEQ ID NO:31. In another embodiment, an antigen-binding domain described herein, which specifically binds to GITR (e.g., human GITR), comprises a heavy chain comprising the amino acid sequence set forth in SEQ ID NO:32. In another embodiment, an antigen-binding domain described herein, which specifically binds to GITR (e.g., human GITR), comprises a heavy chain comprising the amino acid sequence set forth in SEQ ID NO:33. In another embodiment, an antigen-binding domain described herein, which specifically binds to GITR (e.g., human GITR), comprises a heavy chain comprising the amino acid sequence set forth in SEQ ID NO:34. In another embodiment, an antigen-binding domain described herein, which specifically binds to GITR (e.g., human GITR), comprises a heavy chain comprising the amino acid sequence set forth in SEQ ID NO:35. In another embodiment, an antigen-binding domain described herein, which specifically binds to GITR (e.g., human GITR), comprises a heavy chain comprising the amino acid sequence set forth in SEQ ID NO:39.

In a specific embodiment, an antigen-binding domain described herein, which immunospecifically binds to GITR (e.g., human GITR) comprises a VL domain and a VH domain comprising any amino acid sequences described herein, wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In another specific embodiment, an antigen-binding domain described herein, which immunospecifically binds to GITR (e.g., human GITR) comprises a VL domain and a VH domain comprising any amino acid sequences described herein, wherein the constant regions comprise the amino acid sequences of the constant regions of an IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule. In a particular embodiment, the constant regions comprise the amino acid sequences of the constant regions of a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In another specific embodiment, an antigen-binding domain described herein, which immunospecifically binds to GITR (e.g., human GITR), comprises a VL domain and a VH domain comprising any amino acid sequences described herein, wherein the constant regions comprise the amino acid sequences of the constant regions of a human $IgG_1$ (e.g., allotypes G1m3, G1m17,1 or G1m17,1,2), human $IgG_2$, or human $IgG_4$. In a particular embodiment, an antigen-binding domain described herein, which immunospecifically binds to GITR (e.g., human GITR), comprises a VL domain and a VH domain comprising any amino acid sequences described herein, wherein the constant regions comprise the amino acid sequences of the constant region of a human IgG$_1$ (allotype Glm3). Non-limiting examples of human constant regions are described in the art, e.g., see Kabat E A et al., (1991) supra.

In another embodiment, an antigen-binding domain described herein, which specifically binds to GITR (e.g., human GITR), comprises a light chain comprising the amino acid sequence set forth in SEQ ID NO:37 and a heavy chain comprising the amino acid sequence set forth in SEQ ID NO:31, 32, 33, 34, 35, or 39.

In certain embodiments, an antigen-binding domain described herein, which immunospecifically binds to GITR (e.g., human GITR), comprises a VL domain having at least 70%, at least 75%, at least 80%, at least 85%, at least 90%, at least 95%, or at least 98% sequence identity to the amino acid sequence of the VL domain of pab1876w, pab1967w, pab1975w, or pab1979w (i.e., SEQ ID NO:19, 21, or 23), e.g., wherein the antigen-binding domain comprises VL CDRs that are identical to the VL CDRs of pab1876w, pab1967w, pab1975w, or pab1979w.

In certain embodiments, an antigen-binding domain described herein, which immunospecifically binds to GITR (e.g., human GITR), comprises a VH domain having at least 70%, at least 75%, at least 80%, at least 85%, at least 90%, at least 95%, or at least 98% sequence identity to the amino acid sequence of the VH domain of pab1876w, pab1967w, pab1975w, or pab1979w (i.e., SEQ ID NO:18, 20, 22, or 24), e.g., wherein the antigen-binding domain comprises VH CDRs that are identical to the VH CDRs of pab1876w, pab1967w, pab1975w, or pab1979w.

In certain embodiments, an antigen-binding domain described herein, which immunospecifically binds to GITR (e.g., human GITR), comprises: (i) a VL domain having at least 70%, at least 75%, at least 80%, at least 85%, at least 90%, at least 95%, or at least 98% sequence identity to the amino acid sequence of the VL domain of pab1876w, pab1967w, pab1975w, or pab1979w (i.e., SEQ ID NO:19, 21, or 23); and (ii) a VH domain having at least 70%, at least 75%, at least 80%, at least 85%, at least 90%, at least 95%, or at least 98% sequence identity to the amino acid sequence of the VH domain of pab1876w, pab1967w, pab1975w, or pab1979w (i.e., SEQ ID NO:18, 20, 22, or 24), e.g., wherein the antibody comprises VL CDRs and VH CDRs that are identical to the VL CDRs and VH CDRs of pab1876w, pab1967w, pab1975w, or pab1979w.

In specific aspects, provided herein is an antigen-binding domain which competes (e.g., in a dose dependent manner) for specific binding to GITR (e.g., human GITR), with an antigen-binding domain comprising a VH and VL domain having the amino acid sequences set forth in SEQ ID NOs:18 and 19; SEQ ID NOs:20 and 21, SEQ ID NOs:22 and 23 or SEQ ID NOs:24 and 23, respectively.

In a specific embodiment, an antigen-binding domain described herein is one that is competitively blocked (e.g., in a dose dependent manner) by an antigen-binding domain comprising a VH and VL domain having the amino acid sequences set forth in SEQ ID NOs:18 and 19; SEQ ID NOs:20 and 21, SEQ ID NOs:22 and 23 or SEQ ID NOs:24 and 23, respectively for specific binding to GITR (e.g., human GITR).

Assays known to one of skill in the art or described herein (e.g., X-ray crystallography, hydrogen/deuterium exchange coupled with mass spectrometry (e.g., liquid chromatography electrospray mass spectrometry), alanine scanning, ELISA assays, etc.) can be used to determine if two antibodies bind to the same epitope.

In a specific embodiment, an antigen-binding domain described herein immunospecifically binds to the same epitope as that bound by pab1876w, pab1967w, pab1975w, or pab1979w, or an epitope that overlaps the epitope.

In a specific aspect, the binding between an antigen-binding domain described herein and a variant GITR is substantially weakened relative to the binding between the antigen-binding domain and a human GITR sequence of residues 26 to 241 of SEQ ID NO: 41, wherein the variant GITR comprises the sequence of residues 26 to 241 of SEQ ID NO: 41 except for the presence of a D60A or G63A mutation, numbered according to SEQ ID NO: 41. In some embodiments, the variant GITR comprises the sequence of residues 26 to 241 of SEQ ID NO: 41 except for the presence of a D60A and a G63A mutation, numbered according to SEQ ID NO: 41.

In a specific aspect, an antigen-binding domain described herein binds to an epitope of a human GITR sequence comprising, consisting essentially of, or consisting of at least one residue in amino acids 60-63 of SEQ ID NO:41. In some embodiments, the epitope comprises, consists essentially of, or consists of amino acids 60-63 of SEQ ID NO:41.

In a specific embodiment, an antigen-binding domain described herein binds to an epitope of human GITR comprising, consisting essentially of, or consisting of a residue selected from the group consisting of: residues 60, 62, and 63, and a combination thereof of SEQ ID NO:41. In some embodiments, the epitope comprises, consists essentially of, or consists of any one residue, or any two, or three residues, selected from the group consisting of: residues 60, 62, and 63 of SEQ ID NO:41.

In a specific aspect, an antigen-binding domain described herein exhibits, as compared to binding to a human GITR sequence of residues 26 to 241 of SEQ ID NO: 41, reduced or absent binding to a protein identical to residues 26 to 241 of SEQ ID NO: 41 except for the presence of an amino acid mutation (e.g., substitution) selected from the group consisting of: D60A and G63A, numbered according to SEQ ID NO: 41. In some embodiments, the substitution is D60A, numbered according to SEQ ID NO: 41. In some embodiments, the substitution is G63A, numbered according to SEQ ID NO: 41.

In certain embodiments, the epitope of an antigen-binding domain described herein is used as an immunogen to produce antibodies. See, e.g., Section 7.3 infra for methods for producing antibodies.

In specific aspects, an antigen-binding domain described herein, which immunospecifically binds to GITR (e.g., human GITR), functions as an agonist when present in a monospecific bivalent format.

In certain embodiments, an antigen-binding domain described herein, which immunospecifically binds to GITR (e.g., human GITR), increases GITR (e.g., human GITR) activity, when present in a monospecific bivalent form, by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to GITR (e.g., human GITR) activity without any antibody or with an unrelated antibody (e.g., an antibody that does not immunospecifically bind to GITR). In certain embodiments, an antigen-binding domain described herein, which immunospecifically binds to GITR (e.g., human GITR), increases GITR (e.g., human GITR) activity, when present in a monospecific bivalent form, by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to GITR (e.g., human GITR) activity without any antibody or with an unrelated antibody (e.g., an antibody that does not immunospecifically bind to GITR). Non-limiting examples of GITR (e.g., human GITR) activity can include GITR (e.g., human GITR) signaling, cell proliferation, cell survival, and cytokine production (e.g., IL-2, TNF-α, IFN-γ, IL-4, IL-10, and/or IL-13). In certain embodiments, an antigen-binding domain described herein, which immunospecifically binds to GITR (e.g., human GITR), induces, enhances, or increases a GITR (e.g., human GITR) activity, when present in a monospecific bivalent form. In specific embodiments, an increase in a GITR activity is assessed as described in the Examples, infra.

In certain embodiments, a multispecific (e.g., bispecific) antibody provided herein comprises an antigen-binding domain that binds to GITR as described in International Application No. PCT/US2015/032895, which is herein incorporated by reference in its entirety.

7.2.3 Antigen-Binding Domains

In certain aspects, an antigen-binding domain described herein may be described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antigen-binding domain can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antigen-binding domains that specifically bind to GITR or OX40 (e.g., human GITR or OX40) and comprise the Chothia VL CDRs of a VL of pab1876w, pab1967w, pab1975w, pab1979w, pab2049w, or pab1949w. In certain aspects, provided herein are antigen-binding domains that specifically bind to GITR or OX40 (e.g., human GITR or OX40) and comprise the Chothia VH CDRs of a VH of pab1876, pab1967, pab1975, pab1979, pab2049, or pab1949. In certain aspects, provided herein are antigen-binding domains that specifically bind to GITR or OX40 (e.g., human GITR or OX40) and comprise the Chothia VL CDRs of a VL of pab1876, pab1967, pab1975w, pab1979w, pab2049w, or pab1949w and comprise the Chothia VH CDRs of a VH of pab1876w, pab1967w, pab1975w, pab1979w, pab2049w, or pab1949w. In certain embodiments, antigen-binding domains that specifically bind to GITR or OX40 (e.g., human GITR or OX40) comprise one or more CDRs, in which the Chothia and Kabat CDRs have the same amino acid sequence. In certain embodiments, provided herein are antigen-binding domains that specifically bind to GITR or OX40 (e.g., human GITR or OX40) and comprise combinations of Kabat CDRs and Chothia CDRs.

In certain aspects, the CDRs of an antigen-binding domain can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are antigen-binding domains that specifically bind to GITR or OX40 (e.g., human GITR or OX40) and comprise CDRs of pab1876w, pab1967w, pab1975w, pab1979w, pab2049w, or pab1949w as determined by the IMGT numbering system, for example, as described in Lefranc M-P (1999) supra and Lefranc M-P et al., (1999) supra).

In certain aspects, the CDRs of an antigen-binding domain can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dithel, eds., Chapter 31, pp. 422-439, Springer-Verlag, Berlin (2001). In a particular embodiment, provided herein are antigen-binding domains that specifically bind to GITR or OX40 (e.g., human GITR or OX40) and comprise CDRs of pab1876w, pab1967w, pab1975w, pab1979w, pab2049w, or pab1949w as determined by the method in MacCallum R M et al.

In certain aspects, the CDRs of an antibody can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are antigen-binding domains that specifically bind to GITR or OX40 (e.g., human GITR or OX40) and comprise CDRs of pab1876w, pab1967w, pab1975w, pab1979w, pab2049w, or pab1949w as determined by the AbM numbering scheme.

In a specific embodiment, the position of one or more CDRs along the VH (e.g., CDR1, CDR2, or CDR3) and/or VL (e.g., CDR1, CDR2, or CDR3) region of an antigen-binding domain described herein may vary by one, two, three, four, five, or six amino acid positions so long as immunospecific binding to GITR or OX40 (e.g., human GITR or OX40) is maintained (e.g., substantially maintained, for example, at least 50%, at least 60%, at least 70%, at least 80%, at least 90%, at least 95%). For example, in one embodiment, the position defining a CDR of an antigen-binding domain described herein can vary by shifting the N-terminal and/or C-terminal boundary of the CDR by one, two, three, four, five, or six amino acids, relative to the CDR position of an antigen-binding domain described herein, so long as immunospecific binding to GITR or OX40 (e.g., human GITR or OX40) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antigen-binding domain described herein may vary (e.g., be shorter or longer) by one, two, three, four, five, or more amino acids, so long as immunospecific binding to GITR or OX40 (e.g., human GITR or OX40) is maintained (e.g., substantially maintained, for example, at least 50%, at least 60%, at least 70%, at least 80%, at least 90%, at least 95%).

In one embodiment, a VL CDR1, VL CDR2, VL CDR3, VH CDR1, VH CDR2, and/or VH CDR3 described herein may be one, two, three, four, five or more amino acids shorter than one or more of the CDRs described herein (e.g., SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53) so long as immunospecific binding to GITR or OX40 (e.g., human GITR or OX40) is maintained (e.g., substantially maintained, for example, at least 50%, at least 60%, at least 70%, at least 80%, at least 90%, at least 95%). In another embodiment, a VL CDR1, VL CDR2, VL CDR3, VH CDR1, VH CDR2, and/or VH CDR3 described herein may be one, two, three, four, five or more amino acids longer than one or more of the CDRs described herein (e.g., SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53) so long as immunospecific binding to GITR or OX40 (e.g., human GITR or OX40) is maintained (e.g., substantially maintained, for example, at least 50%, at least 60%, at least 70%, at least 80%, at least 90%, at least 95%). In another embodiment, the amino terminus of a VL CDR1, VL CDR2, VL CDR3, VH CDR1, VH CDR2, and/or VH CDR3 described herein may be extended by one, two, three, four, five or more amino acids compared to one or more of the CDRs described herein (e.g., SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53) so long as immunospecific binding to GITR OR OX40 (e.g., human GITR OR OX40) is maintained (e.g., substantially maintained, for example, at least 50%, at least 60%, at least 70%, at least 80%, at least 90%, at least 95%). In another embodiment, the carboxy terminus of a VL CDR1, VL CDR2, VL CDR3, VH CDR1, VH CDR2, and/or VH CDR3 described herein may be extended by one, two, three, four, five or more amino acids compared to one or more of the CDRs described herein (e.g., SEQ ID NO:1-6) so long as immunospecific binding to GITR OR OX40 (e.g., human GITR OR OX40) is maintained (e.g., substantially maintained, for example, at least 50%, at least 60%, at least 70%, at least 80%, at least 90%, at least 95%). In another embodiment, the amino terminus of a VL CDR1, VL CDR2, VL CDR3, VH CDR1, VH CDR2, and/or VH CDR3 described herein may be shortened by one, two, three, four, five or more amino acids compared to one or more of the CDRs described herein (e.g., SEQ ID NO:1-6) so long as immunospecific binding to GITR OR OX40 (e.g., human GITR OR OX40) is maintained (e.g., substantially maintained, for example, at least 50%, at least 60%, at least 70%, at least 80%, at least 90%, at least 95%). In one embodiment, the carboxy terminus of a VL CDR1, VL CDR2, VL CDR3, VH CDR1, VH CDR2, and/or VH CDR3 described herein may be shortened by one, two, three, four, five or more amino acids compared to one or more of the CDRs described herein (e.g., SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53) so long as immunospecific binding to GITR OR OX40 (e.g., human GITR OR OX40) is maintained (e.g., substantially maintained, for example, at least 50%, at least 60%, at least 70%, at least 80%, at least 90%, at least 95%). Any method known in the art can be used to ascertain whether immunospecific binding to GITR OR OX40 (e.g., human GITR OR OX40) is maintained, for example, the binding assays and conditions described in the "Examples" section (Section 8) provided herein.

In another particular embodiment, an antigen-binding domain described herein, which immunospecifically binds to GITR or OX40 (e.g., human GITR or OX40), comprises a heavy chain and a light chain, wherein (i) the heavy and light chains comprise a VH domain and a VL domain, respectively, wherein the VH CDR1, VH CDR2, VH CDR3, VL CDR1, VL CDR2, and VL CDR3 of the VH and VL domains comprise the amino acid sequences set forth in SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53, respectively; (ii) the light chain further comprises a constant light chain domain comprising the amino acid sequence of the constant domain of a human kappa light chain; and (iii) the heavy chain further comprises a constant heavy chain domain comprising the amino acid sequence of the constant domain of a human $IgG_1$ (optionally $IgG_1$ (allotype Glm3)) heavy chain.

In another particular embodiment, an antigen-binding domain described herein, which immunospecifically binds to GITR or OX40 (e.g., human GITR or OX40), comprises a heavy chain and a light chain, wherein (i) the heavy and light chains comprise a VH domain and a VL domain, respectively comprising the amino acid sequences set forth in SEQ ID NOs:18 and 19, SEQ ID NOs:20 and 21, SEQ ID NOs:22 and 23, SEQ ID NOs:24 and 23, SEQ ID NOs:25 and 26, SEQ ID NOs:54 and 55, or SEQ ID NOs:54 and 56, respectively; (ii) the light chain further comprises a constant domain comprising the amino acid sequence of the constant domain of a human kappa light chain; and (iii) the heavy chain further comprises a constant domain comprising the amino acid sequence of the constant domain of a human IgG$_1$ (optionally IgG$_1$ (allotype Glm3)) heavy chain.

In another particular embodiment, an antigen-binding domain described herein, which immunospecifically binds to GITR or OX40 (e.g., human GITR or OX40), comprises a heavy chain and a light chain, wherein (i) the heavy and light chains comprise a VH domain and a VL domain, respectively, wherein the VH CDR1, VH CDR2, VH CDR3, VL CDR1, VL CDR2, and VL CDR3 of the VH and VL domains comprise the amino acid sequences set forth in SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53, respectively; (ii) the light chain further comprises a constant light chain domain comprising the amino acid sequence of the constant domain of a human kappa light chain; and (iii) the heavy chain further comprises a constant heavy chain domain comprising the amino acid sequence of the constant domain of a human IgG$_4$ heavy chain.

In another particular embodiment, an antigen-binding domain described herein, which immunospecifically binds to GITR or OX40 (e.g., human GITR or OX40), comprises a heavy chain and a light chain, wherein (i) the heavy and light chains comprise a VH domain and a VL domain, respectively comprising the amino acid sequences set forth in SEQ ID NOs:18 and 19, SEQ ID NOs:20 and 21, SEQ ID NOs:22 and 23, SEQ ID NOs:24 and 23, SEQ ID NOs:25 and 26, SEQ ID NOs:54 and 55, or SEQ ID NOs:54 and 56, respectively; (ii) the light chain further comprises a constant domain comprising the amino acid sequence of the constant domain of a human kappa light chain; and (iii) the heavy chain further comprises a constant domain comprising the amino acid sequence of the constant domain of a human IgG$_4$ heavy chain.

In another particular embodiment, an antigen-binding domain described herein, which immunospecifically binds to GITR or OX40 (e.g., human GITR or OX40), comprises a heavy chain and a light chain, wherein (i) the heavy and light chains comprise a VH domain and a VL domain, respectively, wherein the VH CDR1, VH CDR2, VH CDR3, VL CDR1, VL CDR2, and VL CDR3 of the VH and VL domains comprise the amino acid sequences set forth in SEQ ID NOs:1-6, SEQ ID NOs:87, 88, 3, 90, 5, and 92; SEQ ID NOS:7, 10, 3, 14, 5, and 16; SEQ ID NOs:8, 11, 3, 15, 5, and 17; SEQ ID NOs:9, 12, 3, 14, 5, and 16; SEQ ID NOs:9, 13, 3, 14, 5, and 16; SEQ ID NOs:47-52, or SEQ ID NOs:47-51 and 53, respectively; (ii) the light chain further comprises a constant light chain domain comprising the amino acid sequence of the constant domain of a human kappa light chain; and (iii) the heavy chain further comprises a constant heavy chain domain comprising the amino acid sequence of the constant domain of a human IgG$_2$ heavy chain.

In another particular embodiment, an antigen-binding domain described herein, which immunospecifically binds to GITR or OX40 (e.g., human GITR or OX40), comprises a heavy chain and a light chain, wherein (i) the heavy and light chains comprise a VH domain and a VL domain, respectively comprising the amino acid sequences set forth in SEQ ID NOs:18 and 19, SEQ ID NOs:20 and 21, SEQ ID NOs:22 and 23, SEQ ID NOs:24 and 23, SEQ ID NOs:25 and 26, SEQ ID NOs:54 and 55, or SEQ ID NOs:54 and 56, respectively; (ii) the light chain further comprises a constant domain comprising the amino acid sequence of the constant domain of a human kappa light chain; and (iii) the heavy chain further comprises a constant domain comprising the amino acid sequence of the constant domain of a human IgG$_2$ heavy chain.

In another particular embodiment, an antigen-binding domain described herein, which immunospecifically binds to GITR or OX40 (e.g., human GITR or OX40), comprises a heavy chain and a light chain, wherein (a) a heavy chain comprising the amino acid sequence of SEQ ID NO: 59 with an amino acid substitution of N to A or Q at amino acid position 297; and (b) a light chain comprising the amino acid sequence of SEQ ID NO: 67 or 69.

In another particular embodiment, an antigen-binding domain described herein, which immunospecifically binds to GITR or OX40 (e.g., human GITR or OX40), comprises (a) a heavy chain comprising the amino acid sequence of SEQ ID NO: 59 or 29 with an amino acid substitution selected from the group consisting of: S to E at amino acid position 267, L to F at amino acid position 328, and both S to E at amino acid position 267 and L to F at amino acid position 328; and (b) a light chain comprising the amino acid sequence of SEQ ID NO: 67 or 69, or SEQ ID NO:37.

In specific embodiments, an antigen-binding domains described herein, which immunospecifically binds to GITR or OX40 (e.g., human GITR or OX40), comprises framework regions (e.g., framework regions of the VL domain and/or VH domain) that are human framework regions or derived from human framework regions. Non-limiting examples of human framework regions are described in the art, e.g., see Kabat E A et al., (1991) supra). In certain embodiment, an antigen-binding domain described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), are grafted onto homologous human or non-human primate acceptor frameworks. In one embodiment, the non-human primate acceptor frameworks are from Old World apes. In a specific embodiment, the Old World ape acceptor framework is from *Pan troglodytes, Pan paniscus* or *Gorilla gorilla*. In a particular embodiment, the non-human primate acceptor frameworks are from the chimpanzee *Pan troglodytes*. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are derived from the *cynomolgus* monkey *Macaca cynomolgus*. Non-human primate framework sequences are described in U.S. Patent Application Publication No. US 2005/0208625.

In another aspect, provided herein are antibodies that contain antigen-binding domains that bind the same or an overlapping epitope of GITR or OX40 (e.g., an epitope of human GITR or OX40) as an antibody described herein (e.g., pab1949w, pab2049w, or pab1876w). In certain embodiments, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antigen-binding fragment is determined using alanine scanning mutagenesis studies. In addition, antigen-binding fragments that recognize and bind to the same or overlapping epitopes of GITR and/or OX40 (e.g., human GITR and/or OX40) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as GITR or OX40. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., GITR or OX40 such as human GITR or OX40) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In one embodiment, a competition assay is performed using surface plasmon resonance (BIAcore®), e.g., by an 'in tandem approach' such as that described by Abdiche Y N et al., (2009) Analytical Biochem 386: 172-180, whereby GITR or OX40 antigen is immobilized on the chip surface, for example, a CM5 sensor chip and the anti-GITR or OX40 antibodies are then run over the chip. To determine if an antibody competes with an anti-GITR or OX40 antigen-binding domain described herein, the antibody containing the anti-GITR or OX40 antigen-binding domain is first run over the chip surface to achieve saturation and then the potential, competing antibody is added. Binding of the competing antibody can then be determined and quantified relative to a non-competing control.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein (e.g., antibody pab1949w, pab2049w, or pab1876w), or a chimeric or Fab antibody thereof, or an antibody comprising VH CDRs and VL CDRs of an antibody described herein (e.g., pab1949w, pab2049w, or pab1876w).

In another aspect, provided herein are antigen-binding domains that compete (e.g., in a dose dependent manner) for binding to GITR or OX40 (e.g., human OX40) with an antigen-binding domain described herein, as determined using assays known to one of skill in the art or described herein (e.g., ELISA competitive assays or surface plasmon resonance). In another aspect, provided herein are antigen-binding domains that competitively inhibit (e.g., in a dose dependent manner) an antigen-binding domain described herein (e.g., pab1949w, pab2049w, or pab1876w) from binding to GITR or OX40 (e.g., human GITR or OX40), as determined using assays known to one of skill in the art or described herein (e.g., ELISA competitive assays, or suspension array or surface plasmon resonance assay). In specific aspects, provided herein is an antigen-binding fragment which competes (e.g., in a dose dependent manner) for specific binding to GITR or OX40 (e.g., human GITR or OX40), with an antibody comprising the amino acid sequences described herein (e.g., VL and/or VH amino acid sequences of pab1949w, pab2049w, or pab1876w), as determined using assays known to one of skill in the art or described herein (e.g., ELISA competitive assays, or suspension array or surface plasmon resonance assay).

In certain embodiments, provided herein is an antigen-binding fragment that competes with an antigen-binding fragment described herein for binding to GITR or OX40 (e.g., human GITR or OX40) to the same extent that the antigen-binding fragment described herein self-competes for binding to GITR or OX40 (e.g., human GITR or OX40). In some embodiments, provided herein is a first antigen-binding antibody fragment that competes with an antigen-binding antibody fragment described herein for binding to GITR or OX40 (e.g., human GITR or OX40), wherein the first antigen-binding antibody fragment competes for binding in an assay comprising the following steps: (a) incubating GITR and/or OX40-transfected cells with the first antigen-binding antibody fragment in unlabeled form in a container; and (b) adding an antigen-binding antibody fragment described herein in labeled form in the container and incubating the cells in the container; and (c) detecting the binding of the antigen-binding antibody fragment described herein in labeled form to the cells. In certain embodiments, provided herein is a first antigen-binding antibody fragment that competes with an antigen-binding antibody fragment described herein for binding to GITR or OX40 (e.g., human GITR or OX40), wherein the competition is exhibited as reduced binding of the first antigen-binding antibody fragment to GITR or OX40 by more than 80% (e.g., 85%, 90%, 95%, or 98%, or between 80% to 85%, 80% to 90%, 85% to 90%, or 85% to 95%).

7.3 Antibody Production

Multispecific (e.g., bispecific) antibodies that immunospecifically bind to GITR and/or OX40 (e.g., human GITR and human OX40) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, a multispecific (e.g., bispecific) antibody described herein is a multispecific (e.g., bispecific) antibody (e.g., recombinant antibody) prepared, expressed, created or isolated by any means that involves creation, e.g., via synthesis, genetic engineering of DNA sequences. In certain embodiments, such a multispecific (e.g., bispecific) antibody comprises sequences (e.g., DNA sequences or amino acid sequences) that do not naturally exist within the antibody germline repertoire of an animal or mammal (e.g., human) in vivo.

Bispecific, bivalent antibodies, and methods of making them, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

A bispecific antibody as described herein can be generated according to the DuoBody technology platform (Genmab A/S) as described, e.g., in International Publication Nos. WO 2011/131746, WO 2011/147986, WO 2008/119353, and WO 2013/060867, and in Labrijn A F et al., (2013) PNAS 110(13): 5145-5150. The DuoBody technology can be used to combine one half of a first monospecific antibody containing two heavy and two light chains with one half of a second monospecific antibody containing two heavy and two light chains. The resultant heterodimer contains one heavy chain and one light chain from the first antibody paired with one heavy chain and one light chain from the second antibody. When both of the monospecific antibodies recognize different epitopes on different antigens, the resultant heterodimer is a bispecific antibody.

The DuoBody technology requires that each of the monospecific antibodies includes a heavy chain constant region with a single point mutation in the CH3 domain. The point mutations allow for a stronger interaction between the CH3 domains in the resultant bispecific antibody than between the CH3 domains in either of the monospecific antibodies. The single point mutation in each monospecific antibody is at residue 366, 368, 370, 399, 405, 407, or 409, numbered according to the EU numbering system, in the CH3 domain of the heavy chain constant region, as described, e.g., in International Publication No. WO 2011/131746. Moreover, the single point mutation is located at a different residue in one monospecific antibody as compared to the other monospecific antibody. For example, one monospecific antibody can comprise the mutation F405L (i.e., a mutation from phenylalanine to leucine at residue 405), while the other monospecific antibody can comprise the mutation K409R (i.e., a mutation from lysine to arginine at residue 409), numbered according to the EU numbering system. The heavy chain constant regions of the monospecific antibodies can be an $IgG_1$, $IgG_2$, $IgG_3$, or $IgG_4$ isotype (e.g., a human $IgG_1$ isotype), and a bispecific antibody produced by the DuoBody technology can retain Fc-mediated effector functions.

Another method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., IgG1 or IgG3) or different subclasses (e.g., IgG1 and IgG3, or IgG3 and IgG4).

In one embodiment, a bispecific antibody that binds to GITR and/or OX40 comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain;" R409D, K370E mutations in the "knobs chain" and D399K, E357K mutations in the "hole chain;" R409D, K370E mutations in the "knobs chain" and D399K, E357K mutations in the "hole chain;" a T366W mutation in the "knobs chain" and T366S, L368A, Y407V mutations in the "hole chain;" R409D, K370E mutations in the "knobs chain" and D399K, E357K mutations in the "hole chain;" Y349C, T366W mutations in one of the chains and E356C, T366S, L368A, Y407V mutations in the counterpart chain; Y349C, T366W mutations in one chain and S354C, T366S, L368A, Y407V mutations in the counterpart chain; Y349C, T366W mutations in one chain and S354C, T366S, L368A, Y407V mutations in the counterpart chain; and Y349C, T366W mutations in one chain and S354C, T366S, L368A, Y407V mutations in the counterpart chain (numbering according to the EU numbering system). Bispecific antibodies that bind to GITR and/or OX40 can, in some instances contain, IgG1 and IgG1, IgG4 and IgG2, IgG4 and IgG2, IgG4 and IgG3, or IgG1 and IgG3 chain heterodimers. Such heterodimeric heavy chain antibodies, can routinely be engineered by, for example, modifying selected amino acids forming the interface of the CH3 domains in human IgG4 and the IgG1 or IgG3 so as to favor heterodimeric heavy chain formation.

In particular embodiments, a multispecific (e.g., bispecific) antibody can be a chimeric antibody or a humanized antibody. In certain embodiments, a multispecific (e.g., bispecific) antibody can be a F(ab')$_2$ fragment. A F(ab')$_2$ fragment contains the two antigen-binding arms of a tetrameric antibody molecule linked by disulfide bonds in the hinge region.

Multispecific (e.g., bispecific) antibodies described herein can be generated by any technique known to those of skill in the art. For example, F(ab')$_2$ fragments described herein can be produced by proteolytic cleavage of immunoglobulin molecules, using enzymes such as pepsin.

In a certain aspect, provided herein is a method of making an antibody or an antigen-binding fragment which immunospecifically binds to GITR and/or OX40 (e.g., human GITR and/or OX40) comprising culturing a cell or cells described herein. In a certain aspect, provided herein is a method of making an antibody or antigen-binding fragment which immunospecifically binds to GITR and/or OX40 (e.g., human GITR and/or OX40) comprising expressing (e.g., recombinantly expressing) the antibody or antigen-binding fragment using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment obtained from the cell or host cell.

Antigen-binding fragments of antibodies can be prepared, e.g., from monoclonal antibodies, using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Further, the antibodies or antigen-binding fragments thereof described herein can also be generated using various phage display methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody or fragment that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate antibodies, including human antibodies, and expressed in any desired host, including mammalian cells, insect cells, plant cells, yeast, and bacteria, e.g., as described below. Techniques to recombinantly produce antibodies such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

In particular embodiments, a human antibody comprises an antigen-binding domain described herein which binds to the same epitope of GITR or OX40 (e.g., human GITR or OX40) as an anti-GITR or OX40 antigen-binding fragment thereof described herein. In particular embodiments, a human antibody comprises an antigen-binding fragment which competitively blocks (e.g., in a dose-dependent manner) any one of the antigen-binding fragments described herein, (e.g., pab1949w, pab2049w, pab1876w, pab1967w, pab1975w, or pab1979w) from binding to GITR or OX40 (e.g., human GITR or OX40). Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., OX40). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies or antigen-binding fragments which specifically bind to GITR or OX40 (e.g., human GIT or OX40) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., OX40 (e.g., human OX40)). Such methods are known and are described in the art, see, e.g., Shinmoto H et al., (2004) Cytotechnology 46: 19-23; Naganawa Y et al., (2005) Human Antibodies 14: 27-31.

7.3.1 Polynucleotides

In certain aspects, provided herein are polynucleotides comprising a nucleotide sequence encoding an antibody described herein or a fragment thereof (e.g., a variable light chain region and/or variable heavy chain region) that immunospecifically binds to a GITR and/or OX40 (e.g., human GITR and/or OX40) antigen, and vectors, e.g., vectors comprising such polynucleotides for recombinant expression in host cells (e.g., *E. coli* and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which immunospecifically bind to a GITR and/or OX40 polypeptide (e.g., human GITR and/or OX40) and comprises an amino acid sequence as described herein, as well as antibodies that compete with such antibodies for binding to a GITR and/or OX40 polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain or light chain variable domain comprising the VL CDRs of antibodies described herein (see, e.g., Tables 1, 4, and 7). The polynucleotides can comprise nucleotide sequences encoding a heavy chain or heavy chain variable domain comprising the VH CDRs of antibodies described herein (see, e.g., Tables 1, 5, and 8). In specific embodiments, a polynucleotide described herein encodes a VL domain comprising the amino acid sequence set forth in SEQ ID NO:19, 21, 23, 26, 55, or 56. In specific embodiments, a polynucleotide described herein encodes a VH domain comprising the amino acid sequence set forth in SEQ ID NO:18, 20, 22, 24, 25, and 54.

In particular embodiments, provided herein are polynucleotides comprising a nucleotide sequence encoding an anti-GITR or OX40 antigen-binding domain comprising three VL chain CDRs, e.g., containing VL CDR1, VL CDR2, and VL CDR3 of any one of antibodies described herein (e.g., see Tables 1, 4, and 7). In specific embodiments, provided herein are polynucleotides comprising three VH chain CDRs, e.g., containing VH CDR1, VH CDR2, and VH CDR3 of any one of antibodies described herein (e.g., see Tables 1, 5, and 8). In specific embodiments, provided herein are polynucleotides comprising a nucleotide sequence encoding an anti-GITR or OX40 antigen-binding domain comprising three VH chain CDRs, e.g., containing VL CDR1, VL CDR2, and VL CDR3 of any one of antibodies described herein (e.g., see Tables 1, 4, and 7) and three VH chain CDRs, e.g., containing VH CDR1, VH CDR2, and VH CDR3 of any one of antibodies described herein (e.g., see Tables 1, 5, and 8).

In certain embodiments, a polynucleotide described herein comprises a nucleotide sequence encoding an antibody or antigen-binding domain provided herein comprising a light chain variable region comprising an amino acid sequence described herein (e.g., SEQ ID NO:19, 21, 23, 26, 55, or 56), wherein the antibody or antigen-binding domain immunospecifically binds to GITR or OX40 (e.g., human GITR or OX40).

In certain embodiments, a polynucleotide described herein comprises a nucleotide sequence encoding an antibody or antigen-binding domain provided herein comprising a heavy chain variable region comprising an amino acid sequence described herein (e.g., SEQ ID NO:18, 20, 22, 24, 25, or 54), wherein the antibody or antigen-binding domain immunospecifically binds to GITR or OX40 (e.g., human GITR or OX40).

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody, which immunospecifically binds to GITR and/or OX40 (e.g., human GITR and/or OX40), wherein the antibody comprises a light chain, wherein the amino acid sequence of the VL domain can comprise the amino acid sequence set forth in SEQ ID NO:19, 21, 23, 26, 55, or 56 and wherein the constant region of the light chain comprises the amino acid sequence of a human kappa light chain constant region. In another particular embodiment, a polynucleotide provided herein comprises a nucleotide sequence encoding an antibody, which immunospecifically binds to GITR and/or OX40 (e.g., human GITR and/or OX40), and comprises a light chain, wherein the amino acid sequence of the VL domain can comprise the amino acid sequence set forth in SEQ ID NO:19, 21, 23, 26, 55, or 56, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to GITR and/or OX40 (e.g., human GITR and/or OX40), wherein the antibody comprises a heavy chain, wherein the amino acid sequence of the VH domain can comprise the amino acid sequence set forth in SEQ ID NO:18, 20, 22, 24, 25, or 54, and wherein the constant region of the heavy chain comprises the amino acid sequence of a human gamma (γ) heavy chain constant region.

In a certain embodiment, a polynucleotide provided herein comprises a nucleotide sequence(s) encoding a VH domain and/or a VL domain of an antibody described herein (such as SEQ ID NO:18, 20, 22, 24, 25, or 54 for the VH domain and/or SEQ ID NO:19, 21, 23, 26, 55, or 56 for the VL domain), which immunospecifically binds to GITR and/or OX40 (e.g., human OX40).

In yet another specific embodiment, a polynucleotide provided herein comprises a nucleotide sequence encoding an antibody described herein, which immunospecifically binds GITR and/or OX40 (e.g., human OX40), wherein the antibody comprises a VL domain and a VH domain comprising any amino acid sequences described herein, wherein the constant regions comprise the amino acid sequences of the constant regions of a human IgG$_1$ (e.g., allotype 1, 17, or 3), human IgG$_2$, or human IgG$_4$.

In a specific embodiment, provided herein are polynucleotides comprising a nucleotide sequence encoding an anti-OX40 antibody or domain thereof, designated herein, see, e.g., Tables 1-9.

Also provided herein are polynucleotides encoding an anti-GITR and/or OX40 antibody or a fragment thereof that are optimized, e.g., by codon/RNA optimization, replacement with heterologous signal sequences, and elimination of mRNA instability elements. Methods to generate optimized nucleic acids encoding an anti-GIR and/or OX40 antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-GITR and/or OX40 antibody described herein or a fragment thereof (e.g., VL domain or VH domain) can hybridize to an antisense (e.g., complementary) polynucleotide of an unoptimized polynucleotide sequence encoding an anti-GITR and/or OX40 antibody described herein or a fragment thereof (e.g., VL domain or VH domain). In specific embodiments, an optimized nucleotide sequence encoding an anti-GITR and/or OX40 antibody described herein or a fragment hybridizes under high stringency conditions to antisense polynucleotide of an unoptimized polynucleotide sequence encoding an anti-GITR and/or OX40 antibody described herein or a fragment thereof. In a specific embodiment, an optimized nucleotide sequence encoding an anti-GITR and/or OX40 antibody described herein or a fragment thereof hybridizes under high stringency, intermediate stringency, or lower stringency hybridization conditions to an antisense polynucleotide of an unoptimized nucleotide sequence encoding an anti-GITR and/or OX40 antibody described herein or a fragment thereof. Information regarding hybridization conditions has been described, see, e.g., U.S. Patent Application Publication No. US 2005/0048549 (e.g., paragraphs 72-73), which is incorporated herein by reference.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain (e.g., SEQ ID NO:18, 20, 22, 24, 25, 54) and/or VL domain (e.g., SEQ ID NO:19, 21, 23, 25, 55, or 56) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

7.3.2 Cells and Vectors

In certain aspects, provided herein are cells (e.g., host cells) expressing (e.g., recombinantly) antibodies described herein which specifically bind to GITR and/or OX40 (e.g., human GITR and/or OX40) and related polynucleotides and expression vectors. Provided herein are vectors (e.g., expression vectors) comprising polynucleotides comprising nucleotide sequences encoding anti-GITR and/or OX40 antibodies or a fragment for recombinant expression in host cells, preferably in mammalian cells. Also provided herein are host cells comprising such vectors for recombinantly expressing anti-GITR and/or OX40 antibodies described herein (e.g., human or humanized antibody). In a particular aspect, provided herein are methods for producing an antibody described herein, comprising expressing such antibody in a host cell.

Recombinant expression of an antibody or fragment thereof described herein (e.g., a heavy or light chain of an antibody described herein) that specifically binds to GITR and/or OX40 (e.g., human OX40) involves construction of an expression vector containing a polynucleotide that encodes the antibody or fragment. Once a polynucleotide encoding an antibody or fragment thereof (e.g., heavy or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., an antibody comprising the CDRs of pab1949w, pab2049w, pab1876w, pab1967w, pab1975w, or pab1979w) or a fragment thereof. Thus, provided herein are host cells containing a polynucleotide encoding an antibody described herein (e.g., an antibody comprising the CDRs of pab1949w, pab2049w, pab1876w, pab1967w, pab1975w, or pab1979w) or fragments thereof (e.g., a heavy or light chain thereof, or fragment thereof), operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein (e.g., an antibody comprising the CDRs of pab1949w, pab2049w, pab1876w, pab1967w, pab1975w, or pab1979w), or a fragment thereof. In specific embodiments, a host cell contains two different vectors, a first vector comprising a polynucleotide encoding a heavy chain or a heavy chain variable region of an antibody described herein (e.g., an antibody comprising the CDRs of pab1949w, pab2049w, pab1876w, pab1967w, pab1975w, or pab1979w), or a fragment thereof, and a second vector comprising a polynucleotide encoding a light chain or a light chain variable region of an antibody described herein (e.g., an antibody comprising the CDRs of pab1949w, pab2049w, pab1876w, pab1967w, pab1975w, or pab1979w), or a fragment thereof. In other embodiments, a first host cell comprises a first vector comprising a polynucleotide encoding a heavy chain or a heavy chain variable region of an antibody described herein (e.g., an antibody comprising the CDRs of pab1949w, pab2049w, pab1876w, pab1967w, pab1975w, or pab1979w), or a fragment thereof, and a second host cell comprises a second vector comprising a polynucleotide encoding a light chain or a light chain variable region of an antibody described herein (e.g., an antibody comprising the CDRs of pab1949w, pab2049w, pab1876w, pab1967w, pab1975w, or pab1979w). In specific embodiments, a heavy chain/heavy chain variable region expressed by a first cell associated with a light chain/light chain variable region of a second cell to form an anti-GITR and/or OX40 antibody described herein (e.g., antibody comprising the CDRs pab1949w, pab2049w, pab1876w, pab1967w, pab1975w, or pab1979w). In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-GITR and/or OX40 antibody described herein (e.g., antibody comprising the CDRs of pab1949w, pab2049w, pab1876w, pab1967w, pab1975w, or pab1979w), and a second vector comprising a polynucleotide encoding a heavy chain/heavy chain variable region of an anti-OX40 antibody described herein (e.g., antibody comprising the CDRs of pab1949w, pab2049w, pab1876w, pab1967w, pab1975w, or pab1979w).

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein (e.g., an antibody comprising the CDRs of any one of antibodies pab1949w, pab2049w, pab1876w, pab1967w, pab1975w, or pab1979w) are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies described herein are produced by CHO cells or NS0 cells. In a specific embodiment, the expression of nucleotide sequences encoding antibodies described herein which immunospecifically bind GITR and/or OX40 (e.g., human GITR and/or OX40) is regulated by a constitutive promoter, inducible promoter or tissue specific promoter.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-GITR and/or OX40 antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-GITR and/or OX40 antibody described herein can be engineered.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the antibody or fragment is recombinantly produced, it is also generally substantially free of culture medium, i.e., culture medium represents less than about 20%, 10%, 2%, 1%, 0.5%, or 0.1% of the volume of the protein preparation. When the antibody or fragment is produced by chemical synthesis, it is generally substantially free of chemical precursors or other chemicals, i.e., it is separated from chemical precursors or other chemicals which are involved in the synthesis of the protein. Accordingly, such preparations of the antibody or fragment have less than about 30%, 20%, 10%, or 5% (by dry weight) of chemical precursors or compounds other than the antibody or fragment of interest. In a specific embodiment, antibodies described herein are isolated or purified.

7.4 Pharmaceutical Compositions

Provided herein are compositions comprising an antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

Pharmaceutical compositions described herein that comprise an agonistic antibody described herein can be useful in enhancing, inducing, or activating a GITR and/or OX40 activity and treating a condition, such as cancer or an infectious disease. Examples of cancer that can be treated in accordance with the methods described herein include, but are not limited to, B cell lymphomas (e.g., B cell chronic lymphocytic leukemia, B cell non-Hodgkin's lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphoblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

Pharmaceutical compositions described herein that comprise an antagonistic antibody described herein can be useful in reducing, inhibiting, or deactivating a GITR and/or OX40 activity and treating a condition, such as an inflammatory or autoimmune disease or disorder or an infectious disease.

Pharmaceutical compositions described herein that comprise an antagonistic antibody described herein can be useful in reducing, deactivating, or inhibiting GITR and/or OX40 activity and treating a condition selected from the group consisting of infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, uveitis, autoimmune uveitis, immune mediated inflammatory disorders of the central and peripheral nervous system such as multiple sclerosis, lupus (such as systemic lupus erythematosus) and Guillain-Barr syndrome, dermatitis, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease, transplant rejection, heart disease (i.e., cardiovascular disease) including ischaemic diseases such as myocardial infarction as well as atherosclerosis, intravascular coagulation, bone resorption, osteoporosis, osteoarthritis, periodontitis, hypochlorhydia, and neuromyelitis optica.

The compositions to be used for in vivo administration can be sterile. This is readily accomplished by filtration through, e.g., sterile filtration membranes.

7.5 Uses and Methods

7.5.1 Therapeutic Uses and Methods

In one aspect, presented herein are methods for modulating one or more immune functions or responses in a subject, comprising to a subject in need thereof administering a multispecific (e.g., bispecific) antibody that binds to GITR and/or OX40 described herein, or a composition comprising such an antibody. In a specific aspect, presented herein are methods for activating, enhancing or inducing one or more immune functions or responses in a subject, comprising administering to a subject in need thereof a multispecific (e.g., bispecific) antibody that binds to GITR and/or OX40 or a composition comprising such an antibody. In a specific embodiment, presented herein are methods for preventing and/or treating diseases in which it is desirable to activate or enhance one or more immune functions or responses, comprising administering to a subject in need thereof a multispecific (e.g., bispecific) antibody that binds to GITR and/or OX40 described herein or a composition thereof. In a certain embodiment, presented herein are methods of treating an infectious disease comprising administering to a subject in need thereof a multispecific (e.g., bispecific) antibody that binds to GITR and/or OX40 or a composition thereof. In a certain embodiment, presented herein are methods of treating cancer comprising administering to a subject in need thereof a multispecific (e.g., bispecific) antibody that binds to GITR and/or OX40 or a composition thereof. The cancer can be selected from a group consisting of melanoma, renal cancer, and prostate cancer. The cancer can be selected from a group consisting of melanoma, renal cancer, prostate cancer, colon cancer, and lung cancer. In a certain embodiment, presented herein are methods of treating melanoma comprising administering to a subject in need thereof a multispecific (e.g., bispecific) antibody that binds to GITR and/or OX40 or a composition thereof. In a certain embodiment, presented herein are methods of treating renal cancer comprising administering to a subject in need thereof a multispecific (e.g., bispecific) antibody that binds to GITR and/or OX40 or a composition thereof. In a certain embodiment, presented herein are methods of treating prostate cancer comprising administering to a subject in need thereof a multispecific (e.g., bispecific) antibody that binds to GITR and/or OX40 or a composition thereof. In certain embodiments, presented herein are methods of treating colon cancer comprising administering to a subject in need thereof a multispecific (e.g., bispecific) antibody that binds to GITR and/or OX40 or a composition thereof. In certain embodiments, presented herein are methods of treating lung cancer comprising administering to a subject in need thereof a multispecific (e.g., bispecific) antibody that binds to GITR and/or OX40 or a composition thereof. In certain embodiments, presented herein are methods of treating non-small cell lung cancer (NSCLC) comprising administering to a subject in need thereof a multispecific (e.g., bispecific) antibody that binds to GITR and/or OX40 or a composition thereof.

In a certain embodiment, presented herein are methods of treating a cancer selected from the group consisting of: B cell lymphomas (e.g., B cell chronic lymphocytic leukemia, B cell non-Hodgkin's lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphoblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In another embodiment, a multispecific (e.g., bispecific) antibody that binds to GITR and/or OX40 is administered to a patient diagnosed with cancer to increase the proliferation and/or effector function of one or more immune cell populations (e.g., T cell effector cells, such as CD4$^+$ and CD8$^+$ T cells) in the patient.

In a specific embodiment, a multispecific (e.g., bispecific) antibody that binds to GITR and/or OX40 described herein activates or enhances or induces one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the multispecific (e.g., bispecific) antibody that binds to GITR and/or OX40 described herein using assays well known in the art, e.g., ELISPOT, ELISA, and cell proliferation assays. In a specific embodiment, the immune function is cytokine production (e.g., IL-2, TNF-α, IFN-γ, IL-4, IL-10, and/or IL-13 production). In another embodiment, the immune function is T cell proliferation/expansion, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a memory response.

In specific embodiments, non-limiting examples of immune functions that can be enhanced or induced by a multispecific (e.g., bispecific) antibody that binds to GITR and/or OX40 are proliferation/expansion of effector lymphocytes (e.g., increase in the number of effector T lymphocytes), and inhibition of apoptosis of effector lymphocytes (e.g., effector T lymphocytes). In particular embodiments, an immune function enhanced or induced by a multispecific (e.g., bispecific) antibody that binds to GITR and/or OX40 described herein is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer (NK) cells), macrophages, monocytes, dendritic cells, mast cells, eosinophils, basophils or polymorphonucleated leukocytes. In one embodiment, a multispecific (e.g., bispecific) antibody that binds to GITR and/or OX40 described herein activates or enhances the proliferation/expansion or number of lymphocyte progenitors. In some embodiments, a multispecific (e.g., bispecific) antibody that binds to GITR and/or OX40 described herein increases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer cells (NK cells), macrophages, monocytes, dendritic cells, mast cells, eosinophils, basophils or polymorphonucleated leukocytes by approximately at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with a multispecific (e.g., bispecific) antibody that binds to GITR and/or OX40 described herein).

In some embodiments, a multispecific (e.g., bispecific) antibody that binds to GITR and/or OX40 described herein is administered to a subject in combination with a compound that targets an immunomodulatory enzyme(s) such as IDO (indoleamine-(2,3)-dioxygenase) and TDO (tryptophan 2,3-dioxygenase). In particular embodiments, such compound is selected from the group consisting of epacadostat (Incyte Corp), F001287 (Flexus Biosciences), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919.

In some embodiments, an a multispecific (e.g., bispecific) antibody that binds to GITR and/or OX40 described herein is administered to a subject in combination with a vaccine.

In some embodiments, a multispecific (e.g., bispecific) antibody that binds to GITR and/or OX40 described herein is administered to a subject in combination with a heat shock protein based tumor vaccine or a heat shock protein based pathogen vaccine. In a specific embodiment, a multispecific (e.g., bispecific) antibody that binds to GITR and/or OX40 is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In some embodiments, HSPPCs used in methods disclosed herein comprise one or more heat shock proteins from the hsp60, hsp70, or hsp90 family of stress proteins complexed with antigenic peptides. In some embodiments, HSPPCs comprise hsc70, hsp70, hsp90, hsp110, grp170, gp96, calreticulin, or combinations of two or more thereof.

In a specific embodiment, a multispecific (e.g., bispecific) antibody that binds to GITR and/or OX40 is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In some embodiments, this fingerprint contains unique antigens that are present only in that particular subject's specific cancer cells and injection of the vaccine is intended to stimulate the subject's immune system to recognize and attack any cells with the specific cancer fingerprint.

In some embodiments, the HSPPC, e.g., HSPPC-96, is produced from the tumor tissue of a subject. In a specific embodiment, the HSPPC (e.g., HSPPC-96) is produced from tumor of the type of cancer or metastasis thereof being treated. In another specific embodiment, the HSPPC (e.g., HSPPC-96) is autologous to the subject being treated. In some embodiments, the tumor tissue is non-necrotic tumor tissue. In some embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In some embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In some embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference in their entireties for all purposes, U.S. Pat. Nos. 6,391,306, 6,383,492, 6,403,095, 6,410,026, 6,436,404, 6,447,780, 6,447,781 and 6,610,659.

In one aspect, the methods for modulating one or more immune functions or responses in a subject as presented herein are methods for deactivating, reducing or inhibiting one or more immune functions or responses in a subject, comprising to a subject in need thereof administering an antagonistic multispecific (e.g., bispecific) antibody that binds to GITR and/or OX40 or a composition thereof. In a specific embodiment, presented herein are methods for preventing and/or treating diseases in which it is desirable to deactivate, reduce, or inhibit one or more immune functions or responses, comprising administering to a subject in need thereof an antagonistic multispecific (e.g., bispecific) antibody that binds to GITR and/or OX40 or a composition thereof.

In a certain embodiment, presented herein are methods of treating an autoimmune or inflammatory disease or disorder comprising administering to a subject in need thereof an effective amount of an antagonistic multispecific (e.g., bispecific) antibody that binds to GITR and/or OX40 or a composition thereof. In certain embodiments, the disease or disorder is selected from the group consisting of: infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, uveitis, autoimmune uveitis, immune mediated inflammatory disorders of the central and peripheral nervous system such as multiple sclerosis, lupus (such as systemic lupus erythematosus) and Guillain-Barr syndrome, dermatitis, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease, transplant rejection, heart disease (i.e., cardiovascular disease) including ischaemic diseases such as myocardial infarction as well as atherosclerosis, intravascular coagulation, bone resorption, osteoporosis, osteoarthritis, periodontitis, hypochlorhydia, and neuromyelitis optica. In certain embodiments, the autoimmune or inflammatory disease or disorder is transplant rejection, graft-versus-host disease, vasculitis, asthma, rheumatoid arthritis, dermatitis, inflammatory bowel disease, uveitis, lupus, colitis, diabetes, multiple sclerosis, or airway inflammation. In certain embodiments, the subject is a human.

In another embodiment, an antagonistic multispecific (e.g., bispecific) antibody that binds to GITR and/or OX40 is administered to a patient diagnosed with an autoimmune or inflammatory disease or disorder to decrease the proliferation and/or effector function of one or more immune cell populations (e.g., T cell effector cells, such as CD4$^+$ and CD8$^+$ T cells) in the patient. In certain embodiments, the autoimmune or inflammatory disease or disorder is transplant rejection, graft-versus-host disease, vasculitis, asthma, rheumatoid arthritis, dermatitis, inflammatory bowel disease, uveitis, lupus, colitis, diabetes, multiple sclerosis, or airway inflammation.

In a specific embodiment, an antagonistic multispecific (e.g., bispecific) antibody that binds to GITR and/or OX40 described herein deactivates or reduces or inhibits one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the antagonistic multispecific (e.g., bispecific) antibody that binds to GITR and/or OX40 described herein using assays well known in the art, e.g., ELISPOT, ELISA, and cell proliferation assays. In a specific embodiment, the immune function is cytokine production (e.g., IL-2, TNF-α, IFN-γ, IL-4, IL-10, and/or IL-13 production). In another embodiment, the immune function is T cell proliferation/expansion, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a memory response.

In specific embodiments, non-limiting examples of immune functions that can be reduced or inhibited by a an antagonistic multispecific (e.g., bispecific) antibody that binds to GITR and/or OX40 are proliferation/expansion of effector lymphocytes (e.g., decrease in the number of effector T lymphocytes), and stimulation of apoptosis of effector lymphocytes (e.g., effector T lymphocytes). In particular embodiments, an immune function reduced or inhibited by an antagonistic multispecific (e.g., bispecific) antibody that binds to GITR and/or OX40 described herein is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer (NK) cells), macrophages, monocytes, dendritic cells, mast cells, eosinophils, basophils or polymorphonucleated leukocytes. In one embodiment, an antagonistic multispecific (e.g., bispecific) antibody that binds to GITR and/or OX40 described herein deactivates or reduces the proliferation/expansion or number of lymphocyte progenitors. In some embodiments, an antagonistic multispecific (e.g., bispecific) antibody that binds to GITR and/or OX40 described herein decreases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer cells (NK cells), macrophages, monocytes, dendritic cells, mast cells, eosinophils, basophils or polymorphonucleated leukocytes by approximately at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an antagonistic multispecific (e.g., bispecific) antibody that binds to GITR and/or OX40 antibody described herein).

7.5.1.1 Routes of Administration & Dosage

An antibody or composition described herein can be delivered to a subject by a variety of routes.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Generally, human antibodies have a longer half-life within the human body than antibodies from other species due to the immune response to the foreign polypeptides. Thus, lower dosages of human antibodies and less frequent administration is often possible.

7.5.2 Detection & Diagnostic Uses

An anti-OX40 antibody described herein (see, e.g., Section 7.2) can be used to assay OX40 protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-OX40 antibody described herein can be labeled and used in combination with an anti-OX40 antibody to detect OX40 protein levels.

Assaying for the expression level of OX40 protein is intended to include qualitatively or quantitatively measuring or estimating the level of a OX40 protein in a first biological sample either directly (e.g., by determining or estimating absolute protein level) or relatively (e.g., by comparing to the disease associated protein level in a second biological sample). OX40 polypeptide expression level in the first biological sample can be measured or estimated and compared to a standard OX40 protein level, the standard being taken from a second biological sample obtained from an individual not having the disorder or being determined by averaging levels from a population of individuals not having the disorder. As will be appreciated in the art, once the "standard" OX40 polypeptide level is known, it can be used repeatedly as a standard for comparison.

As used herein, the term "biological sample" refers to any biological sample obtained from a subject, cell line, tissue, or other source of cells potentially expressing OX40. Methods for obtaining tissue biopsies and body fluids from animals (e.g., humans) are well known in the art. Biological samples include peripheral mononuclear blood cells.

An anti-OX40 antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one embodiment, an anti-OX40 antibody can be used in immunohistochemistry of biopsy samples.

In another embodiment, an anti-OX40 antibody can be used to detect levels of OX40, or levels of cells which contain OX40 on their membrane surface, which levels can then be linked to certain disease symptoms. Anti-OX40 antibodies described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-OX40 antibodies described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-OX40 antibody can carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-OX40 antibody to OX40 (e.g., human OX40). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-OX40 antibody under conditions that allow for the formation of a complex between the antibody and OX40. Any complexes formed between the antibody and OX40 are detected and compared in the sample and the control. In light of the specific binding of the antibodies described herein for OX40, the antibodies thereof can be used to specifically detect OX40 expression on the surface of cells. The antibodies described herein can also be used to purify OX40 via immunoaffinity purification.

Also included herein is an assay system which may be prepared in the form of a test kit for the quantitative analysis of the extent of the presence of, for instance, OX40 or OX40/OX40L complexes. The system or test kit may comprise a labeled component, e.g., a labeled antibody, and one or more additional immunochemical reagents. See, e.g., Section 7.6 below for more on kits.

7.6 Kits

Provided herein are kits comprising one or more antibodies described herein or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises an antibody described herein, preferably a purified antibody, in one or more containers. In a specific embodiment, kits described herein contain a substantially isolated OX40 antigen (e.g., human OX40) that can be used as a control. In another specific embodiment, the kits described herein further comprise a control antibody which does not react with a OX40 antigen. In another specific embodiment, kits described herein contain one or more elements for detecting the binding of an antibody to a OX40 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized OX40 antigen. The OX40 antigen provided in the kit can also be attached to a solid support. In a more specific embodiment, the detecting means of the above described kit includes a solid support to which a OX40 antigen is attached. Such a kit can also include a non-attached reporter-labeled anti-human antibody or anti-mouse/rat antibody. In this embodiment, binding of the antibody to the OX40 antigen can be detected by binding of the said reporter-labeled antibody.

The following examples are offered by way of illustration and not by way of limitation.

8. EXAMPLES

The examples in this Section (i.e., Section 8) are offered by way of illustration, and not by way of limitation.

8.1 Example 1: Characterization of GITR and OX40 Expression on Intratumoral Regulatory T Cells The expression of GITR and OX40 on intratumoral regulatory T cells (Treg) and effector T cells (Teff) was characterized using flow cytometry. Briefly, cryopreserved tumor cells from multiple tumor types (ovarian, stage IIC; colorectal, stage IIIB; endometrial, stage IB; renal, stage III; and non-small cell lung cancer, stage II) were obtained from Conversant Bio, LLC. The tumor cells were isolated prior to therapeutic interventions. After being thawed, cells were treated with human Fc-receptor block (FcR block, Biolegend®) for 15 minutes at room temperature to reduce non-specific binding. Samples were washed twice. An antibody cocktail, containing antibodies recognizing CD4 (BV605, OKT4, lot #B185762), CD127 (APC, A019D5, lot #B193084) and CD25 (PECy7, M-A251 lot #B190207), Zombie Green™ fixable viability dye (FITC, lot #B201900) as well as anti-OX40 antibody (PE, BER-ACT35, lot #B203538), anti-GITR antibody (PE, 110416, lot #LAV0614061), or a cognate isotype control antibody (PE, MOPC-21, lot #B197832) all at 2.5 µg/ml, was diluted in FACS buffer (PBS, 2 mM EDTA, 0.5% BSA, pH 7.2) and added to each sample. The samples were incubated for 30 minutes at 4° C. Prior to staining, additional samples were set aside for single stain compensation controls (CD45-FITC, CD45-PE, CD45-PECy7, CD45-APC, and CD45-BV605; all clone H130). Samples were then washed three times in FACS buffer and incubated in 1× fix-perm buffer (Foxp3 staining kit, eBioscience) for 45 minutes at room temperature in the dark. Following fixation, cells were washed three times in 1× permeabilization buffer (Foxp3 staining kit, eBioscience) and incubated with anti-FOXP3 or rat IgG2a antibodies at 2.5 µg/ml diluted in 1× permeabilization buffer for 45 minutes at 4° C. Samples were washed two times in 1× permeabilization buffer, resuspended in FACS buffer, and analyzed using the LSRFortessa flow cytometer (BD Biosciences). FACS plots were analyzed using a combination of FACS DIVA and WEHI Weasel software.

Effector T cells were defined as CD4+ CD127+ CD25+/−FOXP3−. Regulatory T cells were defined as CD4+ CD127− CD25+ FOXP3+. As shown in FIG. 1A, intratumoral regulatory T cells from endometrial cancer tumor tissue, renal cell carcinoma (RCC) tumor tissue, and non-small cell lung cancer (NSCLC) tumor tissue showed elevated expression of GITR and OX40, whereas intratumoral effector T cells from the same tumor tissues did not.

For receptor quantification, beads with a pre-defined number of PE molecules (Quantum™ R-PE MESF; Bangs Laboratories, Inc.) were analyzed using defined instrument settings. Using mean fluorescence intensity (MFI) for both beads and previously analyzed GITR/OX40 antibodies, the predicted number of GITR and OX40 receptors for intratumoral regulatory T cells and effector T cells was calculated.

Regulatory T cells from ovarian tumor tissue, colorectal cancer (CRC) tumor tissue, endometrial cancer tumor tissue, RCC tumor tissue, and NSCLC tumor tissue all showed higher expression of GITR and OX40 than effector T cells from the same tumor tissues (FIG. 1B).

8.2 Example 2: Characterization of Anti-GITR/OX40 Bispecific Antibodies

In this example, anti-GITR/OX40 bispecific antibodies constructed using Genmab DuoBody technology were examined for their binding and functional characteristics. DuoBody pab1876×pab2049 and DuoBody pab1876×pab1949 both comprise a GITR-binding arm (pab1876) and an OX40-binding arm (pab2049 or pab1949). Three additional DuoBody antibodies were used as controls: DuoBody pab1876×isotype, DuoBody pab2049×isotype and DuoBody pab1949×isotype. The SEQ ID NOs corresponding to the heavy chain and light chain sequences of these DuoBody antibodies are listed in Table 10. In addition, the bivalent monospecific antibodies pab1876, pab2049, and pab1949w were also used in some experiments. pab1876w is an $IgG_1$ antibody comprising a heavy chain of SEQ ID NO:29 and a light chain of SEQ ID NO:37. pab1876 comprises the same heavy and light chain sequences as pab1876w except that it contains a T109S substitution in the light chain constant domain (i.e., substitution of threonine with serine at position 109 relative to the wild type light chain constant domain), numbered according to Kabat, which facilitates the cloning of the variable region in frame to the constant region. This mutation is a conservative modification that does not affect antibody binding or function. pab2049w is an $IgG_1$ antibody comprising a heavy chain of SEQ ID NO:59 and a light chain of SEQ ID NO:67. pab2049 comprises the same heavy and light chain sequences as pab2049w except for a T109S mutation in the light chain constant region, numbered according to Kabat. pab1949w is an $IgG_1$ antibody comprising a heavy chain of SEQ ID NO:59 and a light chain of SEQ ID NO:69. pab1949 comprises the same heavy and light chain sequences as pab1949w except for a T109S mutation in the light chain constant region, numbered according to Kabat.

TABLE 10

DuoBody heavy chain (HC) and light chain (LC) sequences

| DuoBody | First arm HC (SEQ ID NO:) | First arm LC (SEQ ID NO:) | Second arm HC (SEQ ID NO:) | Second arm LC (SEQ ID NO:) |
|---|---|---|---|---|
| pab1876 × pab2049 | 31 | 38 | 61 | 68 |
| pab1876 × pab1949 | 31 | 38 | 61 | 70 |
| pab1876 × isotype | 31 | 38 | N/A | N/A |
| pab2049 × isotype | 61 | 68 | N/A | N/A |
| pab1949 × isotype | 61 | 70 | N/A | N/A |
| pab1876 × pab2049 without heavy chain terminal lysine | 76 | 38 | 120 | 68 |
| pab1876 × pab1949 without heavy chain terminal lysine | 76 | 38 | 120 | 70 |
| pab1876 × isotype without heavy chain terminal lysine | 76 | 38 | N/A | N/A |
| pab2049 × isotype without heavy chain terminal lysine | 120 | 68 | N/A | N/A |
| pab1949 × isotype without heavy chain terminal lysine | 120 | 70 | N/A | N/A |

8.2.1 Selectivity of Anti-GITR/OX40 Bispecific Antibody

The selectivity of DuoBody pab1876×pab2049 for GITR and OX40 was assessed against other members of the TNFR superfamily using suspension array technology. A number of recombinant proteins of the TNFR superfamily, including recombinant human GITR-His (Sino Biological, 50 µg/ml), recombinant human OX40-His (Sino Biological, 50 µg/ml), recombinant human lymphotoxin beta receptor (LTBR)-Fc (AcroBiosystems, 65 µg/ml), recombinant human death receptor 6 (DR6)-bio (Sino Biological, 50 µg/ml), recombinant human tumor necrosis factor-like weak inducer of apoptosis receptor (TWEAKR)-Fc (Sino Biological, 50 µg/ml), recombinant human CD137-Fc (SrtA-bio, 50 µg/ml), and recombinant human B-cell activating factor receptor (BAFFR)-Fc (R&D Systems, 50 µg/ml), were coupled to Luminex® beads using goat anti-human IgG F(ab')$_2$ (Jackson Immuno Research, COOH coupling, 100 µg/ml, pH 5.0). DuoBody pab1876×pab2049 was then incubated at multiple concentrations (8333, 833.3, 83.3 and 8.33 ng/ml final) with the antigen-coupled beads for 1 hour at 20° C. (650 RPM in the dark). Following washing to remove non-specific binding (two times in PBS), the beads were incubated with detection antibody (phycoerythrin-coated goat-anti-huIgG F(ab')$_2$, 2.5 µg/ml final) for 1 hour at 20° C. (650 RPM in the dark). Beads were then washed two times and read on a Luminex 200®. Binding above (+) or below (−) threshold was determined by cutoff detection values (based on LX200 controls).

DuoBody pab1876×pab2049 showed specific binding to human GITR and OX40, and no significant binding to other TNFR family members was observed at tested concentrations (Table 11).

TABLE 11

Selectivity of DuoBody pab1876 × pab2049 to TNFR superfamily members

| Target | GITR | OX40 | LTBR | DR6 | TWEAKR | CD137 | BAFFR |
|---|---|---|---|---|---|---|---|
| Binding | + | + | − | − | − | − | − |

8.2.2 Binding of Anti-GITR/OX40 Bispecific Antibody to Cells Expressing GITR and OX40

The binding of DuoBody pab1876×pab2049 to cells co-expressing GITR and OX40, cells expressing only GITR, and cells expressing only OX40 was examined by flow cytometry.

Hut102 cells (human T cell lymphoma, ATCC) were incubated for 72 hours in RPMI media, supplemented with 1 µg/ml phytohaemagglutinin (PHA) and 10% heat-inactivated FBS, at 37° C. and 5% $CO_2$ to induce GITR and OX40 expression. Cells ectopically expressing GITR or OX40 were generated by transduction of lentiviral vectors (EF1a promoter) into Jurkat cells. Stable clones were generated via single-cell sorting (FACS ARIA Fusion). Expression was verified by flow cytometry. For binding analysis, stable Jurkat cells or activated Hut102 cells were incubated with test antibodies (12-point dose titration, 0.01-10,000 ng/ml) diluted in FACS buffer (PBS, 2 mM EDTA, 0.5% BSA, pH 7.2) for 30 minutes at 4° C. Samples were washed two times in FACS buffer and then incubated with APC-conjugated mouse anti-human kappa detection antibody (Life Technologies, HP6062) for 30 minutes at 4° C. Samples were then washed two times and analyzed using the LSRFortessa flow cytometer (BD Biosciences). FACS plots were analyzed using a combination of FACS DIVA and WEHI Weasel software. Data were plotted with Graphpad Prism software.

As shown in FIG. 2A, DuoBody pab1876×pab2049 showed enhanced binding to cells co-expressing GITR and OX40, as compared to the bivalent monospecific antibodies pab1876 and pab2049. The enhanced binding to cells co-expressing GITR and OX40 was contributed to by both arms, as replacing either arm with an isotype arm in the two control DuoBody antibodies, pab1876×isotype and pab2049×isotype, led to reduced binding to activated Hut102 cells. As expected, for cells that only expressed GITR or OX40 but not both, DuoBody pab1876×pab2049 bound more weakly than bivalent monospecific antibodies pab1876 and pab2049 did at all but the highest concentrations tested (FIGS. 2B and 2C).

8.2.3 Effect of Anti-GITR/OX40 Bispecific Antibody on FcγRIIIA Reporter Cell Line Next, the ability of DuoBody pab1876×pab2049 to engage GITR and OX40 and signal via FcγRIIIA was evaluated using a reporter cell line expressing FcγRIIIA (Promega) together with target cells co-expressing GITR and OX40. Engineered Jurkat cells stably expressing the FcγRIIIA V158 variant and an NFAT response element driving expression of firefly luciferase were used as effector cells. Binding of the antibody/antigen complex, wherein the antigen is located on the surface of the target cells, to FcγRIIIA signals to the promoter/reporter construct of the effector cells and results in luciferase gene transcription.

Natural regulatory T cells (nTreg) were activated to generate target cells co-expressing GITR and OX40. PBMCs were isolated from healthy donor buffy coats via Ficoll gradient (Research Blood Components, LLC) and subjected to magnetic-based nTreg enrichment (Mitenyi Biotec, 130-093-631, lot 5150629039). Cells were then activated using Miltenyi Biotec's Treg Expansion Kit (130-095-345, lot 5150420196) for 8 days in RPMI media, supplemented with 10% heat-inactivated FBS, at 37° C. and 5% $CO_2$. Fresh media containing the Treg Expansion Kit was added to the isolated nTregs every 3-4 days. On day 8, cell expression of GITR and OX40 was confirmed by flow cytometry. Briefly, 20,000 cells were treated with human Fc-receptor block for 15 minutes at room temperature to reduce non-specific binding (FcR block, Biolegend). Samples were washed twice and an antibody cocktail, containing antibodies recognizing CD4 (BV605, OKT4, lot B185762), CD127 (APC, A019D5, lot B193084), and CD25 (PECy7, M-A251, lot B195168) and Zombie Green™ fixable viability dye (FITC, lot B201900), as well as anti-OX40 antibody (PE, BER-ACT35, lot #B203538), anti-GITR antibody (PE, 110416, lot #LAV0614061), or a cognate isotype control antibody (PE, MOPC-21, lot #B197832) all at 2.5 µg/ml, was diluted in FACS buffer (PBS, 2 mM EDTA, 0.5% BSA, pH 7.2), added to each sample and incubated for 30 minutes at 4° C. Prior to staining, additional samples were set aside for single stain compensation controls (CD45-FITC, CD45-PE, CD45-PECy7, CD45-APC, and CD45-BV605; all clone H130). Samples were then washed three times in FACS buffer and incubated in 1× fix-perm buffer (Foxp3 staining kit, eBioscience, lot E00029-1691) for 45 minutes at room temperature in the dark. Following fixation, cells were washed three times in 1× permeabilization buffer (Foxp3 staining kit, eBioscience) and incubated with anti-FOXP3 (eFluor450, PCH101, lot E11056-1635) or rat IgG2a (eFluor450, eBR2a, lot E08519-1633) antibodies at 2.5 µg/ml diluted in 1× permeabilization buffer for 45 minutes at 4° C. Samples were washed two times in 1× permeabilization buffer, resuspended in FACS buffer and analyzed using the LSRFortessa flow cytometer (BD Biosciences).

As shown in FIG. 3A, activated nTregs expressed both GITR and OX40 on the cell surface.

To assess impact on FcγRIIIA reporter cells, 125,000 nTregs, activated for 8 days, were incubated with increasing concentrations (6-point dose titration, 0.04 to 10 µg/ml) of DuoBody pab1876×pab2049, the bivalent monospecific antibody pab1876, the bivalent monospecific antibody pab2049, or an isotype control antibody. FcγRIIIA$^{V158}$-expressing NFAT reporter cells were added to the antibody-nTreg mixture at a 1:1 ratio (125,000 cells) in RPMI media, supplemented with 4% heat-inactivated low-IgG FBS, at 37° C. and 5% $CO_2$. After a 20-hour incubation, Bio-Glo™ Luciferase Assay Substrate (Promega, G720A) was added to each sample (1:1 v/v). Luminescence was measured using the EnVision® Multilabel Plate Reader (Perkin-Elmer). FACS plots were analyzed using a combination of FACS DIVA and WEHI Weasel software. Data were plotted with Graphpad Prism software.

Consistent with the observation that DuoBody pab1876×pab2049 showed enhanced binding to cells co-expressing GITR and OX40, as compared to the bivalent monospecific antibodies pab1876 and pab2049 (FIG. 2A), when bound to GITR- and OX40-co-expressing nTregs, DuoBody pab1876×pab2049 demonstrated a stronger activation of FcγRIIIA than pab1876 and pab2049 did (FIG. 3B).

Furthermore, the ability of DuoBody pab1876×pab2049 to engage GITR or OX40 and signal via FcγRIIIA was evaluated using the FcγRIIIA-expressing reporter cell line described above together with target cells expressing GITR or OX40 but not both. Briefly, Jurkat target cells expressing GITR or OX40 were counted and resuspended at a concentration of 6×10⁶ cells/ml in RPMI-1640 with 4% low-IgG FBS. To the inner 60 wells of multiple 96-well white assay plates, 25 µl of the cell suspension was added to each well. Test antibodies were serially diluted with 3-fold dilutions with a starting final concentration of 10 µg/ml. In duplicate wells, 25 µl of each antibody dilution was added to the target cells. Finally, FcγRIIIA$^{V158}$-expressing NFAT reporter cells were resuspended at a concentration of 6×10⁶ cells/ml in RPMI-1640 with 4% low-IgG FBS. 25 µl of these reporter cells were added to each well resulting in a 1:1 effector to target ratio. Plates were incubated for 20 hours at 37° C. and 5% $CO_2$. After this incubation, Bio-Glo Luciferase Assay Reagent (Promega) was thawed at room temperature and 75 µl was added to each well of the 96-well white assay plates. Within 5-10 minutes, luminescence was measured using the EnVision multilabel plate reader (PerkinElmer). Background luminescence (blank outer wells) was subtracted from each sample reading and the adjusted relative light units (RLU) were recorded. Data were plotted with Graphpad Prism software. The antibodies tested were: DuoBody pab1876×pab2049, the bivalent anti-GITR antibody pab1876 (F405L/F405L), the bivalent anti-OX40 antibody pab2049 (K409R/K409R), DuoBody pab1876×isotype, DuoBody pab2049×isotype, and an isotype control antibody. The antibody pab1876 (F405L/F405L) comprises a F405L substitution in both heavy chain constant regions and the antibody pab2049 (K409R/K409R) comprises a K409R substitution in both heavy chain constant regions, numbered according to the EU numbering system.

For cells that only expressed GITR or OX40 but not both, consistent with the observation that DuoBody pab1876×pab2049 bound more weakly than pab1876 and pab2049 did (FIGS. 2B and 2C), when bound to Jurkat cells expressing GITR or OX40 but not both, DuoBody pab1876×pab2049 demonstrated a weaker activation of FcγRIIIA than pab1876 (F405L/F405L) and pab2049 (K409R/K409R) did at all but the highest concentrations tested (FIGS. 3C and 3D).

8.2.4 Effect of Anti-GITR/OX40 Bispecific Antibody on NK Cell-Mediated ADCC Activity In this example, the ability of DuoBody pab1876×pab2049 to induce natural killer (NK) cell-mediated antibody-dependent cellular cytotoxicity (ADCC) towards cells co-expressing GITR and OX40 was examined.

Human PBMCs isolated via ficoll gradient from healthy donor buffy coats (Research Blood Components, LLC) were further enriched for effector T cells or natural Tregs using magnetic bead isolation (MACS, Miltenyi, 130-094-775). The enriched effector T cells or Tregs were activated with CD3-CD28 microbeads (1:1 beads:cells, Invitrogen, 11132D) and recombinant human IL-2 (20 U/ml for effector T cells; 100 U/ml for Tregs) (Peprotech, 200-02) for 7 days in RPMI media, supplemented with 10% heat-inactivated FBS at 37° C. and 5% $CO_2$. Following stimulation, the cells were evaluated for GITR and OX40 expression via flow cytometry. To reduce non-specific binding, the cells were incubated with an FcγR blocking antibody (Biolegend, 422302) for 15 minutes at ambient temperature. The samples were then washed twice and incubated with a lineage antibody panel of CD3, CD4, CD8, and CD25 as well as a fixable live/dead marker for 30 minutes at 4° C. For Treg delineation, the samples were then washed twice, fixed, permeabilized, and incubated with an anti-FOXP3 antibody (eBiosciences, clone #PCH101) for 30 minutes at 4° C. The samples were then washed twice and analyzed using the LSRFortessa flow cytometer (BD Biosciences). The flow cytometry plots were analyzed using a combination of FACS DIVA and WEHI Weasel software. To evaluate ADCC activities, primary NK cells were isolated from healthy donor PBMCs via magnetic bead separation (MACS, Miltenyi, 130-092-657). The NK cells were rested overnight with 20 U/ml of recombinant human IL-2 (Peprotech, 200-02). The NK cells were co-cultured with target cells (effector T cells or Tregs) and incubated with antibodies (titration range: 0.0004-1.9 μg/ml) for four hours at an E:T ratio of 10:1 in RPMI 1640 phenol red-free medium supplemented with heat-inactivated 0.5% FBS. There were five treatment groups: isotype control, pab1876 alone, pab2049 alone, DuoBody pab1876×pab2049, and a combination of pab1876 and pab2049. In the last group, pab1876 and pab2049 were added at equimolar concentrations to achieve a final concentration same as that of other groups. A total of $2 \times 10^5$ target cells (effector T cell or Treg) and $2 \times 10^6$ NK cells were added in each well in a total volume of 100 μl. Following incubation, cell lysis, as evidenced by lactate dehydrogenase (LDH) release, was measured using the CytoTox 96 non-radioactive cytotoxicity assay (Promega, G1780) according to the manufacturer's instructions. Cytotoxicity (% cell lysis) was determined using the following formula: % Cytotoxicity=(Experimental−Effector Spontaneous−Target Spontaneous)/(Target Maximum−Target Spontaneous)*100.

As shown in FIG. 3E, activated Tregs expressed higher levels of GITR and OX40 than activated effector T cells. Consistent with this differential expression pattern, the antibodies against GITR and/or OX40 did not induce significant lysis of activated effector T cells above background levels (FIG. 3F), whereas the same antibodies induced strong NK cell-mediated ADCC activities towards activated Tregs in a dose dependent manner (FIG. 3G). Notably, DuoBody pab1876×pab2049 induced higher levels of lysis of activated Tregs than pab1876 alone, pab2049 alone, or a combination of pab1876 and pab2049.

8.2.5 Effect of Anti-GITR/OX40 Bispecific Antibody on Human T Cells Following *Staphylococcus* Enterotoxin A (SEA) Stimulation The functional activity of DuoBody pab1876×pab2049 on primary human T cells was assessed following *Staphylococcus* Enterotoxin A (SEA) stimulation. Briefly, PBMCs isolated via Ficoll gradient from healthy donor buffy coats (Research Blood Components, LLC) were incubated in RPMI media, supplemented with 100 ng/ml SEA superantigen (Sigma-Aldrich) and 10% heat-inactivated FBS, together with increasing concentrations of test antibodies (7-point dose titration, 0.02-20 μg/ml) for 5 days at 37° C. and 5% $CO_2$. Following incubation, cell-free supernatant was assayed for IL-2 production using an AlphaLISA immunoassay (Perkin-Elmer). Data were collected using the EnVision® Multilabel Plate Reader (Perkin-Elmer) and the concentration of IL-2 was determined using an IL-2 standard curve. Values were interpolated and plotted using Graphpad Prism software.

DuoBody pab1876×pab2049 induced IL-2 production in this primary human PBMC assay using cells from two donors (FIGS. 4A and 4B). Importantly, DuoBody pab1876× pab2049 was able to induce high levels of IL-2 production at pharmacologically relevant antibody concentrations. IL-2 production induced by DuoBody pab1876× pab2049 is a substantially increasing function of antibody concentration across a wide range of antibody concentrations (e.g., between 0.08 and 20 μg/ml in FIG. 4A and between 0.009 and 20 μg/ml in FIG. 4B).

8.3 Example 3: Anti-GITR/OX40 Bispecific Antibodies as Antagonist Antibodies

The activation of GITR and OX40 signaling depends on receptor clustering to form higher order receptor complexes that efficiently recruit apical adapter proteins to drive intracellular signal transduction. Without being bound by theory, one possible mechanism for the agonistic activity of DuoBody pab1876×pab2049 shown in Section 8.2.4 is by clustering GITR and/or OX40 receptors through Fc-Fc receptor (FcR) co-engagement on accessory myeloid or lymphoid cells, e.g., dendritic cells, monocytes, macrophages, natural killer (NK) cells, and/or B cells. Some tumor cells expressing FcRs may also mediate antibody clustering, e.g., hematologic cancers (acute myelogenous leukemia (AML), plasma cell cancers and non-Hodgkin's lymphoma (NHL)) as well as certain solid (epithelial) tumor cells (e.g. melanoma). Consequently, one approach for developing an anti-GITR/OX40 bispecific antagonist antibody is to select a bispecific antibody that competes with GITR ligand (GITRL) and OX40 ligand (OX40L) for binding to their respective receptors, and diminish or eliminate the binding of the Fc region of the bispecific antibody to Fc receptors. In this example, two reporter assays were developed to first, confirm the loss of the agonistic activity of DuoBody pab1876×pab2049 in the absence of FcR interaction, and second, examine the ability of DuoBody pab1876×pab2049 to antagonize GITRL- and OX40L-induced signaling through GITR and OX40 receptors.

8.3.1 Effect of Anti-GITR/OX40 Bispecific Antibody on GITR NF-κB-Luciferase Reporter Cells First, DuoBody pab1876×pab2049 was evaluated for its agonistic activity on GITR using a GITR reporter assay. This reporter assay was built using Jurkat cells which expressed minimum amount, if any, of FcR, diminishing the possibility of FcR-mediated clustering of the GITR molecules.

Cells ectopically expressing GITR as well as NF-κB-luciferase (Nano luciferase, NanoLuc®) reporter were generated by transduction of lentiviral vectors (EF1a promoter) into Jurkat cells. Stable clones were generated via single-cell sorting (FACS ARIA Fusion). Expression of GITR was verified by flow cytometry. To evaluate agonistic activity, Jurkat-huGITR-NF-κB-luciferase cells were incubated with increasing concentrations of DuoBody pab1876×pab2049 or trimeric GITRL (12-point dose titration, 0.05-10,000 ng/ml) for 2 hours in RPMI media, supplemented with 10% heat-inactivated FBS, at 37° C. and 5% $CO_2$. For detection of luciferase activity, samples were incubated with prepared NanoGlo® Luciferase Assay Substrate (Promega, 1:1 v/v) in passive lysis buffer for 5 minutes at room temperature. Data were collected using the EnVision® Multilabel Plate Reader (Perkin-Elmer). Values were plotted using Graphpad Prism software.

In contrast to trimeric GITRL, which induced high levels of NF-κB-luciferase activity as represented by RLU (relative luciferase units), DuoBody pab1876×pab2049 showed minimal agonistic activity of the GITR reporter cells even at the highest concentration tested (FIG. 5A).

Next, the ability of DuoBody pab1876×pab2049 to neutralize GITRL-induced NF-κB signaling was examined as a surrogate readout of the DuoBody's ligand blocking activity.

Briefly, Jurkat-huGITR-NF-κB-luciferase cells were incubated with increasing concentrations of DuoBody pab1876×pab2049 or an isotype control antibody (10-point dose titration, 0.5-10,000 ng/ml) for 30 minutes. Samples were then washed two times with RPMI, resuspended in 1 µg/ml of trimeric GITRL and incubated for additional 2 hours at 37° C. Luciferase activity was detected and analyzed as described above. To determine % GITRL activity, the RLU value for GITRL (1 µg/ml) without addition of antibody was established as 100% activity. Relative values for DuoBody pab1876×pab2049 and the isotype control were calculated accordingly.

As shown in FIG. 5B, pre-incubation of Jurkat-huGITR-NF-κB-luciferase reporter cells with increasing concentrations of DuoBody pab1876×pab2049 significantly reduced GITRL-induced NF-κB-luciferase activity in a dose-dependent manner.

8.3.2 Effect of Anti-GITR/OX40 Bispecific Antibody on OX40 NF-κB-Luciferase Reporter Cells Similarly, an OX40 reporter assay was developed to test the agonistic activity of DuoBody pab1876×pab2049 on OX40-expressing cells. This OX40 reporter assay was also constructed using Jurkat cells where FcR expression was minimal.

Cells ectopically expressing OX40 as well as NF-κB-luciferase (Nano luciferase, NanoLuc®) reporter were generated by transduction of lentiviral vectors (EF1a promoter) into Jurkat cells. Stable clones were generated via single-cell sorting (FACS ARIA Fusion). Expression of OX40 was verified by flow cytometry. To evaluate agonistic activity, Jurkat-huOX40-NF-κB-luciferase cells were incubated with increasing concentrations of multimeric OX40L, DuoBody pab1876×pab2049 or an isotype control antibody (10-point dose titration, 0.5-10,000 ng/ml) for 2 hours in RPMI media, supplemented with 10% heat-inactivated FBS, at 37° C. and 5% $CO_2$. For detection of luciferase activity, samples were incubated with prepared NanoGlo® Luciferase Assay Substrate (Promega, 1:1 v/v) in passive lysis buffer for 5 minutes at room temperature. Data were collected using the EnVision® Multilabel Plate Reader (Perkin-Elmer). Values were plotted using Graphpad Prism software.

While multimeric OX40L induced NF-κB-luciferase activity over a wide range of concentrations, minimal luciferase signal was observed after incubation with DuoBody pab1876×pab2049 (FIG. 6A).

Next, DuoBody pab1876×pab2049 was assessed for its ability to block OX40L-induced NF-κB signaling. Jurkat-huOX40-NF-κB-luciferase cells were incubated with increasing concentrations of DuoBody pab1876×pab2049 or an isotype control antibody (10-point dose titration, 0.5-10, 000 ng/ml) for 30 minutes. Samples were then washed two times with RPMI, resuspended in 1 µg/ml of multimeric OX40L and incubated for additional 2 hours at 37° C. Luciferase activity was detected and analyzed as described above. To determine % OX40L activity, the RLU value for OX40L (1 µg/ml) without addition of antibody was established as 100% activity. Relative values for DuoBody pab1876×pab2049 and the isotype control were calculated accordingly.

As shown in FIG. 6B, pre-incubation of Jurkat-huOX40-NF-κB-luciferase reporter cells with increasing concentrations of DuoBody pab1876×pab2049 significantly reduced OX40L-induced NF-κB-luciferase activity in a dose-dependent manner.

8.4 Example 4: Epitope Mapping of Anti-GITR Antibodies

This example characterizes the binding epitope of the following anti-GITR antibodies: a chimeric parental 231-32-15 antibody and its humanized versions (pab1876, pab1875, pab1967, pab1975, and pab1979). In addition, a reference anti-GITR antibody named m6C8 was also used in some studies for comparison. The antibody m6C8 was generated based on the variable regions of the antibody 6C8 provided in PCT Application Pub. No. WO 2006/105021 (herein incorporated by reference). The SEQ ID NOs corresponding to the heavy chain variable regions and light chain variable regions of these anti-GITR antibodies are listed in Table 12.

TABLE 12

VH and VL sequences of anti-GITR antibodies

| Antibody | VH (SEQ ID NO:) | VL (SEQ ID NO:) |
|---|---|---|
| 231-32-15 | 101 | 102 |
| pab1876 | 18 | 19 |
| pab1875 | 18 | 103 |
| pab1967 | 20 | 21 |
| pab1975 | 22 | 23 |
| pab1979 | 24 | 23 |
| m6C8 | 104 | 105 |

8.4.1 Epitope Competition—Cell Binding Assay

To confirm that the humanized variant antibodies retained the epitope specificity of the chimeric 231-32-15 parental antibody, a cell binding assay was performed. 1624-5 pre-B cells expressing the chimeric parental 231-32-15 antibody were harvested and 1×10⁶ cells were resuspended in 200 µl FACS buffer plus: i) biotinylated GITR (GITR-bio) (1:1000), preincubated for 15 min with 2 µg chimeric parental 231-32-15 antibody; ii) GITR-bio (1:1000), preincubated for 15 min with 2 µg pab1875; iii) GITR-bio (1:1000), preincubated for 15 min with 2 µg pab1876; or iv) GITR-bio (1:1000). The cells were incubated for 20 min at 4° C. and then washed with 4 ml FACS buffer and centrifuged for 5 min at 300 g at 4° C. The cell pellet was resuspended in 200 µl FACS buffer plus streptavidin-PE (1:1000) and then incubated and washed as before. The cells were then resuspended in 200 µl FACS buffer for analysis using a FACS-AriaII (BD Biosciences).

FIG. 7 shows that the humanized variant antibodies retained the epitope specificity of the chimeric parental 231-32-15 antibody. The right-hand profile shows the binding of GITR-bio to 1624-5 pre-B cells expressing the chimeric parental 231-32-25 antibody. However, when GITR-bio was pre-incubated with either chimeric parental 231-32-15, pab1875 or pab1876 antibodies, there was a loss of binding of GITR-bio to the 1624-5 cells (left-hand profile). The overlapping FACS profiles indicate that the humanized variants also show very similar GITR binding properties to each other and to the chimeric parental 231-32-15 antibody.

8.4.2 Epitope Competition—Suspension Array Technology

Anti-GITR antibodies (25 µl) were diluted to 2 µg/ml in assay buffer (Roche 11112589001) and incubated with 1500 Luminex® beads (5 Luminex Corp, no 5 LC10005-01) coupled with anti-human IgG (F(ab)$_2$-specific, JIR, 105-006-097 overnight in 0.5 ml LoBind tubes (Eppendorf, 0030108.116) under shaking conditions, in the dark. This mixture was then transferred to pre-wetted 96-well filter plates (Millipore, MABVN1250). Plates were washed twice with 200 µl/well PBS to remove unbound antibody. At the same time 20 µg/ml of either the same anti-GITR antibodies, different anti-GITR antibodies, or assay buffer were incubated with 20 µl (1 µg/ml) R-PE labeled GITR antigen (R&D systems, di-sulfide-linked homodimer; 689-GR; in-house labeled with AbDSerotec LYNX Kit, LNK022RPE) for 1 hour in the dark at 650 rpm. The bead mixture and the antigen/antibody mixture were mixed 1:1 (20 µl from each) and incubated for one additional hour under shaking conditions (20° C., 650 rpm). Directly before the measurement, 40 µl of assay buffer was added to each well and analysis was performed using a Luminex® 200 system (Millipore) and a readout of 100 beads in 48 µl sample volume. Binding was determined using the MFI values of the non-competed control (100% binding, only assay buffer as competing compound).

When the chimeric parental 231-32-15 antibody was used as the captured antibody, full binding competition was observed with both humanized antibodies pab1875 and pab1876. When the anti-GITR antibody m6C8 was used as the captured antibody, no competition of binding was observed with the chimeric parental 231-32-15 antibody or the two humanized variants pab1875 and pab1876 (data not shown). These results indicate that m6C8 and the anti-GITR antibodies described herein recognize different epitopes on human GITR.

8.4.3 Epitope Competition—Surface Plasmon Resonance

For epitope binning using surface plasmon resonance the "in tandem approach" was used (Abdiche Y N et al., (2009) Analytical Biochemistry, 386: 172-180). For that purpose different chip surfaces were generated on a CM5 sensor chip (GE Healthcare, Series S CM5, BR-1005-30) using immobilization of different densities of GITR antigen (R&D systems, disulfide-linked homodimer; 689-GR). Flow cell 2 contained GITR antigen in low density (667 RU), medium density was assessed in flow cell 3 (1595 RU) and in flow cell 4, high density was achieved (4371 RU). In flow cell 1, ovalbumin (1289 RU, Pierce ThermoFisher 77120) was immobilized for reference. Immobilization was performed according to a standard protocol from the manufacturer (GE Healthcare) for amine coupling (activation of surface with 0.4 M EDC and 0.1 M NHS, GE Healthcare Amine coupling kit, BR-1000-50). Unreacted groups were inactivated with 1 M ethanol-amine-HCl, pH8.5. Afterwards anti-GITR antibodies were run through the different surfaces at a concentration of 300 nM (45 µg/ml) for 240 seconds at 5 µl/min. Using these conditions saturation of the GITR surface should have been reached. A dissociation time of 60 seconds was included before adding the competing antibody (300 nM, 5 µl/min). Regeneration of the chip surface was performed using 10 mM Glycine pH2.0 (GE Healthcare, BR-1003-55) for 60 seconds at 10 µl/min. Binning was performed using the response units (RU) of the non-competed control (100% binding, saturating conditions).

As is shown in FIG. 8, when the chimeric parental 231-32-15 antibody is first bound to GITR, no further binding of this antibody occurs. However, when the chimeric parental 231-32-15 antibody is first bound to GITR and the antibody m6C8 is applied, this antibody is still able to bind to GITR.

8.4.4 Epitope Mapping—PCR Mutagenesis and Alanine Scanning

In order to map the epitope on GITR to which anti-GITR antibodies described herein bind, error prone PCR was used to generate variants of the human GITR antigen. The variant GITR proteins were expressed on the surface of cells in a cellular library and these cells were screened for binding of the anti-GITR antibodies. As a positive control, a polyclonal anti-GITR antibody was used to confirm proper folding of the GITR protein. For variants of the human GITR antigen to which reduced or no antibody binding occurred, alanine scanning mutagenesis was performed to determine the precise epitope residues that were required for binding by the anti-GITR antibodies described herein.

8.4.4.1 Generation of Human GITR Variants

Error prone PCR mutagenesis was used to generate variants of human GITR with random mutations in the extracellular domain. For error prone PCR, the GeneMorphII Random Mutagenesis Kit (Stratagene) was used, according to the manufacturer's instructions. In brief, 20 PCR cycles in a volume of 50 µl was performed using an in-house construct as template (13 ng, construct number 4377 pMA-T-hu-GITR), 0.05 U/µl Mutazyme II DNA polymerase, 1× Mutazyme II reaction buffer, 0.2 µM of each primer and 0.2 mM of each deoxynucleoside-triphosphate (dATP, dCTP, dGTP, and dTTP). The samples were amplified by PCR (Eppendorf, Germany) using the following program: 95° C. for 2 min; 20 cycles of 95° C. for 30 sec, 56° C. for 30 sec, 72° C. for 1 min; and a final extension step of 72° C. for 10 min. The PCR product was gel purified using 1% agarose gel, the DNA band corresponding to the expected size of 720 bp was cut out and gel extraction was done using a Nucleo-Spin Gel and PCR cleanup kit from Macherey&Nagel according to the product manual. Purified DNA was ligated into an in-house expression vector via XhoI/EcoRI sites using T4 DNA ligase and a ratio of 1:3 (vector:insert). Ligation (25° C.) was stopped after 2 hours with a heat denaturation step for 10 min at 65° C. DNA from the ligation reaction was EtOH precipitated using yeast t-RNA. Standard digestion and ligation techniques were used. The ligation reaction was electroporated into DH10B cells (*E. coli* ElectroMax DH10B electrocompetent cells, Invitrogen; 1900V/5 ms). Electroporated bacteria were plated onto LB-agar+100 µg/ml ampicillin plates and approximately 1.9×10$^8$ colonies were obtained.

All electroporated bacteria were then scratched from the plates and used for large-scale DNA plasmid preparation (Macherey&Nagel, NucleoBond Xtra Maxi Plus Kit), according to the manufacturer's instructions to generate a DNA library. A restriction enzyme digestion with XhoI/EcoRI and BsrGI/EcoRI was performed to quality control the library. Single clones were picked and sent for sequencing to determine the final library diversity.

8.4.4.2 Generation of a Cellular Library with Human GITR Variants

Standard techniques of transfection followed by transduction were used to express human GITR mutants on the surface of 1624-5 cells. For the generation of retroviral particles, a DNA library and vectors expressing retroviral proteins Gag, Pol and Env were transfected into a retroviral packaging cell line (HEK cells) using X-tremeGENE 9

DNA transfection reagent (Roche Diagnostics GmbH, Germany). The resulting retroviral particles accumulated in the cell culture supernatant of the retroviral packaging cells. Two days post transfection cell-free viral vector particle-containing supernatants were harvested and subjected to spin-infection of 1624-5 cells. A transduction efficiency (% human GITR expressing cells) of roughly 4% was obtained. Upon continuous culture for at least one additional day, cells were selected using puromycin (1.5 µg/ml). Untransduced cells served as negative controls (NC). After antibiotic selection, most cells stably expressed the human GITR antigen library on the cell surface. Non-viable cells were removed via a Ficoll separation step.

FACS was used to select cells expressing correctly folded human GITR mutants using a polyclonal anti-GITR antibody and to subsequently select individual cells expressing human GITR variants that did not bind to the anti-GITR chimeric parental 231-32-15 antibody. In brief, antibody binding cells were analyzed by FACS and cells that exhibited specific antibody binding were separated from the non-binding cell population by preparative, high-speed FACS (FACSAriaII, BD Biosciences). Antibody reactive or non-reactive cell pools were expanded again in tissue culture and, due to the stable expression phenotype of retrovirally transduced cells, cycles of antibody-directed cell sorting and tissue culture expansion were repeated, up to the point that a clearly detectable anti-GITR antibody (chimeric parental 231-32-15) non-reactive cell population was obtained. This anti-GITR antibody (chimeric parental 231-32-15) non-reactive cell population was subjected to a final, single-cell sorting step. After several days of cell expansion, single cell sorted cells were again tested for non-binding to anti-GITR chimeric parental 231-32-15 antibody and binding to a polyclonal anti-GITR antibody using 96 well plate analysis on a FACSCalibur (BD Biosciences).

8.4.4.3 Epitope Analysis

To connect phenotype (polyclonal anti-GITR+, chimeric parental 231-32-15-) with genotype, sequencing of single cell sorted huGITR variants was performed. FIGS. 9A and 9B show the alignment of sequences from these variants. The amino acid residues in FIGS. 9A and 9B are numbered according to the immature amino acid sequence of human GITR (SEQ ID NO:41). Sequencing identified regions with increased mutations or "hot spots" (e.g., P62 and G63), providing an indication of the epitope on human GITR recognized by anti-GITR chimeric parental 231-32-15 antibody.

To confirm the precise amino acids of human GITR involved in binding to anti-GITR antibodies, alanine replacement of hot spot amino acids was performed. The following positions (numbered according to SEQ ID NO:41) were separately mutated to an Alanine: P28A, T29A, G30A, G31A, P32A, T54A, T55A, R56A, C57A, C58A, R59A, D60A, Y61A, P62A, G63A, E64A, E65A, C66A, C67A, S68A, E69A, W70A, D71A, C72A, M73A, C74A, V75A, and Q76A. Standard techniques of transfection followed by transduction were used to express these human GITR alanine mutants on the surface of 1624-5 cells.

Finally, alanine mutants expressed on 1624-5 cells were tested in flow cytometry (FACSCalibur; BD Biosciences) for the binding of the anti-GITR humanized antibodies pab1876, pab1967, pab1975 and pab1979, and the reference antibody m6C8. Briefly, 1624-5 cells expressing individual human GITR alanine mutants were incubated with 2 µg/ml of the monoclonal anti-GITR antibody pab1876, pab1967, pab1975, pab1979, or m6C8; or a polyclonal anti-GITR antibody (AF689, R&D systems) conjugated with APC, and Fc receptor block (1:200; BD Cat no. 553142) diluted in 100 µl FACS buffer (PBS+2% FCS) for 20 min at 4° C. After washing, the cells were incubated with a secondary anti-IgG antibody if necessary for detection (APC conjugated; BD Cat no. 109-136-097) diluted in 100 µl FACS buffer (PBS+ 2% FCS) for 20 min at 4° C. The cells were then washed and acquired using a flow cytometer (BD Biosciences). The mean fluorescence intensity (MFI) value of the tested monoclonal antibody was divided by the MFI value of the polyclonal antibody, generating an MFI ratio (monoclonal antibody/polyclonal antibody) for individual GITR alanine mutants. An average MFI ratio ("AMFI ratio") was calculated based on the individual MFI ratios for all the mutants. FIG. 10A is a table summarizing the binding of pab1876, pab1967, pab1975, pab1979 and the reference antibody m6C8 to 1624-5 cells expressing human GITR alanine mutants. An individual MFI ratio that is above 60% of the AMFI ratio is considered to indicate similar binding, after normalization, of that of the polyclonal antibody and is represented by "+" in FIG. 10A. An individual MFI ratio that is between 30% and 60% of the AMFI ratio is represented by "+/−" in FIG. 10A. An individual MFI ratio that is below 30% of the AMFI ratio is represented by "−" in FIG. 10A.

As shown in FIG. 10A, the D60A mutant and the G63A mutant, numbered according to SEQ ID NO:41, specifically disrupted or weakened the binding of pab1876, pab1967, pab1975 and pab1979, but not that of the reference antibody m6C8. The C58A mutant disrupted the binding of all five antibodies and is likely a structural mutation rather than an epitope-specific one. The C74A mutant had weak expression and could not be used for binding comparison.

Furthermore, the anti-GITR antibodies 231-32-15, pab1876, and m6C8 were compared for their binding to wild type versus mutant human GITR. Briefly, wild type human GITR and two GITR alanine mutants (the D60A mutant and the G63A mutant, numbered according to SEQ ID NO:41) were expressed on the surface of 1624-5 cells as described above and tested in a flow cytometry analysis as described above where cells were first stained using 2 µg/ml of the monoclonal antibodies 231-32-15, pab1876, and m6C8, or a polyclonal antibody conjugated to APC, and then stained using a secondary anti-IgG antibody if necessary for detection (APC conjugated; 1:1000; BD Cat No. 109-136-097). All the mean fluorescence intensity (MFI) values were calculated as the mean of two measurements. The MFI value of the tested monoclonal antibody for a particular cell type was divided by the MFI value of the polyclonal antibody for the same cell type, generating a total of nine MFI ratios (monoclonal antibody/polyclonal antibody): MFI ratio$_{231-32-15,\ WT}$, MFI ratio$_{pab1876,\ WT}$, MFI ratio$_{m6C8,\ WT}$, MFI ratio$_{231-32-15,\ D60A}$, MFI ratio$_{pab1876,\ D60A}$, MFI ratio$_{m6C8,\ D60A}$, MFI ratio$_{231-32-15,\ G63A}$, MFI ratio$_{pab1876,\ G63A}$, and MFI ratio$_{m6C8,\ G63A}$. The percentage of binding of an antibody to the GITR alanine mutants relative to the wild type GITR was calculated by dividing a particular MFI ratio for the GITR alanine mutants by the corresponding MFI ratio for the wild type (e.g., dividing MFI ratio$_{pab1876,\ D60A}$ by MFI ratio$_{pab1876,\ WT}$). The percentage of reduction in binding was determined by calculating, e.g., 100%*(1−(MFI ratio$_{pab1876,\ D60A}$/MFI ratio$_{pab1876,\ WT}$)).

As shown in FIG. 10B, the D60A mutant and the G63A mutant specifically disrupted or weakened the binding of 231-32-15 and pab1876, but not that of m6C8. The percentages shown in FIG. 10B are the percentages of GITR positive cells in each plot. When tested using the cells expressing GITR D60A, antibody binding was reduced by 82% and 88% for 231-32-15 and pab1876, respectively, compared with a 10% reduction for m6C8. Similarly, when tested using the cells expressing GITR G63A, the binding of 231-32-15 and pab1876 was reduced by 37% and 59%, respectively, whereas the binding of m6C8 was increased by 62%.

As further evidence for the binding characteristics of the anti-GITR antibodies, the binding of the antibodies to *cynomolgus* GITR was compared. The immature protein of *cynomolgus* GITR comprises the amino acid sequence of SEQ ID NO:44. To increase protein expression, the first residue of the signal peptide of *cynomolgus* GITR was replaced by methionine, generating V1M *cynomolgus* GITR. A mutant *cynomolgus* GITR V1M/Q62P/S63G, where the amino acid residues at the positions 62 and 63 (GlnSer), numbered according to SEQ ID NO:44, were replaced by the corresponding residues in human GITR (ProGly), was then generated. FIG. 11A is a sequence alignment between human GITR, V1M *cynomolgus* GITR, and V1M/Q62P/S63G *cynomolgus* GITR. The three proteins shown in FIG. 11A were expressed on the surface of 1624-5 cells as described above and tested in a flow cytometry analysis as described above where cells were first stained using 2 µg/ml of the monoclonal antibodies 231-32-15, pab1876, and m6C8, or a polyclonal antibody conjugated to APC, and then stained using a secondary anti-IgG antibody (APC conjugated; 1:1000; BD Cat no. 109-136-097).

As shown in FIG. 11B, the anti-GITR antibodies 231-32-15 and pab1876 displayed binding only to the cells expressing V1M/Q62P/S63G *cynomolgus* GITR, but not the cells expressing V1M *cynomolgus* GITR.

8.5 Example 5: Epitope Mapping of Anti-OX40 Antibodies

This example characterizes the epitope of the anti-OX40 antibodies pab1949w, pab2049 and a reference anti-OX40 antibody pab1928. The antibody pab1928 was generated based on the variable regions of the antibody Hu106-122 provided in U.S. Patent Publication No. US 2013/0280275 (herein incorporated by reference). pab1928 comprises a heavy chain of the amino acid sequence of SEQ ID NO:106 and a light chain of the amino acid sequence of SEQ ID NO:107.

8.5.1 Epitope Mapping—Alanine Scanning

The binding characteristics of pab1949w, pab2049 and the reference antibody pab1928 were assessed by alanine scanning. Briefly, the QuikChange HT Protein Engineering System from Agilent Technologies (G5901A) was used to generate human OX40 mutants with alanine substitutions in the extracellular domain. The human OX40 mutants were expressed on the surface of 1624-5 cells using standard techniques of transfection followed by transduction as described above.

Cells expressing correctly folded human OX40 mutants, as evidenced by binding to a polyclonal anti-OX40 antibody in flow cytometry, were further selected for a sub-population that expressed human OX40 mutants that did not bind the monoclonal anti-OX40 antibody pab1949w, pab2049, or pab1928. Cells that exhibited specific antibody binding were separated from the non-binding cell population by preparative, high-speed FACS (FACSAriaII, BD Biosciences). Antibody reactive or non-reactive cell pools were expanded again in tissue culture and, due to the stable expression phenotype of retrovirally transduced cells, cycles of antibody-directed cell sorting and tissue culture expansion were repeated, up to the point that a clearly detectable anti-OX40 antibody (pab1949w, pab2049, or pab1928) non-reactive cell population was obtained. This anti-OX40 antibody non-reactive cell population was subjected to a final, single-cell sorting step. After several days of cell expansion, single cell sorted cells were again tested for binding to a polyclonal anti-OX40 antibody and non-binding to monoclonal antibody pab1949w, pab2049 or pab1928 using flow cytometry. Briefly, 1624-5 cells expressing individual human OX40 alanine mutants were incubated with the monoclonal anti-OX40 antibody pab1949w, pab2049 or pab1928. For each antibody, two antibody concentrations were tested (pab1949w: 2 µg/ml and 0.5 µg/ml; pab2049: 1.8 µg/ml and 0.3 µg/ml; pab1928: 1.1 µg/ml and 0.4 µg/ml). The polyclonal anti-OX40 antibody (AF3388, R&D systems) conjugated with APC was diluted at 1:2000. Fc receptor block (1:200; BD Cat no. 553142) was added, and the samples were incubated for 20 minutes at 4° C. After washing, the cells were incubated with a secondary anti-IgG antibody if necessary for detection (PE conjugated; BD Cat no. 109-116-097) for 20 min at 4° C. The cells were then washed and acquired using a flow cytometer (BD Biosciences).

To connect phenotype (polyclonal anti-OX40 antibody+, monoclonal anti-OX40 antibody−) with genotype, sequencing of single cell sorted human OX40 mutants was performed. FIG. 12 is a table showing the human OX40 alanine mutants that still bind the polyclonal anti-OX40 antibody but do not bind the monoclonal anti-OX40 antibody pab1949w, pab2049, or pab1928. All the residues are numbered according to the mature amino acid sequence of human OX40 (SEQ ID NO:72). "+" indicates binding and "−" indicates loss of binding based on flow cytometry analysis.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. A method of producing a multispecific antibody comprising a first antigen-binding region that specifically binds human OX40 and a second antigen-binding region that specifically binds human GITR, wherein:
   (a) the first antigen-binding region comprises a first heavy chain comprising CDRs VH-CDR1, VH-CDR2, and VH-CDR3, and a first light chain comprising CDRs VL-CDR1, VL-CDR2, and VL-CDR3, wherein the first heavy chain comprises the VH-CDR1, VH-CDR2, and VH-CDR3 amino acid sequences of the VH amino acid sequence of SEQ ID NO: 54, and the first light chain comprises the VL-CDR1, VL-CDR2, and VL-CDR3 amino acid sequences of the VL amino acid sequence of SEQ ID NO: 55; and
   (b) the second antigen-binding region comprises a second heavy chain comprising CDRs VH-CDR1, VH-CDR2, and VH-CDR3, and a second light chain comprising CDRs VL-CDR1, VL-CDR2, and VL-CDR3, wherein the second heavy chain comprises the VH-CDR1, VH-CDR2, and VH-CDR3 amino acid sequences of the VH amino acid sequence of SEQ ID NO: 18, and the second light chain comprises the VL-CDR1, VL-CDR2, and VL-CDR3 amino acid sequences of the VL amino acid sequence of SEQ ID NO: 19,
   the method comprising:
   (c) culturing a first host cell comprising a first polynucleotide encoding the first heavy chain and a second polynucleotide encoding the first light chain under suitable conditions such that the first heavy chain and the first light chain are expressed, and the first antigen-binding region is produced;
   (d) culturing a second host cell comprising a third polynucleotide encoding the second heavy chain and a fourth polynucleotide encoding the second light chain under suitable conditions such that second heavy chain and the second light chain are expressed, and the second antigen-binding region is produced; and
   (e) contacting the first and the second antigen-binding regions produced in steps (c) and (d), under suitable conditions so that the multispecific antibody is produced.

2. The method of claim 1, wherein:
   (a) the VH-CDR1, VH-CDR2, VH-CDR3, VL-CDR1, VL-CDR2, and VL-CDR3 of the first antigen-binding region comprise the amino acid sequences of SEQ ID NOs: 47, 48, 49, 50, 51, and 52, respectively; and
   (b) the VH-CDR1, VH-CDR2, VH-CDR3, VL-CDR1, VL-CDR2, and VL-CDR3 of the second antigen-binding region comprise the amino acid sequences of SEQ ID NOs: 7, 10, 3, 14, 5, and 16, respectively.

3. The method of claim 1, wherein the first heavy chain comprises the amino acid sequence of SEQ ID NO: 54, and/or the first light chain comprises the amino acid sequence of SEQ ID NO: 55.

4. The method of claim 1, wherein the first heavy chain comprises the amino acid sequence of SEQ ID NO: 54, and the first light chain comprises the amino acid sequence of SEQ ID NO: 55.

5. The method of claim 1, wherein the second heavy chain comprises the amino acid sequence of SEQ ID NO: 18, and/or the second light chain comprises the amino acid sequence of SEQ ID NO: 19.

6. The method of claim 1, wherein the second heavy chain comprises the amino acid sequence of SEQ ID NO: 18, and the second light chain comprises the amino acid sequence of SEQ ID NO: 19.

7. The method of claim 1, wherein:
(a) the first heavy chain comprises the amino acid sequence of SEQ ID NO: 54, and the first light chain comprises the amino acid sequence of SEQ ID NO: 55; and
(b) the second heavy chain comprises the amino acid sequence of SEQ ID NO: 18, and the second light chain comprises the amino acid sequence of SEQ ID NO: 19.

8. The method of claim 1, wherein the first heavy chain and/or the second heavy chain comprises a heavy chain constant region selected from the group consisting of human $IgG_1$, $IgG_2$, $IgG_3$, $IgG_4$, $IgA_1$, and $IgA_2$.

9. The method of claim 8, wherein the first heavy chain and/or the second heavy chain comprises an $IgG_1$ heavy chain constant region.

10. The method of claim 9, wherein:
(a) the first heavy chain comprises serine, alanine, and valine at amino acid positions 366, 368, and 407, respectively, and the second heavy chain comprises tryptophan at amino acid position 366; or
(b) the first heavy chain comprises tryptophan at amino acid position 366, and the second heavy chain comprises serine, alanine, and valine at amino acid positions 366, 368, and 407, respectively,
numbered according to the EU numbering system.

11. The method of claim 10, wherein the first heavy chain and/or the second heavy chain comprises aspartate, leucine, and glutamate at amino acid positions 239, 330, and 332, respectively, numbered according to the EU numbering system.

12. The method of claim 1, wherein the first light chain and/or the second light chain comprises a human kappa light chain constant region or a human lambda light chain constant region.

13. The method of claim 9, wherein:
(a) the first heavy chain comprises the amino acid sequence of SEQ ID NO: 54, and the first light chain comprises the amino acid sequence of SEQ ID NO: 67; and
(b) the second heavy chain comprises the amino acid sequence of SEQ ID NO: 18, and the second light chain comprises the amino acid sequence of SEQ ID NO: 37.

14. The method of claim 13, wherein:
(a) the first heavy chain comprises serine, alanine, and valine at amino acid positions 366, 368, and 407, respectively, and the second heavy chain comprises tryptophan at amino acid position 366; or
(b) the first heavy chain comprises tryptophan at amino acid position 366, and the second heavy chain comprises serine, alanine, and valine at amino acid positions 366, 368, and 407, respectively,
numbered according to the EU numbering system.

15. The method of claim 14, wherein the first heavy chain and/or the second heavy chain comprises aspartate, leucine, and glutamate at amino acid positions 239, 330, and 332, respectively, numbered according to the EU numbering system.

16. The method of claim 14, wherein the first heavy chain comprises serine, alanine, and valine at amino acid positions 366, 368, and 407, respectively, and the second heavy chain comprises tryptophan at amino acid position 366, numbered according to the EU numbering system.

17. The method of claim 16, wherein the first heavy chain comprises aspartate, leucine, and glutamate at amino acid positions 239, 330, and 332, respectively, numbered according to the EU numbering system.

18. The method of claim 16, wherein the second heavy chain comprises aspartate, leucine, and glutamate at amino acid positions 239, 330, and 332, respectively, numbered according to the EU numbering system.

19. The method of claim 16, wherein the first heavy chain and the second heavy chain comprise aspartate, leucine, and glutamate at amino acid positions 239, 330, and 332, respectively, numbered according to the EU numbering system.

20. The method of claim 14, wherein the first heavy chain comprises tryptophan at amino acid position 366, and the second heavy chain comprises serine, alanine, and valine at amino acid positions 366, 368, and 407, respectively, numbered according to the EU numbering system.

21. The method of claim 20, wherein the first heavy chain comprises aspartate, leucine, and glutamate at amino acid positions 239, 330, and 332, respectively, numbered according to the EU numbering system.

22. The method of claim 20, wherein the second heavy chain comprises aspartate, leucine, and glutamate at amino acid positions 239, 330, and 332, respectively, numbered according to the EU numbering system.

23. The method of claim 20, wherein the first heavy chain and the second heavy chain comprise aspartate, leucine, and glutamate at amino acid positions 239, 330, and 332, respectively, numbered according to the EU numbering system.

24. A method of producing a multispecific antibody comprising a first antigen-binding region that specifically binds human OX40 and a second antigen-binding region that specifically binds human GITR, wherein:
(a) the first antigen-binding region comprises a first heavy chain comprising CDRs VH-CDR1, VH-CDR2, and VH-CDR3, and a first light chain comprising CDRs VL-CDR1, VL-CDR2, and VL-CDR3, wherein the first heavy chain comprises the VH-CDR1, VH-CDR2, and VH-CDR3 amino acid sequences of the VH amino acid sequence of SEQ ID NO: 54, and the first light chain comprises the VL-CDR1, VL-CDR2, and VL-CDR3 amino acid sequences of the VL amino acid sequence of SEQ ID NO: 55; and
(b) the second antigen-binding region comprises a second heavy chain comprising CDRs VH-CDR1, VH-CDR2, and VH-CDR3, and a second light chain comprising CDRs VL-CDR1, VL-CDR2, and VL-CDR3, wherein the second heavy chain comprises the VH-CDR1, VH-CDR2, and VH-CDR3 amino acid sequences of the VH amino acid sequence of SEQ ID NO: 18, and the second light chain comprises the VL-CDR1, VL-CDR2, and VL-CDR3 amino acid sequences of the VL amino acid sequence of SEQ ID NO: 19,
the method comprising culturing a host cell comprising a first polynucleotide encoding the first heavy chain, a second polynucleotide encoding the first light chain, a third polynucleotide encoding the second heavy chain, and a fourth polynucleotide encoding the second light chain, under suitable conditions such that the first heavy chain, the second heavy chain, the first light chain, and the second light chain are expressed, and the multispecific antibody is produced.

25. The method of claim 24, wherein:
(a) the VH-CDR1, VH-CDR2, VH-CDR3, VL-CDR1, VL-CDR2, and VL-CDR3 of the first antigen-binding region comprise the amino acid sequences of SEQ ID NOs: 47, 48, 49, 50, 51, and 52, respectively; and
(b) the VH-CDR1, VH-CDR2, VH-CDR3, VL-CDR1, VL-CDR2, and VL-CDR3 of the second antigen-binding region comprise the amino acid sequences of SEQ ID NOs: 7, 10, 3, 14, 5, and 16, respectively.

26. The method of claim 24, wherein the first heavy chain comprises the amino acid sequence of SEQ ID NO: 54, and/or the first light chain comprises the amino acid sequence of SEQ ID NO: 55.

27. The method of claim 24, wherein the first heavy chain comprises the amino acid sequence of SEQ ID NO: 54, and the first light chain comprises the amino acid sequence of SEQ ID NO: 55.

28. The method of claim 24, wherein the second heavy chain comprises the amino acid sequence of SEQ ID NO: 18, and/or the second light chain comprises the amino acid sequence of SEQ ID NO: 19.

29. The method of claim 24, wherein the second heavy chain comprises the amino acid sequence of SEQ ID NO: 18, and the second light chain comprises the amino acid sequence of SEQ ID NO: 19.

30. The method of claim 24, wherein:
(a) the first heavy chain comprises the amino acid sequence of SEQ ID NO: 54, and the first light chain comprises the amino acid sequence of SEQ ID NO: 55; and/or
(b) the second heavy chain comprises the amino acid sequence of SEQ ID NO: 18, and the second light chain comprises the amino acid sequence of SEQ ID NO: 19.

31. The method of claim 24, wherein the first heavy chain and/or the second heavy chain comprises a heavy chain constant region selected from the group consisting of human $IgG_1$, $IgG_2$, $IgG_3$, $IgG_4$, $IgA_1$, and $IgA_2$.

32. The method of claim 31, wherein the first heavy chain and/or the second heavy chain comprises an $IgG_1$ heavy chain constant region.

33. The method of claim 32, wherein:
(a) the first heavy chain comprises serine, alanine, and valine at amino acid positions 366, 368, and 407, respectively, and the second heavy chain comprises tryptophan at amino acid position 366; or
(b) the first heavy chain comprises tryptophan at amino acid position 366, and the second heavy chain comprises serine, alanine, and valine at amino acid positions 366, 368, and 407, respectively,
numbered according to the EU numbering system.

34. The method of claim 33, wherein the first heavy chain and/or the second heavy chain comprises aspartate, leucine, and glutamate at amino acid positions 239, 330, and 332, respectively, numbered according to the EU numbering system.

35. The method of claim 24, wherein the first light chain and/or the second light chain comprises a human kappa light chain constant region or a human lambda light chain constant region.

36. The method of claim 24, wherein:
(a) the first heavy chain comprises the amino acid sequence of SEQ ID NO: 54, and the first light chain comprises the amino acid sequence of SEQ ID NO: 67; and
(b) the second heavy chain comprises the amino acid sequence of SEQ ID NO: 18, and the second light chain comprises the amino acid sequence of SEQ ID NO: 37.

37. The method of claim 36, wherein:
(a) the first heavy chain comprises serine, alanine, and valine at amino acid positions 366, 368, and 407, respectively, and the second heavy chain comprises tryptophan at amino acid position 366; or
(b) the first heavy chain comprises tryptophan at amino acid position 366, and the second heavy chain comprises serine, alanine, and valine at amino acid positions 366, 368, and 407, respectively,
numbered according to the EU numbering system.

38. The method of claim 37, wherein the first heavy chain and/or the second heavy chain comprises aspartate, leucine, and glutamate at amino acid positions 239, 330, and 332, respectively, numbered according to the EU numbering system.

39. The method of claim 37, wherein the first heavy chain comprises serine, alanine, and valine at amino acid positions 366, 368, and 407, respectively, and the second heavy chain comprises tryptophan at amino acid position 366, numbered according to the EU numbering system.

40. The method of claim 39, wherein the first heavy chain comprises aspartate, leucine, and glutamate at amino acid positions 239, 330, and 332, respectively, numbered according to the EU numbering system.

41. The method of claim 39, wherein the second heavy chain comprises aspartate, leucine, and glutamate at amino acid positions 239, 330, and 332, respectively, numbered according to the EU numbering system.

42. The method of claim 39, wherein the first heavy chain and the second heavy chain comprise aspartate, leucine, and glutamate at amino acid positions 239, 330, and 332, respectively, numbered according to the EU numbering system.

43. The method of claim 37, wherein the first heavy chain comprises tryptophan at amino acid position 366, and the second heavy chain comprises serine, alanine, and valine at amino acid positions 366, 368, and 407, respectively, numbered according to the EU numbering system.

44. The method of claim 43, wherein the first heavy chain comprises aspartate, leucine, and glutamate at amino acid positions 239, 330, and 332, respectively, numbered according to the EU numbering system.

45. The method of claim 43, wherein the second heavy chain comprises aspartate, leucine, and glutamate at amino acid positions 239, 330, and 332, respectively, numbered according to the EU numbering system.

46. The method of claim 43, wherein the first heavy chain and the second heavy chain comprise aspartate, leucine, and glutamate at amino acid positions 239, 330, and 332, respectively, numbered according to the EU numbering system.

* * * * *